(12) United States Patent
Weiner et al.

(10) Patent No.: US 7,232,672 B2
(45) Date of Patent: Jun. 19, 2007

(54) P450 ENZYMES, NUCLEIC ACIDS ENCODING THEM AND METHODS OF MAKING AND USING THEM

(75) Inventors: David Weiner, Del Mar, CA (US); Mark J. Burk, San Diego, CA (US); Tim Hitchman, San Diego, CA (US); Catherine Pujol, Santee, CA (US); Toby Richardson, San Diego, CA (US); Jay M. Short, Rancho Santa Fe, CA (US)

(73) Assignee: Diversa Corporation, San Diego, CA (US)

( * ) Notice: Subject to any disclaimer, the term of this patent is extended or adjusted under 35 U.S.C. 154(b) by 39 days.

(21) Appl. No.: 10/214,446

(22) Filed: Aug. 5, 2002

(65) Prior Publication Data

US 2003/0180742 A1 Sep. 25, 2003

Related U.S. Application Data

(60) Provisional application No. 60/309,497, filed on Aug. 3, 2001.

(51) Int. Cl.
| | |
|---|---|
| *C12N 9/02* | (2006.01) |
| *C12N 1/20* | (2006.01) |
| *C12N 15/00* | (2006.01) |
| *C12N 21/04* | (2006.01) |
| *C12Q 1/00* | (2006.01) |
| *C12Q 1/68* | (2006.01) |
| *C12P 21/04* | (2006.01) |
| *C12N 5/00* | (2006.01) |

(52) U.S. Cl. .............. 435/189; 435/4; 435/6; 435/69.1; 435/71.1; 435/252.3; 435/320.1; 435/325; 435/440; 536/23.2; 536/23.7

(58) Field of Classification Search ............... 435/189, 435/440, 71.1, 252.3, 320.1, 6, 69.1, 4, 325, 435/7.1; 536/23.2, 23.1, 23.7
See application file for complete search history.

(56) References Cited

U.S. PATENT DOCUMENTS

| | | | |
|---|---|---|---|
| 6,060,253 | A | 5/2000 | Gleboin et al. |
| 6,207,648 | B1 | 3/2001 | Waxman et al. |
| 6,217,860 | B1 | 4/2001 | Woo et al. |
| 6,242,203 | B1 | 6/2001 | Melvin et al. |
| 6,274,360 | B1 | 8/2001 | Demain et al. |
| 6,284,219 | B1 | 9/2001 | Ajami et al. |
| 6,288,087 | B1 | 9/2001 | King |
| 6,300,544 | B1 | 10/2001 | Halkier et al. |

(Continued)

OTHER PUBLICATIONS

Kappel et al. Current Opinion in Biotechnology 3 :548-553, 1992.*

(Continued)

*Primary Examiner*—P. Achutamurthy
*Assistant Examiner*—Yong D. Pak
(74) *Attorney, Agent, or Firm*—Morrison & Foerster LLP

(57) ABSTRACT

The invention is directed to polypeptides having P450 activity, polynucleotides encoding the polypeptides, antibodies that bind to these polypeptides, and methods for making and using these polynucleotides and polypeptides. The P450 enzymes can be used to catalyze the hydrolysis of epoxides and arene oxides to their corresponding diols.

55 Claims, 14 Drawing Sheets

Sharpless asymmetric epoxidation:

Jacobsen asymmetric epoxidation:

Julia asymmetric epoxidation:

U.S. PATENT DOCUMENTS

| | | |
|---|---|---|
| 6,306,624 B1 | 10/2001 | Petkovich et al. |
| 6,306,907 B1 | 10/2001 | Nishikawa et al. |
| 6,312,917 B1 | 11/2001 | Thakker et al. |
| 6,380,465 B1 | 4/2002 | Barrett |
| 6,387,647 B1 | 5/2002 | Kirsch et al. |
| 6,420,131 B1 | 7/2002 | Miller et al. |

OTHER PUBLICATIONS

Mullins et al. Hypertension 22(4):630-633, 1993.*

International Search Report, mailed on Mar. 22, 2004, for PCT application No. PCT/US02/24910, 2 pages.

Rodriguez et al., Database GenBank, US National Library of Medicine (Bethesda, MD USA) (1996) L37200.

Rodriguez et al., FEMS Lett. (1995) 127(1-2):117-120.

Ueda et al. Database GenBank, US National Library of Medicine (Bethesda, MD, USA) (1998) No. AB018074.

Ueda et al., J. Antibiot. (1995) 48(7):638-646.

Katsuki, et al., "The First Practical Method for Asymmetric Epoxidation", *J. Am. Chem. Soc.*, vol. 102, No. 18, pp. 5974-5976, Aug. 27, 1980.

Zhang, et al., "Enantioselective Epoxidation of Unfunctionalized Olefins Catalyzed by (Salen)manganese Complexes", *J. Am. Chem. Soc.*, vol. 112, No. 7, pp. 2801-2803, Mar. 28, 1990.

Sharpless, et al. "High Stereo- and Regioselectivities in the Transition Metal Catalyzed Epoxidations of Olefine Alcohols by *tert*-Butyl Hydroperoxide", *J. Am. Chem. Soc.*, vol. 95, No. 18, pp. 6136-6137, Sep. 5, 1973.

Julia, et al., "Synthetic Enzymes"; Highly Stereoselective Epoxidation of Chalcone in Toluene-Water-Poly[(*S*)-Alanine] *Angew. Chem.*, vol. 92, No. 11, pp. 968-969 (original and translation).

* cited by examiner

Sharpless asymmetric epoxidation:

> 90% ee

Jacobsen asymmetric epoxidation:

92% ee

Julia asymmetric epoxidation:

R=Me: 92% ee

P450 ENZYMES, NUCLEIC ACIDS ENCODING THEM AND METHODS OF MAKING AND USING THEM

CROSS-REFERENCE TO RELATED APPLICATIONS

This application claims the benefit of priority under 35 U.S.C. § 119(e) of U.S. Provisional Application U.S. Ser. No. (USSN) 60/309,497, filed Aug. 3, 2001. The aforementioned application is explicitly incorporated herein by reference in its entirety and for all purposes.

TECHNICAL FIELD

This invention relates to molecular and cellular biology and biochemistry. In particular, the invention is directed to polypeptides having a P450 activity, polynucleotides encoding the polypeptides, and methods for making and using these polynucleotides and polypeptides. The present invention relates generally to methods of selecting or screening and identification of P450 enzymes for use in the production of epoxides. The present invention provides methods of producing epoxides using the P450 enzymes of the invention.

BACKGROUND

Chiral molecules, including alcohols, α-hydroxy acids and epoxides, are important for the synthesis of pharmaceuticals, agrochemicals, as well as many fine chemicals. A major challenge in modem organic chemistry is to generate such compounds in high yields, with high stereo- and regioselectivities. Enantiopure epoxides are versatile synthons for the synthesis of numerous pharmaceuticals, agrochemicals and other high value compounds. However, current chemical routes to chiral epoxides suffer from significant shortcomings (listed below) that have prevented their widespread application in process-scale synthesis.

Of the current techniques available, the most widely utilized are the Sharpless epoxidation reaction (Sharpless, K. B. & Michaelson, R. C. J. *J. Am. Chem. Soc.* 1973 95, 6136), the Jacobsen/Katsuki-type epoxidations (Zhang, W., Loebach, J. L., Wilson, S. R., & Jacobsen, E. N. *J. Am. Chem. Soc.* 1990 112, 2801; Katsuki, T. & Sharpless, K. B. *J. Am. Chem. Soc.* 1980 102, 5974), and the Julia polyleucine-catalyzed reaction (Julia, S., Masana, J., & Vega, J. C. *Angew. Chem.* 1980 92, 968) (FIG. 1). All of these methods are limited in their application to process-scale chiral synthesis by problematic features that include the use of expensive metal catalysts, low substrate/catalyst ratios, and limited efficiency and productivity with low to moderate enantioselectivities. Furthermore, each method is restricted in the range of substrates on which it can be effectively used. The Sharpless epoxidation catalyst is constrained to acting on allylic alcohols, the Jacobson reaction only works effectively on cis-disubstituted alkenes and the Julia method only has application to chalcone-like alkenes. It is clear, therefore, that there is a need for asymmetric oxidative catalysts that are capable of yielding the same high enantiomeric excesses of the above methods, but are also able to function on a process scale and under mild reaction conditions. Oxidative enzymes meet these criteria and have the potential to provide commercially viable alternatives to the chemical catalysts.

As mentioned above, there is currently a need in the biotechnology and chemical industry for molecules that can optimally carry out biological or chemical processes (e.g., enzymes). For example, molecules and compounds that are utilized in both established and emerging chemical, pharmaceutical, textile, food and feed, and detergent markets must meet stringent economical and environmental standards. The synthesis of polymers, pharmaceuticals, natural products and agrochemicals is often hampered by expensive processes which produce harmful byproducts and which suffer from poor or inefficient catalysis. Enzymes, for example, have a number of remarkable advantages which can overcome these problems in catalysis: they act on single functional groups, they distinguish between similar functional groups on a single molecule, and they distinguish between enantiomers. Moreover, they are biodegradable and function at very low mole fractions in reaction mixtures. Because of their chemo-, regio- and stereospecificity, enzymes present a unique opportunity to optimally achieve desired selective transformations. These are often extremely difficult to duplicate chemically, especially in single-step reactions. The elimination of the need for protection groups, selectivity, the ability to carry out multi-step transformations in a single reaction vessel, along with the concomitant reduction in environmental burden, has led to the increased demand for enzymes in chemical and pharmaceutical industries. Enzyme-based processes have been gradually replacing many conventional chemical-based methods. A current limitation to more widespread industrial use is primarily due to the relatively small number of commercially available enzymes. Only ~300 enzymes (excluding DNA modifying enzymes) are at present commercially available from the >3000 non DNA-modifying enzyme activities thus far described.

The use of enzymes for technological applications also may require performance under demanding industrial conditions. This includes activities in environments or on substrates for which the currently known arsenal of enzymes was not evolutionarily selected. However, the natural environment provides extreme conditions including, for example, extremes in temperature and pH. A number of organisms have adapted to these conditions due in part to selection for polypeptides than can withstand these extremes.

Enzymes have evolved by selective pressure to perform very specific biological functions within the milieu of a living organism, under conditions of temperature, pH and salt concentration. For the most part, the non-DNA modifying enzyme activities thus far identified have been isolated from mesophilic organisms, which represent a very small fraction of the available phylogenetic diversity. The dynamic field of biocatalysis takes on a new dimension with the help of enzymes isolated from microorganisms that thrive in extreme environments. For example, such enzymes must function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. Environmental samples obtained, for example, from extreme conditions containing organisms, polynucleotides or polypeptides (e.g., enzymes) open a new field in biocatalysis. By rapidly screening for polynucleotides encoding polypeptides of interest, the invention provides not only a source of materials for the development of biologics, therapeutics, and enzymes for industrial applications, but also provides a new materials for further processing by, for example, directed evolution and mutagenesis to develop molecules or polypeptides modified for particular activity, specificity or conditions.

In addition to the need for new enzymes for industrial use, there has been a dramatic increase in the need for bioactive compounds with novel activities. This demand has arisen largely from changes in worldwide demographics coupled with the clear and increasing trend in the number of pathogenic organisms that are resistant to currently available antibiotics. For example, while there has been a surge in demand for antibacterial drugs in emerging nations with young populations, countries with aging populations, such as the U.S., require a growing repertoire of drugs against cancer, diabetes, arthritis and other debilitating conditions. The death rate from infectious diseases has increased 58% between 1980 and 1992 and it has been estimated that the emergence of antibiotic resistant microbes has added in excess of $30 billion annually to the cost of health care in the U.S. alone. (Adams et al., *Chemical and Engineering News,* 1995; Amann et al., *Microbiological Reviews,* 59, 1995). As a response to this trend pharmaceutical companies have significantly increased their screening of microbial diversity for compounds with unique activities or specificity. Accordingly, the invention can be used to obtain and identify polynucleotides and related sequence specific information from, for example, infectious microorganisms present in the environment such as, for example, in the gut of various macroorganisms.

Identifying novel enzymes in an environmental sample is one solution to this problem. By rapidly identifying polypeptides having an activity of interest and polynucleotides encoding the polypeptide of interest the invention provides methods, compositions and sources for the development of biologics, diagnostics, therapeutics, and compositions for industrial applications.

Oxidative enzymes have been studied extensively over the last few decades. A wide variety of oxidations are catalyzed by these enzymes, including oxidation of alcohols, hydroxylation and epoxidation (FIG. 2). Those reactions that involve insertion of molecular oxygen into an organic molecule (oxygenation) are typically the most difficult to achieve in a stereo and regioselective manner using conventional synthetic chemistry. Use of enzymes to catalyze these transformations is potentially an extremely powerful synthetic tool because they introduce reactive, chemical functionality into previously unactivated positions. Furthermore, these oxygenases can introduce this functionality with high stereospecificity under mild reaction conditions. However, compared to the widely used hydrolases and despite the potential advantages, there have been relatively few commercialized applications of oxidative enzymes to biocatalysis and biotransformation.

P450s are oxidative enzymes that are widespread in nature and are involved in processes such as detoxifying xenobiotics, catabolism of unusual carbon sources and biosynthesis of secondary metabolites. These oxygenases activate molecular oxygen using an iron-heme center and utilize a redox electron shuttle to support the epoxidation reaction. However, to date there have been few reports of syntheses of epoxides using oxidative enzymes (or epoxidases). This is probably due to the difficulty in discovering suitable epoxidases from the limited biodiversity accessible through traditional methods.

SUMMARY

The invention provides isolated or recombinant nucleic acids comprising a nucleic acid sequence having at least 50%, 55%, 60%, 65%, 70%, 75%, 80%, 85%, 90%, 95%, 98%, 99%, or more, sequence identity to SEQ ID NO:3, SEQ ID NO:5, SEQ ID NO:7, SEQ ID NO:9, SEQ ID NO:11, SEQ ID NO:13, SEQ ID NO:23, SEQ ID NO:25, SEQ ID NO:41, SEQ ID NO:45, SEQ ID NO:47, SEQ ID NO:49, SEQ ID NO:51, or SEQ ID NO:53 over a region of at least about 100, 200, 300, 400, 500, 600, 700, 800, 900, 1000, 1100, 1200, 1300, 1400, or more, residues, wherein the nucleic acid encodes at least one polypeptide having a P450 activity, and the sequence identities are determined by analysis with a sequence comparison algorithm or by a visual inspection.

The invention provides isolated or recombinant nucleic acids comprising a nucleic acid sequence having at least 60%, 65%, 70%, 75%, 80%, 85%, 90%, 95%, 98%, 99%, or more sequence identity to SEQ ID NO:1, SEQ ID NO:15, SEQ ID NO:17, SEQ ID NO:21, SEQ ID NO:33, SEQ ID NO:37, SEQ ID NO:39, SEQ ID NO:43, or SEQ ID NO:55 over a region of at least about 100, 200, 300, 400, 500, 600, 700, 800, 900, 1000, 1100, 1200, 1300, 1400, or more, residues, wherein the nucleic acid encodes at least one polypeptide having a P450 activity, and the sequence identities are determined by analysis with a sequence comparison algorithm or by a visual inspection.

The invention provides isolated or recombinant nucleic acids comprising a nucleic acid sequence having at least 70%, 75%, 80%, 85%, 90%, 95%, 98%, 99%, or more, sequence identity to SEQ ID NO:29, SEQ ID NO:31, or SEQ ID NO:35 over a region of at least about 100, 200, 300, 400, 500, 600, 700, 800, 900, 1000, 1100, 1200, 1300, 1400, or more, residues, wherein the nucleic acid encodes at least one polypeptide having a P450 activity, and the sequence identities are determined by analysis with a sequence comparison algorithm or by a visual inspection.

The invention provides isolated or recombinant nucleic acids comprising a nucleic acid sequence having at least 80%, 85%, 90%, 95%, 98%, 99%, or more, sequence identity to SEQ ID NO:27 over a region of at least about 100, 200, 300, 400, 500, 600, 700, 800, 900, 1000, 1100, 1200, or more, residues, wherein the nucleic acid encodes at least one polypeptide having a P450 activity, and the sequence identities are determined by analysis with a sequence comparison algorithm or by a visual inspection.

The invention provides isolated or recombinant nucleic acids comprising a nucleic acid sequence having at least 90%, 95%, 98%, 99%, or more, sequence identity to SEQ ID NO:19 over a region of at least about 100, 200, 300, 400, 500, 600, 700, 800, 900, 1000, 1100, 1200, or more, residues, wherein the nucleic acid encodes at least one polypeptide having a P450 activity, and the sequence identities are determined by analysis with a sequence comparison algorithm or by a visual inspection.

In one aspect, the invention provides isolated or recombinant nucleic acids, wherein the nucleic acid sequence comprises a sequence as set forth in SEQ ID NO:1, a sequence as set forth in SEQ ID NO:3, a sequence as set forth in SEQ ID NO:5, a sequence as set forth in SEQ ID NO:7, a sequence as set forth in SEQ ID NO:9, a sequence as set forth in SEQ ID NO:11, a sequence as set forth in SEQ ID NO:13, a sequence as set forth in SEQ ID NO:15, a sequence as set forth in SEQ ID NO:17, a sequence as set forth in SEQ ID NO:19, a sequence as set forth in SEQ ID NO:21, a sequence as set forth in SEQ ID NO:23, a sequence as set forth in SEQ ID NO:25, a sequence as set forth in SEQ ID NO:27, a sequence as set forth in SEQ ID NO:29, a sequence as set forth in SEQ ID NO:31, a sequence as set forth in SEQ ID NO:33, a sequence as set forth in SEQ ID NO:35, a sequence as set forth in SEQ ID NO:37, a sequence as set forth in SEQ ID NO:39, a sequence as set forth in SEQ ID NO:41, a sequence as set forth in SEQ ID NO:43, a sequence as set forth in SEQ ID NO:45, a sequence as set forth in SEQ ID NO:47, a sequence as set forth in SEQ ID NO:49, a sequence as set forth in SEQ ID NO:51, a sequence as set forth in SEQ ID NO:53, or a sequence as set forth in SEQ ID NO:55.

In one aspect, the invention provides isolated or recombinant nucleic acids, wherein the nucleic acid encodes a polypeptide comprising a sequence as set forth in SEQ ID NO:2, a sequence as set forth in SEQ ID NO:4, a sequence as set forth in SEQ ID NO:6, a sequence as set forth in SEQ ID NO:8, a sequence as set forth in SEQ ID NO:10, a sequence as set forth in SEQ ID NO:12, a sequence as set forth in SEQ ID NO:14, a sequence as set forth in SEQ ID NO:16, a sequence as set forth in SEQ ID NO:18, a sequence as set forth in SEQ ID NO:20, a sequence as set forth in SEQ ID NO:22, a sequence as set forth in SEQ ID NO:24, a sequence as set forth in SEQ ID NO:26, a sequence as set forth in SEQ ID NO:28, a sequence as set forth in SEQ ID NO:30, a sequence as set forth in SEQ ID NO:32, a sequence as set forth in SEQ ID NO:34, a sequence as set forth in SEQ ID NO:36, a sequence as set forth in SEQ ID NO:38, a sequence as set forth in SEQ ID NO:40, a sequence as set forth in SEQ ID NO:42, a sequence as set forth in SEQ ID NO:44, a sequence as set forth in SEQ ID NO:46, a sequence as set forth in SEQ ID NO:48, a sequence as set forth in SEQ ID NO:50, a sequence as set forth in SEQ ID NO:52, a sequence as set forth in SEQ ID NO:54, or a sequence as set forth in SEQ ID NO:56.

In one aspect, the sequence comparison algorithm is a BLAST version 2.2.2 algorithm where a filtering setting is set to Blastall -p Blastp -d "nr pataa" -F F, and all other options are set to default.

In one aspect, the P450 activity comprises a monooxygenation reaction. In one aspect, the P450 activity comprises catalysis of incorporation of oxygen into a substrate. In one aspect, the P450 activity can further comprise hydroxylation of aliphatic or aromatic carbons. In another aspect, the P450 activity can comprise epoxidation. Alternatively, the P450 activity can comprise N—, O—, or S-dealkylation. In one aspect, the P450 activity can comprise dehalogenation. In another aspect the P450 activity can comprise oxidative deamination. Alternatively, the P450 activity can comprise N-oxidation or N-hydroxylation. In one aspect, the P450 activity can comprise sulphoxide formation.

In one aspect, the epoxidase activity further comprises an alkene substrate. The epoxidase activity can further comprise production of a chiral product. In one aspect, the epoxidase activity can be enantioselective.

The invention provides isolated or recombinant nucleic acids, wherein the P450 activity is thermostable. In one aspect, the polypeptide can retain a P450 activity under conditions comprising a temperature range of between about 37° C. to about 70° C. in another aspect, the P450 activity can be thermotolerant. The polypeptide can retain a P450 activity after exposure to a temperature in the range from greater than 37° C. to about 90° C. In another aspect, the polypeptide can retain a P450 activity after exposure to a temperature in the range from greater than 37° C. to about 50° C.

The invention provides isolated or recombinant nucleic acids, wherein the nucleic acid comprises a sequence that hybridizes under stringent conditions to a nucleic acid comprising: a sequence as set forth in SEQ ID NO:1, a sequence as set forth in SEQ ID NO:3, a sequence as set forth in SEQ ID NO:5, a sequence as set forth in SEQ ID NO:7, a sequence as set forth in SEQ ID NO:9, a sequence as set forth in SEQ ID NO:11, a sequence as set forth in SEQ ID NO:13, a sequence as set forth in SEQ ID NO:15, a sequence as set forth in SEQ ID NO:17, a sequence as set forth in SEQ ID NO:19, a sequence as set forth in SEQ ID NO:21, a sequence as set forth in SEQ ID NO:23, a sequence as set forth in SEQ ID NO:25, a sequence as set forth in SEQ ID NO:27, a sequence as set forth in SEQ ID NO:29, a sequence as set forth in SEQ ID NO:31, a sequence as set forth in SEQ ID NO:33, a sequence as set forth in SEQ ID NO:35, a sequence as set forth in SEQ ID NO:37, a sequence as set forth in SEQ ID NO:39, a sequence as set forth in SEQ ID NO:41, a sequence as set forth in SEQ ID NO:43, a sequence as set forth in SEQ ID NO:45, a sequence as set forth in SEQ ID NO:47, a sequence as set forth in SEQ ID NO:49, a sequence as set forth in SEQ ID NO:51, a sequence as set forth in SEQ ID NO:53, or a sequence as set forth in SEQ ID NO:55, wherein the nucleic acid encodes a polypeptide having a P450 activity. The nucleic acid can be at least 100, 200, 300, 400, 500, 600, 700, 800, 900, 1000, 1100, 1200, 1300 residues in length or the full length of the gene or transcript. In one aspect, the stringent conditions include a wash step comprising a wash in 0.2×SSC at a temperature of about 65° C. for about 15 minutes.

The invention provides a nucleic acid probe for identifying a nucleic acid encoding a polypeptide with a P450 activity, wherein the probe comprises at least 1, 20, 30, 40, 50, 60, 70, 80, 90, 100, 150, 200, 250, 300, 350, 400, 450, 500, 550, 600, 650, 700, 750, 800, 850, 900, 950, 1000, or more consecutive bases of a sequence comprising: a sequence as set forth in SEQ ID NO:1, a sequence as set forth in SEQ ID NO:3, a sequence as set forth in SEQ ID NO:5, a sequence as set forth in SEQ ID NO:7, a sequence as set forth in SEQ ID NO:9, a sequence as set forth in SEQ ID NO:11, a sequence as set forth in SEQ ID NO:13, a sequence as set forth in SEQ ID NO:15, a sequence as set forth in SEQ ID NO:17, a sequence as set forth in SEQ ID NO:19, a sequence as set forth in SEQ ID NO:21, a sequence as set forth in SEQ ID NO:23, a sequence as set forth in SEQ ID NO:25, a sequence as set forth in SEQ ID NO:27, a sequence as set forth in SEQ ID NO:29, a sequence as set forth in SEQ ID NO:31, a sequence as set forth in SEQ ID NO:33, a sequence as set forth in SEQ ID NO:35, a sequence as set forth in SEQ ID NO:37, a sequence as set forth in SEQ ID NO:39, a sequence as set forth in SEQ ID NO:41, a sequence as set forth in SEQ ID NO:43, a sequence as set forth in SEQ ID NO:45, a sequence as set forth in SEQ ID NO:47, a sequence as set forth in SEQ ID NO:49, a sequence as set forth in SEQ ID NO:51, a sequence as set forth in SEQ ID NO:53, or a sequence as set forth in SEQ ID NO:55, wherein the probe identifies the nucleic acid by binding or hybridization. The probe can comprise an oligonucleotide comprising at least about 10 to 50, about 20 to 60, about 30 to 70, about 40 to 80, or about 60 to 100 consecutive bases of a nucleic acid of the invention, e.g., a sequence comprising a sequence as set forth in SEQ ID NO:1, a sequence as set forth in SEQ ID NO:3, a sequence as set forth in SEQ ID NO:5, a sequence as set forth in SEQ ID NO:7, a sequence as set forth in SEQ ID NO:9, a sequence as set forth in SEQ ID NO:11, a sequence as set forth in SEQ ID NO:13, a sequence as set forth in SEQ ID NO:15, a sequence as set forth in SEQ ID NO:17, a sequence as set forth in SEQ ID NO:19, a sequence as set forth in SEQ ID NO:21, a sequence as set forth in SEQ ID NO:23, a sequence as set forth in SEQ ID NO:25, a sequence as set forth in SEQ ID NO:27, a sequence as set forth in SEQ ID NO:29, a sequence as set forth in SEQ ID NO:31, a sequence as set forth in SEQ ID NO:33, a sequence as set forth in SEQ ID NO:35, a sequence as set forth in SEQ ID NO:37, a sequence as set forth in SEQ ID NO:39, a sequence as set forth in SEQ ID NO:41, a sequence as set forth in SEQ ID NO:43, a sequence as set forth in SEQ ID NO:45, a sequence as set forth in SEQ ID NO:47, a sequence as set forth in SEQ ID NO:49, a sequence as set forth in SEQ ID NO:51, a sequence as set forth in SEQ ID NO:53, or a sequence as set forth in SEQ ID NO:55.

The invention provides a nucleic acid probe for identifying a nucleic acid encoding a polypeptide having a P450 activity, wherein the probe comprises a nucleic acid comprising a nucleic acid sequence having at least 50%, 55%, 60%, 65%, 70%, 75%, 80%, 85%, 90%, 95%, 98%, 99%, or more sequence identity to SEQ ID NO:3, SEQ ID NO:5, SEQ ID NO:7, SEQ ID NO:9, SEQ ID NO:11, SEQ ID NO:13, SEQ ID NO:23, SEQ ID NO:25, SEQ ID NO:41, SEQ ID NO:45, SEQ ID NO:47, SEQ ID NO:49, SEQ ID NO:51, or SEQ ID NO:53 over a region of at least about 100 residues, wherein the sequence identities are determined by analysis with a sequence comparison algorithm or by visual inspection.

The invention provides a nucleic acid probe comprising a nucleic acid sequence having at least 60%, 65%, 70%, 75%, 80%, 85%, 90%, 95%, 98%, 99%, or more sequence identity to SEQ ID NO:1, SEQ ID NO:15, SEQ ID NO:17, SEQ ID NO:21, SEQ ID NO:33, SEQ ID NO:37, SEQ ID NO:39, SEQ ID NO:43, or SEQ ID NO:55 over a region of at least about 100 residues, wherein the sequence identities are determined by analysis with a sequence comparison algorithm or by visual inspection.

The invention provides a nucleic acid probe comprising a nucleic acid sequence having at least 70%, 75%, 80%, 85%, 90%, 95%, 98%, 99%, or more, sequence identity to SEQ ID NO:29, SEQ ID NO:31, or SEQ ID NO:35 over a region of at least about 100 residues, wherein the sequence identities are determined by analysis with a sequence comparison algorithm or by visual inspection.

The invention provides a nucleic acid probe comprising a nucleic acid sequence having at least 80%, 85%, 90%, 95%, 98%, 99%, or more, sequence identity to SEQ ID NO:27 over a region of at least about 100 residues, wherein the sequence identities are determined by analysis with a sequence comparison algorithm or by visual inspection.

The invention provides a nucleic acid probe comprising a nucleic acid sequence having at least 90%, 95%, 98%, 99%, or more, sequence identity to SEQ ID NO:19 over a region of at least about 100 residues, wherein the sequence identities are determined by analysis with a sequence comparison algorithm or by visual inspection.

The probe can comprise an oligonucleotide comprising at least about 10 to 50, about 20 to 60, about 30 to 70, about 40 to 80, or about 60 to 100 consecutive bases of a nucleic acid sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof.

The invention provides an amplification primer sequence pair for amplifying a nucleic acid encoding a polypeptide having a P450 activity, wherein the primer pair is capable of amplifying a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof. In one aspect, one or each member of the amplification primer sequence pair comprises an oligonucleotide comprising at least about 10 to 50 consecutive bases of the sequence.

The invention provides methods of amplifying a nucleic acid encoding a polypeptide having a P450 activity comprising amplification of a template nucleic acid with an amplification primer sequence pair capable of amplifying a nucleic acid sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof.

The invention provides expression cassettes comprising a nucleic acid of the invention, or, a nucleic acid that hybridizes under stringent conditions to a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof.

The invention provides vector comprising a nucleic acid of the invention, or, a nucleic acid that hybridizes under stringent conditions to a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof.

The invention provides cloning vehicles comprising a vector of the invention, or a nucleic acid of the invention. The cloning vehicle can comprise a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

The invention provides transformed cells comprising a vector of the invention, a cloning vehicle of the invention, or a nucleic acid of the invention, e.g., a nucleic acid comprising: (i) a nucleic acid sequence having at least 50% sequence identity to SEQ ID NO:3, SEQ ID NO:5, SEQ ID NO:7, SEQ ID NO:9, SEQ ID NO:11, SEQ ID NO:13, SEQ ID NO:23, SEQ ID NO:25, SEQ ID NO:41, SEQ ID NO:45, SEQ ID NO:47, SEQ ID NO:49, SEQ ID NO:51, or SEQ ID NO:53 over a region of at least about 100 residues, a nucleic acid sequence having at least 60% sequence identity to SEQ ID NO:1, SEQ ID NO:15, SEQ ID NO:17, SEQ ID NO:21, SEQ ID NO:33, SEQ ID NO:37, SEQ ID NO:39, SEQ ID NO:43, or SEQ ID NO:55 over a region of at least about 100 residues, a nucleic acid sequence having at least 70% sequence identity to SEQ ID NO:29, SEQ ID NO:31, or SEQ ID NO:35 over a region of at least about 100 residues, a nucleic acid sequence having at least 80% sequence identity to SEQ ID NO:27 over a region of at least about 100 residues, or a nucleic acid sequence having at least 90% sequence identity to SEQ ID NO:19 over a region of at least about 100 residues, wherein the sequence identities are determined by analysis with a sequence comparison algorithm or by a visual inspection; or, (ii) a nucleic acid that hybridizes under stringent conditions to a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof. The transformed cells can be a bacterial cell, a mammalian cell, a fungal cell, a yeast cell, an insect cell or a plant cell.

The invention provides transgenic non-human animals comprising a nucleic acid of the invention or a vector of the invention. In one aspect, the animal is a mouse.

The invention provides transgenic plants comprising a nucleic acid of the invention or a vector of the invention. The transgenic plant can be corn plant, a potato plant, a tomato plant, a wheat plant, an oilseed plant, a rapeseed plant, a soybean plant or a tobacco plant.

The invention provides transgenic seeds comprising a nucleic acid of the invention or a vector of the invention. The transgenic seed can be a corn seed, a wheat kernel, an oilseed, a rapeseed, a soybean seed, a palm kernel, a sunflower seed, a sesame seed, a peanut or a tobacco plant seed.

The invention provides an antisense oligonucleotide comprising a nucleic acid sequence complementary to or capable of hybridizing under stringent conditions to a nucleic acid of the invention, e.g., (i) a nucleic acid sequence having at least 50% sequence identity to SEQ ID NO:3, SEQ ID NO:5, SEQ ID NO:7, SEQ ID NO:9, SEQ ID NO:11, SEQ ID NO:13, SEQ ID NO:23, SEQ ID NO:25, SEQ ID NO:41, SEQ ID NO:45, SEQ ID NO:47, SEQ ID NO:49, SEQ ID NO:51, or SEQ ID NO:53 over a region of at least about 100 residues; a nucleic acid sequence having at least 60% sequence identity to SEQ ID NO:1, SEQ ID NO:15, SEQ ID NO:17, SEQ ID NO:21, SEQ ID NO:33, SEQ ID NO:37, SEQ ID NO:39, SEQ ID NO:43, or SEQ ID NO:55 over a region of at least about 100 residues; a nucleic acid sequence having at least 70% sequence identity to SEQ ID NO:29, SEQ ID NO:31, or SEQ ID NO:35 over a region of at least about 100 residues; nucleic acid sequence having at least 80% sequence identity to SEQ ID NO:27 over a region of at least about 100 residues, or a nucleic acid sequence having at least 90% sequence identity to SEQ ID NO:19 over a region of at least about 100 residues, wherein the sequence identities are determined by analysis with a sequence comparison algorithm or by a visual inspection; or, (ii) a nucleic acid that hybridizes under stringent conditions to a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55. In one aspect, the antisense oligonucleotide can be between about 10 to 50, about 20 to 60, about 30 to 70, about 40 to 80, or about 60 to 100 bases in length.

The invention provides methods of inhibiting the translation of a P450 message in a cell comprising administering to the cell or expressing in the cell an antisense oligonucleotide comprising a nucleic acid sequence complementary to or capable of hybridizing under stringent conditions to a nucleic acid of the invention.

The invention provides isolated or recombinant polypeptides comprising (a) a polypeptide comprising: an amino acid sequence having at least 50%, 55%, 60%, 65%, 70%, 75%, 80%, 85%, 90%, 95%, 98%, 99%, or more identity to SEQ ID NO:4, SEQ ID NO:6, SEQ ID NO:8, SEQ ID NO:10, SEQ ID NO:12, SEQ ID NO:14, SEQ ID NO:24, SEQ ID NO:26, SEQ ID NO:42, SEQ ID NO:44, SEQ ID NO:46, SEQ ID NO:48, SEQ ID NO:50, SEQ ID NO:52, or SEQ ID NO:54, over a region of at least about 100, 150, 200, 250, 300, 350, 400, 450, 500, or more, residues; an amino acid sequence having at least 60%, 65%, 70%, 75%, 80%, 85%, 90%, 95%, 98%, 99%, or more, identity to SEQ ID NO:2, SEQ ID NO:16, SEQ ID NO:18, SEQ ID NO:22, SEQ ID NO:30, SEQ ID NO:32, SEQ ID NO:34, SEQ ID NO:36, SEQ ID NO:38, SEQ ID NO:40, SEQ ID NO:44, or SEQ ID NO:56 over a region of at least about 100, 150, 200, 250, 300, 350, 400, 450, 500, or more, residues; an amino acid sequence having at least 80%, 85%, 90%, 95%, 98%, 99%, or more, identity to SEQ ID NO:28 over a region of at least about 100, 150, 200, 250, 300, 350, 400, 450, 500, or more, residues; or an amino acid sequence having at least 90%, 95%, 98%, 99%, identity to SEQ ID NO:20 over a region of at least about 100, 150, 200, 250, 300, 350, 400, 450, 500, or more, residues, or (b) a polypeptide encoded by a nucleic acid of the invention, e.g., a nucleic acid comprising: (i) a nucleic acid sequence having at least 50% sequence identity to SEQ ID NO:3, SEQ ID NO:5, SEQ ID NO:7, SEQ ID NO:9, SEQ ID NO:11, SEQ ID NO:13, SEQ ID NO:23, SEQ ID NO:25, SEQ ID NO:41, SEQ ID NO:45, SEQ ID NO:47, SEQ ID NO:49, SEQ ID NO:51, or SEQ ID NO:53 over a region of at least about 100 residues; a nucleic acid sequence having at least 60% sequence identity to SEQ ID NO:1, SEQ ID NO:15, SEQ ID NO:17, SEQ ID NO:21, SEQ ID NO:33, SEQ ID NO:37, SEQ ID NO:39, SEQ ID NO:43, or SEQ ID NO:55 over a region of at least about 100 residues a nucleic acid sequence having at least 70% sequence identity to SEQ ID NO:29, SEQ ID NO:31, or SEQ ID NO:35 over a region of at least about 100 residues; a nucleic acid sequence having at least 80% sequence identity to SEQ ID NO:27 over a region of at least about 100 residues, or a nucleic acid sequence having at least 90% sequence identity to SEQ ID NO:19 over a region of at least about 100 residues, wherein the sequence identities are determined by analysis with a sequence comparison algorithm or by a visual inspection; or, (ii) a nucleic acid that hybridizes under stringent conditions to a nucleic acid comprising a sequence as set forth in SEQ ID NO:1, or a subsequence thereof, a sequence as set forth in SEQ ID NO:3, or a subsequence thereof, a sequence as set forth in SEQ ID NO:5, or a subsequence thereof, a sequence as set forth in SEQ ID NO:7, or a subsequence thereof, a sequence as set forth in SEQ ID NO:9, or a subsequence thereof, a sequence as set forth in SEQ ID NO:11, or a subsequence thereof, a sequence as set forth in SEQ ID NO:13, or a subsequence thereof, a sequence as set forth in SEQ ID NO:15, or a subsequence thereof, a sequence as set forth in SEQ ID NO:17, or a subsequence thereof, a sequence as set forth in SEQ ID NO:19, or a subsequence thereof, a sequence as set forth in SEQ ID NO:21, or a subsequence thereof, a sequence as set forth in SEQ ID NO:23, or a subsequence thereof, a sequence as set forth in SEQ ID NO:25, or a subsequence thereof, a sequence as set forth in SEQ ID NO:27, or a subsequence thereof, a sequence as set forth in SEQ ID NO:29, or a subsequence thereof, a sequence as set forth in SEQ ID NO:31, or a subsequence thereof, a sequence as set forth in SEQ ID NO:33, or a subsequence thereof, a sequence as set forth in SEQ ID NO:35, or a subsequence thereof, a sequence as set forth in SEQ ID NO:37, or a subsequence thereof, a sequence as set forth in SEQ ID NO:39, or a subsequence thereof, a sequence as set forth in SEQ ID NO:41, or a subsequence thereof, a sequence as set forth in SEQ ID NO:43, or a subsequence thereof, a sequence as set forth in SEQ ID NO:45, or a subsequence thereof, a sequence as set forth in SEQ ID NO:47, or a subsequence thereof, a sequence as set forth in SEQ ID NO:51, or a subsequence thereof, a sequence as set forth in SEQ ID NO:53, or a subsequence thereof, a sequence as set forth in SEQ ID NO:55, or a subsequence thereof. The invention provides the isolated or recombinant polypeptide having a P450 activity.

The invention provides isolated or recombinant polypeptides comprising an amino acid sequence as set forth in SEQ ID NO:2, an amino acid sequence as set forth in SEQ ID NO:4, an amino acid sequence as set forth in SEQ ID NO:6, an amino acid sequence as set forth in SEQ ID NO:8, an amino acid sequence as set forth in SEQ ID NO:10, an amino acid sequence as set forth in SEQ ID NO:12, an amino acid sequence as set forth in SEQ ID NO:14, an amino acid sequence as set forth in SEQ ID NO:16, an amino acid sequence as set forth in SEQ ID NO:18, an amino acid sequence as set forth in SEQ ID NO:20, an amino acid sequence as set forth in SEQ ID NO:22, an amino acid sequence as set forth in SEQ ID NO:24, an amino acid sequence as set forth in SEQ ID NO:26, an amino acid sequence as set forth in SEQ ID NO:28, an amino acid sequence as set forth in SEQ ID NO:30, an amino acid sequence as set forth in SEQ ID NO:32, an amino acid sequence as set forth in SEQ ID NO:34, an amino acid sequence as set forth in SEQ ID NO:36, an amino acid sequence as set forth in SEQ ID NO:38, an amino acid sequence as set forth in SEQ ID NO:40, an amino acid sequence as set forth in SEQ ID NO:42, an amino acid sequence as set forth in SEQ ID NO:44, an amino acid sequence as set forth in SEQ ID NO:46, an amino acid sequence as set forth in SEQ ID NO:48, an amino acid sequence as set forth in SEQ ID NO:50, an amino acid sequence as set forth in SEQ ID NO:52, an amino acid sequence as set forth in SEQ ID NO:54, an amino acid sequence as set forth in SEQ ID NO:56, or a subsequence thereof.

In one aspect, the P450 activity is monooxygenation. The P450 activity can comprise catalysis of incorporation of oxygen into a substrate. In one aspect, the P450 activity can comprise hydroxylation of aliphatic or aromatic carbons. In another aspect, the P450 activity can comprise epoxidation. In an alternative aspect, the P450 activity can comprise N—, O—, or S-dealkylation. In one aspect, the P450 activity can comprise dehalogenation. In another aspect, the P450 activity can comprise oxidative deamination. Alternatively, the P450 activity can comprise N-oxidation or N-hydroxylation. In one aspect, the P450 activity comprises sulphoxide formation.

The invention provides isolated or recombinant polypeptides, wherein the epoxidase activity further comprises an alkene substrate. In one aspect, the epoxidase activity further comprises formation of a chiral product. In one aspect, the epoxidase activity is enantioselective.

The invention provides isolated or recombinant polypeptides, wherein the P450 activity is thermostable. The polypeptide can retain a P450 activity under conditions comprising a temperature range of between about 37° C. to about 70° C. In another aspect, the P450 activity can be thermotolerant. The polypeptide can retain a P450 activity after exposure to a temperature in the range from greater than 37° C. to about 90° C. or in the range from greater than 37° C. to about 50° C.

The invention provides isolated or recombinant polypeptides comprising the polypeptide of the invention that lacks a signal sequence.

The invention provides isolated or recombinant polypeptides, wherein the P450 activity comprises a specific activity at about 37° C. in the range from about 100 to about 1200 units per milligram of protein. In one aspect, the P450 activity comprises a specific activity from about 500 to about 1000 units per milligram of protein. In another aspect, the P450 activity comprises a specific activity at 37° C. in the range from about 500 to about 700 units per milligram of protein. In one aspect, the P450 activity comprises a specific activity at 37° C. in the range from about 750 to about 1000 units per milligram of protein.

In one aspect, the thermotolerance can comprise retention of at least half of the specific activity of the P450 at 37° C. after being heated to the elevated temperature. In another aspect, the thermotolerance comprises retention of specific activity at 37° C. in the range from about 500 to about 1200 units per milligram of protein after being heated to the elevated temperature.

In one aspect, the polypeptide of the invention comprises at least one glycosylation site. In one aspect, glycosylation can be an N-linked glycosylation. In one aspect, the P450 is glycosylated after being expressed in a *P. pastoris* or a *S. pombe*.

In one aspect, the polypeptide can retain a P450 activity under conditions comprising about pH 4.5 or pH 5. Alternatively, the polypeptide can retain a P450 activity under conditions comprising about pH 9.0, pH 9.5, or pH 10.

The invention provides protein preparations comprising a polypeptide of the invention, wherein the protein preparation comprises a liquid, a solid or a gel.

The invention provides heterodimers comprising a polypeptide as set forth in claim 73 and a second domain. In one aspect, the second domain is a polypeptide and the heterodimer is a fusion protein. The second domain can be an epitope or a tag.

The invention provides immobilized polypeptides having a P450 activity, wherein the polypeptide comprises a polypeptide of the invention, a polypeptide encoded by the nucleic acid of the invention, or a polypeptide comprising a polypeptide of the invention and a second domain. The polypeptide can be immobilized on a cell, a metal, a resin, a polymer, a ceramic, a glass, a microelectrode, a graphitic particle, a bead, a gel, a plate, an array or a capillary tube.

The invention provides arrays comprising an immobilized polypeptide of the invention or a polypeptide comprising a polypeptide of the invention and a second domain. The invention provides arrays comprising an immobilized nucleic acid of the invention. The invention provides arrays comprising an antibody of the invention.

The invention provides isolated or recombinant antibodies that specifically binds to a polypeptide of the invention or to a polypeptide encoded by a nucleic acid of the invention. The antibody can be a monoclonal or a polyclonal antibody.

The invention provides hybridomas comprising an antibody of the invention, e.g., an antibody that specifically binds to a polypeptide of the invention or to a polypeptide encoded by a nucleic acid of the invention.

The invention provides methods of isolating or identifying a polypeptide with a P450 activity comprising the steps of: (a) providing an antibody of the invention; (b) providing a sample comprising polypeptides; and (c) contacting the sample of step (b) with the antibody of step (a) under conditions wherein the antibody can specifically bind to the polypeptide, thereby isolating or identifying a polypeptide having a P450 activity.

The invention provides methods of making an anti-P450 polypeptide antibody comprising administering to a non-human animal a nucleic acid of the invention, or a polypeptide of the invention in an amount sufficient to generate a humoral immune response, thereby making an anti-P450 antibody.

The invention provides methods of producing a recombinant polypeptide comprising the steps of: (a) providing a nucleic acid of the invention, operably linked to a promoter; and (b) expressing the nucleic acid of step (a) under conditions that allow expression of the polypeptide, thereby producing a recombinant polypeptide. In one aspect, the method further comprises transforming a host cell with the nucleic acid of step (a) followed by expressing the nucleic acid of step (a), thereby producing a recombinant polypeptide in a transformed cell.

The invention provides methods for identifying a polypeptide having a P450 activity comprising the following steps: (a) providing a polypeptide of the invention or a polypeptide encoded by a nucleic acid of the invention; (b) providing a P450 substrate; and (c) contacting the polypeptide or a fragment or variant thereof of step (a) with the substrate of step (b) and detecting a decrease in the amount of substrate or an increase in the amount of a reaction product, wherein a decrease in the amount of the substrate or an increase in the amount of the reaction product detects a polypeptide having a P450 activity. In one aspect, the substrate is an alkene.

The invention provides methods for identifying a P450 substrate comprising the following steps: (a) providing a polypeptide of the invention or a polypeptide encoded by a nucleic acid of the invention; (b) providing a test substrate; and (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate as a P450 substrate.

The invention provides methods of determining whether a test compound specifically binds to a polypeptide comprising the following steps: (a) expressing a nucleic acid or a vector comprising the nucleic acid under conditions permissive for translation of the nucleic acid to a polypeptide, wherein the nucleic acid comprises a nucleic acid of the invention, or, providing a polypeptide of the invention; (b) providing a test compound; (c) contacting the polypeptide with the test compound; and (d) determining whether the test compound of step (b) specifically binds to the polypeptide.

The invention provides methods for identifying a modulator of a P450 activity comprising the following steps: (a) providing a polypeptide of the invention or a polypeptide encoded by a nucleic acid of the invention; (b) providing a test compound; (c) contacting the polypeptide of step (a) with the test compound of step (b) and measuring an activity of the P450, wherein a change in the P450 activity measured in the presence of the test compound compared to the activity in the absence of the test compound provides a determination that the test compound modulates the P450 activity. In one aspect, the P450 activity can be measured by providing a P450 substrate and detecting a decrease in the amount of the substrate or an increase in the amount of a reaction product, or, an increase in the amount of the substrate or a decrease in the amount of a reaction product. A decrease in the amount of the substrate or an increase in the amount of the reaction product with the test compound as compared to the amount of substrate or reaction product without the test compound identifies the test compound as an activator of the P450 activity. An increase in the amount of the substrate or a decrease in the amount of the reaction product with the test compound as compared to the amount of substrate or reaction product without the test compound identifies the test compound as an inhibitor of the P450 activity.

The invention provides computer systems comprising a processor and a data storage device wherein said data storage device has stored thereon a polypeptide sequence or a nucleic acid sequence, wherein the polypeptide sequence comprises a polypeptide of the invention, or subsequence thereof, and the nucleic acid comprises a nucleic acid of the invention, or subsequence thereof. In one aspect, the computer system can further comprise a sequence comparison algorithm and a data storage device having at least one reference sequence stored thereon. In one aspect, the sequence comparison algorithm comprises a computer program that indicates polymorphisms. In another aspect, the computer system further comprises an identifier that identifies one or more features in said sequence.

The invention provides computer readable media having stored thereon a polypeptide sequence or a nucleic acid sequence, wherein the polypeptide sequence comprises a polypeptide of the invention, or subsequence thereof, and the nucleic acid comprises a nucleic acid of the invention, or subsequence thereof.

The invention provides methods for identifying a feature in a sequence comprising the steps of: (a) reading the sequence using a computer program which identifies one or more features in a sequence, wherein the sequence comprises a polypeptide sequence or a nucleic acid sequence, wherein the polypeptide sequence comprises sequence as set forth in claim 73 or subsequence thereof, and the nucleic acid comprises a sequence as set forth in claim 1 or claim 39 or subsequence thereof; and (b) identifying one or more features in the sequence with the computer program.

The invention provides methods for comparing a first sequence to a second sequence comprising the steps of: (a) reading the first sequence and the second sequence through use of a computer program which compares sequences, wherein the first sequence comprises a polypeptide sequence or a nucleic acid sequence, wherein the polypeptide sequence comprises a polypeptide of the invention, or subsequence thereof, and the nucleic acid comprises a nucleic acid of the invention or subsequence thereof; and (b) determining differences between the first sequence and the second sequence with the computer program. In one aspect, the step of determining differences between the first sequence and the second sequence further comprises the step of identifying polymorphisms. In another aspect, the method further comprises an identifier that identifies one or more features in a sequence. In one aspect, the method can comprise reading the first sequence using a computer program and identifying one or more features in the sequence.

The invention provides methods for isolating or recovering a nucleic acid encoding a polypeptide with a P450 activity from an environmental sample comprising the steps of: (a) providing an amplification primer sequence pair for amplifying a nucleic acid encoding a polypeptide with a P450 activity, wherein the primer pair is capable of amplifying SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, or a subsequence thereof; (b) isolating a nucleic acid from the environmental sample or treating the environmental sample such that nucleic acid in the sample is accessible for hybridization to the amplification primer pair; and, (c) combining the nucleic acid of step (b) with the amplification primer pair of step (a) and amplifying nucleic acid from the environmental sample, thereby isolating or recovering a nucleic acid encoding a polypeptide with a P450 activity from an environmental sample. In one aspect, each member of the amplification primer sequence pair comprises an oligonucleotide comprising at least about 10 to 50 consecutive bases of a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, or a subsequence thereof.

The invention provides methods for isolating or recovering a nucleic acid encoding a polypeptide with a P450 activity from an environmental sample comprising the steps of: (a) providing a polynucleotide probe comprising a polypeptide of the invention, or a subsequence thereof; (b) isolating a nucleic acid from the environmental sample or treating the environmental sample such that nucleic acid in the sample is accessible for hybridization to a polynucleotide probe of step (a); (c) combining the isolated nucleic acid or the treated environmental sample of step (b) with the polynucleotide probe of step (a); and (d) isolating a nucleic acid that specifically hybridizes with the polynucleotide probe of step (a), thereby isolating or recovering a nucleic acid encoding a polypeptide with an epoxide hydrolase activity from an environmental sample. The environmental sample can comprise a water sample, a liquid sample, a soil sample, an air sample or a biological sample. The biological sample can be derived from a bacterial cell, a protozoan cell, an insect cell, a yeast cell, a plant cell, a fungal cell or a mammalian cell.

The invention provides methods of generating a variant of a nucleic acid encoding a polypeptide with a P450 activity comprising the steps of: (a) providing a template nucleic acid comprising a nucleic acid of the invention, and (b) modifying, deleting or adding one or more nucleotides in the template sequence, or a combination thereof, to generate a variant of the template nucleic acid. In one aspect, the method can further comprise expressing the variant nucleic acid to generate a variant P450 polypeptide. In one aspect, the modifications, additions or deletions are introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis™ (GSSM™), synthetic ligation reassembly (SLR) and a combination thereof. In another aspect, the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In one aspect, the method can be iteratively repeated until a P450 having an altered or different activity or an altered or different stability from that of a polypeptide encoded by the template nucleic acid is produced. In one aspect, the variant P450 polypeptide can be thermotolerant, and retains some activity after being exposed to an elevated temperature. In another aspect, the variant P450 polypeptide has increased glycosylation as compared to the P450 encoded by a template nucleic acid. In one aspect, the variant P450 polypeptide has a P450 activity under a high temperature, wherein the P450 encoded by the template nucleic acid is not active under the high temperature. In one aspect, the method can be iteratively repeated until a P450 coding sequence having an altered codon usage from that of the template nucleic acid is produced. In another aspect, the method can be iteratively repeated until a P450 gene having higher or lower level of message expression or stability from that of the template nucleic acid is produced.

The invention provides methods for modifying codons in a nucleic acid encoding a polypeptide with a P450 activity to increase its expression in a host cell, the method comprising the following steps: (a) providing a nucleic acid encoding a polypeptide with a P450 activity comprising a nucleic acid of the invention; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying codons in a nucleic acid encoding a P450 polypeptide, the method comprising the following steps: (a) providing a nucleic acid encoding a polypeptide with a P450 activity comprising a nucleic acid of the invention; and, (b) identifying a codon in the nucleic acid of step (a) and replacing it with a different codon encoding the same amino acid as the replaced codon, thereby modifying codons in a nucleic acid encoding a P450.

The invention provides methods for modifying codons in a nucleic acid encoding a P450 polypeptide to increase its expression in a host cell, the method comprising the following steps: (a) providing a nucleic acid encoding a P450 polypeptide comprising a nucleic acid of the invention; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying a codon in a nucleic acid encoding a polypeptide having a P450 activity to decrease its expression in a host cell, the method comprising the following steps: (a) providing a nucleic acid encoding a P450 polypeptide comprising a nucleic acid of the invention; and (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in genes in the host cell, thereby modifying the nucleic acid to decrease its expression in a host cell. The host cell can be a bacterial cell, a fungal cell, an insect cell, a yeast cell, a plant cell or a mammalian cell.

The invention provides methods for producing a library of nucleic acids encoding a plurality of modified P450 active sites or substrate binding sites, wherein the modified active sites or substrate binding sites are derived from a first nucleic acid comprising a sequence encoding a first active site or a first substrate binding site the method comprising the following steps: (a) providing a first nucleic acid encoding a first active site or first substrate binding site, wherein the first nucleic acid sequence comprises a sequence that hybridizes under stringent conditions to a sequence as set forth in SEQ ID NO:1, SEQ ID NO:3, SEQ ID, NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, or a subsequence thereof, and the nucleic acid encodes a P450 active site or a P450 substrate binding site; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified P450 active sites or substrate binding sites. In one aspect, the method can comprise mutagenizing the first nucleic acid of step (a) by a method comprising an optimized directed evolution system. In another aspect, the method can comprise mutagenizing the first nucleic acid of step (a) by a method comprising gene site-saturation mutagenesis (GSSM), synthetic ligation reassembly (SLR), error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis™ (GSSM™), synthetic ligation reassembly (SLR) and a combination thereof. In one aspect, the method can comprise mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid muitimer creation and a combination thereof.

The invention provides methods for making a small molecule comprising the following steps: (a) providing a plurality of biosynthetic enzymes capable of synthesizing or modifying a small molecule, wherein one of the enzymes comprises a P450 encoded by a nucleic acid comprising a nucleic acid of the invention; (b) providing a substrate for at least one of the enzymes of step (a); and (c) reacting the substrate of step (b) with the enzymes under conditions that facilitate a plurality of biocatalytic reactions to generate a small molecule by a series of biocatalytic reactions.

The invention provides methods for modifying a small molecule comprising the following steps: (a) providing a P450 enzyme, wherein the enzyme comprises a polypeptide of the invention, or, is encoded by a nucleic acid of the invention; (b) providing a small molecule; and (c) reacting the enzyme of step (a) with the small molecule of step (b) under conditions that facilitate an enzymatic reaction catalyzed by the P450 enzyme, thereby modifying a small molecule by a P450 enzymatic reaction. The method can comprise a plurality of small molecule substrates for the enzyme of step (a), thereby generating a library of modified small molecules produced by at least one enzymatic reaction catalyzed by the P450 enzyme. In another aspect, the method can further comprise a plurality of additional enzymes under conditions that facilitate a plurality of biocatalytic reactions by the enzymes to form a library of modified small molecules produced by the plurality of enzymatic reactions. Alternatively, the method can further comprise the step of testing the library to determine if a particular modified small molecule which exhibits a desired activity is present within the library. The step of testing the library can further comprise the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

The invention provides methods for determining a functional fragment of a P450 enzyme comprising the steps of: (a) providing a P450 enzyme, wherein the enzyme comprises a polypeptide of the invention, or, is encoded by a nucleic acid of the invention, and (b) deleting a plurality of amino acid residues from the sequence of step (a) and testing the remaining subsequence for a P450 activity, thereby determining a functional fragment of a P450 enzyme. In one aspect, the P450 activity can be measured by providing a P450 substrate and detecting a decrease in the amount of the substrate or an increase in the amount of a reaction product.

The invention provides methods for whole cell engineering of new or modified phenotypes by using real-time metabolic flux analysis, the method comprising the following steps: (a) making a modified cell by modifying the genetic composition of a cell, wherein the genetic composition is modified by addition to the cell of a nucleic acid of the invention; (b) culturing the modified cell to generate a plurality of modified cells; (c) measuring at least one metabolic parameter of the cell by monitoring the cell culture of step (b) in real time; and, (d) analyzing the data of step (c) to determine if the measured parameter differs from a comparable measurement in an unmodified cell under similar conditions, thereby identifying an engineered phenotype in the cell using real-time metabolic flux analysis. In one aspect, the genetic composition of the cell can be modified by a method comprising deletion of a sequence or modification of a sequence in the cell, or, knocking out the expression of a gene. In one aspect, the method can further comprise selecting a cell comprising a newly engineered phenotype. In one aspect, the method can further comprise culturing the selected cell, thereby generating a new cell strain comprising a newly engineered phenotype.

The invention provides methods for oxygenases an alkene comprising the following steps: (a) providing a polypeptide having a P450 activity, wherein the polypeptide comprises a polypeptide of the invention, or, a polypeptide encoded by a nucleic acid of the invention; (b) providing a composition comprising an alkene; and (c) contacting the polypeptide of step (a) with the composition of step (b) under conditions wherein the polypeptide oxygenases the alkene.

The invention provides methods for producing a compound of a desired chirality comprising the following steps: (a) providing a polypeptide having a enantioselective P450 activity, wherein the polypeptide comprises a polypeptide of the invention, or, a polypeptide encoded by a nucleic acid of the invention; (b) providing a composition comprising a P450 substrate; (c) contacting the polypeptide of step (a) with the composition of step (b) under conditions wherein the polypeptide catalyzes the conversion of the P450 substrate to the chiral epoxide; and (d) converting the chiral epoxide to a chiral product. In one aspect, the chiral product comprises a diol, an amino alcohol, a halohydrin or a branched-chain alkyl moiety. In one aspect, the chiral product is an antibiotic.

The invention provides methods of increasing thermotolerance or thermostability of a P450 polypeptide, the method comprising glycosylating a P450 polypeptide, wherein the polypeptide comprises at least thirty contiguous amino acids of a polypeptide of the invention, or a polypeptide encoded by a polypeptide of the invention, thereby increasing the thermotolerance or thermostability of the P450 polypeptide. In one aspect, the P450 specific activity is thermostable or thermotolerant at a temperature in the range from greater than about 37° C. to about 90° C.

The invention provides methods for overexpressing a recombinant P450 polypeptide in a cell comprising expressing a vector comprising a nucleic acid comprising a nucleic acid sequence at least 50% sequence identity to the nucleic acid of the invention over a region of at least about 100 residues, wherein the sequence identities are determined by analysis with a sequence comparison algorithm or by visual inspection, wherein overexpression is effected by use of a high activity promoter, a dicistronic vector or by gene amplification of the vector.

The invention provides growth-based methods for selecting a cell comprising a nucleic acid encoding a P450 comprising the following steps: (a) providing a plurality of cells, wherein the cells lack a composition essential for growth; (b) providing a precursor or substrate, wherein the precursor or substrate is capable of being converted by a P450 to a composition essential for growth of the cell and the essential composition must comprise an epoxide to induce growth of the cell; (c) growing the cells in a medium lacking the epoxide, and adding the precursor or substrate of step (b); and (d) screening the cells for growth, wherein the cells in the growth stimulated clone are identified as comprising a nucleic acid encoding a P450 capable of converting the precursor or substrate to the composition comprising the epoxide, thereby selecting a cell comprising a nucleic acid encoding a P450. In one aspect, the precursor or substrate comprises an alkene.

The invention provides growth-based methods for selecting a nucleic acid encoding a P450 comprising the following steps: (a) providing a nucleic acid encoding a polypeptide; (b) providing a precursor or substrate, wherein the precursor or substrate is capable of being converted by a P450 to a composition essential for growth of the cell and the composition must comprise an epoxide to induce growth of the cell; (c) providing a plurality of cells, wherein the cells cannot make the composition of step (b); (d) inserting the nucleic acid into the cells and growing the cells under conditions wherein the nucleic acid is expressed and its encoded polypeptide is translated, and the cells are grown in a medium lacking the composition comprising the epoxide essential for growth, and adding the precursor or substrate of step (b); and (e) screening the cells for growth, wherein the nucleic acid in the growth stimulated clone is identified as encoding a P450 capable of converting the precursor or substrate to the composition comprising the epoxide essential for growth, thereby selecting a nucleic acid encoding a P450. In one aspect, the precursor or substrate comprises an alkene.

The invention provides methods for identifying a nucleic acid encoding a P450 comprising the following steps: (a) providing a nucleic acid library, e.g., a library comprising a polynucleotide of the invention; (b) providing a precursor or substrate, wherein the precursor or substrate is capable of being converted by a P450 to a composition essential for growth and the essential composition must comprise an epoxide to induce growth of the cell; (c) providing a plurality of cells, wherein the cells cannot make the composition of step (b); (d) inserting in a cell a member of the gene library and culturing the cells in a medium lacking the composition comprising the epoxide essential for growth; (e) adding the precursor or substrate of step (b) to the culture; (f) selecting a growing cell and identifying the inserted library member of step (d), wherein the cell is capable of growth by enzymatic conversion of the precursor to the composition comprising the epoxide essential for growth, and the enzyme is encoded by the library member, thereby identifying a nucleic acid encoding a P450. In one aspect, the precursor or substrate comprises an alkene.

The invention provides growth-based methods for selecting a cell comprising a nucleic acid encoding a P450 comprising the following steps: (a) providing a plurality of cells comprising an epoxide hydrolase, wherein the cells lack a composition essential for growth; (b) providing a precursor or substrate, wherein the precursor or substrate is capable of being converted by a P450 to an epoxide, wherein the epoxide is capable of being converted by an epoxide hydrolase to a composition essential for growth of the cell; (c) growing the cells in a medium lacking the epoxide and composition essential for growth, and adding the precursor or substrate of step (b); and, (d) screening the cells for growth, wherein the cells in the growth stimulated clone are identified as comprising the nucleic acid encoding a P450 enzyme capable of converting the precursor or substrate to the epoxide, thereby selecting a cell comprising a nucleic acid encoding a P450 enzyme having an epoxidase activity. In one aspect, the precursor or substrate comprises an alkene.

The invention provides growth-based methods for selecting a nucleic acid encoding a P450 enzyme comprising the following steps: (a) providing a nucleic acid encoding a polypeptide, e.g., a polynucleotide of the invention; (b) providing a precursor or substrate, wherein the precursor or substrate is capable of being converted by a P450 to an epoxide, wherein the epoxide is capable of being converted by an epoxide hydrolase to a composition essential for growth of the cell; (c) providing a plurality of cells comprising an epoxide hydrolase, wherein the cells cannot make the composition of step (b); (d) inserting the nucleic acid into the cells and growing the cells under conditions wherein the nucleic acid is expressed and its encoded polypeptide is translated, and the cells are grown in a medium lacking the composition comprising the epoxide essential for growth, and adding the substrate of step (c); and, (e) screening the cells for growth, wherein the nucleic acid in the growth stimulated clone is identified as encoding a P450 capable of converting the precursor or substrate to the composition comprising the epoxide, thereby selecting a nucleic acid encoding a P450 having an epoxidase activity.

In one aspect, the precursor or substrate comprises an alkene. In one aspect, the precursor or substrate comprises allyl alcohol, 3,3-dimethyl acrylate or trans-3-methyl-2-pentenoate. In one aspect, the nucleic acid can be a member of a gene library. The library can be obtained from a mixed population of organisms. In one aspect, the library can be obtained from a mixed population of organisms. In one aspect, the mixed population of organisms can be derived from a soil sample, a water sample or an air sample. In one aspect, the cells are from *Xanthobacter* strain Py2.

The invention provides direct activity assay methods for screening for a polypeptide having a P450 activity, comprising the following steps: (a) providing a polypeptide, e.g., a polypeptide of the invention; (b) providing a precursor or substrate, wherein the precursor or substrate is capable of being converted by an epoxidase to an epoxide; (c) combining the polypeptide of step (a) with the precursor or substrate of step (b) under conditions wherein the polypeptide can convert the precursor or substrate to an epoxide; (d) monitoring spectroscopic properties of the precursor or substrate and the epoxide; and (e) screening the polypeptide for epoxidase activity, wherein the polypeptide is identified as having an epoxidase activity capable of converting the precursor or substrate to the epoxide as detected by modification of the spectroscopic properties of the precursor or substrate as it is converted to the epoxide, thereby selecting a polypeptide having a P450 activity. In one aspect, the spectroscopic property is fluorescence. In one aspect, the polypeptide is identified as having an epoxidase activity capable of converting the precursor or substrate to the epoxide, wherein the precursor has having a yellow fluorescent activity, and the epoxide has a blue fluorescent activity, and the extent of the conversion is monitored by the ratio of blue to yellow fluorescence as the precursor is converted to the epoxide.

The invention provides direct activity assay methods for screening for a polypeptide having a P450 activity, e.g., a polypeptide of the invention, comprising the following steps: (a) providing a plurality of polypeptides; (b) providing a precursor or substrate covalently linked to umbelliferone, wherein the precursor or substrate is capable of being converted by a P450 to an epoxide; (c) combining the polypeptides of step (a) with the precursor or substrate of step (b) under conditions wherein the polypeptides can convert the precursor or substrate to an epoxide linked to umbelliferone; (d) converting the epoxide linked to umbelliferone of step (c) to umbelliferone; (e) measuring the fluorescence quantum yield; and (f) screening the polypeptides for a P450 activity, wherein the polypeptide is identified as having a P450 activity capable of converting the precursor or substrate to the epoxide as detected by an increase in the fluorescence quantum yield due to formation of umbelliferone, thereby selecting a polypeptide having a P450 activity. In one aspect, the conversion of the epoxide linked to umbelliferone to umbelliferone further comprises the following steps: (a) providing a polypeptide having an epoxide hydrolase activity; (b) combining the epoxide linked to umbelliferone with the polypeptide of step (a) under conditions wherein the polypeptide of step (a) can convert the epoxide linked to umbelliferone to a vicinal diol linked to umbelliferone; (c) subjecting the vicinal diol linked to umbelliferone of step (b) to periodate oxidation resulting in the formation of an aldehyde linked to umbelliferone; (d) subjecting the aldehyde of step (c) to BSA-catalyzed β-elimination resulting in the formation of umbelliferone.

DESCRIPTION OF DRAWINGS

Like reference symbols in the various drawings indicate like elements.

DETAILED DESCRIPTION

The invention provides polypeptides having a P450 activity, polynucleotides encoding the polypeptides, and methods for making and using these polynucleotides and polypeptides. The polypeptides of the invention can be used as monooxygenases activating molecular oxygen using an iron-heme center and utilizing a redox electron shuttle to support the oxidation reaction.

In one aspect, the invention provides P450 enzymes from wide varieties of biodiversity sources, such as enzymes or gene libraries from environmental samples. The invention provides methods to rapidly select or screen enzymes and genes to obtain suitable P450 enzymes. The invention provides methods to access untapped biodiversity and to rapidly screen for sequences and activities of interest utilizing recombinant DNA technology. This invention combines the benefits associated with the ability to rapidly screen natural compounds with the flexibility and reproducibility afforded with working with the genetic material of organisms. The invention provides methods to synthesize useful chiral epoxides using the enzymes of the present invention. The invention provides useful chiral epoxides and their derivatives produced using the P450 enzymes developed by the methods of the invention.

P450 oxygenases, also sometimes referred to as P450 epoxidases (hereinafter "P450s") are oxidative enzymes that are widespread in nature and are involved in processes such as detoxifying xenobiotics, catabolism of unusual carbon sources and biosynthesis of secondary metabolites. P450 activities of the enzymes of the invention include all known P450 activities, including detoxifying xenobiotics, catabolism of unusual carbon sources and biosynthesis of secondary metabolites. For other exemplary uses of the enzymes of the invention, and how to make and use the enzymes of the invention, see, e.g., U.S. Pat. Nos. 6,420,131; 6,387,647; 6,380,465; 6,312,917; 6,306,907; 6,306,624; 6,300,544; 6,288,087; 6,284,219; 6,274,360; 6,242,203; 6,217,860; 6,207,648 and 6,060,253.

Figure 1:
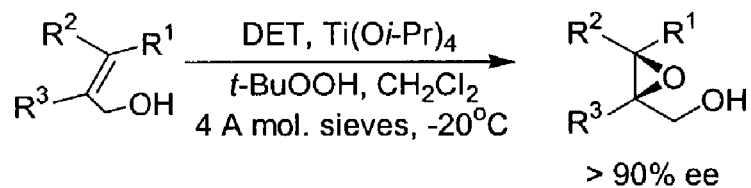
FIG. 1 is a schematic representation of asymmetric chemical oxidations.
Figure 1:
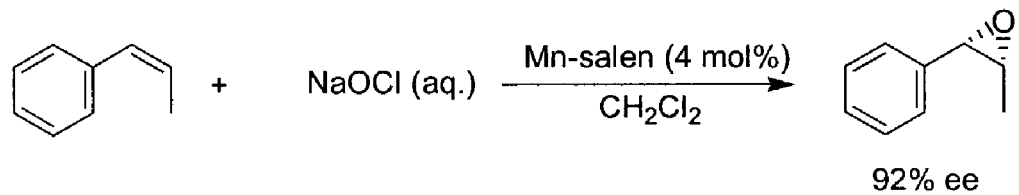
Figure 1:
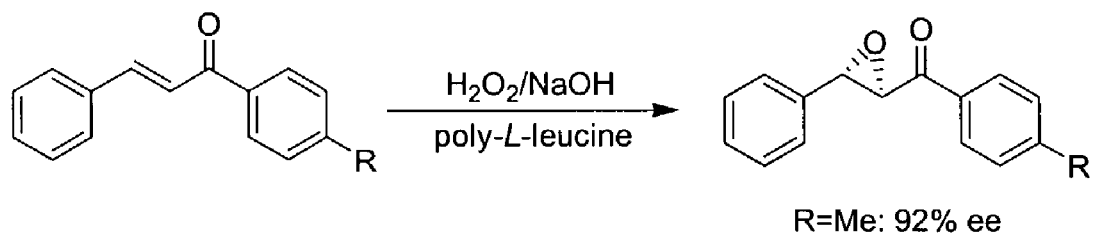
Figure 2:
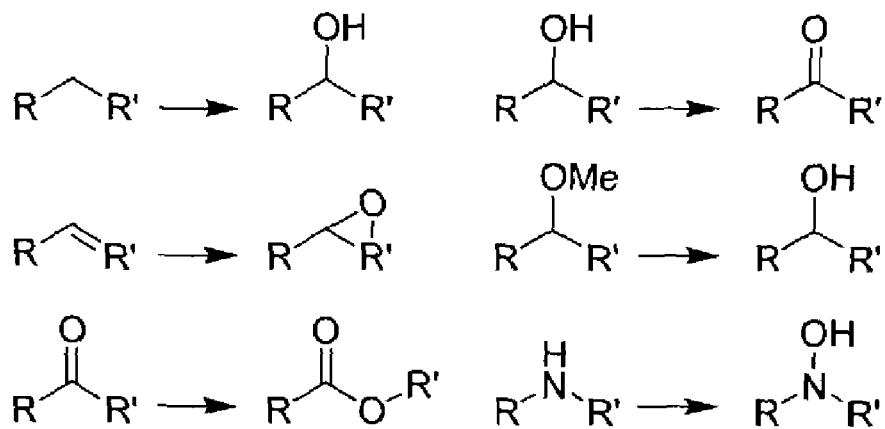
FIG. 2 is an illustration of examples of oxidative reaction catalyzed by oxidative enzymes.
Figure 3:
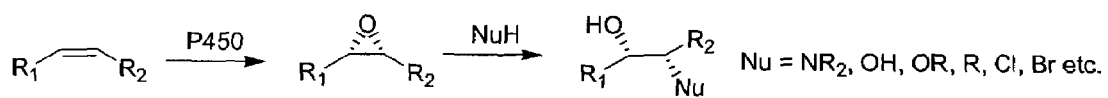
FIG. 3 is an illustration of synthetic utility of epoxides

In bacteria, the electrons required to reduce the heme iron at the end of each reaction cycle are provided by a partner enzyme system, comprising ferredoxin (FDX) and ferredoxin reductase (FDR) activities. Examples of P450 are known to catalyze epoxidations. Epoxidations, in particular, are catalyzed by very few other enzyme classes. Using P450s to mediate this transformation allows stereochemical information to be introduced into an achiral molecule. The resultant chirality can then be transferred to other functionalities by opening the epoxide using a variety of nucleophiles (FIG. 3). Thus, the range of ultimate products is not limited to diols resulting from hydrolysis, but can be extended to amino alcohols, halohydrins and branched-chain alkyl moieties. Furthermore, this process occurs without the loss of material associated with kinetic resolution methods such as enzymatic epoxide hydrolysis.

Definitions

The term "P450" encompasses oxygen-activation catalysts which incorporate one atom of oxygen into a broad range of substrates with reduction of other oxygen atom to water. Thus, the P450 enzymes may have the following activities: hydroxylation of aliphatic & aromatic carbons, epoxidation, N, O— and S-dealkylation, dehalogenation, oxidative deamination, N-oxidation and N-hydroxylation, or sulphoxide formation.

A "P450 variant" has an amino acid sequence which is derived from the amino acid sequence of a "precursor P450". The precursor P450 include naturally-occurring P450 and recombinant P450. The amino acid sequence of the P450 variant is "derived" from the precursor P450 amino acid sequence by the substitution, deletion or insertion of one or more amino acids of the precursor amino acid sequence. Such modification is of the "precursor DNA sequence" which encodes the amino acid sequence of the precursor P450 rather than manipulation of the precursor P450 enzyme per se. Suitable methods for such manipulation of the precursor DNA sequence include methods disclosed herein, as well as methods known to those skilled in the art.

The term "antibody" includes a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267–273; Yarmush (1992) J. Biochem. Biophys. Methods 25:85–97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544–546), which consists of a VH domain; and (vi) an isolated complementarity determining region (CDR). Single chain antibodies are also included by reference in the term "antibody."

The terms "array" or "microarray" or "biochip" or "chip" as used herein is a plurality of target elements, each target element comprising a defined amount of one or more polypeptides (including antibodies) or nucleic acids immobilized onto a defined area of a substrate surface, as discussed in further detail, below.

As used herein, the terms "computer," "computer program" and "processor" are used in their broadest general contexts and incorporate all such devices, as described in detail, below.

The term "expression cassette" as used herein refers to a nucleotide sequence which is capable of affecting expression of a structural gene (i.e., a protein coding sequence, such as a P450 polypeptide of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers. "Operably linked" as used herein refers to linkage of a promoter upstream from a DNA sequence such that the promoter mediates transcription of the DNA sequence. Thus, expression cassettes also include plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and includes both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

"Plasmids" can be commercially available, publicly available on an unrestricted basis, or can be constructed from available plasmids in accord with published procedures. Equivalent plasmids to those described herein are known in the art and will be apparent to the ordinarily skilled artisan.

The term "gene" means a nucleic acid sequence comprising a segment of DNA involved in producing a transcription product (e.g., a message), which in turn is translated to produce a polypeptide chain, or regulates gene transcription, reproduction or stability. Genes can include, inter alia, regions preceding and following the coding region, such as leader and trailer, promoters and enhancers, as well as, where applicable, intervening sequences (introns) between individual coding segments (exons).

The phrases "nucleic acid" or "nucleic acid sequence" as used herein refer to an oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189–197; Strauss-Soukup (1997) Biochemistry 36:8692–8698; Samstag (1996) Antisense Nucleic Acid Drug Dev 6:153–156.

"Amino acid" or "amino acid sequence" as used herein refer to an oligopeptide, peptide, polypeptide, or protein sequence, or to a fragment, portion, or subunit of any of these, and to naturally occurring or synthetic molecules.

The terms "polypeptide" and "protein" as used herein, refer to amino acids joined to each other by peptide bonds or modified peptide bonds, i.e., peptide isosteres, and may contain modified amino acids other than the 20 gene-encoded amino acids. The term "polypeptide" also includes peptides and polypeptide fragments, motifs and the like. The term also includes glycosylated polypeptides. The peptides and polypeptides of the invention also include all "mimetic" and "peptidomimetic" forms, as described in further detail, below.

As used herein, the term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

As used herein, the term "recombinant" means that the nucleic acid is adjacent to a "backbone" nucleic acid to which it is not adjacent in its natural environment. In one aspect, nucleic acids represent 5% or more of the number of nucleic acid inserts in a population of nucleic acid "backbone molecules." "Backbone molecules" according to the invention include nucleic acids such as expression vectors, self-replicating nucleic acids, viruses, integrating nucleic acids, and other vectors or nucleic acids used to maintain or manipulate a nucleic acid insert or interest. In one aspect, the enriched nucleic acids represent 15%, 20%, 30%, 40%, 50%, 60%, 70%, 80%, 90% or more of the number of nucleic acid inserts in the population of recombinant backbone molecules. "Recombinant" polypeptides or proteins refer to polypeptides or proteins produced by recombinant DNA techniques; e.g., produced from cells transformed by an exogenous DNA construct encoding the desired polypeptide or protein. "Synthetic" polypeptides or protein are those prepared by chemical synthesis, as described in further detail, below.

A promoter sequence is "operably linked to" a coding sequence when RNA polymerase which initiates transcription at the promoter will transcribe the coding sequence into mRNA, as discussed further, below.

"Oligonucleotide" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Hybridization" refers to the process by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low), as set forth herein.

The term "variant" refers to polynucleotides or polypeptides of the invention modified at one or more base pairs, codons, introns, exons, or amino acid residues (respectively) yet still retain the biological activity of a P450 of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof. Techniques for producing variant P450 having activity at a pH or temperature, for example, that is different from a wild-type P450, are included herein.

The term "saturation mutagenesis" or "GSSM" includes a method that uses degenerate oligonucleotide primers to introduce point mutations into a polynucleotide, as described in detail, below.

The term "optimized directed evolution system" or "optimized directed evolution" includes a method for reassembling fragments of related nucleic acid sequences, e.g., related genes, and explained in detail, below.

The term "synthetic ligation reassembly" or "SLR" includes a method of ligating oligonucleotide fragments in a non-stochastic fashion, and explained in detail, below.

Generating and Manipulating Nucleic Acids

The invention provides nucleic acids, including expression cassettes such as expression vectors, encoding the polypeptides of the invention. The invention also includes methods for discovering new P450 sequences using the nucleic acids of the invention. Also provided are methods for modifying the nucleic acids of the invention by, e.g., synthetic ligation reassembly, optimized directed evolution system and/or saturation mutagenesis.

The nucleic acids of the invention can be made, isolated and/or manipulated by, e.g., cloning and expression of cDNA libraries, amplification of message or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

General Techniques

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105: 661; Belousov (1997) Nucleic Acids Res. 25:3440–3444; Frenkel (1995) Free Radic. Biol. Med. 19:373–380; Blommers (1994) Biochemistry 33:7886–7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1–3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333–335; yeast artificial chromosomes (YAC); bacterial artificial chromosomes (BAC); P1 artificial chromosomes, see, e.g., Woon (1998) Genomics 50:306–316; P1-derived vectors (PACs), see, e.g., Kern (1997) Biotechniques 23:120–124; cosmids, recombinant viruses, phages or plasmids.

In one aspect, a nucleic acid encoding a polypeptide of the invention is assembled in appropriate phase with a leader sequence capable of directing secretion of the translated polypeptide or fragment thereof.

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787–1797; Dobeli (1998) Protein Expr. Purif. 12:404–414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441–53.

Transcriptional and Translational Control Sequences

The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lacI, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I.

Promoters suitable for expressing a polypeptide in bacteria include the E. coli lac or trp promoters, the lacd promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Expression Vectors and Cloning Vehicles

The invention provides expression vectors and cloning vehicles comprising nucleic acids of the invention, e.g., sequences encoding the proteins of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, Aspergillus and yeast). Vectors of the invention can include chromosomal, non-chromosomal and synthetic DNA sequences. Large numbers of suitable vectors are known to those of skill in the art, and are commercially available. Exemplary vectors are include: bacterial: pQE vectors (Qiagen), pBluescript plasmids, pNH vectors, (lambda-ZAP vectors (Stratagene); ptrc99a, pKK223-3, pDR540, pR1T2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

The expression vector may comprise a promoter, a ribosome binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in E. coli, and the S. cerevisiae TRP1 gene. Promoter regions can be selected from any desired gene using chloramphenicol transferase (CAT) vectors or other vectors with selectable markers.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

A DNA sequence may be inserted into a vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector may be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which may be used include the commercially available plasmids comprising genetic elements of the well known cloning vector pBR322 (ATCC 37017), pKK223-3 (Pharmacia Fine Chemicals, Uppsaia, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

Host Cells and Transformed Cells

The invention also provides a transformed cell comprising a nucleic-acid sequence of the invention, e.g., a sequence encoding a polypeptide of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include E. coli, Streptomyces, Bacillus subtilis, Salmonella typhimurium and various species within the genera Pseudomonas, Streptomyces, and Staphylococcus. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampieillin resistance in *E. coli*.

Amplification of Nucleic Acids

In practicing the invention, nucleic acids encoding the polypeptides of the invention, or modified nucleic acids, can be reproduced by, e.g., amplification. The invention provides amplification primer sequence pairs for amplifying nucleic acids encoding P450 polypeptides, where the primer pairs are capable of amplifying nucleic acid sequences including the exemplary SEQ ID NO:1, or a subsequence thereof; a sequence as set forth in SEQ ID NO:3, or a subsequence thereof; a sequence as set forth in SEQ ID NO:5, or a subsequence thereof; and, a sequence as set forth in SEQ ID NO:7, or a subsequence thereof, a sequence as set forth in SEQ ID NO:9, or a subsequence thereof. One of skill in the art can design amplification primer sequence pairs for any part of or the full length of these sequences; for example:

```
The exemplary SEQ ID NO:1 is
gtgaccacca ccacgaccaa cgaccccgac accccccagg tccacttctg ggccgtcccc   60
gacctcaccg gcctcgactt cgacccgctg ctcgccaaac tgctgcacga ggacccgtc   120 acccgcgtcc ggctgccgca cggcgaaggc cacgcctggc tcgtcacccg ctacgaggac   180
gtcaagttcg tctccgtcga cccgcgcttc agccgccagg ccgtctgggg ccgttccatc   240
acccgcctag ccccccactt catcccgatg gagggcgccg tcggcttcgc cgacccgccg   300
gaccacaccc ggatgcgccg cgtcgtcgcc cgcgccttca gcgcccgcgc cctgcgctcc   360
ctgcgcgacc acgccagga cgtcatggac cggctcctcg accgggtcga ggagcacggc   420
gcgcccgccg acctcatgga gctcgtcaac cgcccccttcc ccctcgccat ggtcagcgaa   480
ctcatgggcg tccccgaggg cgaccagccg ctgatggccc actggtccga caccatcatc   540
tcggccggcg ccggccggga ggccagcgag acggccaagg ccgagatggg ccggtacttc   600
accgaactca tcggccgcaa ccacggcacc ggcaaggaga ccctcgccgc cgtcctcgcc   660
gacgccgtcg acgacgacac cctcacgag cacgaggccg tcggcctcgc cgtcctcatc   720
```

-continued

```
cagatcggcg gcgcccacgc cgtccggaac aacagcgcca acatggtgta cgcgctgctc    780
acccaccccg agcacctcgc ccggctgcgc gcggagccgg agctcgtccc ccaggccgtc    840
gacgagctcc tccgctacat cccgcaccgc aacgccgtcg gcctctcccg gatcgccctg    900
gaggacgtcg aggtcggcgg ggtcaccatc ccctccggcg accccgtcta cgtctcctac    960
ctgacggcca accgcgaccc cgccgtcttc cccgaccccg agcggctcga cttcgaccgc   1020
gcgtacaacc cccacgtcgc cttcggccac ggcccccact actgcccggg ctccgccctc   1080
gcccgcatcg agtcggagat cctcgtcgac acgctgtgga cccgcttccc gaacctgcgg   1140
ctcgccgtcc ccgaggacca gctgcgctgg cagcgcggcg ccctcatccg cggccccgag   1200
accctcccgg tcacctggtg a                                            1221
```

Thus, an exemplary amplification primer sequence pair is residues 1 to 21 of SEQ ID NO:1 and the complementary strand of the last 21 residues of SEQ ID NO:1.

The exemplary SEQ ID NO:1 encodes a polypeptide having the sequence

Met Thr Thr Thr Thr Thr Asn Asp Pro Asp Thr Pro Gln Val His Phe Trp Ala Val Pro       (SEQ ID NO:2)

Asp Leu Thr Gly Leu Asp Phe Asp Pro Leu Leu Ala Lys Leu Leu His Glu Asp Pro Val

Thr Arg Val Arg Leu pro His Gly Glu Gly His Ala Trp Leu Val Thr Arg Tyr Glu Asp

Val Lys Phe Val Ser Val Asp pro Arg Phe Ser Arg Gln Ala Val Trp Gly Arg Ser Ile Thr Arg Val Ala pro His Phe Ile Pro Met Glu Gly Ala Val Gly Phe Ala Asp Pro Pro Asp His Thr Arg Met Arg Arg Val Val Ala Arg Ala Phe Ser Ala Arg Ala Leu Arg Ser Leu Arg Asp His Ala Gln Asp Val Met Asp Arg Leu Leu Asp Arg Val Glu Glu His Gly Ala Pro Ala Asp Leu Met Glu Leu Val Asn Arg Pro Phe Pro Leu Ala Met Val Ser Glu Leu Met Gly Val Pro Glu Gly Asp Gln Pro Leu Met Ala His Trp Ser Asp Thr Ile Ile Ser Ala Gly Ala Gly Arg Glu Ala Ser Glu Thr Ala Lys Ala Glu Met Gly Arg Tyr Phe Thr Glu Leu Ile Gly Arg Asn His Gly Thr Gly Lys Glu Thr Leu Ala Ala Val Leu Ala Asp Ala Val Asp Asp Asp Thr Leu Glu His Glu Ala Val Gly Leu Ala Val Leu Ile Gln Ile Gly Gly Ala His Ala Val Arg Asn Asn Ser Ala Asn Met Val Tyr Ala Leu Leu Thr His Pro Glu His Leu Ala Arg Leu Arg Ala Glu Pro Glu Leu Val pro Gln Ala Val Asp Glu Leu Leu Arg Tyr Ile Pro His Arg Asn Ala Val Gly Leu Ser Arg Ile Ala Leu Glu Asp Val Glu Val Gly Gly Val Thr Ile Pro Ser Gly Asp Pro Val Tyr Val Ser Tyr Leu Thr Ala Asn Arg Asp Pro Ala Val Phe Pro Asp Pro Glu Arg Leu Asp Phe Asp Arg Ala Tyr Asn Pro His Val Ala Phe Gly His Gly Pro His Tyr Cys Pro Gly Ser Ala Leu Ala Arg Ile Glu Ser Glu Ile Leu Val Asp Thr Leu Trp Thr Arg Phe Pro Asn Leu Arg Leu Ala Val Pro Glu Asp Gln Leu Arg Trp Gln Arg Gly Ala Leu Ile Arg Gly Pro Glu Thr Leu Pro Val Thr Trp The exemplary SEQ ID NO:3 is

```
atgaccggtc aagaccagac aatcgttcac gatgtcccgg taaacgtcgc tcaacagccc     60 aaccctacc cgctcttcga acgcatccgc gagcacggcg tcgtccagcg ggtacggctg     120
aatcccactc ttgaagtctg gatggtcacc ggatacgacg aggcggtggc ggcgctcacc    180 gaccccggc tcagcagcag ccccgtcggc gtcaacggac tcgaggagga gatggcccac    240
caggagcgca ccaacgtcct gatggccagc atgctcgtcg ccaacggcga ggaccacacc    300
```

-continued

```
cggctgcgca acctcgtctc gaaggccttc accgcccgcc gggtggagca gctcgcgccg    360
cgcgtccagg cgcacaccga cgccttcctc gacgcggtcg cggcgcgcgg atccgccgac    420
ctggtctcgg agttcgccct gccgctcccc atggccgtac tcagcgacct catcggcatc    480
ccggccgagg ggcagcccga cttcgcccgc ctcgcggtcg gcctcatcat gccgccgaac    540
accccgagc ggctcgccaa gggagcccgc gcccgcgccg aactcaccga gttcttcgag    600
ccgttgatcg cccagcgcaa gaaggagccg aaggacgacc tgctgagcgc gctctgcgcg    660
gcgcaggccg aggagcggat cagcgaccgc gagctgacgg cgatgacgat cctgctcacg    720
ctcgccgggc acgagacgac ggccagcctg atcgccaacg gcgtgcacgc cctgctgcgg    780
caccccggagc agttcgccac cctgcgcgac gaccccctcgc tgctgccggg cgcgatcgag   840
gaactcctgc gctacgaggg cccggtgagc cggggcgtcg cccgcttcac caccgacccg    900
tacgagatcg gcggggtcac cgtaccggcc ggcgagatga tcatcatcgg gctcgccgcg    960
gccaatcgcg acccggcccg ctacgaccgt cccgacatcc tcgacgttgc acgccgtgag   1020
gtgccgcaac agctcgcttt cggccatggc gtgcacttct gcctgggtgc gccgctggcc   1080
cgcgcggagg cccggatcgc catcggcacc ctgctgcgcc gcttccccga tctgcggctc   1140
gccgacccgg acgcggacct cagccggcgc gagggcatcc tgcgcggcat ggcgaccctg   1200
cccgtgacct tcacgcccga ggcctga 1227
```

Thus, an exemplary amplification primer sequence pair is residues 1 to 21 of SEQ ID NO:3 and the complementary strand of the last 21 residues of SEQ ID NO:3.

```
The exemplary SEQ ID NO:3 encodes a polypeptide having the sequence

Met Thr Gly Gln Asp Gln Thr Ile Val His Asp Val Pro Val Asn Val Ala Gln Gln Pro Asn    (SEQ ID NO:4)

Pro Tyr Pro Leu Phe Glu Arg Ile Arg Glu His Gly Val Val Gln Arg Val Arg Leu Asn Pro

Thr Leu Giu Val Trp Met Val Thr Gly Tyr Asp Glu Ala Val Ala Ala Leu Thr Asp Pro

Arg Leu Ser Ser Ser Pro Val Gly Val Asn Gly Leu Glu Glu Glu Met Ala His Gln Glu

Arg Thr Asn Val Leu Met Ala Ser Met Leu Val Ala Asn Gly Glu Asp His Thr Arg Leu

Arg Asn Leu Val Ser Lys Ala Phe Thr Ala Arg Arg Val Glu Gln Leu Ala Pro Arg Val

Gln Ala His Thr Asp Ala Phe Leu Asp Ala Val Ala Ala Arg Gly Ser Ala Asp Leu Val

Ser Glu Phe Ala Leu Pro Leu Pro Met Ala Val Leu Ser Asp Leu Ile Gly Ile Pro Ala Glu

Gly Gln Pro Asp Phe Ala Arg Leu Ala Val Gly Leu Ile Met Pro Pro Asn Thr Pro Glu Arg

Leu Ala Lys Gly Ala Arg Ala Arg Ala Glu Leu Thr Glu Phe Phe Glu Pro Leu Ile Ala Gln

Arg Lys Lys Glu Pro Lys Asp Asp Leu Leu Ser Ala Leu Cys Ala Ala Gln Ala Glu Glu

Arg Ile Ser Asp Arg Glu Leu Thr Ala Met Thr Ile Leu Leu Thr Leu Ala Gly His Glu Thr

Thr Ala Ser Leu Ile Ala Asn Gly Val His Ala Leu Leu Arg His Pro Glu Gln Phe Ala Thr

Leu Arg Asp Asp Pro Ser Leu Leu Pro Gly Ala Ile Glu Glu Leu Leu Arg Tyr Glu Gly

Pro Val Ser Arg Gly Val Ala Arg Phe Thr Thr Asp Pro Tyr Glu Ile Gly Gly Val Thr Val

Pro Ala Gly Glu Met Ile Ile Ile Gly Leu Ala Ala Ala Asn Arg Asp Pro Ala Arg Tyr Asp

Arg Pro Asp Ile Leu Asp Val Ala Arg Arg Glu Val Pro Gln Gln Leu Ala Phe Gly His Gly

Val His Phe Cys Leu Gly Ala Pro Leu Ala Arg Ala Glu Ala Arg Ile Ala Ile Gly Thr Leu
```

-continued

Leu Arg Arg Phe Pro Asp Leu Arg Leu Ala Asp Pro Asp Ala Asp Leu Ser Arg Arg Glu

Gly Ile Leu Arg Gly Met Ala Thr Leu Pro Val Thr Phe Thr Pro Glu Ala

The exemplary SEQ ID NO:5 is

| | | | | |
|---|---|---|---|---|
| atgagcgacg | agccgaaccg | cgagccgggc | cggggcatag | cgggcgaccg | ggcggcggcg | 60 |
| ccgcccgggg | acccctggac | gcggctgccg | tccatggcgc | cggcggagcc | ggtggccgac | 120 |
| ggtaagggcg | gcccccggtc | cgccgccgcg | ccgggacggg | tgcggaccgt | gcccgatccg | 180 |
| gccgtcctcg | gtggctcccg | ggccaggacc | gtcgcgccca | gtcccctcga | ccccggcgcc | 240 |
| tcgcgcgacc | cgcaccgcat | ccaccggacg | ctgcgggagg | acttcccgct | cacgtacgac | 300 |
| ccgctgctgc | gggcctgggt | gctcagccgg | tacgccgacg | tggccaccgc | cctcaccgac | 360 |
| agccgcttca | cccacgggca | ccggcccggc | gacccgccgt | gcgcgcgggc | ccatgtcgac | 420 |
| gtcgacgtgg | cggccctgcg | gtcggtcacg | gagcgcaccg | cgtacgtgct | ggcccgccgg | 480 |
| atcgccgagc | ggccccaggc | cgatctggtg | gccgacttct | gccactggct | gcccgccggg | 540 |
| accgtggccg | ccgccgtcgg | cgtcccctac | cgcgacatga | tgcggctcgt | ccgcggccgg | 600 |
| gcggccggcg | ctctcgcggg | ggagtgcggc | gggcagatcg | ccgtacggga | gaaggcgctt | 660 |
| gcgtccttcc | tcggcaacgt | cctcgccgat | cccgatcagg | tcgccgccct | gcgggacgcg | 720 |
| ccggccgggc | tggtggcccg | cgcctggacg | gagtcgctgc | gccgcgaccc | gcccgtgcag | 780 |
| atcgccgtgc | gcaggacgag | cgccgaggtg | ccggtgagcg | gcggtgtcgt | cccggcgggc | 840 |
| gtgcccgtgg | cgctgctcgt | gggctcggcg | ggccgggacc | cggagcggtt | ccgcgagccg | 900 |
| gaccgtttcg | atcccttccg | tgccgacccg | ggccagttga | cgtacggctc | cggcttctgc | 960 |
| ccggcggtgc | tcctggccgg | tcttgaggcg | gagtacgcgc | tgcgggccct | gttcacggcg | 1020 |
| atgcccggc | tccgcctcgc | cgagggcttc | cgcccggtgt | gggcgggtct | catcacgcgg | 1080 |
| gcgccgcgga | gcctgatcgt | ccggccggga | ggctga | | | 1116 |

Thus, an exemplary amplification primer sequence pair is residues 1 to 21 of SEQ ID NO:5 and the complementary strand of the last 21 residues of SEQ ID NO:5.

The exemplary SEQ ID NO:5 encodes a polypeptide having the sequence

Met Ser Asp Glu Pro Asn Arg Glu Pro Gly Arg Gly Ile Ala Gly Asp Arg Ala Ala Pro    (SEQ ID NO:6)

Pro Gly Asp Pro Trp Thr Arg Leu Pro Ser Met Ala Pro Ala Glu Pro Val Ala Asp Gly Lys

Gly Gly Pro Arg Ser Ala Ala Pro Gly Arg Val Arg Thr Val Pro Asp Pro Ala Val Leu

Gly Gly Ser Arg Ala Arg Thr Val Ala Pro Ser Pro Leu Asp Pro Gly Ala Ser Arg Asp Pro

His Arg Ile His Arg Thr Leu Arg Glu Asp Phe Pro Leu Thr Tyr Asp Pro Leu Leu Arg

Ala Trp Val Leu Ser Arg Tyr Ala Asp Val Ala Thr Ala Leu Thr Asp Ser Arg Phe Thr His

Gly His Arg Pro Gly Asp Pro Pro Cys Ala Arg Ala His Val Asp Val Asp Val Ala Ala

Leu Arg Ser Val Thr Glu Arg Thr Ala Tyr Val Leu Ala Arg Arg Ile Ala Glu Arg Pro Gln

Ala Asp Leu Val Ala Asp Phe Cys His Trp Leu Pro Ala Gly Thr Val Ala Ala Val

Gly Val Pro Tyr Arg Asp Met Met Arg Leu Val Arg Gly Arg Ala Ala Gly Ala Leu Ala

Gly Glu Cys Gly Gly Gln Ile Ala Val Arg Glu Lys Ala Leu Ala Ser Phe Leu Gly Asn Val

Leu Ala Asp Pro Asp Gln Val Ala Ala Leu Arg Asp Ala Pro Ala Gly Leu Val Ala Arg

Ala Trp Thr Glu Ser Leu Arg Arg Asp Pro Pro Val Gln Ile Ala Val Arg Arg Thr Ser Ala

-continued

Glu Val Pro Val Ser Gly Gly Val Val Pro Ala Gly Val Pro Val Ala Leu Leu Val Gly Ser

Ala Gly Arg Asp Pro Glu Arg Phe Arg Glu Pro Asp Arg Phe Asp Pro Phe Arg Ala Asp

Pro Gly Gln Leu Thr Tyr Gly Ser Gly Phe Cys Pro Ala Val Leu Leu Ala Gly Leu Glu

Ala Glu Tyr Ala Leu Arg Ala Leu Phe Thr Ala Met Pro Arg Leu Arg Leu Ala Glu Gly

Phe Arg Pro Val Trp Ala Gly Leu Ile Thr Arg Ala Pro Arg Ser Leu Ile Val Arg Pro Gly

Gly

The exemplary SEQ ID NO:7 is

| | |
|---|---|
| atgcccccca acaccgtccc gaccccggtg ccaggaggcc gaccgctgat cgggcacgcc | 60 |
| cgccaactgc tgtggcgcag gctgccgttc ctggagtcgc tgcgggacca cggcgacatc | 120 |
| gtggtgatcc gcctcggccc gtggcggatc catgtgctca acgacccggc gctcgtccgc | 180 |
| gacgtcctca ccaaacgctc cccggacttc gggctgagcc ccagttcca ggtgatgaaa | 240 |
| cgcgtcatcg gcaacgggct cctcgccacc gacggcccct tccaccgccg gcagcgcaaa | 300 |
| ctgatcctcc ccgccctgca ccacaccagg atccgcgcct acgcccgcac catgacccgc | 360 |
| ctcgccgacg cccgtaccgc ccgctggcag gacgggcaga ccctgcgcgt cgacgcggag | 420 |
| ttcaccgaac tggccaccga gatcgtgctg cgctgcctgt tctccaccga gatcggcggc | 480 |
| gccgacgtgg ccgccgtggt ggccgccctg cccgacctga tgagctgggc cggcagccgc | 540 |
| ggcctcgacc cgaccgggct gctcggcgcc gtccccaccc cgctgggccg ccgcttccgg | 600 |
| cgctccatgg cggtgctgga cgcgctgctc gcccgggtca tcggggcccg ccgggcggac | 660 |
| ggcccggcca ccgaccaccc cgacctgctc gccgcgctgc tcgccgcccg cgacgcggag | 720 |
| accggggagc ccatgtccga ccggcagatc cgcgacgagg ccatgtcgtt cctggtggcc | 780 |
| ggggccgaat cggtctcccg caccctgacc tggagcgccc tgctgctggc cggcgacccc | 840 |
| gaggcggccc gccggctcca ccaggaggcc gatcgcgaac tgtccggccg cccggcccac | 900 |
| ttcgaggacc tgccgaggct gcgccacacc cgcatggtgc tccaggaggc gctgcgcctg | 960 |
| tacccgcccg gctacctgat ctcccgggcg gcgctgcgcg acaccacgct cggcccctac | 1020 |
| cgcatcccgg ccggcgccac cgtgatgttc tcctactacg ccctccagcg ggaccccgc | 1080 |
| cgcttcccgg accggcccg gttcgacccg ttgcgctggt cgcccaagcg cggcggcgcc | 1140 |
| gaccgggagg cgttcacgcc gttcggcctc ggcccgcacg gctgcctcgg cgagagcttc | 1200 |
| gcgtggaccg agatgtccat cgtgctcgcc accctcgccg cccgctggga gctgcgctcc | 1260 |
| gcctcgccgc gcccggtgcg gccggtgccc accttctccc tgaccatggc cggcgccccg | 1320 |
| atgaccgtca ccgcgcggcc ggtgcgcacc ggccccgtcc acaccctgct ggccagccgt | 1380 |
| aacggaggat ga | 1392 |

Thus, an exemplary amplification primer sequence pair is residues 1 to 21 of SEQ ID NO:7 and the complementary strand of the last 21 residues of SEQ ID NO:7.

The exemplary SEQ ID NO:7 encodes a polypeptide having the sequence

Met Pro Pro Asn Thr Val Pro Thr Pro Val Pro Gly Gly Arg Pro Leu Ile Gly His Ala Arg    (SEQ ID NO:8)

Gln Leu Leu Trp Arg Arg Leu Pro Phe Leu Glu Ser Leu Arg Asp His Gly Asp Ile Val

Val Ile Arg Leu Gly Pro Trp Arg Ile His Val Leu Asn Asp Pro Ala Leu Val Arg Asp Val

Leu Thr Lys Arg Ser Pro Asp Phe Gly Leu Ser Pro Gln Phe Gln Val Met Lys Arg Val Ile

-continued

Gly Asn Gly Leu Leu Ala Thr Asp Gly Pro Phe His Arg Arg Gln Arg Lys Leu Ile Leu
Pro Ala Leu His His Thr Arg Ile Arg Ala Tyr Ala Arg Thr Met Thr Arg Leu Ala Asp Ala
Arg Thr Ala Arg Trp Gln Asp Gly Gln Thr Leu Arg Val Asp Ala Glu Phe Thr Glu Leu
Ala Thr Glu Ile Val Leu Arg Cys Leu Phe Ser Thr Glu Ile Gly Gly Ala Asp Val Ala Ala
Val Val Ala Ala Leu Pro Asp Leu Met Ser Trp Ala Gly Ser Arg Gly Leu Asp Pro Thr
Gly Leu Leu Gly Ala Val Pro Thr Pro Leu Gly Arg Arg Phe Arg Arg Ser Met Ala Val
Leu Asp Ala Leu Leu Ala Arg Val Ile Gly Ala Arg Arg Ala Asp Gly Pro Ala Thr Asp
His Pro Asp Leu Leu Ala Ala Leu Leu Ala Ala Arg Asp Ala Glu Thr Gly Glu Pro Met
Ser Asp Arg Gln Ile Arg Asp Glu Ala Met Ser Phe Leu Val Ala Gly Ala Glu Ser Val Ser
Arg Thr Leu Thr Trp Ser Ala Leu Leu Leu Ala Gly Asp Pro Glu Ala Ala Arg Arg Leu
His Gln Glu Ala Asp Arg Glu Leu Ser Gly Arg Pro Ala His Phe Glu Asp Leu Pro Arg
Leu Arg His Thr Arg Met Val Leu Gln Glu Ala Leu Arg Leu Tyr Pro Pro Gly Tyr Leu Ile
Ser Arg Ala Ala Leu Arg Asp Thr Thr Leu Gly Pro Tyr Arg Ile Pro Ala Gly Ala Thr Val
Met Phe Ser Tyr Tyr Ala Leu Gln Arg Asp Pro Arg Arg Phe Pro Asp Pro Ala Arg Phe
Asp Pro Leu Arg Trp Ser Pro Lys Arg Gly Gly Ala Asp Arg Glu Ala Phe Thr Pro Phe
Gly Leu Gly Pro His Gly Cys Leu Gly Glu Ser Phe Ala Trp Thr Glu Met Ser Ile Val Leu
Ala Thr Leu Ala Ala Arg Trp Glu Leu Arg Ser Ala Ser Pro Arg Pro Val Arg Pro Val Pro
Thr Phe Ser Leu Thr Met Ala Gly Ala Pro Met Thr Val Thr Ala Arg Pro Val Arg Thr Gly
Pro Val His Thr Leu Leu Ala Ser Arg Asn Gly Gly

The exemplary SEQ ID NO:9 is

| | |
|---|---:|
| gtggacccga ttctggatct ggcccgaccg tcgatcctgc ggaaccccta cccctcgtac | 60 |
| gaccggatgc gcgagaccgg cccggtcttc tggcacgaac tgctcggttc gtgggtcctg | 120 |
| acccggcacg ccgactgcct cgcggtgctc accgacagca accgtttcgc ctccgactgg | 180 |
| cgccgggccg gggaggacat ccccgccccg ctgctcagcg tgcagaccct cgacccgccg | 240 |
| gagcacaccg ccatccggca cctcctcctc gacggtttcc gggcccagga ccggcgggcg | 300 |
| ctccatgacg acctggaggg gcagatcgcc gatctgctcg cggagttggc cggccggccg | 360 |
| tccttcgacc tggtcgggga gctcgccgaa ccgatcgccc tccgcttcgt gaccgccttc | 420 |
| ctcggcgtcc cggcccccgc gctcgactgg ttcgtgccca tgtcccgtac cgtcgtcgac | 480 |
| ggcatggacg ccgggctgtg gcccgagaag cacgagccgg ccgtcgccgc ccgcgcccag | 540 |
| ctcgcggagt acgcgggcgg ctggctcgcc gacccgccga aggacggcct catcgcctac | 600 |
| gtggccgagc acgcggcgga cagcggcgtg cagaaacgg ttctgcggaa cagtctgcgc | 660 |
| gccgttctcc acgcgggcta cgaatccgcc tcccggctgc tcggcaacgc cgcggccgcc | 720 |
| ctcctcacca cccccggcgc gctcgccgcg ttccgggcga ccccgccac ggccgtggac | 780 |
| gaactcatcc ggtacgacgc acccgtccag gcggacgccc gggtctgcgt caccgacacc | 840 |
| gaactgggtg gcgtcacgat gaaggcgggt gatccggtca cgctcttcct gggcgcggcc | 900 |
| aaccacgacc cgctccgctt cgaccacccc acagagctgc gactcgaccg cgccccgaac | 960 |
| ccgcaccctcg ggttcggccg cggggcccat gcctgtctgg gcgcgtccat ggcgatccgg | 1020 |
| ctcaccggat cggtcctcgg gaccctggcc acggaccacc ccggcgcacg ggcggtcgcg | 1080 |
| gaaccggaac accggcgcaa cctgacccctt cgcggtctcg accgcttcga ggtctgcctg | 1140 |
| cgtccagaca cgggggagga ggtacgacca tga | 1173 |

Thus, an exemplary amplification primer sequence pair is residues 1 to 21 of SEQ ID NO:9 and the complementary strand of the last 21 residues of SEQ ID NO:9.

The exemplary SEQ ID NO:9 encodes a polypeptide having the sequence

Met Asp Pro Ile Leu Asp Leu Ala Arg Pro Ser Ile Leu Arg Asn Pro Tyr Pro Ser Tyr (SEQ ID NO:10)
Asp Arg Met Arg Glu Thr Gly Pro Val Phe Trp His Glu Leu Leu Gly Ser Trp Val Leu
Thr Arg His Ala Asp Cys Leu Ala Val Leu Thr Asp Ser Asn Arg Phe Ala Ser Asp Trp
Arg Arg Ala Gly Glu Asp Ile Pro Ala Pro Leu Leu Ser Val Gln Thr Leu Asp Pro Pro Glu
His Thr Ala Ile Arg His Leu Leu Asp Gly Phe Arg Ala Gln Asp Arg Arg Ala Leu
His Asp Asp Leu Glu Gly Gln Ile Ala Asp Leu Leu Ala Glu Leu Ala Gly Arg Pro Ser
Phe Asp Leu Val Gly Glu Leu Glu Pro Ile Ala Leu Arg Phe Val Thr Ala Phe Leu Gly Val
Pro Ala Pro Ala Leu Asp Trp Phe Val Pro Met Ser Arg Thr Val Val Asp Gly Met Asp
Ala Gly Leu Trp Pro Glu Lys His Glu Pro Ala Val Ala Ala Arg Ala Gln Leu Ala Glu Tyr
Ala Gly Gly Trp Leu Ala Asp Pro Pro Lys Asp Gly Leu Ile Ala Tyr Val Ala Glu His Ala
Ala Asp Ser Gly Val Ala Glu Thr Val Leu Arg Asn Ser Leu Arg Ala Val Leu His Ala
Gly Tyr Glu Ser Ala Ser Arg Leu Leu Gly Asn Ala Ala Ala Leu Leu Thr Thr Pro Gly
Ala Leu Ala Ala Phe Arg Ala Thr Pro Ala Thr Ala Val Asp Glu Leu Ile Arg Tyr Asp Ala
Pro Val Gln Ala Asp Ala Arg Val Cys Val Thr Asp Thr Glu Leu Gly Gly Val Thr Met
Lys Ala Gly Asp Pro Val Thr Leu Phe Leu Gly Ala Ala Asn His Asp Pro Leu Arg Phe
Asp His Pro Thr Glu Leu Arg Leu Asp Arg Ala Pro Asn Pro His Leu Gly Phe Gly Arg
Gly Ala His Ala Cys Leu Gly Ala Ser Met Ala Ile Arg Leu Thr Gly Ser Val Leu Gly Thr
Leu Ala Thr Asp His Pro Gly Ala Arg Ala Val Ala Glu Pro Glu His Arg Arg Asn Leu
Thr Leu Arg Gly Leu Asp Arg Phe Glu Val Cys Leu Arg Pro Asp Thr Gly Glu Glu Val
Arg Pro

The exemplary SEQ ID NO:11 is

```
atgactttga agttcaaccc ctactgcgaa gagttttacc agaacccgtg gcagaacttc        60
cgggcgcttc gaacgcagga cccggtccac tatatcgagg aattcgatgc ctgggctctg       120
ttcggtttcg aggatgtgtg gcgcgcgggc atggaccggg aaagcttcac cgctacctac       180
ggcagctctc cacaggcgct gctgatcgac cgggtaaagc agccggagat cttcctgttc       240
atggacatac cgaaccacat gatccaccgg gcattattg cgaaggatta cggccgcaac        300
gccatgccgc ttctcgaggg gaagatccgc gccacggcaa agaggcgat tacgccctac        360
ctgaagtccg gtgagatgga cgtttacgcc ttcgcccgta cagtggcgct tttcaccatc       420
gctgacatga tcggtctgcg gccggaagag gtcgtccgta tccggtccct tatcgatatt       480
ttcttcgggc gcacaccagg ccatcgaggc acaaccccgg acggcgtggc ggcctttcac       540
gaagtaaccg cctacgtcct tgatctgatc ggccactacc gggcgaaggg cgcaccggag       600
ggcagccaca tcgacaactg gctcaaggca gagccggatg gccggcccct cgacgatcag       660
gcgctgtgcg ccaatatctt ttcgctgtcg attacgggct cggacaccgt gcccctgtca       720
tcggcggcgg caatctatta tctgtcggag catccggcgc agctggaggc ggtgcgctcc       780
gaccgcgcgc tgattcccgc cgccttcgct gagaccgtgc gctacgatca gccgaccaat       840
gtactgggcc gactgcttgc cattgacacc gacaaatacg gcaagccgat gaaaaaggt       900
caagcggtcc tgttcatgta tgcgtcggca aaccgtgacc cgctggaatt cgaacacccc       960
```

-continued

```
gacacgttca atatataccg cgatccccgg cgcaccctgt ccttcggctc cggcatccat    1020
atctgtctgg gccagcttct ggccaaactg gaaggtcaga tcattctgga aacgctgttt    1080
gagcatatcc cggactttac ggtccagtat aaggaggtgc ggcgcattcc cggcgaattt    1140
ctccaggggt tcgggtcat gccgatccgc ttcccgctgc gaacctga                  1188
```

Thus, an exemplary amplification primer sequence pair is residues 1 to 21 of SEQ ID NO:11 and the complementary strand of the last 21 residues of SEQ ID NO:11.

The exemplary SEQ ID NO:11 encodes a polypeptide having the sequence

```
Met Thr Leu Lys Phe Asn Pro Tyr Cys Glu Glu Phe Tyr Gln Asn Pro Trp Gln Asn Phe    (SEQ ID NO:12)
Arg Ala Leu Arg Thr Gln Asp Pro Val His Tyr Ile Glu Glu Phe Asp Ala Trp Ala Leu Phe
Gly Phe Glu Asp Val Trp Arg Ala Gly Met Asp Arg Glu Ser Phe Thr Ala Thr Tyr Gly
Ser Ser Pro Gln Ala Leu Leu Ile Asp Arg Val Lys Gln Pro Glu Ile Phe Leu Phe Met Asp
Ile Pro Asn His Met Ile His Arg Gly Ile Ile Ala Lys Asp Tyr Gly Arg Asn Ala Met Pro
Leu Leu Glu Gly Lys Ile Arg Ala Thr Ala Lys Glu Ala Ile Thr Pro Tyr Leu Lys Ser Gly
Glu Met Asp Val Tyr Ala Phe Ala Arg Thr Val Ala Leu Phe Thr Ile Ala Asp Met Ile Gly
Leu Arg Pro Glu Glu Val Val Arg Ile Arg Ser Leu Ile Asp Ile Phe Phe Gly Arg Thr Pro
Gly His Arg Gly Thr Thr Pro Asp Gly Val Ala Ala Phe His Glu Val Thr Ala Tyr Val Leu
Asp Leu Ile Gly His Tyr Arg Ala Lys Gly Ala Pro Glu Gly Ser His Ile Asp Asn Trp Leu
Lys Ala Glu Pro Asp Gly Arg Pro Leu Asp Asp Gln Ala Leu Cys Ala Asn Ile Phe Ser
Leu Ser Ile Thr Gly Ser Asp Thr Val Pro Leu Ser Ser Ala Ala Ala Ile Tyr Tyr Leu Ser
Glu His Pro Ala Gln Leu Glu Ala Val Arg Ser Asp Arg Ala Leu Ile Pro Ala Ala Phe Ala
Glu Thr Val Arg Tyr Asp Gln Pro Thr Asn Val Leu Gly Arg Leu Leu Ala Ile Asp Thr
Asp Lys Tyr Gly Lys Pro Met Lys Lys Gly Gln Ala Val Leu Phe Met Tyr Ala Ser Ala
Asn Arg Asp Pro Leu Glu Phe Glu His Pro Asp Thr Phe Asn Ile Tyr Arg Asp Pro Arg
Arg Thr Leu Ser Phe Gly Ser Gly Ile His Ile Cys Leu Gly Gln Leu Leu Ala Lys Leu Glu
Gly Gln Ile Ile Leu Glu Thr Leu Phe Glu His Ile Pro Asp Phe Thr Val Gln Tyr Lys Glu
Val Arg Arg Ile Pro Gly Glu Phe Leu Gln Gly Phe Gly Val Met Pro Ile Arg Phe Pro Leu
Arg Thr
```

The exemplary SEQ ID NO:13 is

```
atgagcgagt ccctccacac cgtcaccacg ctgccgaccg agcgtcagac cgggtgcccc    60
ttcgacccgc cggcggaact gatcgacgca cgccaacacg gtggcatcag ccggtgcacc    120
catcccggcg gcaagcccgg ctatctgatc accggttacg acctcgtccg atccgtactg    180
gccgatcccc ggttcagctc gcgcaaggac ctcctgaacg tcgtcgactt cgagctcccg    240
cccgcccctc cggcgagtt cctcctcatg gacgagcccc agcattcgcg ctaccggaag    300
ccgctcgtcg gcaagttcac cgtgcggcgc atgcgactgc tcaccgaacg catcgagcag    360
atcaccacgg aatgcctgga cgccatggag gaggccgggc cgtcggcgga cctcgtggcc    420
gcgttcgcca agccgatccc caccatcgtc atctgcgagc tgctgggcgt tccgtacgag    480
gaccgtgcct cgttccagga gcagatcgac acgttcatga cggcgagac gagcgacgag    540
gacctcatcg cggcgtacac cgccacccag acctacctcg ccgagctggt ggccgccaag    600
```

-continued

```
cgcgcgaaac ccaccgacga cgtgctgagc gaactgaccg acagcgacct caccgacgag      660
gaactgcagg gcatcagcct gatcctgctc gcggccggct tcgacacgac cgcgaacatg      720
ctctccctcg gtaccttcgc ccttctgcag caccggccc aactggccgc gctgcaggcc       780
gaccccggcc tcatcgacca ggccgtcgaa gagctgctgc ggtacctcag cgtcgcgaag      840
acgttcatgc ggaccgcgct cgtcgacgtc gaggtcggcg gccacaccgt cgaggcgggc      900
acgaccgtcg tcctgtcgta cagcacggcc aaccgcgacc ccgagcgctt cgacgacccc     960
cacgtgctcg acgtgcaccg gaagcagggc gggcacctgg ccttcggcca cggcatccac     1020
ctgtgcctgg gtcagcaact cgcccgcgtc gagatgcgga tcgcgatcgc cgcgctgctc     1080
gaccgcttcc ccacgctgcg cctcgccgtc ccgccgagg aggtcgccct gcggcccgag      1140
accgcggaca tctacggggt gaagagcctt cccgtcacct gggacgtatg a              1191
```

Thus, an exemplary amplification primer sequence pair is residues 1 to 21 of SEQ ID NO:13 and the complementary strand of the last 21 residues of SEQ ID NO:13.

The exemplary SEQ ID NO:13 encodes a polypeptide having the sequence

Met Ser Glu Ser Leu His Thr Val Thr Thr Leu Pro Thr Glu Arg Gln Thr Gly Cys Pro    (SEQ ID NO:14)
Phe Asp Pro Pro Ala Glu Leu Ile Asp Ala Arg Gln His Gly Gly Ile Ser Arg Cys Thr His
Pro Gly Gly Lys Pro Gly Tyr Leu Ile Thr Gly Tyr Asp Leu Val Arg Ser Val Leu Ala Asp
Pro Arg Phe Ser Ser Arg Lys Asp Leu Leu Asn Val Val Asp Phe Glu Leu Pro Pro Ala
Pro Pro Gly Glu Phe Leu Leu Met Asp Glu Pro Gln His Ser Arg Tyr Arg Lys Pro Leu
Val Gly Lys Phe Thr Val Arg Arg Met Arg Leu Leu Thr Glu Arg Ile Glu Gln Ile Thr Thr
Glu Cys Leu Asp Ala Met Glu Glu Ala Gly Pro Ser Ala Asp Leu Val Ala Ala Phe Ala
Lys Pro Ile Pro Thr Ile Val Ile Cys Glu Leu Leu Gly Val Pro Tyr Glu Asp Arg Ala Ser
Phe Gln Glu Gln Ile Asp Thr Phe Met Ser Gly Glu Thr Ser Asp Glu Asp Leu Ile Ala Ala
Tyr Thr Ala Thr Gln Thr Tyr Leu Ala Glu Leu Val Ala Ala Lys Arg Ala Lys Pro Thr Asp
Asp Val Leu Ser Glu Leu Thr Asp Ser Asp Leu Thr Asp Glu Glu Leu Gln Gly Ile Ser
Leu Ile Leu Leu Ala Ala Gly Phe Asp Thr Thr Ala Asn Met Ser Leu Gly Thr Phe Ala
Leu Leu Gln His Pro Ala Gln Leu Ala Ala Leu Gln Ala Asp Pro Gly Leu Ile Asp Gln Ala
Val Glu Glu Leu Leu Arg Tyr Leu Ser Val Ala Lys Thr Phe Met Arg Thr Ala Leu Val
Asp Val Glu Val Gly Gly His Thr Val Glu Ala Gly Thr Thr Val Val Leu Ser Tyr Ser Thr
Ala Asn Arg Asp Pro Glu Arg Phe Asp Asp Pro His Val Leu Asp Val His Arg Lys Gln
Gly Gly His Leu Ala Phe Gly His Gly Ile His Leu Cys Leu Gly Gln Gln Leu Ala Arg Val
Glu Met Arg Ile Ala Ile Ala Ala Leu Leu Asp Arg Phe Pro Thr Leu Arg Leu Ala Val Pro
Ala Glu Glu Val Ala Leu Arg Pro Glu Thr Ala Asp Ile Tyr Gly Val Lys Ser Leu Pro Val
Thr Trp Asp Val

The exemplary SEQ ID NO:15 is

```
gtggccgctt ccgccgccgc cccgccggcg gcccgcacct gggcggtgga cgacctgccc       60
gccctcgcct tcgacccgct gctcaccgaa ctcctggaga aggagcccgt cgcccgcatc      120
aggctgccgt tcgccgcgcg gaacgaggcc tggctggtga cgcggtacga ggacgtgcgc     180
gcggtgacct ccgaccccg gttcagccgg acggcgctgc tcgaccagca ggtcaccaag      240
```

-continued

```
atgaccggcc acatggtggc ctcgaaggcg gccctcaact acgccgatcc gccgtaccac      300
acccagctgc gcaaggcggt gaccaaggcg ttcaccgggc agagcaccag gcggctgcgt      360
ccgcttgccc aggcgggcac cgaccggctc ctggacgcga tggaggcggc gggccgcccc      420
gccgacctga tgaagcatct gcacggcccg ctgccgatgg cggtggtgtg cgatctgctc      480
ggcatcccgg aggaggaccg ggcggagctg gcctcctggc cggacctgat cctgtcctcg      540 ggcccggcc cggagagcag caaggcggcc aaggcccaga tccacggcta cgtcatccgg       600
ctgctcgacc ggcggcgcgc ggagccccag gacgatctgg cgggcgtgct cgcggagtcc      660
ctcgccgagg ggcggatcac cgccgaggag gccgtctccc tggcgatggc gatcctgatc      720
agcggcgcgc acgcggtacg gaacaacagc gccaacatgg tgtacgtgct gctcacccgg      780
ccggagctcg cggaccggct gcgcgccgag cccggactgc tcccgcaggc cgtggacgag      840
ctgctgcgct ggatcccgca ccgcaacggc gtcgggctgc ccggatcgc gacggaggac       900 gtcgaggtcg gcgggtgct gatccggcg ggtgaggcgg tctacgcctc ctacctcgcg        960
gccaaccggg acccggcggc cttcgaggac ccggaccgcc tcgacttcga ccgggagggc      1020
atcgggcacg tgtcgttcgg tcacggcccg caccactgca tgggcgcgat gctcacccgc      1080
atggagtccg aggtgatgct gtcgacgctg ctcgaccgct atccgcggct gcggctcgcg      1140
gggagcgccg aggacgtggt gtggcagtcg aaggggctca tccgcggccc gaaggaactc      1200
ctcgtgacct ggtga                                                       1215
```

Thus, an exemplary amplification primer sequence pair is residues 1 to 21 of SEQ ID NO:15 and the complementary strand of the last 21 residues of SEQ ID NO:15.

The exemplary SEQ ID NO:15 encodes a polypeptide having the sequence

Met Ala Ala Ser Ala Ala Ala Pro Pro Ala Ala Arg Thr Trp Ala Val Asp Asp Leu Pro    (SEQ ID NO:16)

Ala Leu Ala Phe Asp Pro Leu Leu Thr Glu Leu Leu Glu Lys Glu Pro Val Ala Arg Ile

Arg Leu Pro Phe Ala Ala Arg Asn Glu Ala Trp Leu Val Thr Arg Tyr Glu Asp Val Arg

Ala Val Thr Ser Asp Pro Arg Phe Ser Arg Thr Ala Leu Leu Asp Gln Gln Val Thr Lys

Met Thr Gly His Met Val Ala Ser Lys Ala Ala Leu Asn Tyr Ala Asp Pro Pro Tyr His Thr

Gln Leu Arg Lys Ala Val Thr Lys Ala Phe Thr Gly Gln Ser Thr Arg Arg Leu Arg Pro

Leu Ala Gln Ala Gly Thr Asp Arg Leu Leu Asp Ala Met Glu Ala Ala Gly Arg Pro Ala

Asp Leu Met Lys His Leu His Gly Pro Leu Pro Met Ala Val Val Cys Asp Leu Leu Gly

Ile Pro Glu Glu Asp Arg Ala Glu Leu Ala Ser Trp Pro Asp Leu Ile Leu Ser Ser Gly Pro

Gly Pro Glu Ser Ser Lys Ala Ala Lys Ala Gln Ile His Gly Tyr Val Ile Arg Leu Leu Asp

Arg Arg Arg Ala Glu Pro Gln Asp Asp Leu Ala Gly Val Leu Ala Glu Ser Leu Ala Glu

Gly Arg Ile Thr Ala Glu Glu Ala Val Ser Leu Ala Met Ala Ile Leu Ile Ser Gly Ala His

Ala Val Arg Asn Asn Ser Ala Asn Met Val Tyr Val Leu Thr Arg Pro Glu Leu Ala Asp

Arg Leu Arg Ala Glu Pro Gly Leu Leu Pro Gln Ala Val Asp Glu Leu Leu Arg Trp Ile

Pro His Arg Asn Gly Val Gly Leu Pro Arg Ile Ala Thr Glu Asp Val Glu Val Gly Gly Val

Leu Ile Arg Ala Gly Glu Ala Val Tyr Ala Ser Tyr Leu Ala Ala Asn Arg Asp Pro Ala Ala

Phe Glu Asp Pro Asp Arg Leu Asp Phe Asp Arg Glu Gly Ile Gly His Val Ser Phe Gly

His Gly Pro His His Cys Met Gly Ala Met Leu Thr Arg Met Glu Ser Glu Val Met Leu

-continued

Ser Thr Leu Leu Asp Arg Tyr Pro Arg Leu Arg Leu Ala Gly Ser Ala Glu Asp Val Val

Trp Gln Ser Lys Gly Leu Ile Arg Gly Pro Lys Glu Leu Leu Val Thr Trp

The exemplary SEQ ID NO:17 is

```
atggccgcct gccccatct ccccgaaggg caccttcccg aggggttcga cgccaccgac      60
cccgacctgc tgcgcgaacg cgtccccttc ccggagttca cccggctgcg gcagaccgca     120
ccggtgtggt ggtgcccgca gccgcccggc gtcaccggct tcgcggacgg cgggtactgg     180
gccgtcacgc gccacgccga cgtcaagtac gtctccaccc accccgagct gttctcctcg     240
aacgagaaca ccgccgtcat ccgcttcaac gagcacatca cccgggacca gatcgaggtc     300
cagaagctga tcatgctcaa catggacccg cccgagcaca cccgggtccg ccagatcgtc     360
cagcgcggct tcacccccg cgcgatccgc agcctggaaa ccgccctgcg cgaccgggcc      420
cacgccatcg tcgacgaggc ccggcgcggc gcggacgccg acggcacctt cgacttcgtc     480
acccgggtcg ccgtcgaact gccctccag gccatcgccg aactcatcgg cgtcccccag      540
gaggaccgct cccggatctt cgactggtcg aacaagatgg tcgcgtacga cgaccccgaa     600
tacgccatca ccgaggagat cggcgccgag ccgccatgg aactcatcgg ctactcgatg      660
aacatggccg ccgcccgcaa ggagtgcccc gccgccgaca tcgtcagcca gctcgtcgcc     720
gccgagggcc agggcaacct ctcctccgac gagttcggct tcttcgtgct gctgctcgcc     780
gtcgccggga acgagaccac ccgcaacgcc atcagccacg gcatgcacgc cttcctcacc     840
caccccgacg agtgggagct cttcaagcgc gagcggcccg cgaccgccgc cgaggagatc     900
gtccgctggg ccaccccgt cgtctccttc cagcggaccg cgacccagga caccgaactc      960
ggcggacaga gatcaccaa gggcgaccgc gtcggcctct tctactcctc cgccaacaac     1020
gaccccgagg tcttcaccga ccccgaacgc ttcgacatca cccgcgaccc caaccccccac    1080
ctcggcttcg gcggcggcgg ccccacttc tgcctcggca gtccctcgc catcaaggag      1140
atcgagctga tcttcaacgc gatcgcggac gccctgcccg acctcaccct cgcgggcgaa     1200
ccgcgccgac tgcgggccgc ctggctgaac ggcgtcaagg aactccgggt ccgcgcctcc     1260
gcgtga                                                                1266
```

Thus, an exemplary amplification primer sequence pair is residues 1 to 21 of SEQ ID NO:17 and the complementary strand of the last 21 residues of SEQ ID NO:17.

The exemplary SEQ ID NO:17 encodes a polypeptide having the sequence

Met Ala Ala Cys Pro His Leu Pro Glu Gly His Leu Pro Glu Gly Phe Asp Ala Thr Asp (SEQ ID NO:18)

Pro Asp Leu Leu Arg Glu Arg Val Pro Phe Pro Glu Phe Thr Arg Leu Arg Gln Thr Ala

Pro Val Trp Trp Cys Pro Gln Pro Pro Gly Val Thr Gly Phe Ala Asp Gly Gly Tyr Trp Ala

Val Thr Arg His Ala Asp Val Lys Tyr Val Ser Thr His Pro Glu Leu Phe Ser Ser Asn Glu

Asn Thr Ala Val Ile Arg Phe Asn Glu His Ile Thr Arg Asp Gln Ile Glu Val Gln Lys Leu

Ile Met Leu Asn Met Asp Pro Pro Glu His Thr Arg Val Arg Gln Ile Val Gln Arg Gly Phe

Thr Pro Arg Ala Ile Arg Ser Leu Glu Thr Ala Leu Arg Asp Arg Ala His Ala Ile Val Asp

Glu Ala Arg Arg Gly Ala Asp Ala Asp Gly Thr Phe Asp Phe Val Thr Arg Val Ala Val

Glu Leu Pro Leu Gln Ala Ile Ala Glu Leu Ile Gly Val Pro Gln Glu Asp Arg Ser Arg Ile

Phe Asp Trp Ser Asn Lys Met Val Ala Tyr Asp Asp Pro Glu Tyr Ala Ile Thr Glu Glu Ile

-continued

Gly Ala Glu Ala Ala Met Glu Leu Ile Gly Tyr Ser Met Asn Met Ala Ala Ala Arg Lys

Glu Cys Pro Ala Ala Asp Ile Val Ser Gln Leu Vat Ala Ala Glu Gly Gln Gly Asn Leu Ser

Ser Asp Glu Phe Gly Phe Phe Val Leu Leu Leu Ala Val Ala Gly Asn Glu Thr Thr Arg

Asn Ala Ile Ser His Gly Met His Ala Phe Leu Thr His Pro Asp Glu Trp Glu Leu Phe Lys

Arg Glu Arg Pro Ala Thr Ala Ala Glu Glu Ile Val Arg Trp Ala Thr Pro Vat Val Ser Phe

Gln Arg Thr Ala Thr Gln Asp Thr Glu Leu Gly Gly Gln Lys Ile Thr Lys Gly Asp Arg

Val Gly Leu Phe Tyr Ser Ser Ala Asn Asn Asp Pro Glu Val Phe Thr Asp Pro Glu Arg

Phe Asp Ile Thr Arg Asp Pro Asn Pro His Leu Gly Phe Gly Gly Gly Pro His Phe Cys

Leu Gly Lys Ser Leu Ala Ile Lys Glu Ile Glu Leu Ile Phe Asn Ala Ile Ala Asp Ala Leu

Pro Asp Leu Thr Leu Ala Gly Glu Pro Arg Arg Leu Arg Ala Ala Trp Leu Asn Gly Val

Lys Glu Leu Arg Val Arg Ala Ser Ala

The exemplary SEQ ID NO:19 is

| | |
|---|---|
| gtgagcacca ccccgaacc cgcctcctgc cccgtgtcgt ccccgctcc cgagctcttc | 60 |
| acctgggagt tcgcgagcga tccgtatccc gcgtacgcct ggctgcggga gcacgcgccc | 120 |
| gtgcaccgga cgacgctgcc cagcggggtc gaggcgtggc tggtgacgcg gtacggggac | 180 |
| gcccggcagg cgctggccga ccagcggctc tccaagaacc cggcgcacca cgacgagtcc | 240 |
| ccgcacgcca agggcaagac gggcattccg ggcgagcgca aggccgagct gatgacgcat | 300 |
| ctgctcaaca tcgacccgcc ggaccacacc cggctgcggc ggctcgtctc gaaggccttc | 360 |
| accccgcgcc gggtcgccga gttcacgccg cgggtgcagg agctgaccga ccggctgatc | 420 |
| gacgccttcg tgacgaaggg gagcgcggac ctcatccacg acttcgcctt cccgctgccc | 480 |
| atctacgcga tctgcgacct gctcggcgtg cccgaggagg accaggacga cttccgggac | 540 |
| tgggccggga tgatgatccg gcacggcggc gggccgcgcg gcggggtcgc gcggtcggtg | 600 |
| aagaagatgc gcggctatct cgccgagctg atccaccgca agcgcgaagc gcccggggac | 660 |
| gacctcatct cggggctcat caaggcctcc gaccacgggg agacctcac cgagaacgag | 720 |
| gcggccgcca tggccttcat cctgctcttc gccggcttcg agaccaccgt caacctcatc | 780 |
| ggcaacggcg tgtaccagct gctgcgccac cccgggcagc gcgagcggct gcagacctcg | 840 |
| ctcgcggccg gcgagaccgg gctcctggag accgggatcg aggagctgct gcggtacgac | 900 |
| gggccggtgg agatggccac ctggcggtac gcgaccgagc cgctgaccct cggcgggcag | 960 |
| gacatcccgc ggggcgaccc ggtgctcgtg gtcctcgcgg ccgccgaccg ggaccggag | 1020 |
| cggttcgacc ggccggacgt gctcgacctc gcccggcgcg acaaccagca cctggggtac | 1080 |
| gggcacggca tccactactg cctgggcgcg ccgctcgcgc ggctcgaagg gcagaccgcg | 1140 |
| ctcgcgaccc tgctgactcg gcttccggac ctgcgacttg ccgccgatcc ggccgaactg | 1200 |
| cggtggcgcg gcgggctcat catgcggggt ttgcgcacgc ttccggtgga gttctcccct | 1260 |
| tccgtacggg tccactga | 1278 |

Thus, an exemplary amplification primer sequence pair is residues 1 to 21 of SEQ ID NO:19 and the complementary strand of the last 21 residues of SEQ ID NO:19.

The exemplary SEQ ID NO:19 encodes a polypeptide having the sequence

Met Ser Thr Thr Pro Glu Pro Ala Ser Cys Pro Val Ser Ser Pro Ala Pro Glu Leu Phe Thr   (SEQ ID NO:20)
Trp Glu Phe Ala Ser Asp Pro Tyr Pro Ala Tyr Ala Trp Leu Arg Glu His Ala Pro Val His
Arg Thr Thr Leu Pro Ser Gly Val Glu Ala Trp Leu Val Thr Arg Tyr Gly Asp Ala Arg
Gln Ala Leu Ala Asp Gln Arg Leu Ser Lys Asn Pro Ala His His Asp Glu Ser Pro His Ala
Lys Gly Lys Thr Gly Ile Pro Gly Glu Arg Lys Ala Glu Leu Met Thr His Leu Leu Asn Ile
Asp Pro Pro Asp His Thr Arg Leu Arg Arg Leu Val Ser Lys Ala Phe Thr Pro Arg Arg
Val Ala Glu Phe Thr Pro Arg Val Gln Glu Leu Thr Asp Arg Leu Ile Asp Ala Phe Val Thr
Lys Gly Ser Ala Asp Leu Ile His Asp Phe Ala Phe Pro Leu Pro Ile Tyr Ala Ile Cys Asp
Leu Leu Gly Val Pro Glu Glu Asp Gln Asp Asp Phe Arg Asp Trp Ala Gly Met Met Ile
Arg His Gly Gly Gly Pro Arg Gly Gly Val Ala Arg Ser Val Lys Lys Met Arg Gly Tyr
Leu Ala Glu Leu Ile His Arg Lys Arg Glu Ala Pro Gly Asp Asp Leu Ile Ser Gly Leu Ile
Lys Ala Ser Asp His Gly Glu His Leu Thr Glu Asn Glu Ala Ala Met Ala Phe Ile Leu
Leu Phe Ala Gly Phe Glu Thr Thr Val Asn Leu Ile Gly Asn Gly Val Tyr Gln Leu Leu
Arg His Pro Gly Gln Arg Glu Arg Leu Gln Thr Ser Leu Ala Ala Gly Glu Thr Gly Leu
Leu Glu Thr Gly Ile Glu Glu Leu Leu Arg Tyr Asp Gly Pro Val Glu Met Ala Thr Trp
Arg Tyr Ala Thr Glu Pro Leu Thr Leu Gly Gly Gln Asp Ile Pro Ala Gly Asp Pro Val Leu
Val Val Leu Ala Ala Ala Asp Arg Asp Pro Glu Arg Phe Asp Arg Pro Asp Val Leu Asp
Leu Ala Arg Arg Asp Asn Gln His Leu Gly Tyr Gly His Gly Ile His Tyr Cys Leu Gly
Ala Pro Leu Ala Arg Leu Glu Gly Gln Thr Ala Leu Ala Thr Leu Leu Thr Arg Leu Pro
Asp Leu Arg Leu Ala Ala Asp Pro Ala Glu Leu Arg Trp Arg Gly Gly Leu Ile Met Arg
Gly Leu Arg Thr Leu Pro Val Glu Phe Ser Pro Ser Val Arg Val His

The exemplary SEQ ID NO:21 is

| | |
|---|---|
| atgtacacca ttcccctac gccacagttc gacaacgaac ttgtcgatcc ggcgacctgg | 60 |
| gccgacgagg ccagaatcca tgcctacctg gcctggctgc gggagcacga cccggtgcgc | 120 |
| cggctcgagc ctgagggcta cgagcccttc tacgccatca cgaagcatgc cgacctgatg | 180 |
| gccatcgaac gcgacaagca ggtgttcatc aacgacccgc gccctaccct ggcgccggaa | 240 |
| gcggtcaccg cggcgatcga gcaactcacc gggcgccggc acctggtccg gtcgctggtg | 300 |
| cagatggacg agccggacca catgaagtac cggatgctca ccgcgtcctt cttcacccgt | 360 |
| cagaagctcg cggcgatgaa gccggaggtg gagcgtctcg cggcgcacta tgtggatcgg | 420 |
| atggcggagt tcggcggcga atgcgacttc gttcgggacg tggcggtctg gtaccgctg | 480 |
| cgggtggtga tgagtgcgct cggcgttccg ccggaggacg agccgctgat gatgaagctg | 540 |
| acccaggagt tgttcggatc cagcgacccc gaggtccagc ggtccttcga catcatggcg | 600 |
| atcggcgacg tggtacggga cttcgaggcg tacttcaccg gcatctcgga agatcgccgg | 660 |
| cgcaatcccc gtgacgacat cgccacgctc attgcccacg ccaaaatcga cggggaaccc | 720 |
| attggtgacc tggaggcggc aggctattac atcatcatcg ccaccgccgg ccacgacacc | 780 |
| acctcctcga gtacgccgg cgggctgctc gcgctgatgg agaaccccga ggagttccag | 840 |
| aaactgcgcg gcgacacgga tcggcatgtg gccggcgcgg tcgacgaaat gattcgctgg | 900 |

-continued

```
gtatccccag tgcgtcactt catgcgcacc gccaccgagg actacgcaat ccgcggcaag        960
accatcgcca agggcgaatc ggtgatcctg tggtatccgt cggcgaaccg cgatgccgag       1020
gtgttcaacg acccgttcgc gttccgcgtc gagcggccgg cggcgcgcaa tttggccttc       1080
ggctacggcg ctcacgtctg tctcggtcaa catctggcgc ggatggaaat gcagacgttc       1140
taccgcgaac tgctgtcgcg ggtggggcac gtagagctgg cgggcgagcc ccgctacgcc       1200
caggctgcct tcgtcggcgg actcaagagc ctgccgattc gctaccgcat gaagtga          1257
```

Thus, an exemplary amplification primer sequence pair is residues 1 to 21 of SEQ ID NO:21 and the complementary strand of the last 21 residues of SEQ ID NO:21.

```
The exemplary SEQ ID NO:21 encodes a polypeptide having the sequence
Met Tyr Thr Ile Pro Pro Thr Pro Gln Phe Asp Asn Glu Leu Val Asp Pro Ala Thr Trp      (SEQ ID NO:22)
Ala Asp Glu Ala Arg Ile His Ala Tyr Leu Ala Trp Leu Arg Glu His Asp Pro Val Arg Arg
Leu Glu Pro Glu Gly Tyr Glu Pro Phe Tyr Ala Ile Thr Lys His Ala Asp Leu Met Ala Ile
Glu Arg Asp Lys Gln Val Phe Ile Asn Asp Pro Arg Pro Thr Leu Ala Pro Glu Ala Val Thr
Ala Ala Ile Glu Gln Leu Thr Gly Arg Arg His Leu Val Arg Ser Leu Val Gln Met Asp
Glu Pro Asp His Met Lys Tyr Arg Met Leu Thr Ala Ser Phe Phe Thr Arg Gln Lys Leu
Ala Aia Met Lys Pro Glu Val Glu Arg Leu Ala Ala His Tyr Val Asp Arg Met Ala Glu
Phe Gly Gly Glu Cys Asp Phe Val Arg Asp Val Ala Val Trp Tyr Pro Leu Arg Val Val
Met Ser Ala Leu Gly Val Pro Pro Glu Asp Glu Pro Leu Met Met Lys Leu Thr Gln Glu
Leu Phe Gly Ser Ser Asp Pro Glu Val Gln Arg Ser Phe Asp Ile Met Ala Ile Gly Asp Val
Val Arg Asp Phe Glu Ala Tyr Phe Thr Gly Ile Ser Glu Asp Arg Arg Arg Asn Pro Arg
Asp Asp Ile Ala Thr Leu Ile Ala His Ala Lys Ile Asp Gly Glu Pro Ile Gly Asp Leu Glu
Ala Ala Gly Tyr Tyr Ile Ile Ile Ala Thr Ala Gly His Asp Thr Thr Ser Ser Ser Thr Ala Gly
Gly Leu Leu Ala Leu Met Glu Asn Pro Glu Glu Phe Gln Lys Leu Arg Gly Asp Thr Asp
Arg His Val Ala Gly Ala Val Asp Glu Met Ile Arg Trp Val Ser Pro Val Arg His Phe Met
Arg Thr Ala Thr Glu Asp Tyr Ala Ile Arg Gly Lys Thr Ile Ala Lys Gly Glu Ser Val Ile
Leu Trp Tyr Pro Ser Ala Asn Arg Asp Ala Glu Val Phe Asn Asp Pro Phe Ala Phe Arg
Val Glu Arg Pro Ala Ala Arg Asn Leu Ala Phe Gly Tyr Gly Ala His Val Cys Leu Gly
Gln His Leu Ala Arg Met Glu Met Gln Thr Phe Tyr Arg Glu Leu Leu Ser Arg Val Gly
His Val Glu Leu Ala Gly Glu Pro Arg Tyr Ala Gln Ala Ala Phe Val Gly Gly Leu Lys Ser
Leu Pro Ile Arg Tyr Arg Met Lys
The exemplary SEQ ID NO:23 is
atggcgtcca ccaacagatt gagcccgatc ccgcatccgc cgactaaacc ggtggtcggc         60
aacatgctgt cgctggactc gacggcgccg gtgcagaacc tggcacggct ggcgaaggaa       120
ctggggccga tcttctggtt ggacatgatg ggggcgccga tcgtcatcgt ctccggccac       180
gatctcgtgg aagagctcag cgacgagaaa cgtttcgaca aggcggtacg cggggcgctg       240
cgccgcgtac gtgcggtcgg cggcgacggg ctgttcaccg ccgatacgtc ggagccgaac       300
tggagcaagg cgcataacat cctgctgcag ccgttcggca accgcgccat gcagtcctac       360
cacccgagca tggtcgatat cgccgaacag ctcgtgaaga aatgggagcg gctgaacgtc       420
```

-continued

```
gacgacgaga tcgacgtcgt tcatgatatg accgcattga cgctcgacac catcggactg        480
tgcgggttcg attaccgctt caattcattt taccggcgtg attaccatcc gttcgtcgcg        540
tcgttggtcc gttcgctcga aaccatcatg atgatccgcg gcctgccgtt ggaaaatctg        600
tggatgcaga agcgtcggcg cgacctcgcc gccgacgttg gcttcatgaa caaaatggtc        660
gacgagatca ttgccgagcg gcgcaggagc gctgaagccg agggcaagaa agacatgctc        720
ggcgcaatga tgaccggcgt cgaccgcacc accggtgaac agcttgatga cgtcaacatc        780
cgctatcaga tcaacacgtt tctgatcgcg gggcatgaaa ccaccagcgg cctgttgtcg        840
tgcacgctgt atgcgttgtt gaagcatcct gaaattctca ggaaggccta cgaggaagtc        900
gaccgggtgc tcgggcccga tatcaacgcc aggccgacct atcagcaggt gacacagctc        960
acgtacatca cgcagattct gaaggaggcg ctgcggttgt ggccgccggc gccggcctat       1020
ggcatctcgc cgctcaagga cgagaccatc ggcggcaagt acaaattaaa gaagaacacg       1080
ttcatccacg tattggtgct ggcactgcac cgcgatcgca gcgtgtgggg atccaatccc       1140
gatgcgttcg atccggaaaa tttcagccgc gaggccgagg cggcgcggcc catcaacgcc       1200
tggaagccgt tcggcaacgg tcagcgcgcc tgcatcggcc gtggctttgc gatgcatgaa       1260
gcggcgcttg cgatcggtat gatcctgcaa cgcttcaagc tggtcgacgt caaccgttac       1320
cagatggtgt tgaaggagac gctgacgatc aagcctgacg gcttcaagat caaggtgcgg       1380
ccgcgggccg aacgggatcg cggcgcttac ggcggcgcgg catctgtagc gatggccccg       1440
aacacgccga cggcgcccca cgagcgaacg cgtctgggc acaacacgcc gctgttggtg        1500
ctttatggat cgaacctcgg caccgcggaa gaactcgcga cccgcgttgc cgatctcgcc       1560
gaagtcaacg gctttgccac caaactggcc ccgctcgatg atttcgtcgg caagctgccg       1620
gagcaaggcg gcgttctgat tttctgtgcg tcctacaatg gtgtaccgcc cgacaacgcc       1680
acgcagttcg tcaaatggct tggcggcgat atcccaaagg atagttttgc caaggtgcgt       1740
tacgcggtgt tcggctgcgg caacagcgac tgggccgcga cctatcagtc agtgccgcgc       1800
ctgatcgacg agcaattggc ggcgcacggc gcgcgcagcg tttatacgcg aggcgagggc       1860
gacgcccgca gcgatcttga cgggcaattc gagagctggt ttgcagccgc agctccggcg       1920
gcaaccaggg agtttggtct cgagtcgaat ttcagccgca cgctgatga tgcgccgctc        1980
tacacgatcg aaccggtggc accatcagtg gtcaatacga tcgtcaccca gggcggcgtc       2040
ttgccgatga aggtagtggc caactgaa ctgcaaaaaca agctgggcac caatccctct        2100
gatcgttcga cccggcatgt cgaggtgcag ctacctccag gcatcagcta tcgtgtcggc       2160
gatcatctca gcgtcgtgcc gcgcaatgat ccggcgctgg tcgatgccgt cgcgcgccgc       2220
ttcggctttc tgccggccga ccagatccgg ttgcaggtcg ccgaaggccg ccgtgcgcaa       2280
ctgccggtcg gcgacgccgt ttcggtcggg cggctgttga ccgagttcgt cgagttgcag       2340
caggtcgcga cccgcaagca aatccagatc ttgtcggaac acacgcgttg tccgatgacc       2400
aagcccaaac tggtgggcct ggccggagac gacgcagctt ccgcggaacg ctaccgcgcc       2460
gaggtgctcg gcaagcgcaa atcggtgttc gacctgctgg aggaacatcc ggcctgcgaa       2520
ttgccgttcc acgcgtttct ggaaatgctg tcgctgctgg cgccgcgcta ttattcgatc       2580
tcgtcgtcgc cggcgggcga gcccgcgcgt tgcagcgtta ccgcggccgt ggtcgcatcg       2640
cctgcgagtt cgggacgcgg tatctaccgg ggcgtcgtt cgaactatct tgccgggcgc        2700
cgcgcaggtg acaccatcca cgccaccgtg cgcgaaacca aggccggctt ccggctgccg       2760
aatgatccgt ccgtgccgat catcatgatc ggccccggca cgggtctggc gccgtttcgt       2820
```

-continued

```
ggtttcctgc aggagcgtgc cgcgttgcag gcaaagggcg ctacgcttgg tccggcgatg    2880
ctgtttttcg gctgccgtca ccccgaacag gattatctct atgccgatga actaaaggcg    2940 acgccgccg acgggattac cgagttgcac accgcgttct cgcgcggcga cggaccgaag     3000
acgtatgtgc agcatctgat cgtggccgag aaggatcggg tctgcagcct gatcgagcaa    3060
ggcgcgatca tctacgtttg tggcgacggc ggacggatgg aaccggacgt gaaagccacg    3120
cttgtcggga tctatcgcga acgctccggc gccgatgccg gcactgcgca gcgctggatc    3180
gaagacctcg gcgccaaaaa ccgctacgtc ctcgacgtct gggcaggtgg ataa           3234
```

Thus, an exemplary amplification primer sequence pair is residues 1 to 21 of SEQ ID NO:23 and the complementary strand of the last 21 residues of SEQ ID NO:23.

```
The exemplary SEQ ID NO:23 encodes a polypeptide having the sequence
Met Ala Ser Thr Asn Arg Leu Ser Pro Ile Pro His Pro Pro Thr Lys Pro Val Val Gly Asn      (SEQ ID NO:24)
Met Leu Ser Leu Asp Ser Thr Ala Pro Val Gln Asn Leu Ala Arg Leu Ala Lys Glu Leu
Gly Pro Ile Phe Trp Leu Asp Met Met Gly Ala Pro Ile Val Ile Val Ser Gly His Asp Leu
Val Glu Glu Leu Ser Asp Glu Lys Arg Phe Asp Lys Ala Val Arg Gly Ala Leu Arg Arg
Val Arg Ala Val Gly Gly Asp Gly Leu Phe Thr Ala Asp Thr Ser Glu Pro Asn Trp Ser
Lys Ala His Asn Ile Leu Leu Gln Pro Phe Gly Asn Arg Ala Met Gln Ser Tyr His Pro Ser
Met Val Asp Ile Ala Glu Gln Leu Val Lys Lys Trp Glu Arg Leu Asn Val Asp Asp Glu
Ile Asp Val Val His Asp Met Thr Ala Leu Thr Leu Asp Thr Ile Gly Leu Cys Gly Phe Asp
Tyr Arg Phe Asn Ser Phe Tyr Arg Arg Asp Tyr His Pro Phe Val Ala Ser Leu Val Arg Ser
Leu Glu Thr Ile Met Met Ile Arg Gly Leu Pro Leu Glu Asn Leu Trp Met Gln Lys Arg
Arg Arg Asp Leu Ala Ala Asp Val Gly Phe Met Asn Lys Met Val Asp Glu Ile Ile Ala
Glu Arg Arg Arg Ser Ala Glu Ala Glu Gly Lys Lys Asp Met Leu Gly Ala Met Met Thr
Gly Val Asp Arg Thr Thr Gly Glu Gln Leu Asp Asp Val Asn Ile Arg Tyr Gln Ile Asn Thr
Phe Leu Ile Ala Gly His Glu Thr Thr Ser Gly Leu Leu Ser Cys Thr Leu Tyr Ala Leu Leu
Lys His Pro Glu Ile Leu Arg Lys Ala Tyr Glu Glu Val Asp Arg Val Leu Gly Pro Asp Ile
Asn Ala Arg Pro Thr Tyr Gln Gln Val Thr Gln Leu Thr Tyr Ile Thr Gln Ile Leu Lys Glu
Ala Leu Arg Leu Trp Pro Pro Ala Pro Ala Tyr Gly Ile Ser Pro Leu Lys Asp Glu Thr Ile
Gly Gly Lys Tyr Lys Leu Lys Lys Asn Thr Phe Ile Thr Val Leu Val Leu Ala Leu His Arg
Asp Arg Ser Val Trp Gly Ser Asn Pro Asp Ala Phe Asp Pro Glu Asn Phe Ser Arg Glu
Ala Glu Ala Ala Arg Pro Ile Asn Ala Trp Lys Pro Phe Gly Asn Gly Gln Arg Ala Cys Ile
Gly Arg Gly Phe Ala Met His Glu Ala Ala Leu Ala Ile Gly Met Ile Leu Gln Arg Phe Lys
Leu Val Asp Val Asn Arg Tyr Gln Met Val Leu Lys Glu Thr Leu Thr Ile Lys Pro Asp
Gly Phe Lys Ile Lys Val Arg Pro Arg Ala Glu Arg Asp Arg Gly Ala Tyr Gly Gly Ala Ala
Ser Val Ala Met Ala Pro Asn Thr Pro Thr Ala Pro His Glu Arg Thr Arg Leu Gly His Asn
Thr Pro Leu Leu Val Leu Tyr Gly Ser Asn Leu Gly Thr Ala Glu Glu Leu Ala Thr Arg
Val Ala Asp Leu Ala Glu Val Asn Gly Phe Ala Thr Lys Leu Ala Pro Leu Asp Asp Phe
Val Gly Lys Leu Pro Glu Gln Gly Gly Val Leu Ile Phe Cys Ala Ser Tyr Asn Gly Val Pro
Pro Asp Asn Ala Thr Gln Phe Val Lys Trp Leu Gly Gly Asp Ile Pro Lys Asp Ser Phe Ala
```

-continued

Lys Val Arg Tyr Ala Val Phe Gly Cys Gly Asn Ser Asp Trp Ala Ala Thr Tyr Gln Ser Val

Pro Arg Leu Ile Asp Glu Gln Leu Ala Ala His Gly Ala Arg Ser Val Tyr Thr Arg Gly Glu

Gly Asp Ala Arg Ser Asp Leu Asp Gly Gln Phe Glu Ser Trp Phe Ala Ala Ala Ala Pro

Ala Ala Thr Arg Glu Phe Gly Leu Glu Ser Asn Phe Ser Arg Ser Ala Asp Asp Ala Pro

Leu Tyr Thr Ile Glu Pro Val Ala Pro Ser Val Val Asn Thr Ile Val Thr Gln Gly Gly Val

Leu Pro Met Lys Val Val Ala Asn Ser Glu Leu Gln Asn Lys Leu Gly Thr Asn Pro Ser

Asp Arg Ser Thr Arg His Val Glu Val Gln Leu Pro Pro Gly Ile Ser Tyr Arg Val Gly Asp

His Leu Ser Val Val Pro Arg Asn Asp Pro Ala Leu Val Asp Ala Val Ala Arg Arg Phe

Gly Phe Leu Pro Ala Asp Gln Ile Arg Leu Gln Val Ala Glu Gly Arg Arg Ala Gln Leu

Pro Val Gly Asp Ala Val Ser Val Gly Arg Leu Leu Thr Glu Phe Val Glu Leu Gln Gln

Val Ala Thr Arg Lys Gln Ile Gln Ile Leu Ser Glu His Thr Arg Cys Pro Met Thr Lys Pro

Lys Leu Val Gly Leu Ala Gly Asp Asp Ala Ala Ser Ala Glu Arg Tyr Arg Ala Glu Val

Leu Gly Lys Arg Lys Ser Val Phe Asp Leu Leu Glu Glu His Pro Ala Cys Glu Leu Pro

Phe His Ala Phe Leu Glu Met Leu Ser Leu Leu Ala Pro Arg Tyr Tyr Ser Ile Ser Ser Ser

Pro Ala Gly Glu Pro Ala Arg Cys Ser Val Thr Ala Ala Val Val Ala Ser Pro Ala Ser Ser

Gly Arg Gly Ile Tyr Arg Gly Val Cys Ser Asn Tyr Leu Ala Gly Arg Arg Ala Gly Asp

Thr Ile His Ala Thr Val Arg Glu Thr Lys Ala Gly Phe Arg Leu Pro Asn Asp Pro Ser Val

Pro Ile Ile Met Ile Gly Pro Gly Thr Gly Leu Ala Pro Phe Arg Gly Phe Leu Gln Glu Arg

Ala Ala Leu Gln Ala Lys Gly Ala Thr Leu Gly Pro Ala Met Leu Phe Phe Gly Cys Arg

His Pro Glu Gln Asp Tyr Leu Tyr Ala Asp Glu Leu Lys Ala Phe Ala Ala Asp Gly Ile Thr

Glu Leu His Thr Ala Phe Ser Arg Gly Asp Gly Pro Lys Thr Tyr Val Gln His Leu Ile Val

Ala Glu Lys Asp Arg Val Cys Ser Leu Ile Glu Gln Gly Ala Ile Ile Tyr Val Cys Gly Asp

Gly Gly Arg Met Glu Pro Asp Val Lys Ala Thr Leu Val Gly Ile Tyr Arg Glu Arg Ser Gly

Ala Asp Ala Gly Thr Ala Gln Arg Trp Ile Glu Asp Leu Gly Ala Lys Asn Arg Tyr Val

Leu Asp Val Trp Ala Gly Gly

The exemplary SEQ ID NO:25 is

```
gtgaacgcac cgaagagcac cgcccccggc cgccgcgcgc cccaccgcct cgaccccacc        60
ggccccctgcc cgcacgccgt caacgcccgc ctcctcgcgg agggcgccgt caccccgta       120
ctcctccccg gcgacatcga cggcatggcc gtcctcggcc acgacgccct ccgtgacttc       180
ctctcccacc ccgacgtcgc caagggcccc cagcacttca ccgccctctc cgagggccga       240
ataccccgacg gctggcccct gcgcaccttc gccaccctcc cgggcatgat gaccgccgac       300
ggcgccgacc accgccgtct gcgcgccctg gtgagcagcg ccttcaccgc ccgccgggtg       360
gaggaactgc gcccccgcgt cgcgacggtc gccgccggac tcctcgacgg actcgccgag       420
gccgccgaac ggggcgacgg cgtcgcggac ctccgccgcc actacgccct cccgctgccg       480
ctcggcgtca tctgcgaact cctcggcgtc gaccgggccc accaggaccg gctgcacgag       540
ctctccgcgc tggtcgtcgc gaccgacatc gggcccgacc gcgccgtcgc cgtcaaccgc       600
gagctcctcg aactcctcac cgccatcgcc gccgccaagg ccgccgatcc gcgcgacgac       660
ctcaccagcg cgctcatcgc ggcccgcgac gaggacggcg accggctcgg cccgcacgag       720
ctgatcggca ccctgctcct gctgatcgtc gccggccacg agaccaccct gaacctggtg       780
accaacgccg tgcgggcgct ctgctcccac cgcgaccaac tcgccctggt cctcgacggc       840
```

-continued

```
cgggcgagct ggtcggacgt ggtggaggag acgctccgct gggacagccc ggtcagctac        900
ttcccgttcc gctatcccac ccgggaccct accgtcgacg gcaccctcat ccccgggc          960 accccgtcc tcgccggcta tgcggcggcg ggccgggaca ccaaggccca cggcccggac        1020
gccgaccgct tcgacctcac gcgtacggcg acggtgaagc acctgtcact cggccacggc      1080
ccgcactact gcctgggcgc cccgctcgcc cggatggagg cggccgtcgc cctggagacg      1140
ctgttcaccc gcttccccgg cctggacctg gccgtcccgg agtccgagtt gccccggcac      1200
tccgggttcg tcggcaacag cgtccggacg ctcccggtcc ggcccggcgg ctga            1254
```

Thus, an exemplary amplification primer sequence pair is residues 1 to 21 of SEQ ID NO:25 and the complementary strand of the last 21 residues of SEQ ID NO:25.

```
The exemplary SEQ ID NO:25 encodes a polypeptide having the sequence

Met Asn Ala Pro Lys Ser Thr Ala Pro Gly Arg Arg Ala Pro His Arg Leu Asp Pro Thr    (SEQ ID NO:26)

Gly Pro Cys Pro His Ala Val Asn Ala Arg Leu Leu Ala Glu Gly Ala Val Thr Pro Val Leu

Leu Pro Gly Asp Ile Asp Gly Met Ala Val Leu Gly His Asp Ala Leu Arg Asp Phe Leu

Ser His Pro Asp Val Ala Lys Gly Pro Gln His Phe Thr Ala Leu Ser Glu Gly Arg Ile Pro

Asp Gly Trp Pro Leu Arg Thr Phe Ala Thr Leu Pro Gly Met Met Thr Ala Asp Gly Ala

Asp His Arg Arg Leu Arg Ala Leu Val Ser Ser Ala Phe Thr Ala Arg Arg Val Glu Glu

Leu Arg Pro Arg Val Ala Thr Val Ala Ala Gly Leu Leu Asp Gly Leu Ala Glu Ala Ala

Glu Arg Gly Asp Gly Val Ala Asp Leu Arg Arg His Tyr Ala Leu Pro Leu Pro Leu Gly

Val Ile Cys Glu Leu Leu Gly Val Asp Arg Ala His Gln Asp Arg Leu His Glu Leu Ser

Ala Leu Val Val Ala Thr Asp Ile Gly Pro Asp Arg Ala Val Ala Val Asn Arg Glu Leu

Leu Glu Leu Leu Thr Ala Ile Ala Ala Ala Lys Ala Ala Asp Pro Arg Asp Asp Leu Thr Ser

Ala Leu Ile Ala Ala Arg Asp Glu Asp Gly Asp Arg Leu Gly Pro His Glu Leu Ile Gly Thr

Leu Leu Leu Leu Ile Val Ala Gly His Glu Thr Thr Leu Asn Leu Val Thr Asn Ala Val

Arg Ala Leu Cys Ser His Arg Asp Gln Leu Ala Leu Val Leu Asp Gly Arg Ala Ser Trp

Ser Asp Val Val Glu Glu Thr Leu Arg Trp Asp Ser Pro Val Ser Tyr Phe Pro Phe Arg Tyr

Pro Thr Arg Asp Leu Thr Val Asp Gly Thr Leu Ile Pro Arg Gly Thr Pro Val Leu Ala Gly

Tyr Ala Ala Ala Gly Arg Asp Thr Lys Ala His Gly Pro Asp Ala Asp Arg Phe Asp Leu

Thr Arg Thr Ala Thr Val Lys His Leu Ser Leu Gly His Gly Pro His Tyr Cys Leu Gly Ala

Pro Leu Ala Arg Met Glu Ala Ala Val Ala Leu Glu Thr Leu Phe Thr Arg Phe Pro Gly

Leu Asp Leu Ala Val Pro Glu Ser Glu Leu Pro Arg His Ser Gly Phe Val Gly Asn Ser Val

Arg Thr Leu Pro Val Arg Pro Gly Gly

The exemplary SEQ ID NO:27 is atggacgccg ctgctgaccc cgtgtacgac ccctggtccc ccgagttcgt cgccgatccc         60
taccccgcct acgccgggct gcgcgcggcc ggccgcgcgc actggcacgg gccgacgcgg       120
cagtggctga tcccgcacca cgaggacgtg tcggcactgc tcagggaccg gcggctcggc       180
cgtacgtaca cccatcgctt cacgcacgag gagttcgggc aggaggcccc ggacgccgcg       240
tacgagccgt tccacacgct caacgaccac gggctgctcg acctggaggg cgccgaccac       300
agccgcatcc ggcggctggt gtcgaaggcg ttcacccccga ggaccgtgga ggacctggcg      360
```

```
                                                      -continued
ccgaccgtac ggcggctggc cgccgacctg gtcggcggtc tggtcgcggc cggcggcggc          420
gacctccagg cggcggtggc ggaacccctg ccggtcgcgg tgatcgccga gatgctgggc          480
gtccccgagg gcgacgagga gcgggcgcgg ctgcgcccct ggtcggcggc gatctgcggg          540
atgutcgagc tgaatcccic ggaggagacg gcgcggcggg cggtggcggc ctctgtggag          600
ttctccggct atctgcggga gctgatcgcc cggcggcgca aggagccggg ggacgatctg          660
atctcgtcgc tgatcgcggt ggaggagctg accgagcagg agatgatctc cacctgtgtg          720
ctcctcctga acgcgggtca cgaggcgacc gtgaacacca cggtcaacgg ctggtggacg          780
ctgctcagag agggcgtccg gcccgatccc gaaaagttgt ccacagctgt ggaagaactt          840
ctgcgctacg acacccgct ccagatgttc gagcggtggg tcctcgacga catcgagatc          900
ggcggccaca cccttccgcg cggctccgag gtggccctgc tcctcggctc cgccaaccgc          960
gaccccgccc gcttcggccc gaccgccgac accctcgacc tcacccgcgc cgacaacccc         1020
cacatcacct cggcgccgg catccactac tgcctcggcg ccccgctcgc ccgtctcgaa          1080
ctgacggcgg tcttcggcga gttgctccgc caggcgccgg gcctccggct cgcggcggag         1140
cccgtacgca agccgggata cgtgatccgc ggcttcgagg agctgctcgt cgagctgtga         1200
```

Thus, an exemplary amplification primer sequence pair is residues 1 to 21 of SEQ ID NO:27 and the complementary strand of the last 21 residues of SEQ ID NO:27.

The exemplary SEQ ID NO:27 encodes a polypeptide having the sequence

Met Asp Ala Ala Ala Asp Pro Val Tyr Asp Pro Trp Ser Pro Glu Phe Val Ala Asp Pro    (SEQ ID NO:28)

Tyr Pro Ala Tyr Ala Gly Leu Arg Ala Ala Gly Arg Ala His Trp His Gly Pro Thr Arg Gln

Trp Leu Ile Pro His His Glu Asp Val Ser Ala Leu Leu Arg Asp Arg Arg Leu Gly Arg Thr

Tyr Thr His Arg Phe Thr His Glu Glu Phe Gly Gln Glu Ala Pro Asp Ala Ala Tyr Glu Pro

Phe His Thr Leu Asn Asp His Gly Leu Leu Asp Leu Glu Gly Ala Asp His Ser Arg Ile

Arg Arg Leu Val Ser Lys Ala Phe Thr Pro Arg Thr Val Glu Asp Leu Ala Pro Thr Val

Arg Arg Leu Ala Ala Asp Leu Val Gly Gly Leu Val Ala Ala Gly Gly Gly Asp Leu Gln

Ala Ala Val Ala Glu Pro Leu Pro Val Ala Val Ile Ala Glu Met Leu Gly Val Pro Glu Gly

Asp Glu Glu Arg Ala Arg Leu Arg Pro Trp Ser Ala Ala Ile Cys Gly Met Phe Glu Leu

Asn Pro Ser Glu Glu Thr Ala Arg Arg Ala Val Ala Ala Ser Val Glu Phe Ser Gly Tyr Leu

Arg Glu Leu Ile Ala Arg Arg Arg Lys Glu Pro Gly Asp Asp Leu Ile Ser Ser Leu Ile Ala

Val Glu Glu Leu Thr Glu Gln Glu Met Ile Ser Thr Cys Val Leu Leu Leu Asn Ala Gly His

Glu Ala Thr Val Asn Thr Thr Val Asn Gly Trp Trp Thr Leu Leu Arg Glu Gly Val Arg

Pro Asp Pro Glu Lys Leu Ser Thr Ala Val Glu Glu Leu Leu Arg Tyr Asp Thr Pro Leu

Gln Met Phe Glu Arg Trp Val Leu Asp Asp Ile Glu Ile Gly Gly His Thr Leu Pro Arg Gly

Ser Glu Val Ala Leu Leu Leu Gly Ser Ala Asn Arg Asp Pro Ala Arg Phe Gly Pro Thr

Ala Asp Thr Leu Asp Leu Thr Arg Ala Asp Asn Pro His Ile Thr Phe Gly Ala Gly Ile His

Tyr Cys Leu Gly Ala Pro Leu Ala Arg Leu Glu Leu Thr Ala Val Phe Gly Glu Leu Leu

Arg Gln Ala Pro Gly Leu Arg Leu Ala Ala Glu Pro Val Arg Lys Pro Gly Tyr Val Ile Arg

Gly Phe Glu Glu Leu Leu Val Glu Leu

-continued

The exemplary SEQ ID NO:29 is

| | |
|---|---|
| atgaccctcc cacccgccga acacaccgcc gagaaggcag gggcggtccc gccccgggc | 60 |
| tgcccggccc acgcctccaa gggacccggc ggagcgaccc ggctctacgg ccccgccgcc | 120 |
| gagacggacc ccatgggcct gtacgaggca ctgcgcgcc aacacggccc ggtcgccccc | 180 |
| gtgctgctcg acggagacgt ccgcgcctgg ctcgtgctcg gctacctgga gaaccgcgac | 240 |
| gtggccagcc gcccgacgca gtactcccgc gacccgcgcg tctggcacgg ctggcggagc | 300 |
| ggcgagatcg accccgccac ctcgcccctc gtcccgatga tcggctggcg tcccgactgc | 360 |
| gtgtgcgccg acggcgagga gcaccagcgg ctgcgcgggg cggtcacggc cgggctcagc | 420 |
| cagttcgacc accggggggt ccgccgccac atcacccgct tcgcgcacca gctgatcgac | 480 |
| acgttctgcg aggacggcga ggtggagctg gtcgggcagt tcaccgagca cctgccgatg | 540 |
| ctcacgctga cccatctgct cggcatgtcg gacgagtccg gccccggct cgtgcacgcc | 600 |
| gcccgtgacc tcttcaaggc caccgagacc tcgctcgcca gcaacgccta cgtgatcgag | 660 |
| tgcctcgaac agctcgtcgt cgccaagcgg tcccggccgg ggcaggacat cgcctccgcg | 720 |
| ctgatggcac accccgccgg gctcaccgac gaggaggtgc tgcaccacct gcgcctcatc | 780 |
| ctcctcgcgg ggtacgagac gaccgccaac ctcatgtcca acgtcctgcg catggtggtc | 840 |
| accgaccccc ggttccgagg atcgctggcc ggcggccaga tgaccctgcc cgaggccgtc | 900 |
| gagcaggtcc tctgggacga gccgccgctg atggtgtgcc ccggccggtg ggccaacggc | 960 |
| gacaccaccc tcggcggccg gcagatcaag gcgggcgaca tgctgctgct cggcctggcc | 1020 |
| gccgggaacg tcgacaaggc gatccgcccg gacgcctcga ccccgtcca ccacaaccgc | 1080 |
| gcccacctgt cgttcagcgc cggcacccac gagtgccccg ccaggacat cggccgcatc | 1140 |
| atcgccgacg ccggcatcga catcctgctc acccggctgc ccgacatcgc cctggccgtc | 1200 |
| cccgaggaga gcctgtcctg gcgctcctcc acctgggccc ggcacctgac ggcgctgccc | 1260 |
| gtgcacttcg cccccgcgt ccccgagggg cacgacgtcc cgaacccgct gcccgccccg | 1320 |
| ccggccccga gcttcgggcc ccgtcggcg ccgctgtggc cgtcgcccgg ccccggaccc | 1380 |
| gcccgcccgt cggatcaggc gccgccgccc ggcccggtgc ccggcggcgg ggccacggga | 1440 |
| ggggcgtccg ggcccgcgtc ggaacacggc cccggacccc gcgccacctg cgtacgagg | 1500 |
| gtcatgcgct tcctgcggag gcggtag | 1527 |

Thus, an exemplary amplification primer sequence pair is residues1 to 21 of SEQ ID NO:29 and the complementary strand of the last 21 residues of SEQ ID NO:29.

The exemplary SEQ ID NO:29 encodes a polypeptide having the sequence

Met Thr Leu Pro Pro Ala Glu His Thr Ala Glu Lys Ala Gly Ala Val Pro Pro Gly    (SEQ ID NO:30)

Cys Pro Ala His Ala Ser Lys Gly Pro Gly Gly Ala Thr Arg Leu Tyr Gly Pro Ala Ala Glu

Thr Asp Pro Met Gly Leu Tyr Glu Ala Leu Arg Ala Glu His Gly Pro Val Ala Pro Val

Leu Leu Asp Gly Asp Val Arg Ala Trp Leu Val Leu Gly Tyr Leu Glu Asn Arg Asp Val

Ala Ser Arg Pro Thr Gln Tyr Ser Arg Asp Pro Arg Val Trp His Gly Trp Arg Ser Gly Glu

Ile Asp Pro Ala Thr Ser Pro Leu Val Pro Met Ile Gly Trp Arg Pro Asp Cys Val Cys Ala

Asp Gly Glu Glu His Gln Arg Leu Arg Gly Ala Val Thr Ala Gly Leu Ser Gln Phe Asp

His Arg Gly Val Arg Arg His Ile Thr Arg Phe Ala His Gln Leu Ile Asp Thr Phe Cys Glu

Asp Gly Glu Val Glu Leu Val Gly Gln Phe Thr Glu His Leu Pro Met Leu Thr Leu Thr

His Leu Leu Gly Met Ser Asp Glu Ser Gly Pro Arg Leu Val His Ala Ala Arg Asp Leu

Phe Lys Ala Thr Glu Thr Ser Leu Ala Ser Asn Ala Tyr Val Ile Glu Cys Leu Glu Gln Leu

Val Val Ala Lys Arg Ser Arg Pro Gly Gln Asp Ile Ala Ser Ala Leu Met Ala His Pro Ala

Gly Leu Thr Asp Glu Glu Val Leu His His Leu Arg Leu Ile Leu Leu Ala Gly Tyr Glu

Thr Thr Ala Asn Leu Met Ser Asn Val Leu Arg Met Val Val Thr Asp Pro Arg Phe Arg

Gly Ser Leu Ala Gly Gly Gln Met Thr Leu Pro Glu Ala Val Glu Gln Val Leu Trp Asp

Glu Pro Pro Leu Met Val Cys Pro Gly Arg Trp Ala Asn Gly Asp Thr Thr Leu Gly Gly

Arg Gln Ile Lys Ala Gly Asp Met Leu Leu Leu Gly Leu Ala Ala Gly Asn Val Asp Lys

Ala Ile Arg Pro Asp Ala Ser Thr Pro Val His His Asn Arg Ala His Leu Ser Phe Ser Ala

Gly Thr His Glu Cys Pro Gly Gln Asp Ile Gly Arg Ile Ile Ala Asp Ala Gly Ile Asp Ile

Leu Leu Thr Arg Leu Pro Asp Ile Ala Leu Ala Val Pro Glu Glu Ser Leu Ser Trp Arg Ser

Ser Thr Trp Ala Arg His Leu Thr Ala Leu Pro Val His Phe Ala Pro Arg Val Pro Glu Gly

His Asp Val Pro Asn Pro Leu Pro Ala Pro Pro Ala Pro Ser Phe Gly Pro Pro Ser Ala Pro

Leu Trp Pro Ser Pro Gly Pro Gly Pro Ala Arg Pro Ser Asp Gln Ala Pro Pro Gly Pro

Val Pro Gly Gly Gly Ala Thr Gly Gly Ala Ser Gly Pro Ala Ser Glu His Gly Pro Gly Pro

Arg Ala Thr Trp Arg Thr Arg Val Met Arg Phe Leu Arg Arg Arg

The exemplary SEQ ID NO:31 is

| | |
|---|---:|
| atgtccgtca tcgaactggg ggagtacggc gcggacttca ccgcgaatcc gtacccctac | 60 |
| tacgcgaaac tccgcgaagc gggacccgtc cacgaggtcc ggatgcccga cggcttccag | 120 |
| ttctggctgg tcgtcggcca cgaggagggg gcgcgccgca ccgccgaccc ccggctcgcc | 180 |
| aagtccccct ccgtgatcgg cgtacggccg ccggaggagg acatcatcgg cgtccacctc | 240 |
| ctcgccgcgg acgcgcccga ccacacccgg ctgcgccgcc tggtcaccgg tgagttcacc | 300 |
| ggccgtcggg tggagggcct cgccccccgc atccagcagc tgaccacgga gctcgccgac | 360 |
| gccatggaac cggcaggccg tgccgacctc gtcgacgcct cgcctacccc gctgccgatc | 420 |
| atcgtcatct gcgagctcct cggcgtcccc gccgaggacc gcgacacctt ccgccgctgg | 480 |
| tcgaaccagc tggtcacgcc caccggcgac caggagttcg gccaggcgat ggtggacttc | 540 |
| gcggcctatc tcgacgcgct catcgaggac aagcgggccg ccggacccac cgacgacctg | 600 |
| ctctccgccc tgatcaccgc ccgcgccgag acggcgacc ggctctccgg ccccgaactc | 660 |
| cgcgccatgg cctatctgct gctcatcgcg ggccacgaga ccaccgtcaa cctgatcgcc | 720 |
| aacaccgtcc gcaacctgct cacccacccc gagcagctcg cggccctccg cgccgacccg | 780 |
| gacctcctgg acgggacgat cgaggagtcc ctgcggtacg acggaccggt ggagaccggc | 840 |
| acgttccgct tcacccggga ggccgtcacc atcggcgggc gggagatcgc ggcgggccag | 900 |
| tacgtgctcg tcggcatcgg ggcgctcgac cgcgaccccg ccgcttccc cgaccccgac | 960 |
| cgcttcgaca tccgccggga caccgcggc cacctcgcct tcggccacgg catccactac | 1020 |
| tgcctgggcg ccccgctggc ccgcctggag ggccggatcg ccctccgtac cctcctcgac | 1080 |
| cgcttccccgg acctggaact cgaccccgag ggcgagccct gggaatggct ccccggcctc | 1140 |
| ctgatcgccg cgtccgaca cctcccggtc aggtggtga | 1179 |

Thus, an exemplary amplification primer sequence pair is residues 1 to 21 of SEQ ID NO:31 and the complementary strand of the last 21 residues of SEQ ID NO:31.

The exemplary SEQ ID NO:31 encodes a polypeptide having the sequence

Met Ser Val Ile Glu Leu Gly Glu Tyr Gly Ala Asp Phe Thr Ala Asn Pro Tyr Pro Tyr    (SEQ ID NO:32)
Tyr Ala Lys Leu Arg Glu Ala Gly Pro Val His Glu Vat Arg Met Pro Asp Gly Phe Gln
Phe Trp Leu Val Val Gly His Glu Glu Gly Arg Ala Ala Leu Ala Asp Pro Arg Leu Ala
Lys Ser Pro Ser Val LIe Gly Val Arg Pro Glu Glu Asp Ile Ile Gly Val His Leu Leu
Ala Ala Asp Ala Pro Asp His Thr Arg Leu Arg Arg Leu Val Thr Gly Glu Phe Thr Gly
Arg Arg Val Glu Gly Leu Arg Pro Arg Ile Gtn Gln Leu Thr Thr Glu Leu Ala Asp Ala
Met Glu Pro Ala Gly Arg Ala Asp Leu Val Asp Ala Phe Ala Tyr Pro Leu Pro Ile Ile Val
Ile Cys Glu Leu Leu Gly Val Pro Ala Glu Asp Arg Asp Thr Phe Arg Arg Trp Ser Asn
Gln Leu Val Thr Pro Thr Gly Asp Gln Glu Phe Gly Gln Ala Met Val Asp Phe Ala Ala
Tyr Leu Asp Ala Leu Ile Glu Asp Lys Arg Ala Ala Gly Pro Thr Asp Asp Leu Leu Ser
Ala Leu Ile Thr Ala Arg Ala Glu Asp Gly Asp Arg Leu Ser Gly Pro Glu Leu Arg Ala
Met Ala Tyr Leu Leu Leu Ile Ala Gly His Glu Thr Thr Val Asn Leu Ile Ala Asn Thr Val
Arg Asn Leu Leu Thr His Pro Glu Gln Leu Ala Ala Leu Arg Ala Asp Pro Asp Leu Leu
Asp Gly Thr Ile Glu Glu Ser Leu Arg Tyr Asp Gly Pro Val Glu Thr Gly Thr Phe Arg Phe
Thr Arg Glu Ala Val Thr Ile Gly Gly Arg Glu Ile Ala Ala Gly Gln Tyr Val Leu Val Gly
Ile Gly Ala Leu Asp Arg Asp Pro Ala Arg Phe Pro Asp Pro Asp Arg Phe Asp Ile Arg
Arg Asp Thr Arg Gly His Leu Ala Phe Gly His Gly Ile His Tyr Cys Leu Gly Ala Pro Leu
Ala Arg Leu Glu Gly Arg Ile Ala Leu Arg Thr Leu Leu Asp Arg Phe Pro Asp Leu Glu
Leu Asp Pro Glu Gly Glu Pro Trp Glu Trp Leu Pro Gly Leu Leu Met Arg Gly Val Arg
His Leu Pro Val Arg Trp

The exemplary SEQ ID NO:33 is

```
atgagcgtcg ccgtcgagac cctgccggcc ttccccttcg actgggacgg gacccggctg         60
cccgccgagg tcgaggcgct ccgcgccgaa cccgtacgcc gggtgcggac gatcgccggg        120
gccgaggcct ggctggtctc ctcgtacgag ctgtgcaggc aggtcctgga ggacccgcgg        180
ttcagcctga aggacacctc ggcgccgggc gcgccgcggc agtacgcgct gacgatcccg        240
ccgcacgtgg tgaacaacat gggcaacatc accggggccg ggctgcgcaa ggccgtgatg        300
aaggcgatca acccgaaggc gcccggcctg gaggagtggg tgcgggcgcg ggccggggcc        360
ctggtggacg cgctggtcgc cgagggcgcg cccggggagc tgcggggcgc ctacgccgac        420
ccgtactcgt cggggctgca ctgccggatg ctgggcatcc cggaggagga cgggccgcgg        480
ctgctgcgca gcctggacgt ggccttcatg aacgcccgt ccgagatcga ggcggcccgg         540
ctccactggg accgggacat cgcgtacatg accgagcgtc tcgacgatcc ggcgacgggc        600
gggctgatgg cggagctcgc ggcgctgcgc gaggatcccg agtacgcgca tctgacggac        660
gagatgctgg cgacggtggg cgtgacgctg ttcggggccg gggtgatctc caccgccggg        720
ttcctgacga tggcgctcgt gtcggtgctg acccggccgg acgtgcgggc ggcgctgacc        780
gccggcggcg ggcacggggt cgccggggcg atggacgaac tgctgcgggt gaacctgtcc        840
atcggcgacg gctgccccg gctcgccctg gaggacgtgc ggctcggcga cgtcgaggtg        900
cgggccggtg aactggtcct ggtgctggtg gaggccgcga accacgatcc gctgcacttc        960
```

-continued

```
ccggacccgc tggccttccg gccggaccgg gagaacgccg ccgaccacct ctccttcggc      1020
ggcggtcggc actactgccc ggcgacggcg ctgggcaagc ggcacgccga gatcgccctg      1080
gagacgctcc tcgaccggct gccggagctg cggctcgcgg tgccggtcga gcagctggtg      1140
tggcgcacca acttcatgaa gcggctcccg gagcggctgc cggtggcctg gtag            1194
```

Thus, an exemplary amplification primer sequence pair is residues 1 to 21 of SEQ ID NO:33 and the complementary strand of the last 21 residues of SEQ ID NO:33.

The exemplary SEQ ID NO:33 encodes a polypeptide having the sequence

Met Ser Val Ala Val Glu Thr Leu Pro Ala Phe Pro Phe Asp Trp Asp Gly Thr Arg Leu    (SEQ ID NO:34)

Pro Ala Glu Val Glu Ala Leu Arg Ala Glu Pro Val Arg Arg Val Arg Thr Ile Ala Gly Ala

Glu Ala Trp Leu Val Ser Ser Tyr Glu Leu Cys Arg Gln Val Leu Glu Asp Pro Arg Phe

Ser Leu Lys Asp Thr Ser Ala Pro Gly Ala Pro Arg Gln Tyr Ala Leu Thr Ile Pro Pro His

Val Val Asn Asn Met Gly Asn Ile Thr Gly Ala Gly Leu Arg Lys Ala Val Met Lys Ala Ile

Asn Pro Lys Ala Pro Gly Leu Glu Glu Trp Leu Arg Ala Arg Ala Gly Ala Leu Val Asp

Ala Leu Val Ala Glu Gly Ala Pro Gly Glu Leu Arg Gly Ala Tyr Ala Asp Pro Tyr Ser Ser

Gly Leu His Cys Arg Met Leu Gly Ile Pro Glu Glu Asp Gly Pro Arg Leu Leu Arg Ser

Leu Asp Val Ala Phe Met Asn Ala Pro Ser Glu Ile Glu Ala Ala Arg Leu His Trp Asp Arg

Asp LIe Ala Tyr Met Thr Glu Arg Leu Asp Asp Pro Ala Thr Gly Gly Leu Met Ala Glu

Leu Ala Ala Leu Arg Glu Asp Pro Glu Tyr Ala His Leu Thr Asp Glu Met Leu Ala Thr

Val Gly Val Thr Leu Phe Gly Ala Gly Val Ile Ser Thr Ala Gly Phe Leu Thr Met Ala Leu

Val Ser Val Leu Thr Arg Pro Asp Val Arg Ala Ala Leu Thr Ala Gly Gly His Gly Val

Ala Gly Ala Met Asp Glu Leu Leu Arg Val Asn Leu Ser Ile Gly Asp Gly Leu Pro Arg

Leu Ala Leu Glu Asp Val Arg Leu Gly Asp Val Glu Val Arg Ala Gly Glu Leu Val Leu

Val Leu Val Glu Ala Ala Asn His Asp Pro Leu His Phe Pro Asp Pro Leu Ala Phe Arg

Pro Asp Arg Glu Asn Ala Ala Asp His Leu Ser Phe Gly Gly Gly Arg His Tyr Cys Pro

Ala Thr Ala Leu Gly Lys Arg His Ala Glu Ile Ala Leu Glu Thr Leu Leu Asp Arg Leu Pro

Glu Leu Arg Leu Ala Val Pro Val Glu Gln Leu Val Trp Arg Thr Asn Phe Met Lys Arg

Leu Pro Glu Arg Leu Pro Val Ala Trp

The exemplary SEQ ID NO:35 is

```
gtgatcccgg ccacggagga gaacccggcc gcggcgccgc gggtgccgga cctgtccgac      60
ccgctgctcc accagcgcgg cgaggccgga ccggtcctgg cgcgactgcg gcgcgaggaa      120
ccggtctgcc aggtcacccg ggcggacggc tcgacgttct gggccgtcct gtcgtacgag      180
ctgatcaccc aggtcctcgc cgacgccgcc accttcagct ccaccggcgg gatgcggctc      240
gacgccgatc cggtggcgac cgccgccgcg accggcaaga tgatggtcat caccgacccg      300
ccgctgcacg gcatgatccg ccgggtcgtc agctcggcgt tcaccccccg catggtgctc      360
cgcctcgagg agaccatgcg gaccatctcg gtcgaggtca tcgaggccgc cctcgggcag      420
gactcgatcg acttcaccga ggtgcggcc cggctgccgc tgtcggtcat ctgcgacatg      480
ctcggcgtgc cgcgcgccga ctggacttc atgctgtccc gcacgatgac ggccttcggg      540
gtgaacggcg acgacgggcc cgagcagcag cagcgggtgg cgacggccca caccgacatc      600
```

-continued

```
ttcctgtact acgacgagct gatgcggctg cgcaggaagg agccgcagga ggacatcatc        660
agcgccctcg tgcacggccg gatcgacggc aggccgctga ccgaggagga gatcatcctc        720
aactgcaacg gcctgatctc cggcggcaac gagaccaccc ggcacgccac catcggcgga        780
ctgctcgcgc tcatcgagca ccccgagcag tggcgccggc tccaggagga gccggaggtg        840
ctgccgaccg cggtgcagga gatcctgcgc ttcacgacgc ccgccatgca cgtgctgcgc        900
accgccaccc gggaaacgga actggcgggg cgccggatca aggcgggcga catggtcgcg        960
ctctggctgg cctcgggcaa ccgggacgag accgtcttcg cggacccgga ccgctttgac       1020 atcggcggc gcgaggtgaa ccgcaacctc accttcgcgt acggcagtca cttctgcatc       1080
ggttcggcgc tcgccaccac ggagctgaac accttcttcg acgtcctcag acagcgggtc       1140
gcacggcccg aactgaccgg agaggtacgc cgcatgcgct ccaacctcat cggcggcatc       1200
gagcacctgc cggtccgcct ggtcccccgg gaccgctga                              1239
```

Thus, an exemplary amplification primer sequence pair is residues1 to 21 of SEQ ID NO:35 and the complementary strand of the last 21 residues of SEQ ID NO:35.

The exemplary SEQ ID NO:35 encodes a polypeptide having the sequence

Met Ile Pro Ala Thr Glu Glu Asn Pro Ala Ala Ala Pro Arg Val Pro Asp Leu Ser Asp     (SEQ ID NO:36)

Pro Leu Leu His Gln Arg Gly Glu Ala Gly Pro Val Leu Ala Arg Leu Arg Arg Glu Glu

Pro Val Cys Gln Val Thr Arg Ala Asp Gly Ser Thr Phe Trp Ala Val Leu Ser Tyr Glu Leu

Ile Thr Gln Val Leu Ala Asp Ala Ala Thr Phe Ser Ser Thr Gly Gly Met Arg Leu Asp Ala

Asp Pro Val Ala Thr Ala Ala Ala Thr Gly Lys Met Met Val Ile Thr Asp Pro Pro Leu His

Gly Met Ile Arg Arg Val Val Ser Ser Ala Phe Thr Pro Arg Met Val Leu Arg Leu Glu Glu

Thr Met Arg Thr Ile Ser Val Glu Val Ile Glu Ala Ala Leu Gly Gln Asp Ser Ile Asp Phe

Thr Glu Val Ala Ala Arg Leu Pro Leu Ser Val Ile Cys Asp Met Leu Gly Val Pro Arg Ala

Asp Trp Asp Phe Met Leu Ser Arg Thr Met Thr Ala Phe Gly Val Asn Gly Asp Asp Gly

Pro Glu Gln Gln Gln Arg Val Ala Thr Ala His Thr Asp Ile Phe Leu Tyr Tyr Asp Glu Leu

Met Arg Leu Arg Arg Lys Glu Pro Gln Glu Asp Ile Ile Ser Ala Leu Val His Gly Arg Ile

Met Arg Leu Arg Arg Lys Glu Pro Gln Glu Asp Ile Ile Ser Ala Leu Val His Gly Arg Ile

Asp Gly Arg Pro Leu Thr Glu Glu Glu Ile Ile Leu Asn Cys Asn Gly Leu Ile Ser Gly Gly

Asn Glu Thr Thr Arg His Ala Thr Ile Gly Gly Leu Leu Ala Leu Ile Glu His Pro Glu Gln

Trp Arg Arg Leu Gln Glu Glu Pro Glu Val Leu Pro Thr Ala Val Gln Glu Ile Leu Arg Phe

Thr Thr Pro Ala Met His Val Leu Arg Thr Ala Thr Arg Glu Thr Glu Leu Ala Gly Arg

Arg Ile Lys Ala Gly Asp Met Val Ala Leu Trp Leu Ala Ser Gly Asn Arg Asp Glu Thr

Val Phe Ala Asp Pro Asp Arg Phe Asp Ile Gly Arg Arg Glu Val Asn Arg Asn Leu Thr

Phe Ala Tyr Gly Ser His Phe Cys Ile Gly Ser Ala Leu Ala Thr Thr Glu Leu Asn Thr Phe

Phe Asp Val Leu Arg Gln Arg Val Ala Arg Pro Glu Leu Thr Gly Glu Val Arg Arg Met

Arg Ser Asn Leu Ile Gly Gly Ile Glu His Leu Pro Val Arg Leu Val Pro Arg Asp Arg

The exemplary SEQ ID NO:37 is

```
gtgcagaacg aacagacccc tgccaccgca cccgtcacgc ttcccaccgg gcgagccgcc         60
ggctgcccct tcgacccgcc cgccggactc gccgaggtcc gcgccaccgg cccgctggcc        120
```

-continued

```
cggatgacgt accccgacgg acacatcggc tggctggcca ccggccacgc cgcggtgcgc      180
tccgtcctgg gcgaccccg gttcagctcg cggtacgagc tgatgcacta ccccttcccc       240
ggcggcccg agggcccgcc ggcacccgcc cccgtcggcg acatgaccgg gatggacgca       300
cccgagcaca cccgcttccg gcggctgctc accggcaagt tcaccgtccg ccggatgcgg      360
cagctcaccg accgggtcgc ggagctcacc gccgggcacc tggacgcgat ggagcgcggc      420
ggcccgggcg tcgacctggt cgaggccttc gcacgaccgc tgcccgcgct gatgatctgc      480
gagctgctcg gcgtgccgta cgcggaccgc gagcgcttcc aggagcacgc tcagacgatc     540
atgtcgatgg acgtgtcgcc cgaggagatg gaggccgcgt tcaccgcgtt cctcgggtac     600
atggcggagc tggtcgcggc caagcgggcc gagccctccg acgacctgct cggcgacctg     660
gcccaggact ccgacctcac cgacgaggaa ctcgtcggcg tcggaggctt cctgctcgcc     720
gccggcctcg acaccaccgc caacatgatc gcccacggaa cgttcgcgct cctcacccac    780
ccggaacagg cggacgcgct gcgcgcggac ccggcccttg ccccgggcgc cgtggaggag    840
ctgatgcgct atctgaccgt cgcccacacc ggagtgcgga ccgccctgga ggacgtcgag     900
gtggaaggcg tgctcatcag ggcgggcgag agcgtcaccc tctcccttga ggccgccaac    960
cgggacccgg agcggttccc cgaccccgac accctcgacg tacaccgcaa ggccacgggg    1020
cacctgggct cgggcacgg catccaccag tgcctgggcc agcaactggc ccgcgtcgag    1080
atgacggtgg ccctgcccgc gctgctgagg cggttcccca cgctgcggct cgacgtgccg    1140
gccgaggagg tgccgctgcg gaccgagatg aacgtgtacg gcgtgcaccg gctgcccgtc   1200
acctgggacg aggtctga                                                   1218
```

Thus, an exemplary amplification primer sequence pair is residues 1 to 21 of SEQ ID NO:37 and the complementary strand of the last 21 residues of SEQ ID NO:37.

The exemplary SEQ ID NO:37 encodes a polypeptide having the sequence

Met Gln Asn Glu Gln Thr Pro Ala Thr Ala Pro Val Thr Leu Pro Thr Gly Arg Ala Ala    (SEQ ID NO:38)
Gly Cys Pro Phe Asp Pro Pro Ala Gly Leu Ala Glu Val Arg Ala Thr Gly Pro Leu Ala
Arg Met Thr Tyr Pro Asp Gly His Ile Gly Trp Leu Ala Thr Gly His Ala Ala Val Arg Ser
Val Leu Gly Asp Pro Arg Phe Ser Ser Arg Tyr Glu Leu Met His Tyr Pro Phe Pro Gly Gly
Pro Glu Gly Pro Pro Ala Pro Ala Pro Val Gly Asp Met Thr Gly Met Asp Ala Pro Glu His
Thr Arg Phe Arg Arg Leu Leu Thr Gly Lys Phe Thr Val Arg Arg Met Arg Gln Leu Thr
Asp Arg Val Ala Glu Leu Thr Ala Gly His Leu Asp Ala Met Glu Arg Gly Gly Pro Gly
Val Asp Leu Val Glu Ala Phe Ala Arg Pro Leu Pro Ala Leu Met Ile Cys Glu Leu Leu
Gly Val Pro Tyr Ala Asp Arg Glu Arg Phe Gln Glu His Ala Gln Thr Ile Met Ser Met Asp
Val Ser Pro Glu Glu Met Glu Ala Ala Phe Thr Ala Phe Leu Gly Tyr Met Ala Glu Leu
Val Ala Ala Lys Arg Ala Glu Pro Ser Asp Asp Leu Leu Gly Asp Leu Ala Gln Asp Ser
Asp Leu Thr Asp Glu Glu Leu Val Gly Val Gly Gly Phe Leu Leu Ala Ala Gly Leu Asp
Thr Thr Ala Asn Met Ile Ala His Gly Thr Phe Ala Leu Leu Thr His Pro Glu Gln Ala Asp
Ala Leu Arg Ala Asp Pro Ala Leu Ala Pro Gly Ala Val Glu Glu Leu Met Arg Tyr Leu
Thr Val Ala His Thr Gly Val Arg Thr Ala Leu Glu Asp Val Glu Val Glu Gly Val Leu Ile
Arg Ala Gly Glu Ser Val Thr Leu Ser Leu Glu Ala Ala Asn Arg Asp Pro Glu Arg Phe

-continued

```
Pro Asp Pro Asp Thr Leu Asp Val His Arg Lys Ala Thr Gly His Leu Gly Phe Gly His

Gly Ile His Gln Cys Leu Gly Gln Gln Leu Ala Arg Val Glu Met Thr Val Ala Leu Pro Ala

Leu Leu Arg Arg Phe Pro Thr Leu Arg Leu Asp Val Pro Ala Glu Glu Val Pro Leu Arg

Thr Glu Met Asn Val Tyr Gly Val His Arg Leu Pro Val Thr Trp Asp Glu Val
```

The exemplary SEQ ID NO:39 is

| | |
|---|---|
| atgcgcttac acacagcaga accggccggg accgccgacg ccgaacccgt tccgtacccg | 60 |
| ttcaacgagg cggacggcat ctccctggcc gacgcctacg aggaggcccg cgagcagccc | 120 |
| gggctgctgc gggtccggat ggcctacggt gagccggcct ggctcgccac ccggtacgcc | 180 |
| gacgcccggc tggtcctggg cgaccggcgc ttcagccggg ccgagggcgc ccggcacgac | 240 |
| gagccgcgcc agtccgaggg gcgccgcgac agcgggatcc tcagcatgga cccgccggac | 300 |
| cacaccggt tgcgcaccct ggtggccaag gcgttcacca tgcaccaggt ggagaagttg | 360 |
| cgcccggcg tgcgggagct ggccgacgag ctgatcgaca agatggtcgc caccggcgcc | 420 |
| ccggtcgacc tggtcgagga gttcgcgctg ccggtgccgg tcggggtgat ctgccagctg | 480 |
| ctcggcgtgc cggtcgagga ccgtccgcgc ttccgggcgt ggagcgacgc ggcgctgtcc | 540 |
| accagttccc tgacggccga ggagttcgac gccaaccagg aggaactgcg ggcctacatg | 600 |
| cgggggttga tcgaggatca ccgggcgcgt ccgcgtgagg acctgatcac cgggctgatc | 660 |
| gaggcccggg accgcgacga ccggctgacc gagcaggagt tggtggacct gtgcgtcggc | 720 |
| atcctggtgg ccgccacga gaccaccgcc acgcagatcc ccaacttcgt ggtgacgctg | 780 |
| ctggaccggc ccgagcagtg gaaccggctg cgggaggacc cggagctggt cccgaccgcg | 840 |
| gtcgaggagc tgatgcgttt cgtgccgctg ggcagcggtg cctcgttccc gcggtacgcc | 900 |
| accgaggacg tggaggtcgg cggcacgctg gtgcgcgccg gggagccggt gctggtggcg | 960 |
| gtcggggcgg ccaaccgcga cccggccagg ttcgacgcgc cgcaggagct ggacctggcc | 1020 |
| cgggagggca accagcacct cgggttcggc catggcgtcc accactgcct cggggcgccg | 1080 |
| ctggcccggc tggagttgca ggaggcgctg ggcgcgctgc tgcggcggct gccgggtctg | 1140 |
| cggatcgccg gtgacatcga gtggaagacg cagatgctgg tccgcgggcc gcgcacgctg | 1200 |
| ccggtggggt ggtga | 1215 |

45

Thus, an exemplary amplification primer sequence pair is residues 1 to 21 of SEQ ID NO:39 and the complementary strand of the last 21 residues of SEQ ID NO:39.

---

The exemplary SEQ ID NO:39 encodes a polypeptide having the sequence

```
Met Arg Leu His Thr Ala Glu Pro Ala Gly Thr Ala Asp Ala Glu Pro Val Pro Tyr Pro      (SEQ ID NO:40)

Phe Asn Glu Ala Asp Gly Ile Ser Leu Ala Asp Ala Tyr Glu Glu Ala Arg Glu Gln Pro Gly

Leu Leu Arg Val Arg Met Ala Tyr Gly Glu Pro Ala Trp Leu Ala Thr Arg Tyr Ala Asp

Ala Arg Leu Val Leu Gly Asp Arg Arg Phe Ser Arg Ala Glu Gly Ala Arg His Asp Glu

Pro Arg Gln Ser Glu Gly Arg Arg Asp Ser Gly Ile Leu Ser Met Asp Pro Asp His Thr

Arg Leu Arg Thr Leu Val Ala Lys Ala Phe Thr Met His Gln Val Glu Lys Leu Arg Pro

Ala Val Arg Glu Leu Ala Asp Glu Leu Ile Asp Lys Met Val Ala Thr Gly Ala Pro Val

Asp Leu Val Glu Glu Phe Ala Leu Pro Val Pro Val Gly Val Ile Cys Gln Leu Leu Gly Val
```

-continued

The exemplary SEQ ID NO:39 encodes a polypeptide having the sequence

Pro Val Glu Asp Arg Pro Arg Phe Arg Ala Trp Ser Asp Ala Ala Leu Ser Thr Ser Ser Leu

Thr Ala Glu Glu Phe Asp Ala Asn Gln Glu Glu Leu Arg Ala Tyr Met Arg Gly Leu Ile

Glu Asp His Arg Ala Arg Pro Arg Glu Asp Leu Ile Thr Gly Leu Ile Glu Ala Arg Asp Arg

Asp Asp Arg Leu Thr Glu Gln Glu Leu Val Asp Leu Cys Val Gly Ile Leu Val Ala Gly

His Glu Thr Thr Ala Thr Gln Ile Pro Asn Phe Val Val Thr Leu Leu Asp Arg Pro Glu Gln

Trp Asn Arg Leu Arg Glu Asp Pro Glu Leu Val Pro Thr Ala Val Glu Glu Leu Met Arg

Phe Val Pro Leu Gly Ser Gly Ala Ser Phe Pro Arg Tyr Ala Thr Glu Asp Val Glu Val Gly

Gly Thr Leu Val Arg Ala Gly Glu Pro Val Leu Val Ala Val Gly Ala Ala Asn Arg Asp

Pro Ala Arg Phe Asp Ala Pro Gln Glu Leu Asp Leu Ala Arg Glu Gly Asn Gln His Leu

Gly Phe Gly His Gly Val His His Cys Leu Gly Ala Pro Leu Ala Arg Leu Glu Leu Gln

Glu Ala Leu Gly Ala Leu Leu Arg Arg Leu Pro Gly Leu Arg Ile Ala Gly Asp Lie Glu Trp

Lys Thr Gln Met Leu Val Arg Gly Pro Arg Thr Leu Pro Val Gly Trp

Determining the Degree of Sequence Identity

The invention provides nucleic acids and polypeptides having at least 99%, 98%, 97%, 96%, 95%, 90%, 85%, 80%, 75%, 70%, 65%, 60%, 55% or 50% sequence identity (homology) to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56. In alternative aspects, the sequence identify can be over a region of at least about 5, 10, 20, 30, 40, 50, 100, 150, 200, 250, 300, 350, 400, 450, 500, 550, 600, 650, 700, 750, 800, 850, 900, 950, 1000, or more, consecutive residues, or the full length of the nucleic acid or polypeptide.

The extent of sequence identity (homology) may be determined using any computer program and associated parameters, including those described herein, such as BLAST 2.2.2. or FASTA version 3.0t78, with the default parameters.

Homologous sequences also include RNA sequences in which uridines replace the thymines in the nucleic acid sequences. The homologous sequences may be obtained using any of the procedures described herein or may result from the correction of a sequencing error. It will be appreciated that the nucleic acid sequences as set forth herein can be represented in the traditional single character format (see, e.g., Stryer, Lubert. Biochemistry, 3rd Ed., W. H Freeman & Co., New York) or in any other format which records the identity of the nucleotides in a sequence.

Various sequence comparison programs identified herein are used in this aspect of the invention. Protein and/or nucleic acid sequence identities (homologies) may be evaluated using any of the variety of sequence comparison algorithms and programs known in the art. Such algorithms and programs include, but are not limited to, TBLASTN, BLASTP, FASTA, TFASTA, and CLUSTALW (Pearson and Lipman, Proc. Natl. Acad. Sci. USA 85(8):2444–2448, 1988; Altschul et al., J. Mol. Biol. 215(3):403–410, 1990; Thompson et al., Nucleic Acids Res. 22(2):4673–4680, 1994; Higgins et al., Methods Enzymol. 266:383–402, 1996; Altschul et al., J. Mol. Biol. 215(3):403–410, 1990; Altschul et al., Nature Genetics 3:266–272, 1993).

Homology or identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence (an exemplary sequence SEQ ID NO:1, SEQ ID NO:2, SEQ ID NO:3, SEQ ID NO:4, SEQ ID NO:5, SEQ ID NO:6, SEQ ID NO:7, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56) to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the numbers of contiguous residues. For example, in alternative aspects of the invention, continuous residues ranging anywhere from 20 to the full length of exemplary sequences SEQ ID NO:1, SEQ ID NO:3, SEQ ID NO:5, SEQ ID NO:7, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56 are compared to a reference sequence of the same number of contiguous positions after the two sequences are optimally aligned. If the reference sequence has the requisite sequence identity to SEQ ID NO:1, SEQ ID NO:3, SEQ ID NO:5, SEQ ID NO:7, SEQ ID NO:9, e.g., 50%, 55%, 60%, 65%, 70%, 75%, 80%, 90% or 95% sequence identity to SEQ ID NO:1, SEQ ID NO:3, SEQ ID NO:5, SEQ ID NO:7, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, that sequence is within the scope of the invention. In alternative embodiments, subsequences ranging from about 20 to 600, about 50 to 200, and about 100 to 150 are compared to a reference sequence of the same number of contiguous positions after the two sequences are optimally aligned. Methods of alignment of sequence for comparison are well known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (Gibbs, 1995). Several genomes have been sequenced, e.g., *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Databases containing genomic information annotated with some functional information are maintained by different organization, and are accessible via the internet.

BLAST, BLAST 2.0 and BLAST 2.2.2 algorithms are also used to practice the invention. They are described, e.g., in Altschul (1977) Nuc. Acids Res. 25:3389–3402; Altschul (1990) J. Mol. Biol. 215:403–410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) Proc. Natl. Acad. Sci. USA 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443–1445, 1992; Henikoff and Henikoff, Proteins 17:49–61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, to determine if a nucleic acid has the requisite sequence identity to be within the scope of the invention, the NCBI BLAST 2.2.2 programs is used, default options to blastp. There are about 38 setting options in the BLAST 2.2.2 program. In this exemplary aspect of the invention, all default values are used except for the default filtering setting (i.e., all parameters set to default except filtering which is set to OFF); in its place a "−F F" setting is used, which disables filtering. Use of default filtering often results in Karlin-Altschul violations due to short length of sequence.

The default values used in this exemplary aspect of the invention include:
"Filter for low complexity: ON
Word Size: 3
Matrix: Blosum62
Gap Costs: Existence: 11
Extension: 1"

Other default settings are: filter for low complexity OFF, word size of 3 for protein, BLOSUM62 matrix, gap existence penalty of −11 and a gap extension penalty of −1.

An exemplary NCBI BLAST 2.2.2 program setting is set forth in Example 1, below. Note that the "−W" option defaults to 0. This means that, if not set, the word size defaults to 3 for proteins and 11 for nucleotides.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Computer Systems and Computer Program Products

To determine and identify sequence identities, structural homologies, motifs and the like in silico, the sequence of the invention can be stored, recorded, and manipulated on any medium which can be read and accessed by a computer. Accordingly, the invention provides computers, computer systems, computer readable mediums, computer programs products and the like recorded or stored thereon the nucleic acid and polypeptide sequences of the invention. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

Another aspect of the invention is a computer readable medium having recorded thereon at least one nucleic acid and/or polypeptide sequence of the invention. Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Figure 4:
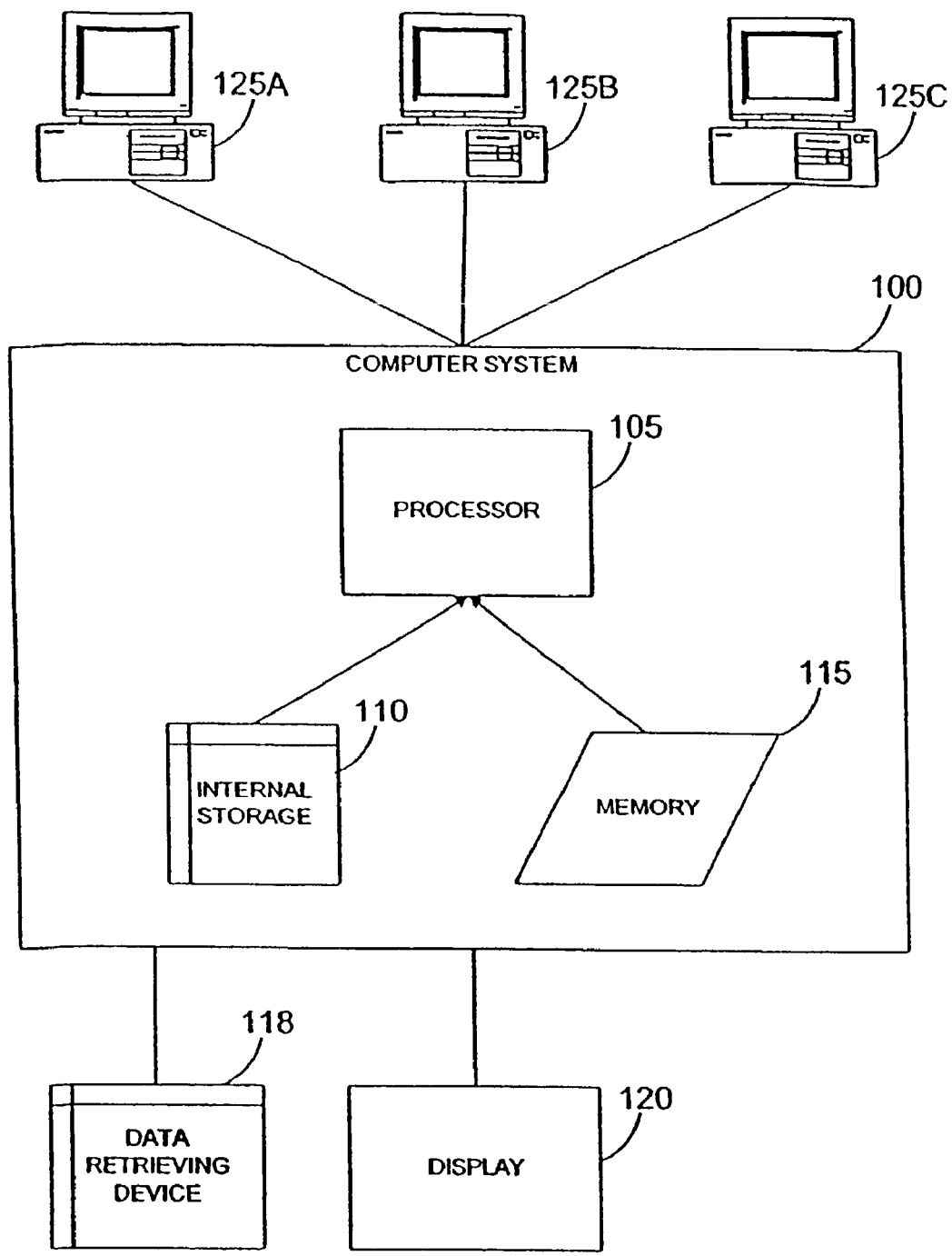
FIG. 4 is a block diagram of a computer system.

Aspects of the invention include systems (e.g., internet based systems), particularly computer systems, which store and manipulate the sequences and sequence information described herein. One example of a computer system 100 is illustrated in block diagram form in FIG. 4. As used herein, "a computer system" refers to the hardware components, software components, and data storage components used to analyze a nucleotide or polypeptide sequence of the invention. The computer system 100 can include a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines. The computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one aspect, the computer system 100 includes a processor 105 connected to a bus which is connected to a main memory 115 (preferably implemented as RAM) and one or more internal data storage devices 110, such as a hard drive and/or other computer readable media having data recorded thereon. The computer system 100 can further include one or more data retrieving device 118 for reading the data stored on the internal data storage devices 110. The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device. The computer system 100 includes a display 120 which is used to display output to a computer user. It should also be noted that the computer system 100 can be linked to other computer systems 125a–c in a network or wide area network to provide centralized access to the computer system 100. Software for accessing and processing the nucleotide or amino acid sequences of the invention can reside in main memory 115 during execution. In some aspects, the computer system 100 may further comprise a sequence comparison algorithm for comparing a nucleic acid sequence of the invention. The algorithm and sequence(s) can be stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of the invention stored on a computer readable medium to reference sequences stored on a computer readable medium to identify homologies or structural motifs.

Figure 5:
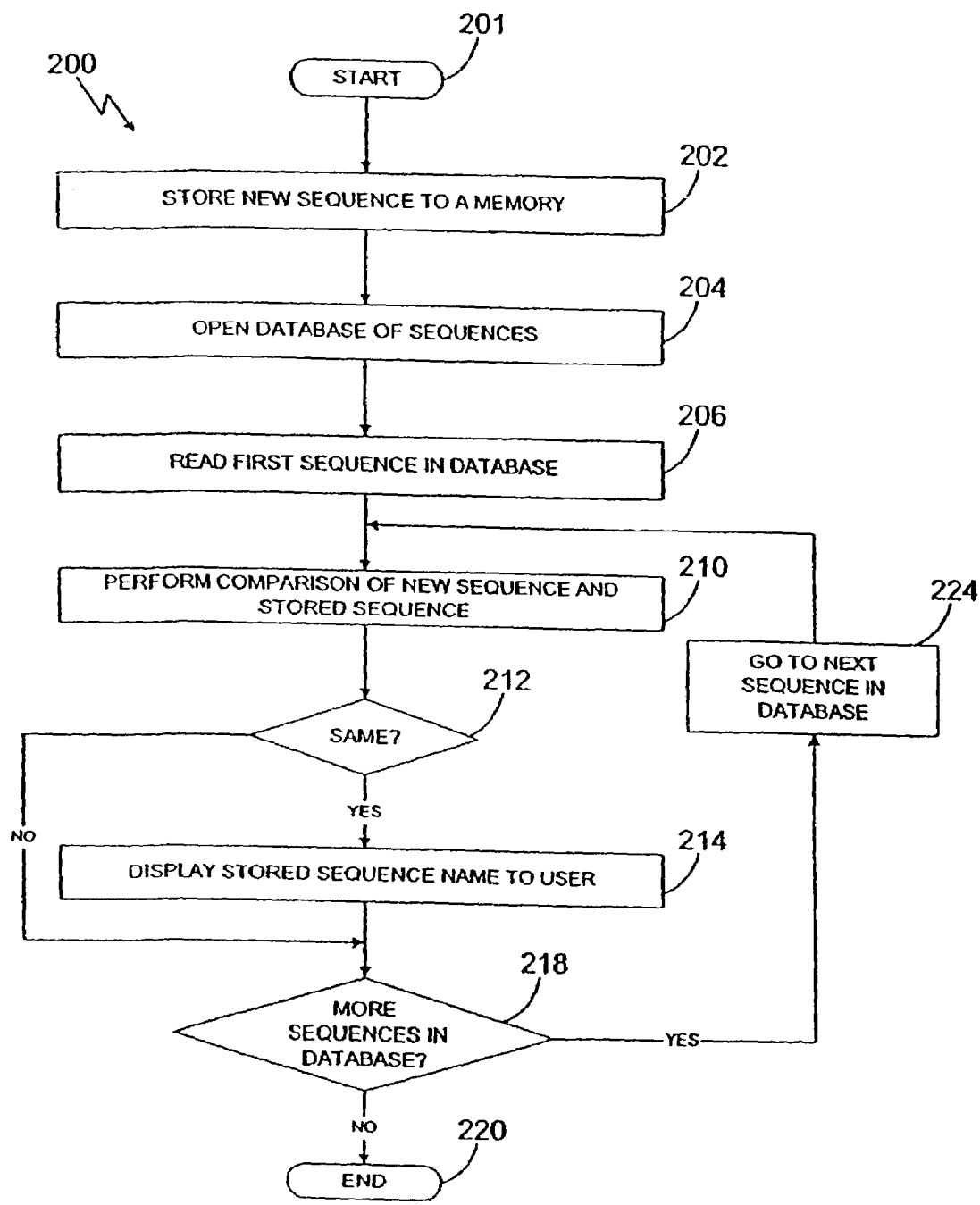
FIG. 5 is a flow diagram illustrating one aspect of a process for comparing a new nucleotide or protein sequence with a database of sequences in order to determine the homology levels between the new sequence and the sequences in the database.
Figure 6:
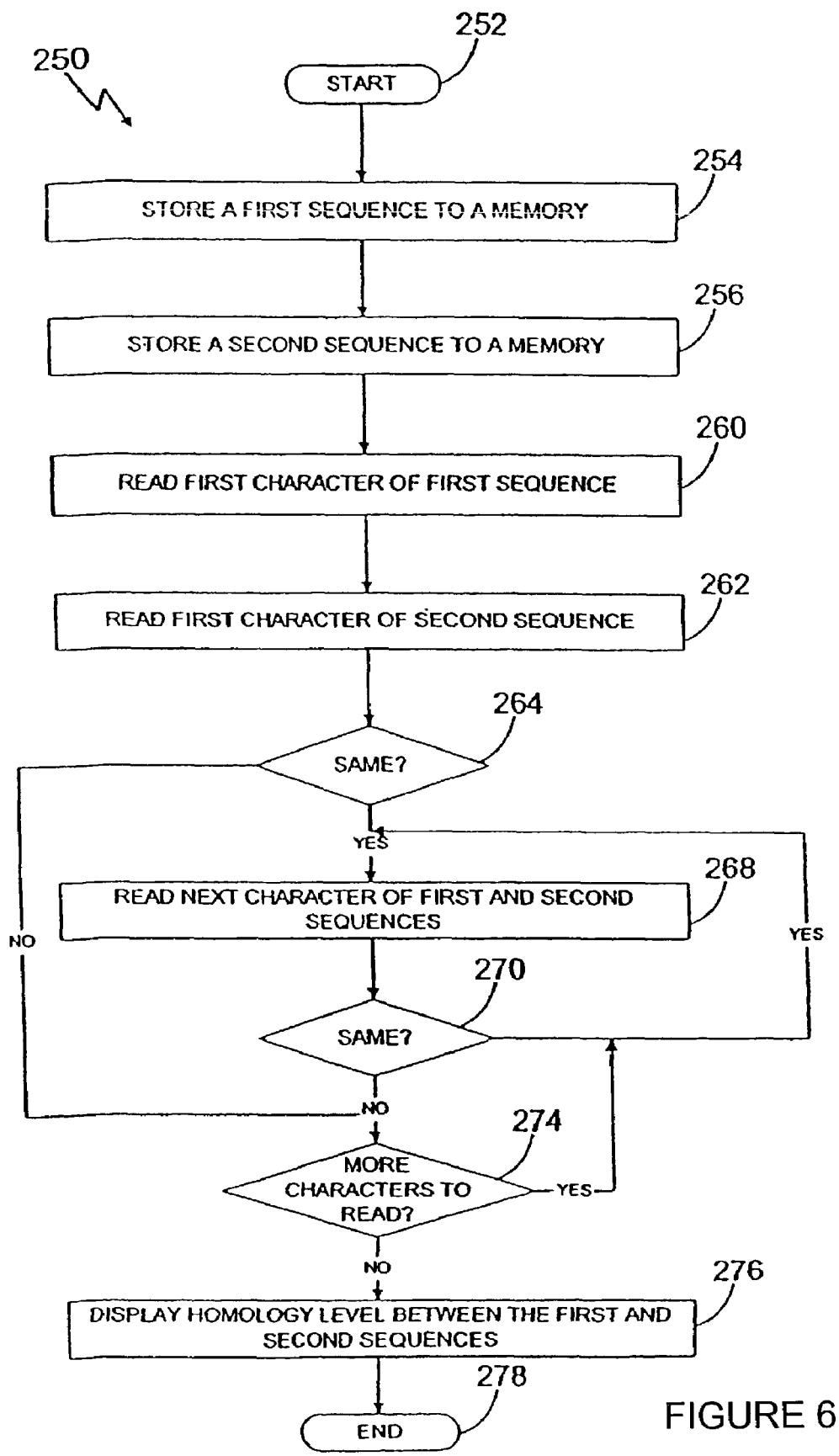
FIG. 6 is a flow diagram illustrating one aspect of a process in a computer for determining whether two sequences are homologous.

The parameters used with the above algorithms may be adapted depending on the sequence length and degree of homology studied. In some aspects, the parameters may be the default parameters used by the algorithms in the absence of instructions from the user. FIG. 5 is a flow diagram illustrating one aspect of a process 200 for comparing a new nucleotide or protein sequence with a database of sequences in order to determine the homology levels between the new sequence and the sequences in the database. The database of sequences can be a private database stored within the computer system 100, or a public database such as GEN-BANK that is available through the Internet. The process 200 begins at a start state 201 and then moves to a state 202 wherein the new sequence to be compared is stored to a memory in a computer system 100. As discussed above, the memory could be any type of memory, including RAM or an internal storage device. The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system. Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200. If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database. It should be noted that if a determination had been made at the decision state 212 that the sequences were not homologous, then the process 200 would move immediately to the decision state 218 in order to determine if any other sequences were available in the database for comparison. Accordingly, one aspect of the invention is a computer system comprising a processor, a data storage device having stored thereon a nucleic acid sequence of the invention and a sequence comparer for conducting the comparison. The sequence comparer may indicate a homology level between the sequences compared or identify structural motifs, or it may identify structural motifs in sequences which are compared to these nucleic acid codes and polypeptide codes. FIG. 6 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it can be a single letter amino acid code so that the first and sequence sequences can be easily compared. A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read. If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with an every character in a second sequence, the homology level would be 100%.

Alternatively, the computer program can compare a reference sequence to a sequence of the invention to determine whether the sequences differ at one or more positions. The program can record the length and identity of inserted, deleted or substituted nucleotides or amino acid residues with respect to the sequence of either the reference or the invention. The computer program may be a program which determines whether a reference sequence contains a single nucleotide polymorphism (SNP) with respect to a sequence of the invention, or, whether a sequence of the invention comprises a SNP of a known sequence. Thus, in some aspects, the computer program is a program which identifies SNPs. The method may be implemented by the computer systems described above and the method illustrated in FIG. 6. The method can be performed by reading a sequence of the invention and the reference sequences through the use of the computer program and identifying differences with the computer program.

Figure 7:
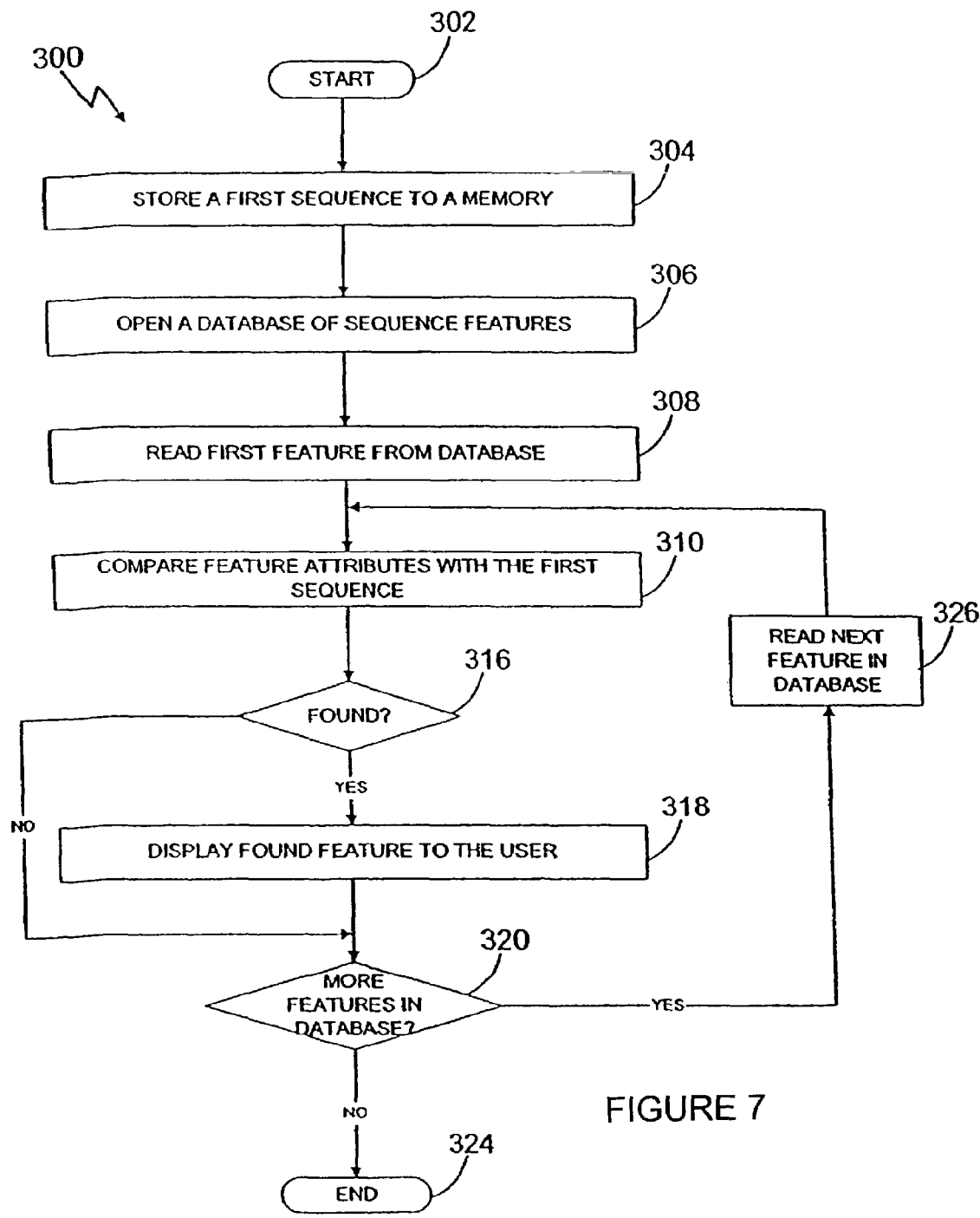
FIG. 7 is a flow diagram illustrating one aspect of an identifier process 300 for detecting the presence of a feature in a sequence.
Figure 8:
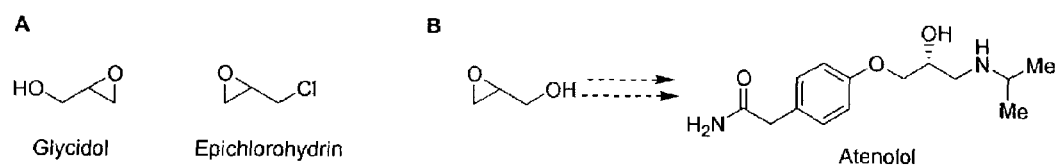
FIG. 8 is an illustration of valuable small molecule epoxides and their application in drug synthesis

In other aspects the computer based system comprises an identifier for identifying features within a nucleic acid or polypeptide of the invention. An "identifier" refers to one or more programs which identifies certain features within a nucleic acid sequence. For example, an identifier may comprise a program which identifies an open reading frame (ORF) in a nucleic acid sequence. FIG. 7 is a flow diagram illustrating one aspect of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art. Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user. The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence. If the feature attribute is not found in the first sequence at the decision state 316, the process 300 moves directly to the decision state 320 in order to determine if any more features exist in the database. Thus, in one aspect, the invention provides a computer program that identifies open reading frames (ORFs).

A polypeptide or nucleic acid sequence of the invention may be stored and manipulated in a variety of data processor programs in a variety of formats. For example, a sequence can be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparison algorithms, identifiers, or sources of reference nucleotide sequences or polypeptide sequences to be compared to a nucleic acid sequence of the invention. The programs and databases used to practice the invention include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237–245, 1990), Catalyst (Molecular Simulations Inc.), Catalyst/SHAPE (Molecular Simulations Inc.), Cerius2.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Hybridization of Nucleic Acids

The invention provides isolated or recombinant nucleic acids that hybridize under stringent conditions to an exemplary sequence of the invention, e.g., SEQ ID NO:1, SEQ ID NO:3, SEQ ID NO:5, SEQ ID NO:7, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56. The stringent conditions can be highly stringent conditions, medium stringent conditions, low stringent conditions, including the high and reduced stringency conditions described herein. In alternative embodiments, nucleic acids of the invention as defined by their ability to hybridize under stringent conditions can be between about five residues and the full length of a sequence of the invention; e.g., they can be at least 5, 10, 15, 20, 25, 30, 35, 40, 50, 55, 60, 65, 70, 75, 80, 90, 100, 150, 200, 250, 300, 350, 400 residues in length. Nucleic acids shorter than full length are also included. These nucleic acids are useful as, e.g., hybridization probes, labeling probes, PCR oligonucleotide probes, iRNA, antisense or sequences encoding antibody binding peptides (epitopes), motifs, active sites and the like.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10x Denhardt's, and 0.5 mg/ml polyriboadenylic acid. Approximately $2 \times 10^7$ cpm (specific activity $4-9 \times 10^8$ cpm/ug) of $^{32}P$ end-labeled oligonucleotide probe are then added to the solution. After 12–16 hours of incubation, the membrane is washed for 30 minutes at room temperature in 1xSET (150 mM NaCl, 20 mM Tris hydrochloride, pH 7.8, 1 mM $Na_2EDTA$) containing 0.5% SDS, followed by a 30 minute wash in fresh 1xSET at $T_m-10°$ C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, $T_m$, is the temperature (under defined ionic strength and pH) at which 50% of the target sequence hybridizes to a perfectly complementary probe. Very stringent conditions are selected to be equal to or about 5° C. lower than the $T_m$ for a particular probe. The melting temperature of the probe may be calculated using the following formulas:

For probes between 14 and 70 nucleotides in length the melting temperature ($T_m$) is calculated using the formula: $T_m=81.5+16.6(\log[Na+])+0.41$ (fraction G+C)−(600/N) where N is the length of the probe.

If the hybridization is carried out in a solution containing formamide, the melting temperature may be calculated using the equation: $T_m=81.5+16.6(\log[Na+])+0.41$(fraction G+C)−(0.63% formamide)−(600/N) where N is the length of the probe.

Prehybridization may be carried out in 6xSSC,5x Denhardt's reagent,0.5% SDS, 100 µg denatured fragmented salmon sperm DNA or 6xSSC, 5x Denhardt's reagent, 0.5% SDS, 100 µg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15–25° C. below the $T_m$. For shorter probes, such as oligonucleotide probes, the hybridization may be conducted at 5–10° C. below the $T_m$. Typically, for hybridizations in 6xSSC, the hybridization is conducted at approximately 68° C. Usually, for hybridizations in 50% formamide containing solutions, the hybridization is conducted at approximately 42° C.

All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2xSSC, 0.1% SDS at room temperature for 15 minutes (low stringency); 0.1xSSC, 0.5% SDS at room temperature for 30 minutes to 1 hour (moderate stringency); 0.1xSSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1xSSC at room temperature. The examples above are merely illustrative of one set of conditions that can be used to wash filters. One of skill in the art would know that there are numerous recipes for different stringency washes. Some other examples are given below.

Nucleic acids which have hybridized to the probe are identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2xSSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6xSSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

For example, the preceding methods may be used to isolate nucleic acids having a sequence with at least about 97%, at least 95%, at least 90%, at least 85%, at least 80%, at least 75%, at least 70%, at least 65%, at least 60%, at least 55%, or at least 50% homology to a nucleic acid sequence of the invention, or fragments comprising at least about 10, 15, 20, 25, 30, 35, 40, 50, 75, 100, 150, 200, 300, 400, or 500 consecutive bases thereof, and the sequences complementary thereto. Homology can be measured using an alignment algorithm. For example, the homologous polynucleotides may have a coding sequence which is a naturally occurring allelic variant of one of the coding sequences described herein. Such allelic variants may have a substitution, deletion or addition of one or more nucleotides when compared to the nucleic acids of the invention or the sequences complementary thereto.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

Probes derived from sequences near the 3' or 5' ends of a nucleic acid sequence of the invention can also be used in chromosome walking procedures to identify clones containing additional, e.g., genomic sequences. Such methods allow the isolation of genes which encode additional proteins of interest from the host organism.

In one aspect, nucleic acid sequences of the invention are used as probes to identify and isolate related nucleic acids.

In some aspects, the so-identified related nucleic acids may be cDNAs or genomic DNAs from organisms other than the one from which the nucleic acid of the invention was first isolated. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter. Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM NaH2PO4, pH 7.0, 5.0 mM Na2EDTA, 0.5% SDS, 10× Denhardt's, and 0.5 mg/ml polyriboadenylic acid. Approximately 2×10$^7$ cpm (specific activity 4–9×10$^8$ cpm/ug) of 32P end-labeled oligonucleotide probe are then added to the solution. After 12–16 hours of incubation, the membrane is washed for 30 minutes at room temperature (RT) in 1×SET (150 mM NaCl, 20 mM Tris hydrochloride, pH 7.8, 1 mM Na2EDTA) containing 0.5% SDS, followed by a 30 minute wash in fresh 1×SET at Tm–10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following exemplary formulas. For probes between 14 and 70 nucleotides in length the melting temperature (Tm) is calculated using the formula: Tm=81.5+16.6(log [Na+])+0.41(fraction G+C)−(600/N) where N is the length of the probe. If the hybridization is carried out in a solution containing formamide, the melting temperature may be calculated using the equation: Tm=81.5+16.6(log [Na+])+0.41(fraction G+C)−(0.63% formamide)−(600/N) where N is the length of the probe. Prehybridization may be carried out in 6× SSC, 5×Denhardt's reagent, 0.5% SDS, 100 μg denatured fragmented salmon sperm DNA or 6×SSC, 5× Denhardt's reagent, 0.5% SDS, 100μg denatured fragmented salmon sperm DNA, 50% formamide. Formulas for SSC and Denhardt's and other solutions are listed, e.g., in Sambrook.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15–25° C. below the Tm. For shorter probes, such as oligonucleotide probes, the hybridization may be conducted at 5–10° C. below the Tm. In one aspect, hybridizations in 6×SSC are conducted at approximately 68° C. In one aspect, hybridizations in 50% formamide containing solutions are conducted at approximately 42° C. All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes.

Nucleic acids which have hybridized to the probe can be identified by autoradiography or other conventional techniques. The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. An example of "moderate" hybridization conditions is when the above hybridization is conducted at 55° C. An example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

These probes and methods of the invention can be used to isolate nucleic acids having a sequence with at least about 99%, 98%, 97%, at least 95%, at least 90%, at least 85%, at least 80%, at least 75%, at least 70%, at least 65%, at least 60%, at least 55%, or at least 50% homology to a nucleic acid sequence of the invention comprising at least about 10, 15, 20, 25, 30, 35, 40, 50, 75, 100, 150, 200, 250, 300, 350, 400, 500, 550, 600, 650, 700, 750, 800, 850, 900, 950, 1000, or more consecutive bases thereof, and the sequences complementary thereto. Homology may be measured using an alignment algorithm, as discussed herein. For example, the homologous polynucleotides may have a coding sequence which is a naturally occurring allelic variant of one of the coding sequences described herein. Such allelic variants may have a substitution, deletion or addition of one or more nucleotides when compared to a nucleic acid of the invention.

Additionally, the probes and methods of the invention may be used to isolate nucleic acids which encode polypeptides having at least about 99%, at least 95%, at least 90%, at least 85%, at least 80%, at least 75%, at least 70%, at least 65%, at least 60%, at least 55%, or at least 50% sequence identity (homology) to a polypeptide of the invention comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters, or a BLAST 2.2.2 program with exemplary settings as set forth herein).

Oligonucleotides Probes and Methods for Using Them

The invention also provides nucleic acid probes for identifying nucleic acids encoding a polypeptide with P450 activity. In one aspect, the probe comprises at least 10 consecutive bases of a sequence as set forth in an exemplary sequence of the invention. Alternatively, a probe of the invention can be at least about 5, 6, 7, 8 or 9 to about 40, about 10 to 50, about 20 to 60 about 30 to 70, consecutive bases of a sequence of the invention. The probes identify a nucleic acid by binding or hybridization. The probes can be used in arrays of the invention, see discussion below, including, e.g., capillary arrays. The probes of the invention can also be used to isolate other nucleic acids or polypeptides.

The probes of the invention can be used to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences present in the sample. Where necessary, conditions which permit the probe to specifically hybridize to complementary sequences may be determined by placing the probe in contact with complementary sequences from samples known to contain the complementary sequence, as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids (see discussion on specific hybridization conditions).

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product. Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel and Sambrook.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). In one aspect, the probes comprise oligonucleotides. In one aspect, the amplification reaction may comprise a PCR reaction. PCR protocols are described in Ausubel and Sambrook (see discussion on amplification reactions). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the 3' or 5' ends of a nucleic acid sequence of the invention can also be used in chromosome walking procedures to identify clones containing additional, e.g., genomic sequences. Such methods allow the isolation of genes which encode additional proteins of interest from the host organism. In one aspect, nucleic acid sequences of the invention are used as probes to identify and isolate related nucleic acids.

In some aspects, the so-identified related nucleic acids may be cDNAs or genomic DNAs from organisms other than the one from which the nucleic acid of the invention was first isolated. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter. Hybridization may be carried out under conditiulons of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM NaH$_2$PO4, pH 7.0, 5.0 mM Na$_2$EDTA, 0.5% SDS, 10× Denhardt's, and 0.5 mg/ml polyriboadenylic acid. Approximately 2×10$^7$ cpm (specific activity 4–9×10$^8$ cpm/ug) of 32P end-labeled oligonucleotide probe are then added to the solution. After 12–16 hours of incubation, the membrane is washed for 30 minutes at room temperature (RT) in 1×SET (150 mM NaCl, 20 mM Tris hydrochloride, pH 7.8, 1 mM Na$_2$EDTA) containing 0.5% SDS, followed by a 30 minute wash in fresh 1×SET at Tm–10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following exemplary formulas. For probes between 14 and 70 nucleotides in length the melting temperature (Tm) is calculated using the formula: Tm=81.5+16.6(log [Na+])+0.41(fraction G+C)–(600/N) where N is the length of the probe. If the hybridization is carried out in a solution containing formamide, the melting temperature may be calculated using the equation: Tm=81.5+16.6(log [Na+])+0.41(fraction G+C)–(0.63% formamide)–(600/N) where N is the length of the probe. Prehybridization may be carried out in 6×SSC, 5× Denhardt's reagent, 0.5% SDS, 100 µg denatured fragmented salmon sperm DNA or 6×SSC, 5× Denhardt's reagent, 0.5% SDS, 100 µg denatured fragmented salmon sperm DNA, 50% formamide. Formulas for SSC and Denhardt's and other solutions are listed, e.g., in Sambrook.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15–25° C. below the Tm. For shorter probes, such as oligonucleotide probes, the hybridization may be conducted at 5–10° C. below the Tm. In one aspect, hybridizations in 6×SSC are conducted at approximately 68° C. In one aspect, hybridizations in 50% formamide containing solutions are conducted at approximately 42° C. All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes.

Nucleic acids which have hybridized to the probe can be identified by autoradiography or other conventional techniques. The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. An example of "moderate" hybridization conditions is when the above hybridization is conducted at 55° C. An example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

These probes and methods of the invention can be used to isolate nucleic acids having a sequence with at least about 99%, 98%, 97%, at least 95%, at least 90%, at least 85%, at least 80%, at least 75%, at least 70%, at least 65%, at least 60%, at least 55%, or at least 50% homology to a nucleic acid sequence of the invention comprising at least about 10, 15, 20, 25, 30, 35, 40, 50, 75, 100, 150, 200, 250, 300, 350, 400, 500, 550, 600, 650, 700, 750, 800, 850, 900, 950, 1000, or more consecutive bases thereof, and the sequences complementary thereto. Homology may be measured using an alignment algorithm, as discussed herein. For example, the homologous polynucleotides may have a coding sequence which is a naturally occurring allelic variant of one of the coding sequences described herein. Such allelic variants may have a substitution, deletion or addition of one or more nucleotides when compared to a nucleic acid of the invention.

Additionally, the probes and methods of the invention may be used to isolate nucleic acids which encode polypeptides having at least about 99%, at least 95%, at least 90%, at least 85%, at least 80%, at least 75%, at least 70%, at least 65%, at least 60%, at least 55%, or at least 50% sequence identity (homology) to a polypeptide of the invention comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters, or a BLAST 2.2.2 program with exemplary settings as set forth herein).

Inhibiting Expression of P450

The invention further provides for nucleic acids complementary to (e.g., antisense sequences to) the nucleic acid sequences of the invention. Antisense sequences are capable of inhibiting the transport, splicing or transcription of P450-encoding genes. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind P450 gene or message, in either case preventing or inhibiting the production or function of P450. The association can be through sequence specific hybridization. Another useful class of inhibitors includes oligonucleotides which cause inactivation or cleavage of P450 message. The oligonucleotide can have enzyme activity which causes such cleavage, such as ribozymes. The oligonucleotide can be chemically modified or conjugated to an enzyme or composition capable of cleaving the complementary nucleic acid. One may screen a pool of many different such oligonucleotides for those with the desired activity.

Antisense Oligonucleotides

The invention provides antisense oligonucleotides capable of binding P450 message which can inhibit proteolytic activity by targeting mRNA. Strategies for designing antisense oligonucleotides are well described in the scientific and patent literature, and the skilled artisan can design such P450 oligonucleotides using the novel reagents of the invention. For example, gene walking/RNA mapping protocols to screen for effective antisense oligonucleotides are well known in the art, see, e.g., Ho (2000) Methods Enzymol. 314:168–183, describing an RNA mapping assay, which is based on standard molecular techniques to provide an easy and reliable method for potent antisense sequence selection. See also Smith (2000) Eur. J. Pharm. Sci. 11: 191–198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol Appl Pharmacol 144:189□197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene (methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense P450 sequences of the invention (see, e.g., Gold (1995) J. of Biol. Chem. 270:13581–13584).

Inhibitory Ribozymes

The invention provides for with ribozymes capable of binding P450 message which can inhibit proteolytic activity by targeting mRNA. Strategies for designing ribozymes and selecting the P450-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary basepairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it is typically released from that RNA and so can bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The enzymatic ribozyme RNA molecule can be formed in a hammerhead motif, but may also be formed in the motif of a hairpin, hepatitis delta virus, group I intron or RnaseP-like RNA (in association with an RNA guide sequence). Examples of such hammerhead motifs are described by Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

Modification of Nucleic Acids

The invention provides methods of generating variants of the nucleic acids of the invention, e.g., those encoding a P450 enzyme methods can be repeated or used in various combinations to generate P450 enzymes having an altered or different activity or an altered or different stability from that of a P450 encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

A nucleic acid of the invention can be altered by any means. For example, random or stochastic methods, or, non-stochastic, or "directed evolution," methods, see, e.g., U.S. Pat. No. 6,361,974. Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photoactivated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) Proc. Natl. Acad. Sci. USA 89:5467–5471; or, combinatorial multiple cassette mutagenesis, see, e.g., Crameri (1995) Biotechniques 18:194–196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturated Mutagenesis™ (GSSM™), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The following publications describe a variety of recursive recombination procedures and/or methods which can be incorporated into the methods of the invention: Stemmer (1999) "Molecular breeding of viruses for targeting and other clinical properties" Tumor Targeting 4:1–4; Ness (1999) Nature Biotechnology 17:893–896; Chang (1999) "Evolution of a cytokine using DNA family shuffling" Nature Biotechnology 17:793–797; Minshull (1999) "Protein evolution by molecular breeding" Current Opinion in Chemical Biology 3:284–290; Christians (1999) "Directed evolution of thymidine kinase for AZT phosphorylation using DNA family shuffling" Nature Biotechnology 17:259–264; Crameri (1998) "DNA shuffling of a family of genes from diverse species accelerates directed evolution" Nature 391:288–291; Crameri (1997) "Molecular evolution of an arsenate detoxification pathway by DNA shuffling," Nature Biotechnology 15:436–438; Zhang (1997) "Directed evolution of an effective fucosidase from a galactosidase by DNA shuffling and screening" Proc. Natl. Acad. Sci. USA 94:4504–4509; Patten et al. (1997) "Applications of DNA Shuffling to Pharmaceuticals and Vaccines" Current Opinion in Biotechnology 8:724–733; Crameri et al. (1996) "Construction and evolution of antibody-phage libraries by DNA shuffling" Nature Medicine 2:100–103; Gates et al. (1996) "Affinity selective isolation of ligands from peptide libraries through display on a lac repressor 'headpiece dimer'" Journal of Molecular Biology 255:373–386; Stemmer (1996) "Sexual PCR and Assembly PCR" In: The Encyclopedia of Molecular Biology. VCH Publishers, New York. pp. 447–457; Crameri and Stemmer (1995) "Combinatorial multiple cassette mutagenesis creates all the permutations of mutant and wildtype cassettes" BioTechniques 18:194–195; Stemmer et al. (1995) "Single-step assembly of a gene and entire plasmid form large numbers of oligodeoxyribonucleotides" Gene, 164:49–53; Stemmer (1995) "The Evolution of Molecular Computation" Science 270: 1510; Stemmer (1995) "Searching Sequence Space" Bio/Technology 13:549–553; Stemmer (1994) "Rapid evolution of a protein in vitro by DNA shuffling" Nature 370:389–391; and Stemmer (1994) "DNA shuffling by random fragmentation and reassembly: In vitro recombination for molecular evolution." Proc. Natl. Acad. Sci. USA 91:10747–10751.

Mutational methods of generating diversity include, for example, site-directed mutagenesis (Ling et al. (1997) "Approaches to DNA mutagenesis: an overview" Anal Biochem. 254(2): 157–178; Dale et al. (1996) "Oligonucleotide-directed random mutagenesis using the phosphorothioate method" Methods Mol. Biol. 57:369–374; Smith (1985) "In vitro mutagenesis" Ann. Rev. Genet. 19:423–462; Botstein & Shortle (1985) "Strategies and applications of in vitro mutagenesis" Science 229:1193–1201; Carter (1986) "Site-directed mutagenesis" Biochem. J. 237:1–7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488–492; Kunkel et al. (1987) "Rapid and efficient site-specific mutagenesis without phenotypic selection" Methods in Enzymol. 154, 367–382; and Bass et al. (1988) "Mutant Trp repressors with new DNA-binding specificities" Science 242:240–245); oligonucleotide-directed mutagenesis (Methods in Enzymol. 100: 468–500 (1983); Methods in Enzymol. 154: 329–350 (1987); Zoller & Smith (1982) "Oligonucleotide-directed mutagenesis using M13-derived vectors: an efficient and general procedure for the production of point mutations in any DNA fragment" Nucleic Acids Res. 10:6487–6500; Zoller & Smith (1983) "Oligonucleotide-directed mutagenesis of DNA fragments cloned into M13 vectors" Methods in Enzymol. 100:468–500; and Zoller & Smith (1987) Oligonucleotide-directed mutagenesis: a simple method using two oligonucleotide primers and a single-stranded DNA template" Methods in Enzymol. 154: 329–350); phosphorothioate-modified DNA mutagenesis (Taylor et al. (1985) "The use of phosphorothioate-modified DNA in restriction enzyme reactions to prepare nicked DNA" Nucl. Acids Res. 13: 8749–8764; Taylor et al. (1985) "The rapid generation of oligonucleotide-directed mutations at high frequency using phosphorothioate-modified DNA" Nucl. Acids Res. 13: 8765–8787 (1985); Nakamaye (1986) "Inhibition of restriction endonuclease Nci I cleavage by phosphorothioate groups and its application to oligonucleotide-directed mutagenesis" Nucl. Acids Res. 14: 9679–9698; Sayers et al. (1988) "Y-T Exonucleases in phosphorothioate-based oligonucleotide-directed mutagenesis" Nucl. Acids Res. 16:791–802; and Sayers et al. (1988) "Strand specific cleavage of phosphorothioate-containing DNA by reaction with restriction endonucleases in the presence of ethidium bromide" Nucl. Acids Res. 16: 803–814); mutagenesis using gapped duplex DNA (Kramer et al. (1984) "The gapped duplex DNA approach to oligonucleotide-directed mutation construction" Nucl. Acids Res. 12: 9441–9456; Kramer & Fritz (1987) Methods in Enzymol. "Oligonucleotide-directed construction of mutations via gapped duplex DNA" 154:350–367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987–6999).

Additional protocols used in the methods of the invention include point mismatch repair (Kramer (1984) "Point Mismatch Repair" Cell 38:879–887), mutagenesis using repair-deficient host strains (Carter et al. (1985) "Improved oligonucleotide site-directed mutagenesis using M13 vectors" Nucl. Acids Res. 13: 4431–4443; and Carter (1987) "Improved oligonucleotide-directed mutagenesis using M13 vectors" Methods in Enzymol. 154: 382–403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415–423), mutagenesis by total gene synthesis (Nambiar et al. (1984) "Total synthesis and cloning of a gene coding for the ribonuclease S protein" Science 223: 1299–1301; Sakamar and Khorana (1988) "Total synthesis and expression of a gene for the a-subunit of bovine rod outer segment guanine nucleotide-binding protein (transducin)" Nucl. Acids Res. 14: 6361–6372; Wells et al. (1985) "Cassette mutagenesis: an efficient method for generation of multiple mutations at defined sites" Gene 34:315–323; and Grundstrom et al. (1985) "Oligonucieotide-directed mutagenesis by microscale 'shot-gun' gene synthesis" Nucl. Acids Res. 13: 3305–3316), double-strand break repair (Mandecki (1986); Arnold (1993) "Protein engineering for unusual environments" Current Opinion in Biotechnology 4:450–455. "Oligonucleotide-directed double-strand break repair in plasmids of *Escherichia coli*: a method for site-specific mutagenesis" Proc. Natl. Acad. Sci. USA, 83:7177–7181). Additional details on many of the above methods can be found in Methods in Enzymology Volume 154, which also describes useful controls for trouble-shooting problems with various mutagenesis methods. See also U.S. Pat. Nos. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library ImLmunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Certain U.S. applications provide additional details regarding various diversity generating methods, including "SHUFFLING OF CODON ALTERED GENES" by Patten et al. filed Sep. 28, 1999, (U.S. Ser. No. 09/407,800); "EVOLUTION OF WHOLE CELLS AND ORGANISMS BY RECURSIVE SEQUENCE RECOMBINATION" by del Cardayre et al., filed Jul. 15, 1998 (U.S. Ser. No. 09/166,188), and Jul. 15, 1999 (U.S. Ser. No. 09/354,922); "OLIGONUCLEOTIDE MEDIATED NUCLEIC ACID RECOMBINATION" by Crameri et al., filed Sep. 28, 1999 (U.S. Ser. No. 09/408,392), and "OLIGONUCLEOTIDE MEDIATED NUCLEIC ACID RECOMBINATION" by Crameri et al., filed Jan. 18, 2000 (PCT/US00/01203); "USE OF CODON-VARIED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g. "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549).

Non-stochastic, or "directed evolution," methods include, e.g., saturation mutagenesis (GSSM), synthetic ligation reassembly (SLR), or a combination thereof are used to modify the nucleic acids of the invention to generate P450 with new or altered properties (e.g., activity under highly acidic or alkaline conditions, high temperatures, and the like). Polypeptides encoded by the modified nucleic acids can be screened for an activity before testing for proteolytic or other activity. Any testing modality or protocol can be used, e.g., using a capillary array platform. See, e.g., U.S. Pat. Nos. 6,361,974; 6,280,926; 5,939,250.

Saturation Mutagenesis, or, GSSM™

In one aspect of the invention, non-stochastic gene modification, a "directed evolution process," is used to generate P450s with new or altered properties. Variations of this method have been termed "gene site-saturation mutagenesis," "site-saturation mutagenesis," "saturation mutagenesis" or simply GSSM™. It can be used in combination with other mutagenization processes. See, e.g., U.S. Pat. Nos. 6,171,820; 6,238,884. In one aspect, GSSM™ comprises providing a template polynucleotide and a plurality of oligonucleotides, wherein each oligonucleotide comprises a sequence homologous to the template polynucleotide, thereby targeting a specific sequence of the template polynucleotide, and a sequence that is a variant of the homologous gene; generating progeny polynucleotides comprising non-stochastic sequence variations by replicating the template polynucleotide with the oligonucleotides, thereby generating polynucleotides comprising homologous gene sequence variations.

In one aspect, codon primers containing a degenerate N, N, G/T sequence are used to introduce point mutations into a polynucleotide, so as to generate a set of progeny polypeptides in which a full range of single amino acid substitutions is represented at each amino acid position, e.g., an amino acid residue in an enzyme active site or ligand binding site targeted to be modified. These oligonucleotides can comprise a contiguous first homologous sequence, a degenerate N, N, G/T sequence, and, optionally, a second homologous sequence. The downstream progeny translational products from the use of such oligonucleotides include all possible amino acid changes at each amino acid site along the polypeptide, because the degeneracy of the N, N, G/T sequence includes codons for all 20 amino acids. In one aspect, one such degenerate oligonucleotide (comprised of, e.g., one degenerate N, N, G/T cassette) is used for subjecting each original codon in a parental polynucleotide template to a full range of codon substitutions. In another aspect, at least two degenerate cassettes are used—either in the same oligonucleotide or not, for subjecting at least two original codons in a parental polynucleotide template to a full range of codon substitutions. For example, more than one N, N, G/T sequence can be contained in one oligonucleotide to introduce amino acid mutations at more than one site. This plurality of N, N, G/T sequences can be directly contiguous, or separated by one or more additional nucleotide sequence(s). In another aspect, oligonucleotides serviceable for introducing additions and deletions can be used either alone or in combination with the codons containing an N, N, G/T sequence, to introduce any combination or permutation of amino acid additions, deletions, and/or substitutions.

In one aspect, simultaneous mutagenesis of two or more contiguous amino acid positions is done using an oligonucleotide that contains contiguous N, N, G/T triplets, i.e. a degenerate (N, N, G/T)n sequence. In another aspect, degenerate cassettes having less degeneracy than the N, N, G/T sequence are used. For example, it may be desirable in some instances to use (e.g. in an oligonucleotide) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N, N, N triplet sequence.

In one aspect, use of degenerate triplets (e.g., N, N, G/T triplets) allows for systematic and easy generation of a full range of possible natural amino acids (for a total of 20 amino acids) into each and every amino acid position in a polypeptide (in alternative aspects, the methods also include generation of less than all possible substitutions per amino acid residue, or codon, position). For example, for a 100 amino acid polypeptide, 2000 distinct species (i.e. 20 possible amino acids per position×100 amino acid positions) can be generated. Through the use of an oligonucleotide or set of oligonucleotides containing a degenerate N, N, G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a non-degenerate oligonucleotide in site-directed mutagenesis leads to only one progeny polypeptide product per reaction vessel. Nondegenerate oligonucleotides can optionally be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In one aspect, each saturation mutagenesis reaction vessel contains polynucleotides encoding at least 20 progeny polypeptide (e.g., P450s) molecules such that all 20 natural amino acids are represented at the one specific amino acid position corresponding to the codon position mutagenized in the parental polynucleotide (other aspects use less than all 20 natural combinations). The 32-fold degenerate progeny polypeptides generated from each saturation mutagenesis reaction vessel can be subjected to clonal amplification (e.g. cloned into a suitable host, e.g., *E. coli* host, using, e.g., an expression vector) and subjected to expression screening. When an individual progeny polypeptide is identified by screening to display a favorable change in property (when compared to the parental polypeptide, such as increased proteolytic activity under alkaline or acidic conditions), it can be sequenced to identify the correspondingly favorable amino acid substitution contained therein.

In one aspect, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e. 2 at each of three positions) and no change at any position.

In another aspect, site-saturation mutagenesis can be used together with another stochastic or non-stochastic means to vary sequence, e.g., synthetic ligation reassembly (see below), shuffling, chimerization, recombination and other mutagenizing processes and mutagenizing agents. This invention provides for the use of any mutagenizing process(es), including saturation mutagenesis, in an iterative manner.

Synthetic Ligation Reassembly (SLR)

The invention provides a non-stochastic gene modification system termed "synthetic ligation reassembly," or simply "SLR," a "directed evolution process," to generate P450s with new or altered properties. SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. patent application Ser. No. (USSN) 09/332,835 entitled "Synthetic Ligation Reassembly in Directed Evolution" and filed on Jun. 14, 1999 ("U.S. Ser. No. 09/332,835"). In one aspect, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over 10100 different chimeras. SLR can be used to generate libraries comprised of over 101000 different progeny chimeras. Thus, aspects of the present invention include non-stochastic methods of producing a set of finalized chimeric nucleic acid molecule shaving an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g. T4 DNA ligase), to achieve covalent bonding of the building pieces.

In one aspect, the design of the oligonucleotide building blocks is obtained by analyzing a set of progenitor nucleic acid sequence templates that serve as a basis for producing a progeny set of finalized chimeric polynucleotides. These parental oligonucleotide templates thus serve as a source of sequence information that aids in the design of the nucleic acid building blocks that are to be mutagenized, e.g., chimerized or shuffled. In one aspect of this method, the sequences of a plurality of parental nucleic acid templates are aligned in order to select one or more demarcation points. The demarcation points can be located at an area of homology, and are comprised of one or more nucleotides. These demarcation points are preferably shared by at least two of the progenitor templates. The demarcation points can thereby be used to delineate the boundaries of oligonucleotide building blocks to be generated in order to rearrange the parental polynucleotides. The demarcation points identified and selected in the progenitor molecules serve as potential chimerization points in the assembly of the final chimeric progeny molecules. A demarcation point can be an area of homology (comprised of at least one homologous nucleotide base) shared by at least two parental polynucleotide sequences. Alternatively, a demarcation point can be an area of homology that is shared by at least half of the parental polynucleotide sequences, or, it can be an area of homology that is shared by at least two thirds of the parental polynucleotide sequences. Even more preferably a serviceable demarcation points is an area of homology that is shared by at least three fourths of the parental polynucleotide sequences, or, it can be shared by at almost all of the parental polynucleotide sequences. In one aspect, a demarcation point is an area of homology that is shared by all of the parental polynucleotide sequences.

In one aspect, a ligation reassembly process is performed exhaustively in order to generate an exhaustive library of progeny chimeric polynucleotides. In other words, all possible ordered combinations of the nucleic acid building blocks are represented in the set of finalized chimeric nucleic acid molecules. At the same time, in another aspect, the assembly order (i.e. the order of assembly of each building block in the 5' to 3 sequence of each finalized chimeric nucleic acid) in each combination is by design (or non-stochastic) as described above. Because of the non-stochastic nature of this invention, the possibility of unwanted side products is greatly reduced.

In another aspect, the ligation reassembly method is performed systematically. For example, the method is performed in order to generate a systematically compartmentalized library of progeny molecules, with compartments that can be screened systematically, e.g. one by one. In other words this invention provides that, through the selective and judicious use of specific nucleic acid building blocks, coupled with the selective and judicious use of sequentially stepped assembly reactions, a design can be achieved where specific sets of progeny products are made in each of several reaction vessels. This allows a systematic examination and screening procedure to be performed. Thus, these methods allow a potentially very large number of progeny molecules to be examined systematically in smaller groups. Because of its ability to perform chimerizations in a manner that is highly flexible yet exhaustive and systematic as well, particularly when there is a low level of homology among the progenitor molecules, these methods provide for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. The saturation mutagenesis and optimized directed evolution methods also can be used to generate different progeny molecular species. It is appreciated that the invention provides freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecular homologous demarcation points and thus to allow an increased number of couplings to be achieved among the building blocks, which in turn allows a greater number of progeny chimeric molecules to be generated.

In another aspect, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g. by mutagenesis) or in an in vivo process (e.g. by utilizing the gene splicing ability of a host organism). It is appreciated that in many instances the introduction of these nucleotides may also be desirable for many other reasons in addition to the potential benefit of creating a serviceable demarcation point.

In one aspect, a nucleic acid building block is used to introduce an intron. Thus, functional introns are introduced into a man-made gene manufactured according to the methods described herein. The artificially introduced intron(s) can be functional in a host cells for gene splicing much in the way that naturally-occurring introns serve functionally in gene splicing.

Optimized Directed Evolution System

The invention provides a non-stochastic gene modification system termed "optimized directed evolution system" to generate P450s with new or altered properties. Optimized directed evolution is directed to the use of repeated cycles of reductive reassortment, recombination and selection that allow for the directed molecular evolution of nucleic acids through recombination. Optimized directed evolution allows generation of a large population of evolved chimeric sequences, wherein the generated population is significantly enriched for sequences that have a predetermined number of crossover events.

A crossover event is a point in a chimeric sequence where a shift in sequence occurs from one parental variant to another parental variant. Such a point is normally at the juncture of where oligonucleotides from two parents are ligated together to form a single sequence. This method allows calculation of the correct concentrations of oligonucleotide sequences so that the final chimeric population of sequences is enriched for the chosen number of crossover events. This provides more control over choosing chimeric variants having a predetermined number of crossover events.

In addition, this method provides a convenient means for exploring a tremendous amount of the possible protein variant space in comparison to other systems. Previously, if one generated, for example, 1013 chimeric molecules during a reaction, it would be extremely difficult to test such a high number of chimeric variants for a particular activity. Moreover, a significant portion of the progeny population would have a very high number of crossover events which resulted in proteins that were less likely to have increased levels of a particular activity. By using these methods, the population of chimerics molecules can be enriched for those variants that have a particular number of crossover events. Thus, although one can still generate 1013 chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

One method for creating a chimeric progeny polynucleotide sequence is to create oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. Additional information can also be found, e.g., in U.S. Ser. No. 09/332,835; U.S. Pat. No. 6,361,974. The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a $\frac{1}{3}$ chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. By utilizing these methods, one can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events. These methods are directed to the use of repeated cycles of reductive reassortment, recombination and selection that allow for the directed molecular evolution of a nucleic acid encoding a polypeptide through recombination. This system allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. The method allows calculation of the correct concentrations of oligonucleotide sequences so that the final chimeric population of sequences is enriched for the chosen number of crossover events. This provides more control over choosing chimeric variants having a predetermined number of crossover events.

In addition, these methods provide a convenient means for exploring a tremendous amount of the possible protein variant space in comparison to other systems. By using the methods described herein, the population of chimerics molecules can be enriched for those variants that have a particular number of crossover events. Thus, although one can still generate 1013 chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

In one aspect, the method creates a chimeric progeny polynucleotide sequence by creating oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. See also U.S. Ser. No. 09/332,835.

The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a $\frac{1}{3}$ chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. One can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events.

Determining Crossover Events

Aspects of the invention include a system and software that receive a desired crossover probability density function (PDF), the number of parent genes to be reassembled, and the number of fragments in the reassembly as inputs. The output of this program is a "fragment PDF" that can be used to determine a recipe for producing reassembled genes, and the estimated crossover PDF of those genes. The processing described herein is preferably performed in MATLABâ (The Mathworks, Natick, Mass.) a programming language and development environment for technical computing.

Iterative Processes

In practicing the invention, these processes can be iteratively repeated. For example a nucleic acid (or, the nucleic acid) responsible for an altered P450 phenotype is identified, re-isolated, again modified, re-tested for activity. This process can be iteratively repeated until a desired phenotype is engineered. For example, an entire biochemical anabolic or catabolic pathway can be engineered into a cell, including proteolytic activity.

Similarly, if it is determined that a particular oligonucleotide has no affect at all on the desired trait (e.g., a new P450 phenotype), it can be removed as a variable by synthesizing larger parental oligonucleotides that include the sequence to be removed. Since incorporating the sequence within a larger sequence prevents any crossover events, there will no longer be any variation of this sequence in the progeny polynucleotides. This iterative practice of determining which oligonucleotides are most related to the desired trait, and which are unrelated, allows more efficient exploration all of the possible protein variants that might be provide a particular trait or activity.

In vivo Shuffling

In vivo shuffling of molecules is use in methods of the invention that provide variants of polypeptides of the invention, e.g., antibodies, P450s, and the like. In vivo shuffling can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In one aspect, the invention provides a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

Producing Sequence Variants

The invention also provides methods of making sequence variants of the nucleic acid and P450 sequences of the invention or isolating P450 using the nucleic acids and polypeptides of the invention. In one aspect, the invention provides for variants of an P450 gene of the invention, which can be altered by any means, including, e.g., random or stochastic methods, or, non-stochastic, or "directed evolution," methods, as described above.

The isolated variants may be naturally occurring. Variant can also be created in vitro. Variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures. Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. These nucleotide differences can result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described, e.g., in Leung, D. W., et al., Technique, 1:11–15, 1989) and Caldwell, R. C. & Joyce G. F., PCR Methods Applic., 2:28–33, 1992. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described, e.g., in Reidhaar-Olson (1988) Science 241: 53–57. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described, e.g., in Stemmer (1994) Proc. Natl. Acad. Sci. USA 91:10747–10751. Briefly, in such procedures a plurality of nucleic acids to be recombined are digested with DNase to generate fragments having an average size of 50–200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10–30 ng/:1 in a solution of 0.2 mM of each dNTP, 2.2 mM MgCl2, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50–55° C. for 30 seconds, 72° C. for 30 seconds (30–45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some aspects, random mutations in a sequence of interest are generated by propagating the sequence of interest in a bacterial strain, such as an E. Coli strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described, e.g., in PCT Publication No. WO 91/16427.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described, e.g., in Arkin (1992) Proc. Natl. Acad. Sci. USA 89:7811–7815.

In some aspects, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described, e.g., in Delegrave (1993) Biotechnology Res. 11:1548–1552. Random and site-directed mutagenesis are described, e.g., in Arnold (1993) Current Opinion in Biotechnology 4:450–455.

In some aspects, the variants are created using shuffling procedures wherein portions of a plurality of nucleic acids which encode distinct polypeptides are fused together to create chimeric nucleic acid sequences which encode chimeric polypeptides as described in, e.g., U.S. Pat. Nos. 5,965,408; 5,939,250.

The invention also provides variants of polypeptides of the invention comprising sequences in which one or more of the amino acid residues (e.g., of an exemplary polypeptide, such as SEQ ID NO:2) are substituted with a conserved or non-conserved amino acid residue (e.g., a conserved amino acid residue) and such substituted amino acid residue may or may not be one encoded by the genetic code. Conservative substitutions are those that substitute a given amino acid in a polypeptide by another amino acid of like characteristics. Thus, polypeptides of the invention include those with conservative substitutions of sequences of the invention, e.g., the exemplary SEQ ID NO:2, including but not limited to the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue. Other variants are those in which one or more of the amino acid residues of the polypeptides of the invention includes a substituent group.

Other variants within the scope of the invention are those in which the polypeptide is associated with another compound, such as a compound to increase the half-life of the polypeptide, for example, polyethylene glycol.

Additional variants within the scope of the invention are those in which additional amino acids are fused to the polypeptide, such as a leader sequence, a secretory sequence, a proprotein sequence or a sequence which facilitates purification, enrichment, or stabilization of the polypeptide.

In some aspects, the variants, fragments, derivatives and analogs of the polypeptides of the invention retain the same biological function or activity as the exemplary polypeptides, e.g., a proteolytic activity, as described herein. In other aspects, the variant, fragment, derivative, or analog includes a proprotein, such that the variant, fragment, derivative, or analog can be activated by cleavage of the proprotein portion to produce an active polypeptide.

Optimizing Codons to Achieve High Levels of Protein Expression in Host Cells

The invention provides methods for modifying P450-encoding nucleic acids to modify codon usage. In one aspect, the invention provides methods for modifying codons in a nucleic acid encoding an P450 to increase or decrease its expression in a host cell. The invention also provides nucleic acids encoding a P450 modified to increase its expression in a host cell, P450 so modified, and methods of making the modified P450s. The method comprises identifying a "non-preferred" or a "less preferred" codon in P450-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors of the invention include bacteria, yeast, fungi, plant cells, insect cells and mammalian cells. Thus, the invention provides methods for optimizing codon usage in all of these cells, codon-altered nucleic acids and polypeptides made by the codon-altered nucleic acids. Exemplary host cells include gram negative bacteria, such as *Escherichia coli* and *Pseudomonas fluorescens*; gram positive bacteria, such as *Streptomyces diversa, Lactobacillus gasseri, Lactococcus lactis, Lactococcus cremoris, Bacillus subtilis*. Exemplary host cells also include eukaryotic organisms, e.g., various yeast, such as Saccharomyces sp., including *Saccharomyces cerevisiae, Schizosaccharomyces pombe, Pichia pastoris*, and *Kluyveromyces lactis, Hansenula polymorpha, Aspergillus niger*, and mammalian cells and cell lines and insect cells and cell lines. Thus, the invention also includes nucleic acids and polypeptides optimized for expression in these organisms and species.

For example, the codons of a nucleic acid encoding a P450 isolated from a bacterial cell are modified such that the nucleic acid is optimally expressed in a bacterial cell different from the bacteria from which the P450 was derived, a yeast, a fungi, a plant cell, an insect cell or a mammalian cell. Methods for optimizing codons are well known in the art, see, e.g., U.S. Pat. No. 5,795,737; Baca (2000) Int. J. Parasitol. 30:113–118; Hale (1998) Protein Expr. Purif. 12:185–188; Narum (2001) Infect. Immun. 69:7250–7253. See also Narum (2001) Infect. Immun. 69:7250–7253, describing optimizing codons in mouse systems; Outchkourov (2002) Protein Expr. Purif. 24:18–24, describing optimizing codons in yeast; Feng (2000) Biochemistry 39:15399–15409, describing optimizing codons in *E. coli*; Humphreys (2000) Protein Expr. Purif. 20:252–264, describing optimizing codon usage that affects secretion in *E. coli*.

Transgenic Non-human Animals

The invention provides transgenic non-human animals comprising a nucleic acid, a polypeptide (e.g., P450), an expression cassette or vector or a transfected or transformed cell of the invention. The transgenic non-human animals can be, e.g., goats, rabbits, sheep, pigs, cows, rats and mice, comprising the nucleic acids of the invention. These animals can be used, e.g., as in vivo models to study P450 activity, or, as models to screen for modulators of P450 activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) J. Immunol. Methods 231:147–157, describing the production of recombinant proteins in the milk of transgenic dairy animals; Baguisi (1999) Nat. Biotechnol. 17:456–461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods of the invention. For example, in one aspect, the transgenic or modified animals of the invention comprise a "knockout animal," e.g., a "knockout mouse," engineered not to express or to be unable to express an P450.

Polypeptides and Peptides

The invention provides isolated or recombinant polypeptides having a sequence identity to an exemplary sequence of the invention, e.g., SEQ ID NO:2; SEQ ID NO:4; SEQ ID NO:6; SEQ ID NO:8, SEQ ID NO:10, SEQ ID NO:12, SEQ ID NO:14, SEQ ID NO:16, SEQ ID NO:18, SEQ ID NO:20; SEQ ID NO:22; SEQ ID NO:22; SEQ ID NO:26; SEQ ID NO:28, SEQ ID NO:30, SEQ ID NO:32, SEQ ID NO:34, SEQ ID NO:36; SEQ ID NO:38, SEQ ID NO:40, SEQ ID NO:42, SEQ ID NO:44, SEQ ID NO:46, SEQ ID NO:48, SEQ ID NO:50; SEQ ID NO:52; SEQ ID NO:54; SEQ ID NO:56. As discussed above, the identity can be over the full length of the polypeptide, or, the identity can be over a region of at least about 50, 60, 70, 80, 90, 100, 150, 200, 250, 300, 350, 400, 450, 500, 550, 600, 650, 700 or more residues. Polypeptides of the invention can also be shorter than the full length of exemplary polypeptides (e.g., SEQ ID NO:2; SEQ ID NO:4; SEQ ID NO:6; SEQ ID NO:8, SEQ ID NO:10, SEQ ID NO:12, SEQ ID NO:14, SEQ ID NO:16; SEQ ID NO:18, SEQ ID NO:20; SEQ ID NO:22; SEQ ID NO:22; SEQ ID NO:26; SEQ ID NO:28, SEQ ID NO:30, SEQ ID NO:32, SEQ ID NO:34, SEQ ID NO:36; SEQ ID NO:38, SEQ ID NO:40, SEQ ID NO:42, SEQ ID NO:44, SEQ ID NO:46, SEQ ID NO:48, SEQ ID NO:50; SEQ ID NO:52; SEQ ID NO:54; SEQ ID NO:56). In alternative aspects, the invention provides polypeptides (peptides, fragments) ranging in size between about 5 and the full length of a polypeptide, e.g., an enzyme, such as a P450; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, or more residues, e.g., contiguous residues of an exemplary P450 of the invention. Peptides of the invention can be useful as, e.g., labeling probes, antigens, toleragens, motifs, P450 active sites.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215–223; Horn (1980) Nucleic Acids Res. Symp. Ser. 225–232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3–13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has an P450 activity.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH2- for —C(=O)—NH—), aminomethylene (CH2—NH), ethylene, olefin (CH=CH), ether (CH2-O), thioether (CH2-S), tetrazole (CN4-), thiazole, retroamide, thioamide, or ester (see, e.g., Spatoia (1983) in Chemistry and Biochemistry of Amino Acids, Peptides and Proteins, Vol. 7, pp 267–357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; K- or L-p-methoxy-biphenylphenylalanine; D- or L-2-indole (alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3 (2-morpholinyl-(4-ethyl) carbodiimide or 1-ethyl-3(4-azonia-4,4-dimetholpentyl)carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl)propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gammacarboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W. H. Freeman and Company, New York (1993); Posttranslational Covalent Modification of Proteins, B. C. Johnson, Ed., Academic Press, New York, pp. 1–12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149–2154, 1963) (See also Stewart, J. M. and Young, J. D., Solid Phase Peptide Synthesis, 2nd Ed., Pierce Chemical Co., Rockford, Ill., pp. 11–12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

P450 Enzymes

P450 oxygenases, also sometimes referred to as P450 epoxidases (hereinafter "P450s") are oxidative enzymes that are widespread in nature and are involved in processes such as detoxifying xenobiotics, catabolism of unusual carbon sources and biosynthesis of secondary metabolites. Oxygenases activate molecular oxygen using an iron-heme center and utilize a redox electron shuttle to support the oxidation reaction. In bacteria, the electrons required to reduce the heme iron at the end of each reaction cycle are provided by a partner enzyme system, comprising ferredoxin (FDX) and ferredoxin reductase (FDR) activities. Examples of P450 are known to catalyze epoxidations. Epoxidations, in particular, are catalyzed by very few other enzyme classes. Using P450s to mediate this transformation allows stereochemical information to be introduced into an achiral molecule. The resultant chirality can then be transferred to other functionalities by opening the epoxide using a variety of nucleophiles (FIG. 3). Thus, the range of ultimate products is not limited to diols resulting from hydrolysis, but can be extended to amino alcohols, halohydrins and branched-chain alkyl moieties. Furthermore, this process occurs without the loss of material associated with kinetic resolution methods such as enzymatic epoxide hydrolysis.

The synthetic utility of chiral epoxides means that they have great commercial potential as intermediates in the synthesis of many fine chemicals and key drug intermediates. Therefore, P450s would potentially have applications in the synthesis of many high value compounds, including antibiotics, antivirals, anticancer agents, insecticides and herbicides.

For instance, Glycidol currently has application in the process-scale synthesis of the antihypertensive agent atenolol (ICI, FIG. 4B). Chiral epoxides also have application in the synthesis of the frontline antineoplastic agents docetaxel (FIG. 5A; Aventis,) and paclitaxel (BMS), which both proceed through cinnamate oxide. Stereospecific preparation of this key intermediate from a commercially viable starting material involves four steps. In contrast, an enzymatic synthesis would require only one step, the epoxidation of the readily available cinnamic acid, and so a partial biocatalytic approach to docetaxel may result in considerable cost savings. Similarly, synthesis of the anti-HIV agent amprenavir (Merck; FIG. 5B) also requires a chiral epoxide intermediate. A simple chemo-enzymatic synthesis of this crucial building block can be envisaged and may provide significant commercial advantages in the preparation of the drug. It is clear therefore, that an efficient and commercially viable route to chiral epoxides would have a significant impact; P450-catalyzed epoxidation could provide such a technology.

It is clear, therefore, that the potential exists to exploit the catalytic power and selectivity of P450s for the synthesis of chiral epoxides. However, to date there have been few reports of biocatalytic syntheses of epoxides. This is probably due to the difficulty in discovering suitable oxygenases from the limited biodiversity accessible through traditional methods.

One of those particular reactions of interest is epoxidation of alkene to form chiral epoxide using oxidative enzymes. Oxidative enzymes (also called epoxidase) such as P450s can efficiently catalyze the synthesis of epoxides with high stereospecificity and may therefore provide a commercial route to chiral epoxides. Therefore, the present invention relates to building a technology platform focused on the production of chiral epoxides by exploiting the catalytic power and selectivity of P450 enzymes. Preferably, the toolbox of enzymes necessary for this platform is obtained from environmental gene libraries. These oxidative enzymes will enable the development of chemo-enzymatic routes to pharmaceuticals such as antibiotics, antivirals, and anticancer agents, as well as agrochemicals and fine chemicals.

As used herein, the bioactivity of interest is activity as a catalyst for epoxidation reactions and, more preferably, activity as a catalyst for the epoxidation of alkenes. As used herein, biomolecule refers P450s.

Preferably, the first step of the efforts for discovering these oxidative enzymes involves developing sensitive, high throughput methods for the discovery of epoxide-forming P450s. To facilitate this effort, a variety of host strains must be provided to optimally support the in vivo synthesis of epoxides by P450s. These host strains may be obtained from host strain libraries. The combination of optimized assays and screening hosts can be applied to demonstrate that epoxidase biocatalysts can be obtained from environmental gene libraries. The host strain libraries and environmental gene libraries can be built using the technologies described in U.S. Pat. Nos. 5,958,672, 6,001,574 and 5,763,239.

Hybrid P450 Enzymes and Peptide Libraries

In one aspect, the invention provides hybrid P450 and fusion proteins, including peptide libraries, comprising sequences of the invention. The peptide libraries comprising sequences of the invention are used to isolate peptide inhibitors of targets (e.g., receptors, enzymes) and to identify formal binding partners of targets (e.g., ligands, such as cytokines, hormones and the like).

The field of biomolecule screening for biologically and therapeutically relevant compounds is rapidly growing. Relevant biomolecules that have been the focus of such screening include chemical libraries, nucleic acid libraries and peptide libraries, in search of molecules that either inhibit or augment the biological activity of identified target molecules. With particular regard to peptide libraries, the isolation of peptide inhibitors of targets and the identification of formal binding partners of targets has been a key focus. Screening of combinatorial libraries of potential drugs on therapeutically relevant target cells is a rapidly growing and important field. However, one particular problem with peptide libraries is the difficulty assessing whether any particular peptide has been expressed, and at what level, prior to determining whether the peptide has a biological effect. Thus, in order to express and subsequently screen functional peptides in cells, the peptides need to be expressed in sufficient quantities to overcome catabolic mechanisms such as proteolysis and transport out of the cytoplasm into endosomes.

In one aspect, the fusion proteins of the invention (e.g., the peptide moiety) are conformationally stabilized (relative to linear peptides) to allow a higher binding affinity for their cellular targets. The present invention provides fusions of P450s of the invention and other peptides, including known and random peptides, that are fused in such a manner that the structure of the P450s is not significantly perturbed and the peptide is metabolically or structurally conformationally stabilized. This allows the creation of a peptide library that is easily monitored, both for its presence within cells and its quantity.

Amino acid sequence variants of the invention can be characterized by the predetermined nature of the variation, a feature that sets them apart from naturally occurring allelic or interspecies variation of the P450 amino acid sequence. In one aspect, the variants of the invention exhibit the same qualitative biological activity as the naturally occurring analogue, although variants can also be selected which have modified characteristics. While the site or region for introducing an amino acid sequence variation is predetermined, the mutation per se need not be predetermined. For example, in order to optimize the performance of a mutation at a given site, random mutagenesis may be conducted at the target codon or region and the expressed P450 variants screened for the optimal combination of desired activity. Techniques for making substitution mutations at predetermined sites in DNA having a known sequence are well known, for example, M13 primer mutagenesis and PCR mutagenesis. Screening of the mutants is done using assays of proteolytic activities. In alternative aspects, amino acid substitutions can be single residues; insertions can be on the order of from about 1 to 20 amino acids, although considerably larger insertions may be tolerated. Deletions can range from about 1 to about 20 residues, although in some cases deletions may be much larger. To obtain a final derivative with the optimal properties, substitutions, deletions, insertions or any combination thereof may be used. Generally, these changes are done on a few amino acids to minimize the alteration of the molecule. However, larger changes may be tolerated in certain circumstances.

The invention provides P450s where the structure of the polypeptide backbone, the secondary or the tertiary structure, e.g., an alpha-helical or beta-sheet structure, has been modified. In one aspect, the charge or hydrophobicity has been modified. In one aspect, the bulk of a side chain has been modified. Substantial changes in function or immunological identity are made by selecting substitutions that are less conservative. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine. The variants can exhibit the same qualitative biological activity (i.e. proteolytic activity) although variants can be selected to modify the characteristics of the P450s as needed.

In one aspect, P450s of the invention comprise epitopes or purification tags, signal sequences or other fusion sequences, etc. In one aspect, the P450s of the invention can be fused to a random peptide to form a fusion polypeptide. By "fused" or "operably linked" herein is meant that the random peptide and the P450 are linked together, in such a manner as to minimize the disruption to the stability of the P450 structure (i.e. it can retain proteolytic activity) or maintains a Tm of at least 42° C. The fusion polypeptide (or fusion polynucleotide encoding the fusion polypeptide) can comprise further components as well, including multiple peptides at multiple loops.

In one aspect, the peptides and nucleic acids encoding them are randomized, either fully randomized or they are biased in their randomization, e.g. in nucleotide/residue frequency generally or per position. "Randomized" means that each nucleic acid and peptide consists of essentially random nucleotides and amino acids, chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids. The library can provide a sufficiently structurally diverse population of randomized expression products to affect a probabilistically sufficient range of cellular responses to provide one or more cells exhibiting a desired response. Thus, the invention provides an interaction library large enough so that at least one of its members will have a structure that gives it affinity for some molecule, protein, or other factor whose activity is necessary for completion of a signaling pathway.

In one aspect, a peptide library of the invention is fully randomized, with no sequence preferences or constants at any position. In another aspect, the library is biased, that is, some positions within the sequence are either held constant, or are selected from a limited number of possibilities. For example, in one aspect, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc. For example, individual residues may be fixed in the random peptide sequence of the insert to create a structural bias. In an alternative aspect, the random libraries can be biased to a particular secondary structure by including an appropriate number of residues (beyond the glycine linkers) which prefer the particular secondary structure.

In one aspect, the bias is towards peptides that interact with known classes of molecules. For example, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from wasps, can be limited to a short peptide region with death-inducing apoptotic or G protein inducing functions. Thus, a number of molecules or protein domains are suitable as starting points for the generation of biased randomized peptides. A large number of small molecule domains are known, that confer a common function, structure or affinity. In addition, areas of weak amino acid homology may have strong structural homology. Exemplary molecules, domains, and/or corresponding consensus sequences used in the invention (e.g., incorporated into fusion proteins of the invention) include SH-2 domains, SH-3 domains, Pleckstrin, death domains, P450 cleavage/recognition sites, enzyme inhibitors, enzyme substrates, Traf, etc. Similarly, there are a number of known nucleic acid binding proteins containing domains suitable for use in the invention, e.g., leucine zipper consensus sequences.

The invention provides a variety of expression vectors comprising nucleic acids of the invention, including those encoding a fusion protein. The expression vectors may be either self-replicating extra chromosomal vectors or vectors which integrate into a host genome. Generally, these expression vectors include transcriptional and translational regulatory nucleic acid operably linked to the nucleic acid encoding the fusion protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site.

Transcriptional and translational regulatory sequences used in the expression cassettes and vectors of the invention include, but are not limited to, promoter sequences, ribosomal binding sites, transcriptional start and stop sequences, translational start and stop sequences, and enhancer or activator sequences. In one aspect, the regulatory sequences include a promoter and transcriptional start and stop sequences. Promoter sequences encode either constitutive or inducible promoters. The promoters may be either naturally occurring promoters or hybrid promoters. Hybrid promoters, which combine elements of more than one promoter, are also known in the art, and are useful in the present invention. In one aspect, the promoters are strong promoters, allowing high expression in cells, particularly mammalian cells, such as the CMV promoter, particularly in combination with a Tet regulatory element.

In addition, the expression vector may comprise additional elements. In one exemplification, the expression vector may have two replication systems, thus allowing it to be maintained in two organisms, for, example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In one aspect, the nucleic acids or vectors of the invention are introduced into the cells for screening, thus, the nucleic acids enter the cells in a manner suitable for subsequent expression of the nucleic acid. The method of introduction is largely dictated by the targeted cell type. Exemplary methods include CaPO4 precipitation, liposome fusion, lipofection (e.g., LIPOFECTIN™), electroporation, viral infection, etc. The candidate nucleic acids may stably integrate into the genome of the host cell (for example, with retroviral introduction) or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

Expression vectors of the invention may also include a selectable marker gene to allow for the selection of bacterial strains that have been transformed, e.g., genes which render the bacteria resistant to drugs such as ampicillin, chloramphenicol, erythromycin, kanamycin, neomycin and tetracycline. Selectable markers can also include biosynthetic genes, such as those in the histidine, tryptophan and leucine biosynthetic pathways.

Screening Methodologies and "On-line" Monitoring Devices

In practicing the methods of the invention, a variety of apparatus and methodologies can be used to in conjunction with the polypeptides and nucleic acids of the invention, e.g., to screen polypeptides for P450 reactivity, to screen compounds as potential modulators of activity (e.g., potentiation or inhibition of enzyme activity), for antibodies that bind to a polypeptide of the invention, for nucleic acids that hybridize to a nucleic acid of the invention, and the like.

Immobilized Enzyme Solid Supports

The P450 enzymes, fragments thereof and nucleic acids that encode the enzymes and fragments can be affixed to a solid support. This is often economical and efficient in the use of P450s in industrial processes. For example, a consortium or cocktail of P450 enzymes (or active fragments thereof), which are used in a specific chemical reaction, can be attached to a solid support and dunked into a process vat. The enzymatic reaction can occur. Then, the solid support can be taken out of the vat, along with the enzymes affixed thereto, for repeated use. In one embodiment of the invention, an isolated nucleic acid of the invention is affixed to a solid support. In another embodiment of the invention, the solid support is selected from the group of a gel, a resin, a polymer, a ceramic, a glass, a microelectrode and any combination thereof.

For example, solid supports useful in this invention include gels. Some examples of gels include Sepharose, gelatin, glutaraldehyde, chitosan-treated glutaraldehyde, albumin-glutaraldehyde, chitosan-Xanthan, toyopearl gel (polymer gel), alginate, alginate-polylysine, carrageenan, agarose, glyoxyl agarose, magnetic agarose, dextran-agarose, poly(Carbamoyl Sulfonate) hydrogel, BSA-PEG hydrogel, phosphorylated polyvinyl alcohol (PVA), monoaminoethyl-N-aminoethyl (MANA), amino, or any combination thereof.

Another solid support useful in the present invention are resins or polymers. Some examples of resins or polymers include cellulose, acrylamide, nylon, rayon, polyester, anion-exchange resin, AMBERLITE™ XAD-7, AMBERLITE™ XAD-8, AMBERLITE™ IRA-94, AMBERLITE™ IRC-50, polyvinyl, polyacrylic, polymethacrylate, or any combination thereof another type of solid support useful in the present invention is ceramic. Some examples include non-porous ceramic, porous ceramic, $SiO_2$, $Al_2O_3$. Another type of solid support useful in the present invention is glass. Some examples include non-porous glass, porous glass, aminopropyl glass or any combination thereof. Another type of solid support that can be used is a microelectrode. An example is a polyethyleneimine-coated magnetite. Graphitic particles can be used as a solid support. Another example of a solid support is a cell, such as a red blood cell.

Methods of Immobilization

There are many methods that would be known to one of skill in the art for immobilizing enzymes or fragments thereof, or nucleic acids, onto a solid support. Some examples of such methods include, e.g., electrostatic droplet generation, electrochemical means, via adsorption, via covalent binding, via cross-linking, via a chemical reaction or process, via encapsulation, via entrapment, via calcium alginate, or via poly (2-hydroxyethyl methacrylate). Like methods are described in Methods in Enzymology, Immobilized Enzymes and Cells, Part C. 1987. Academic Press. Edited by S. P. Colowick and N. O. Kaplan. Volume 136; and Immobilization of Enzymes and Cells. 1997. Humana Press. Edited by G. F. Bickerstaff. Series: Methods in Biotechnology, Edited by J. M. Walker.

Capillary Arrays

Capillary arrays, such as the GIGAMATRIX™, Diversa Corporation, San Diego, Calif., can be used to in the methods of the invention. Nucleic acids or polypeptides of the invention can be immobilized to or applied to an array, including capillary arrays. Arrays can be used to screen for or monitor libraries of compositions (e.g., small molecules, antibodies, nucleic acids, etc.) for their ability to bind to or modulate the activity of a nucleic acid or a polypeptide of the invention. Capillary arrays provide another system for holding and screening samples. For example, a sample screening apparatus can include a plurality of capillaries formed into an array of adjacent capillaries, wherein each capillary comprises at least one wall defining a lumen for retaining a sample. The apparatus can further include interstitial material disposed between adjacent capillaries in the array, and one or more reference indicia formed within of the interstitial material. A capillary for screening a sample, wherein the capillary is adapted for being bound in an array of capillaries, can include a first wall defining a lumen for retaining the sample, and a second wall formed of a filtering material, for filtering excitation energy provided to the lumen to excite the sample.

A polypeptide or nucleic acid, e.g., a ligand, can be introduced into a first component into at least a portion of a capillary of a capillary array. Each capillary of the capillary array can comprise at least one wall defining a lumen for retaining the first component. An air bubble can be introduced into the capillary behind the first component. A second component can be introduced into the capillary, wherein the second component is separated from the first component by the air bubble. A sample of interest can be introduced as a first liquid labeled with a detectable particle into a capillary of a capillary array, wherein each capillary of the capillary array comprises at least one wall defining a lumen for retaining the first liquid and the detectable particle, and wherein the at least one wall is coated with a binding material for binding the detectable particle to the at least one wall. The method can further include removing the first liquid from the capillary tube, wherein the bound detectable particle is maintained within the capillary, and introducing a second liquid into the capillary tube.

The capillary array can include a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a micro titer plate having about 100,000 or more individual capillaries bound together.

Arrays, or "Biochips"

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a P450 gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins. The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

In practicing the methods of the invention, any known array and/or method of making and using arrays can be incorporated in whole or in part, or variations thereof, as described, for example, in U.S. Pat. Nos. 6,277,628; 6,277, 489; 6,261,776; 6,258,606; 6,054,270; 6,048,695; 6,045, 996; 6,022,963; 6,013,440; 5,965,452; 5,959,098; 5,856, 174; 5,830,645; 5,770,456; 5,632,957; 5,556,752; 5,143, 854; 5,807,522; 5,800,992; 5,744,305; 5,700,637; 5,556, 752; 5,434,049; see also, e.g., WO 99/51773; WO 99/09217; WO 97/46313; WO 96/17958; see also, e.g., Johnston (1998) Curr. Biol. 8:R171–R174; Schummer (1997) Biotechniques 23:1087–1092; Kern (1997) Biotechniques 23:120–124; Solinas-Toldo (1997) Genes, Chromosomes & Cancer 20:399–407; Bowtell (1999) Nature Genetics Supp. 21:25–32. See also published U.S. patent applications Nos. 20010018642; 20010019827; 20010016322; 20010014449; 20010014448; 20010012537; 20010008765.

Antibodies and Antibody-based Screening Methods

The invention provides isolated or recombinant antibodies that specifically bind to a P450 of the invention. These antibodies can be used to isolate, identify or quantify the fluorescent polypeptides of the invention or related polypeptides. These antibodies can be used to isolate other polypeptides within the scope the invention or other related P450s.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62–70; Katz (1 997) Annu. Rev. Biophys. Biomol. Struct. 26:27–45.

Polypeptides or peptides can be used to generate antibodies which bind specifically to the polypeptides of the invention. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention.

In immunoaffinity procedures, the antibody is attached to a solid support, such as a bead or other column matrix. The protein preparation is placed in contact with the antibody under conditions in which the antibody specifically binds to one of the polypeptides of the invention. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the invention can be obtained by direct injection of the polypeptides into an animal or by administering the polypeptides to a non-human animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77–96).

Techniques described for the production of single chain antibodies (see, e.g., U.S. Pat. No. 4,946,778) can be adapted to produce single chain antibodies to the polypeptides of the invention. Alternatively, transgenic mice may be used to express humanized antibodies to these polypeptides or fragments thereof.

Antibodies generated against the polypeptides of the invention may be used in screening for similar polypeptides from other organisms and samples. In such techniques, polypeptides from the organism are contacted with the antibody and those polypeptides which specifically bind the antibody are detected. Any of the procedures described above may be used to detect antibody binding.

Kits

The invention provides kits comprising the compositions, e.g., nucleic acids, expression cassettes, vectors, cells, polypeptides (e.g., P450s) and/or antibodies of the invention. The kits also can contain instructional material teaching the methodologies and industrial uses of the invention, as described herein.

Measuring Metabolic Parameters

The methods of the invention provide whole cell evolution, or whole cell engineering, of a cell to develop a new strain having a new phenotype by modifying the genetic composition of the cell, where the genetic composition is modified by addition to the cell of a nucleic acid. To detect the new phenotype, at least one metabolic parameter of a modified cell is monitored in the cell in a "real time" or "on-line" time frame. In one aspect, a plurality of cells, such as a cell culture, is monitored in "real time" or "on-line." In one aspect, a plurality of metabolic parameters is monitored in "real time" or "on-line." Metabolic parameters can be monitored using the fluorescent polypeptides of the invention.

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods of the invention, metabolic networks are established, including the:

identity of all pathway substrates, products and intermediary metabolites identity of all the chemical reactions interconverting the pathway metabolites, the stoichiometry of the pathway reactions, identity of all the enzymes catalyzing the reactions, the enzyme reaction kinetics, the regulatory interactions between pathway components, e.g. allosteric interactions, enzyme-enzyme interactions etc, intracellular compartmeritalization of enzymes or any other supramolecular organization of the enzymes, and, the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available. Metabolic phenotype relies on the changes of the whole metabolic network within a cell. Metabolic phenotype relies on the change of pathway utilization with respect to environmental conditions, genetic regulation, developmental state and the genotype, etc. In one aspect of the methods of the invention, after the on-line MFA calculation, the dynamic behavior of the cells, their phenotype and other properties are analyzed by investigating the pathway utilization. For example, if the glucose supply is increased and the oxygen decreased during the yeast fermentation, the utilization of respiratory pathways will be reduced and/or stopped, and the utilization of the fermentative pathways will dominate. Control of physiological state of cell cultures will become possible after the pathway analysis. The methods of the invention can help determine how to manipulate the fermentation by determining how to change the substrate supply, temperature, use of inducers, etc. to control the physiological state of cells to move along desirable direction. In practicing the methods of the invention, the MFA results can also be compared with transcriptome and proteome data to design experiments and protocols for metabolic engineering or gene shuffling, etc.

In practicing the methods of the invention, any modified or new phenotype can be conferred and detected, including new or improved characteristics in the cell. Any aspect of metabolism or growth can be monitored.

Monitoring Expression of an mRNA Transcript

In one aspect of the invention, the engineered phenotype comprises increasing or decreasing the expression of an mRNA transcript or generating new transcripts in a cell. This increased or decreased expression can be traced by use of a fluorescent polypeptide of the invention. mRNA transcripts, or messages, also can be detected and quantified by any method known in the art, including, e.g., Northern blots, quantitative amplification reactions, hybridization to arrays, and the like. Quantitative amplification reactions include, e.g., quantitative PCR, including, e.g., quantitative reverse transcription polymerase chain reaction, or RT-PCR; quantitative real time RT-PCR, or "real-time kinetic RT-PCR" (see, e.g., Kreuzer (2001) Br. J. Haematol. 114:313–318; Xia (2001) Transplantation 72:907–914).

In one aspect of the invention, the engineered phenotype is generated by knocking out expression of a homologous gene. The gene's coding sequence or one or more transcriptional control elements can be knocked out, e.g., promoters enhancers. Thus, the expression of a transcript can be completely ablated or only decreased.

In one aspect of the invention, the engineered phenotype comprises increasing the expression of a homologous gene. This can be effected by knocking out of a negative control element, including a transcriptional regulatory element acting in cis- or trans-, or, mutagenizing a positive control element. One or more, or, all the transcripts of a cell can be measured by hybridization of a sample comprising transcripts of the cell, or, nucleic acids representative of or complementary to transcripts of a cell, by hybridization to immobilized nucleic acids on an array.

Monitoring Expression of a Polypeptides, Peptides and Amino Acids

In one aspect of the invention, the engineered phenotype comprises increasing or decreasing the expression of a polypeptide or generating new polypeptides in a cell. This increased or decreased expression can be traced by use of a P450 of the invention. Polypeptides, peptides and amino acids also can be detected and quantified by any method known in the art, including, e.g., nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, e.g. immunoprecipitation, immunodiffusion, immuno-electrophoresis, radioimmunoassays (RIAs), enzyme-linked immunosorbent assays (ELISAs), immuno-fluorescent assays, gel electrophoresis (e.g., SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like. Novel bioactivities can also be screened using methods, or variations thereof, described in U.S. Pat. No. 6,057,103. Furthermore, as discussed below in detail, one or more, or, all the polypeptides of a cell can be measured using a protein array.

Assay Development

Several assay methods for obtaining P450s can be used. These assay methods include growth-based assays, direct activity-based assays and sequence-based assays. Preferably, to successfully obtain a range of P450s with desirable characteristics, all three of these assay methods may be used complementarily.

Growth-based Assays

Figure 10:
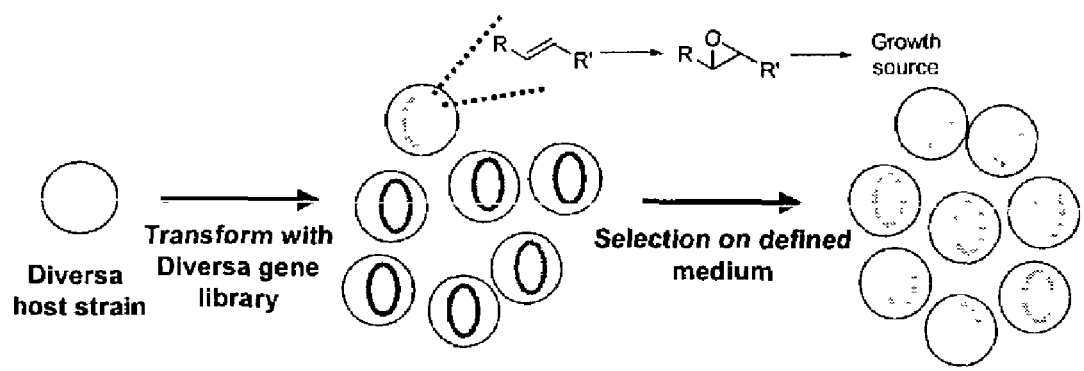
FIG. 10 is an illustration of selections for enzymes that catalyze epoxidations.
Figure 11:
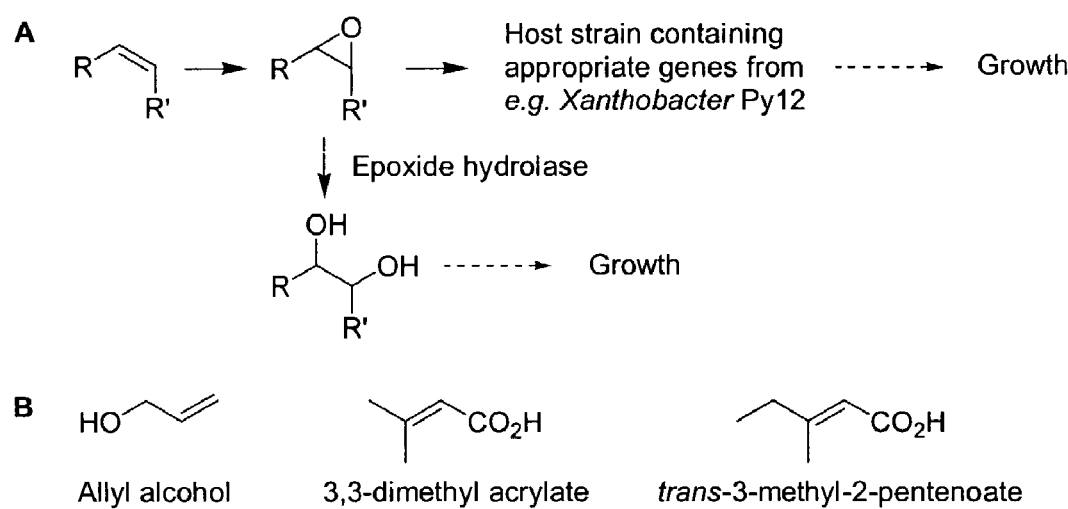
FIG. 11 is a schematic representation of potential selection and selection substrates for epoxidase discovery.

The most direct and high throughput growth-based selection method for identifying enzymes that are capable of catalyzing epoxidation reactions would be to perform growth selections on the appropriate alkenes (FIG. 10). This method requires that the screening host contain enzymes that allow the epoxide derivative of the target alkene to be utilized as a carbon source. Several bacteria (e.g Xanthobacter strain Py2) have already been identified as being able to utilize alkenes as the sole carbon source (see Ensign, S. A. Biochemistry 2001 40, 5845) (FIG. 11A), the first step of which involves oxidation of the alkene to the corresponding epoxide. The epoxide is then channeled into normal cellular metabolism by the sequential action of several other enzymes. Selection for growth directly on target alkene substrates may therefore be feasible, but would rely on genomic clones containing both the epoxide-forming and epoxide-processing genes. Alternatively, a host strain could be constructed to express the epoxide processing enzymes, reducing the discovery effort to epoxidases.

Figure 12:
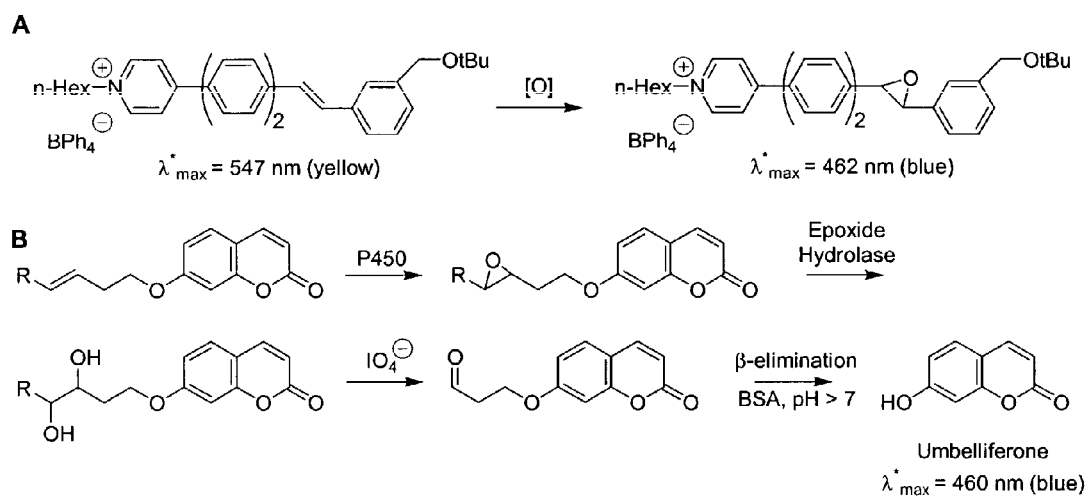
FIG. 12 is an illustration of potential screens for epoxidase discovery.

A second growth-based selection method uses the diol hydrolysis product of the target epoxide as a nutrient source for growth. This method requires a host strain for selection that contains a P450 with appropriate substrate specificity. Alkenes that could be used as selection substrates (FIG. 12) include allyl alcohol, 3,3-dimethyl acrylate and trans-3-methyl-2-pentenoate. Epoxidation of these compounds followed by hydrolysis to the diols would yield glycerol, and key intermediates in the biosynthesis of, for example, valine and isoleucine, respectively. For allyl alcohol the selection would thus rely on the use of glycerol as a sole carbon source for growth.

Direct activity-based Assays

A direct activity assay method (also called "activity screen" method) to identify epoxidase activities would be less amenable to ultra-high throughput methodology, but would require less host-strain modification. Activity screens are applicable to enzyme identification, secondary characterization of hits and analysis of enzyme evolution efforts and are therefore extremely versatile. Suitable activity screens would entail monitoring the modification of the spectroscopic properties of a particular molecule on formation of its epoxide derivative. Sames and coworkers (Moreira, R. Havranek, M. & Sames, D. J. Am. Chem. Soc. 2001,123, 3927) recently described one example of a suitable activity screen of this type (FIG. 12A). In this case a yellow fluorescent alkene is converted to a blue fluorescent epoxide, which allows the extent of reaction to be monitored by the ratio of blue to yellow fluorescence. A second potential fluorescence-based screen method would involve the in vivo coupling of epoxidase and P450 activities (FIG. 12B) (Badalassi, F., Wahler, D., Klein, G., Crotti, P., & Reymond, J.-L. Angew. Chem. Int. Ed., 2000; 39, 4067). The resultant vicinal diol linked to umbelliferone is subjected to periodate oxidation, followed by BSA-catalyzed β-elimination of umbelliferone. In this way epoxide formation is detected by an increase in the fluorescence quantum yield. This method of epoxide/diol detection may require engineering of a host strain to contain a suitable P450.

Sequence Based Assays

A complementary approach to the activity-based discovery of epoxidases is sequence-based discovery of generic P450s followed by assessment of their substrate specificities in secondary assays. This method is certainly feasible given that P450s have several conserved regions that can be used to design oligonucleotide probes for hybridization or PCR screening. The oligonucleotide probes can be designed using conserved sequence motifs that appear to be specific to P450s involved in macrolide biosynthetic pathways. This suggests that it may be possible to combine experimental data and bioinformatic analysis to gain information on the substrate-type of newly discovered P450s and then recycle this information to design more specific probes for target-oriented enzymes. A sequence mining discovery program has the added advantages that it will simultaneously provide information on the total P450s content in the environmental gene libraries and increases the portfolio of cloned enzymes available in the environmental libraries for future uses. Furthermore, biopanning techniques for the high throughput discovery of homologous sequences can be used in this sequence-based discovery method. This will enable the discovery of a large number of potentially useful biocatalysts.

Strain Development

Successful identification of P450s in the environmental gene libraries will depend on engineering specific characteristics into the library host strain. First, it may be necessary in some cases to ensure that the screening host can optimally support activities of exogenous P450s. In addition, it may be necessary in some cases to insert genes encoding for auxiliary enzymes that can process or detoxify the epoxide reaction product.

Expression of heterologous P450s in *E. coli* often results in low or no activity. In many cases this may be due to inefficient interaction between native reductase enzymes present in the host cells and the noncognate oxidase. To overcome this problem, co-expression of P450s with FDX or FDX and FDR may be used to significantly improve the activity of P450s. Therefore, to better discover the suitable enzymes, all the above-mentioned assay methods are preferably performed in a host strain optimized for P450 epoxidase expression. For example, the activity of an actinomycete P450 was supported by co-expression with the putidaredoxin/putidaredoxin reductase pair from *P. putida*. Therefore, preferably this reductase system is used for the development of a P450 screening host strain. If necessary, this host strain could be further optimized by evaluation of different FDX/FDR pairs from a variety of bacterial types. Cross referencing the activity of newly identified P450s with the presence of different FDX/FDR pairs may give a guide as to the most suitable reductive complements, allowing further optimization of the method.

Epoxide Metabolism

Epoxide reaction products may be toxic to *E. coli* host strains and are unlikely to be directly metabolized. Therefore, identification on the basis of product epoxides as growth sources may require additional engineering of the host strain. One approach to this would be to clone and heterologously express (possibly from the *E. coli* chromosome) the Xanthobacter epoxide-processing genes. This pathway comprises an epoxyalkane-coenzyme M transferase, R- and S-specific hydroxypropyl-CoM dehydrogenases and a ketopropyl-CoM oxidoreductase/carboxylase. To better carry out this approach, one may need to introduce, discover or develop Co-enzyme M biosynthesis in *E. coli* and determine the breadth of substrate specificity for each of the enzymes in the pathway. Furthermore, it may be helpful to carry out this approach by obtaining expression and activity of the entire pathway.

Diol Metabolism

Figure 9:
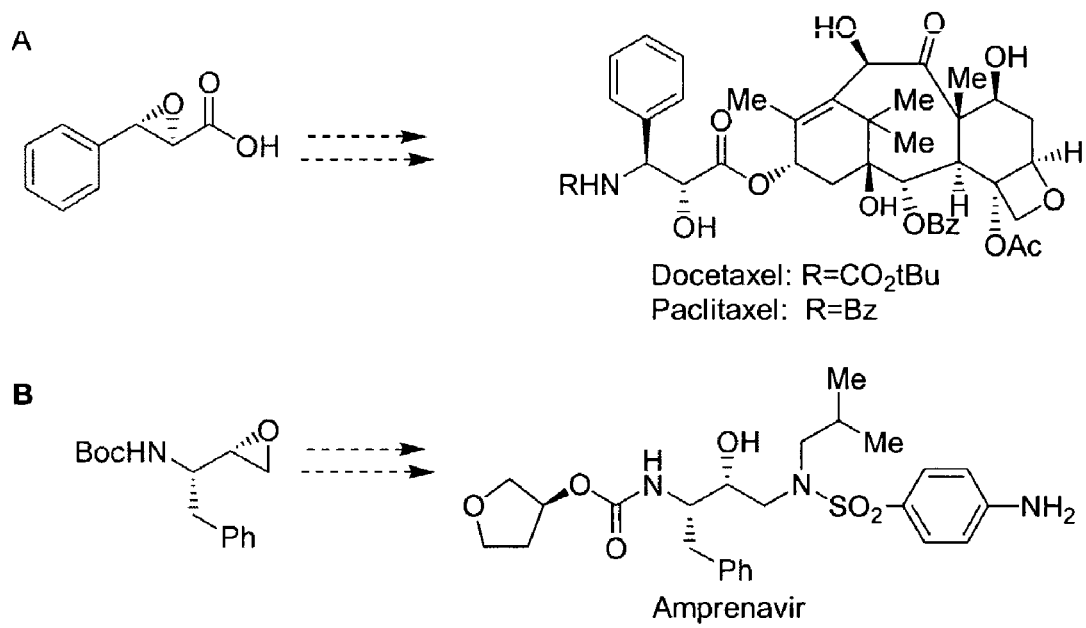
FIG. 9 is an illustration of uses of epoxides in the synthesis of anti-cancer and anti-HIV drugs.

A more preferred approach to an epoxide-based selection is to hydrolyze the epoxide in situ and utilize the resultant diol as sole carbon source for growth. This selection method may require engineering of a host strain to contain a suitable epoxide hydrolase. Insertion of an epoxide hydrolase gene into the generic host strain for P450 epoxidase identification would be advantageous for several reasons. First, it would alleviate any problems with toxicity of the epoxides generated from the alkene substrates. Second, judicious choice of alkenes would facilitate discovery via selection methods by generation of diols that can be metabolized. Third, it will facilitate application of the periodate-coupled fluorogenic assay (FIG. 9B) for both screen-based discovery of epoxidases and later evolution programs for their target-specific optimization.

The screening method can be used to discover a wide range of novel P450s, thereby creating a toolbox of synthetically useful biocatalysts. Optionally, where necessary, evolution technologies, which are discussed below, may be used to optimize the properties of the enzymes.

In one aspect, the assays developed will be applied to screen the environmental gene libraries for the presence of microbial enzymes with the necessary activities and substrate specificities. Positive hits from these screens may then be sequenced and the genes subcloned into expression vectors. The expressed recombinant enzymes can then be characterized with respect to activity and substrate selectivities. Should the identified enzymes require enhancement of one or more of their properties (e.g pH and temperature optima, thermostability, thermotolerance, substrate specificity etc.) they can be optimized using GSSM™ (Gene Site Saturation Mutagenesis), Gene Reassembly™ and other technologies discussed below. These P450s may be used in the chemo-enzymatic synthesis of specific fine chemicals and high value precursors to pharmaceuticals and agrochemicals. The optimized enzymes developed using a method of the present invention may be applied in the development of a commercially viable synthesis route to one or more target compounds. Specifically, the P450s can be used as key intermediates in the synthesis of fine chemicals and enantiomeric pharmaceuticals having the desired purities.

In one aspect, the environmental gene libraries are constructed using DNA isolated from a wide variety of microenvironments around the world. Application of an appropriate discovery method then allows enzymes to be extracted from these libraries according to function, enzyme class or a specific combination of the two. In contrast to traditional discovery programs, the preferred discovery method ensures capture of genes from uncultivated microbes and facilitates screening in well-defined, domesticated laboratory hosts. This expression cloning method results in simultaneous capture of enzyme activities and the corresponding genetic information.

The preferred discovery method involves: isolating and fractionating nucleic acids from nature or other suitable sources; constructing environmental gene libraries; screening the genes in the environmental libraries to discover the desired genes encoding the desired enzymes using the methods described below; optimizing the desired genes to optimize the activity of the desired enzymes using the evolution technologies described in U.S. Pat. No. 5,830,696, U.S. Pat. No. 5,939,250 and U.S. Pat. No. 5,965,408, which are incorporated herein by reference; sequencing the optimized genes; overexpressing the sequenced genes in suitable host strains; producing a large number of the suitable strains containing the optimized genes by fermentation and obtaining the desired enzymes, optionally contained in host strains, after purification.

Newly cloned or discovered enzymes can then be further customized by using the evolution technologies described in U.S. Pat. Nos. 5,830,696, U.S. Pat. No. 5,939,250 and U.S. Pat. No. 5,965,408 and a combinatorial evolution technology described below.

In one aspect, the screening step may be carried out by one or more of expression and sequence-based screening methods including single cell activity screens, microtiter plate-based activity screens, sequence-based screening and growth selection methods. These methods may all be applied to the discovery of P450s utilizing the assays described above.

Figure 13:
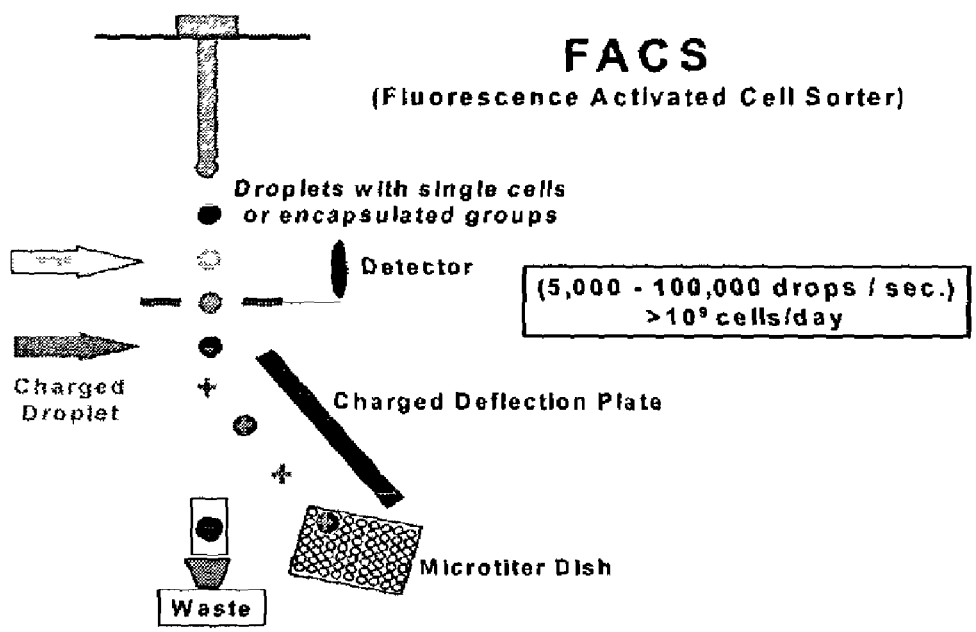
FIG. 13 is an illustration of Fluorescence Activated Cell Sorting (FACS) for ultra high throughput single cell activity and sequence screening.

Single cell activity screening method is a method derived from Fluorescence Activated Cell Sorting (FACS) by substantially modifying the FACS platform for expression and sequence hybridization-based screening of environmental libraries (FIG. 13). In the case of expression screening, fluorescent substrates are soaked into clone libraries and when a clone expresses a gene product that is capable of cleaving the substrate, the fluorescence quantum yield increases. Alternatively, FACS-hybridization cloning methodology permits the recovery of recombinant clones based on sequence homology. This single cell activity screening method allows screening rates of 50,000 clones per second and a daily screening rate of up to $10^9$ clones.

The growth selection method can be one of the most powerful methods for enzyme discovery. In this method the substrate of choice acts as a nutrient source for the host cells only when those cells contain the enzyme activity of interest, allowing them to grow selectively. Genetic manipulation of cell lines may be involved in this growth selection method. The substrate used in this method may also be custom synthesized.

Figure 14:
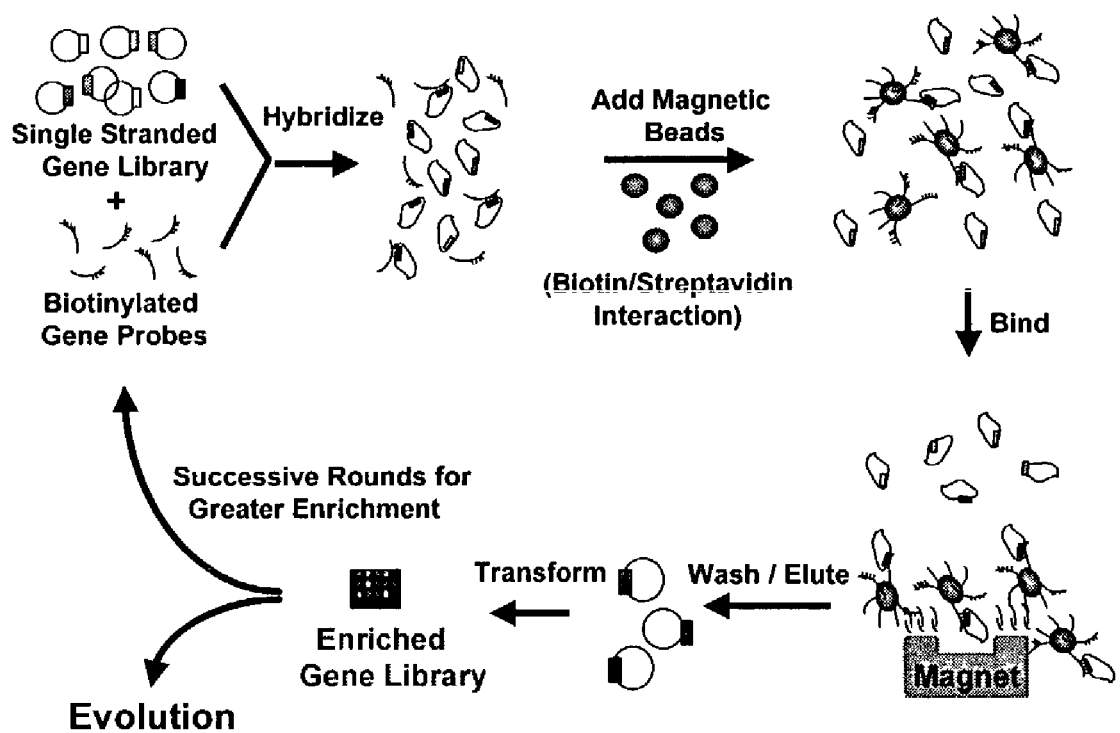
FIG. 14 is an illustration of environmental library bio-panning for sequence-based discovery.

In another aspect, sequence-based discovery methods may be powerful and complementary alternatives to expression cloning. Both solution phase and FACS-based formats can be used for ultra high throughput DNA hybridization-based discovery techniques, such as environmental biopanning, which facilitate screening of the large and complex environmental gene libraries. In the solution based environmental biopanning technique, inserts from mega libraries are rendered single stranded and combined in solution with arrays of biotinylated hybridization probes known as hooks (FIG. 14). Library clones containing related sequences hybridize to the hooks and are captured on streptavidin coated magnetic beads. The eluted sequence-enriched DNA inserts are then either subjected to another cycle of biopanning or back-cloned into lambda. In this way enrichment is achieved greater than 1000-fold for sequences of interest. The FACS-based biopanning approach further facilitates the enzyme identification process by allowing for amplification-free biopanning of both small and large insert clones.

Laboratory evolution of enzymes can be used to further improve, customize or refine the properties of the enzymes. These laboratory evolution technologies include Gene Site Saturation Mutagenesis (GSSM™) and GeneReassembly™, where multiple natural genes can be combined to create a combinatorial evolution library. If necessary, these technologies can be applied to the P450 enzymes discovered using the enzyme discovery method to further optimize these P450 enzymes for characteristics such as thermostability, specific activity or stereospecificity.

In one aspect, the present invention provides rapid screening of libraries derived from more than one organism, such as a mixed population of organisms from, for example, an environmental sample or an uncultivated population of organisms or a cultivated population of organisms.

In one aspect, gene libraries are generated by obtaining nuceic acids from a mixed population of organisms and cloning the nucleic acids into a suitable vector for transforming a plurality of clones to generate a gene library. The gene library thus contains gene or gene fragments present in organisms of the mixed population. The gene library can be an expression library, in which case the library can be screened for an expressed polypeptide having a desired activity. Alternatively, the gene library can be screened for sequences of interest by, for example, PCR or hybridization screening. In one embodiment, nucleic acids from isolates of a sample containing a mixed population of organism are pooled and the pooled nucleic acids are used to generate a gene library.

By "isolates" is meant that a particular species, genus, family, order, or class of organisms is obtained or derived from a sample having more than one organism or from a mixed population of organisms. Nucleic acids from these isolated populations can then be used to generate a gene library. Isolates can be obtained from by selectively filtering or culturing a sample containing more than one organism or a mixed population of organisms. For example, isolates of bacteria can be obtained by filtering the sample through a filter, which excludes organisms based on size or by culturing the sample on media that allows from selective growth or selective inhibition of certain populations of organisms.

An "enriched population" is a population of organisms wherein the percentage of organisms belonging to a particular species, genus, family, order or class of organisms is increased with respect to the population as a whole. For example, selective growth or inhibition media can increase the overall number of organisms. One can enrich for prokaryotic organisms with respect to the total number of organisms in the population. Similarly, a particular species, genus, family, order or class of organisms can be enriched by growing a mixed population on a selective media that inhibits or promotes the growth of a subpopulation within the mixed population.

In another aspect, nucleic acids from a plurality (e.g., two or more) of isolates from a mixed population of organisms are used to generate a plurality of gene libraries containing a plurality of clones, and the gene libraries from at least two isolates are then pooled to obtain a "pooled isolate library."

Once gene libraries are generated, the clones are screened to detect a bioactivity, in this case activity as an epoxidase or a biomolecule of interest (e.g., an epoxidase). Such screening techniques include, for example, contacting a clone, clonal population, or population of nucleic acid sequences with a substrate or substrates having a detectable molecule that provides a detectable signal upon interaction with the bioactivity or biomolecule of interest. The substrate can be an enzymatic substrate, a bioactive molecule, an oligonucleotide, and the like.

In one aspect, gene libraries are generated, clones are either exposed to a chromogenic or fluorogenic substrate or substrate(s) of interest, or hybridized to a labeled probe (e.g., an oligonucleotide having a detectable molecule) having a sequence corresponding to a sequence of interest and positive clones are identified by a detectable signal (e.g., fluorescence emission).

In one aspect, expression libraries generated from a mixed population of organisms are screened for an activity of interest. Specifically, expression libraries are generated, clones are exposed to the substrate or substrate(s) of interest, and positive clone are identified and isolated. The present invention does not require cells to survive. The cells only need to be viable long enough to produce the molecule to be detected, and can thereafter be either viable or nonviable cells, so long as the expressed biomolecule (e.g., an enzyme) remains active.

In certain aspects, the invention provides an approach that combines direct cloning of genes encoding novel or desired bioactivities from environmental samples with a high-throughput screening system designed for the rapid discovery of new molecules, for example, enzymes. The approach is based on the construction of environmental "expression libraries" which can represent the collective genomes of numerous naturally occurring microorganisms archived in cloning vectors that can be propagated in E. coli or other suitable host cells. Because the cloned DNA can be initially extracted directly from environmental samples or from isolates of the environmental samples, the libraries are not limited to the small fraction of prokaryotes that can be grown in pure culture. Additionally, a normalization of the environmental DNA present in these samples could allow a more equal representation of the DNA from all of the species present in a sample. Normalization techniques (described below) can dramatically increase the efficiency of finding interesting genes from minor constituents of the sample that may be under-represented by several orders of magnitude compared to the dominant species in the sample. Normalization can occur in any of the foregoing embodiments following obtaining nucleic acids from the sample or isolate(s).

In another aspect, the invention provides a high-throughput capillary array system for screening that allows one to assess an enormous number of clones to identify and recover cells encoding useful enzymes, as well as other biomolecules (e.g., ligands). In particular, the capillary array-based techniques described herein can be used to screen, identify and recover proteins having a desired bioactivity or other ligands having a desired binding affinity. For example, binding assays may be conducted by using an appropriate substrate or other marker that emits a detectable signal upon the occurrence of the desired binding event.

In addition, fluorescence activated cell sorting can be used to screen and isolate clones having an activity or sequence of interest. Previously, FACS machines have been employed in the studies focused on the analyses of eukaryotic and prokaryotic cell lines and cell culture processes. FACS has also been utilized to monitor production of foreign proteins in both eukaryotes and prokaryotes to study, for example, differential gene expression, and the like. The detection and counting capabilities of the FACS system have been applied in these examples. However, FACS has never previously been employed in a discovery process to screen for and recover bioactivities in prokaryotes. Furthermore, the present invention does not require cells to survive, as do previously described technologies, since the desired nucleic acid (recombinant clones) can be obtained from alive or dead cells. The cells only need to be viable long enough to produce the compound to be detected, and can thereafter be either viable or non-viable cells so long as the expressed biomolecule remains active. The present invention also solves problems that would have been associated with detection and sorting of E. coli expressing recombinant enzymes, and recovering encoding nucleic acids. Additionally, the present invention includes within its embodiments any apparatus capable of detecting fluorescent wavelengths associated with biological material, such apparatus are defined herein as fluorescent analyzers (one example of which is a FACS apparatus).

In some instances it is desirable to identify nucleic acid sequences from a mixed population of organisma, isolates, or enriched populations. In this aspect, it is not necessary to express gene products. Nucleic acid sequences of interest can be identified or "biopanned" by contacting a clone, device (e.g. a gene chip), filter, or nucleic acid sample with a probe labeled with a detectable molecule. The probe will typically have a sequence that is substantially identical to the nucleic acid sequence of interest. Alternatively, the probe will be a fragment or full length nucleic acid sequence encoding a polypeptide of interest. The probe and nucleic acids are incubated under conditions and for such time as to allow the probe and a substantially complementary sequence to hybridize. Hybridization stringency will vary depending on, for example, the length and GC content of the probe. Such factors can be determined empirically (See, for example, Sambrook et al., Molecular Cloning—A Laboratory Manual, Cold Spring Harbor Laboratory, Cold Spring Harbor, N.Y., 1989, and Current Protocols in Molecular Biology, M. Ausubel et al., eds., (Current Protocols, a joint venture between Greene Publishing Associates, Inc. and John Wiley & Sons, Inc., most recent Supplement)). Once hybridized the complementary sequence can be PCR amplified, identified by hybridization techniques (e.g., exposing the probe and nucleic acid mixture to a film), or detecting the nucleic acid using a chip.

Prior to the present invention, the evaluation of complex gene libraries or environmental expression libraries was rate limiting. The present invention allows the rapid screening of complex environmental libraries, containing, for example, genomic sequences from thousands of different organisms or subsets and isolates thereof. The benefits of the present invention can be seen, for example, in screening a complex environmental sample. Screening of a complex sample previously required one to use labor-intensive methods to screen several million clones to cover the genomic biodiversity. The invention represents an extremely high-throughput screening method, which allows one to assess this enormous number of clones. The method disclosed allows the screening anywhere from about 30 million to about 200 million clones per hour for a desired nucleic acid sequence, biological activity, or biomolecule of interest. This allows the thorough screening of environmental libraries for clones expressing novel bioactivities or biomolecules.

Once a sequence or bioactivity of interest is identified (e.g., an enzyme of interest) the sequence or polynucleotide encoding the bioactivity of interest can be evolved, mutated or derived to modify the amino acid sequence to provide, for example, modified activities such as increased thermostability, specificity or activity.

The invention provides methods of identifying a nucleic acid sequence encoding a polypeptide having either known or unknown function. For example, much of the diversity in microbial genomes results from the rearrangement of gene clusters in the genome of microorganisms. These gene clusters can be present across species or phylogenetically related with other organisms.

For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. The gene cluster, the promoter, and additional sequences that function in regulation altogether are referred to as an "operon" and can include up to 20 or more genes, usually from 2 to 6 genes. Thus, a gene cluster is a group of adjacent genes that are either identical or related, usually as to their function.

Some gene families consist of identical members. Clustering is a prerequisite for maintaining identity between genes, although clustered genes are not necessarily identical. Gene clusters range from extremes where a duplication is generated to adjacent related genes to cases where hundreds of identical genes lie in a tandem array. Sometimes no significance is discernable in a repetition of a particular gene. A principal example of this is the expressed duplicate insulin genes in some species, whereas a single insulin gene is adequate in other mammalian species.

Further, gene clusters undergo continual reorganization and, thus, the ability to create heterogeneous libraries of gene clusters from, for example, bacterial or other prokaryote sources is valuable in determining sources of novel proteins, particularly including enzymes such as, for example, the polyketide synthases that are responsible for the synthesis of polyketides having a vast array of useful activities. For example, polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of a huge variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins. Other types of proteins that are the product(s) of gene clusters are also contemplated, including, for example, antibiotics, antivirals, antitumor agents and regulatory proteins, such as insulin.

The ability to select and combine desired components from a library of polyketides and postpolyketide biosynthesis genes for generation of novel polyketides for study is appealing. The method(s) of the present invention make it possible to, and facilitate the cloning of, novel polyketide synthases and other gene clusters, since one can generate gene banks with clones containing large inserts (especially when using the f-factor based vectors), which facilitates cloning of gene clusters.

For example, a gene cluster can be ligated into a vector containing an expression of regulatory sequences, which can control and regulate the production of a detectable protein or protein-related array activity from the ligated gene clusters. Use of vectors which have an exceptionally large capacity for exogenous nucleic acid introduction are particularly appropriate for use with such gene clusters and are described by way of example herein to include the f-factor (or fertility factor) of E. coli. This f-factor of E. coli is a plasmid which affects high-frequency transfer of itself during conjugation and is ideal to achieve and stably propagate large nucleic acid fragments, such as gene clusters from mixed microbial samples.

The nucleic acid isolated or derived from these samples (e.g., a mixed population of microorganisms) or isolates thereof can be inserted into a vector or a plasmid prior to screening of the polynucleotides. Such vectors or plasmids are typically those containing expression regulatory sequences, including promoters, enhancers and the like.

Accordingly, the invention provides novel systems to clone and screen mixed populations of organisms, enriched samples, or isolates thereof for polynucleotides encoding molecules having an activity of interest, enzymatic activities and bioactivities of interest in vitro. The method(s) of the invention allow the cloning and discovery of novel bioactive molecules in vitro, and in particular novel bioactive molecules derived from uncultivated or cultivated samples. Large size gene clusters, genes and gene fragments can be cloned, sequenced and screened using the method(s) of the invention. Unlike previous strategies, the method(s) of the invention allow one to clone screen and identify polynucleotides and the polypeptides encoded by these polynucleotides in vitro from a wide range of environmental samples.

The invention allows one to screen for and identify polynucleotide sequences from complex environmental samples, enriched samples thereof, or isolates thereof. Gene libraries can be generated from cell free samples, so long as the sample contains nucleic acid sequences, or from samples containing cells, cellular material or viral particles. The organisms from which the libraries may be prepared include prokaryotic microorganisms, such as *Eubacteria* and *Archaebacteria*, lower eukaryotic microorganisms such as fungi, algae and protozoa, as well as mixed populations of plants, plant spores and pollen. The organisms may be cultured organisms or uncultured organisms, obtained from environmental samples and includes extremophiles, such as thermophiles, hyperthermophiles, psychrophiles and psychrotrophs.

Sources of nucleic acids used to generate a DNA library can be obtained from environmental samples, such as, but not limited to, microbial samples obtained from Arctic and Antarctic ice, water or permafrost sources, materials of volcanic origin, materials from soil or plant sources in tropical areas, droppings from various organisms including mammals and invertebrates, as well as dead and decaying matter and the like. The nucleic acids used to generate the gene libraries can be obtained, for example, from enriched subpopulations or isolates of the sample. In another embodiment, DNA of a plurality of isolates can be pooled to create a source of nucleic acids for generation of the library. Alternatively, the nucleic acids can be obtained from a plurality of isolates, a plurality of gene libraries generated from the plurality of isolates to obtain a plurality of gene libraries. Two or more of the gene libraries can be pooled or combined to obtain a pooled isolate library. Thus, for example, nucleic acids may be recovered from either a cultured or non-cultured organism and used to produce an appropriate gene library (e.g., a recombinant expression library) for subsequent determination of the identity of the particular biomolecule of interest (e.g., a polynucleotide sequence) or screened for a bioactivity of interest (e.g., an enzyme or biological activity).

The following outlines a general procedure for producing libraries from both culturable and non-culturable organisms, enriched populations, as well as mixed population of organisms and isolates thereof, which libraries can be probed, sequenced or screened to select therefrom nucleic acid sequences having an identified, desired or predicted biological activity (e.g., an enzymatic activity), which selected nucleic acid sequences can be further evolved, mutagenized or derived.

As used herein an environmental sample is any sample containing organisms or polynucleotides or a combination thereof. Thus, an environmental sample can be obtained from any number of sources (as described above), including, for example, insect feces, hot springs, soil and the like. Any source of nucleic acids in purified or non-purified form can be utilized as starting material. Thus, the nucleic acids may be obtained from any source, which is contaminated by an organism or from any sample containing cells. The environmental sample can be an extract from any bodily sample such as blood, urine, spinal fluid, tissue, vaginal swab, stool, amniotic fluid or buccal mouthwash from any mammalian organism. For non-mammalian (e.g., invertebrates) organisms the sample can be a tissue sample, salivary sample, fecal material or material in the digestive tract of the organism. An environmental sample also includes samples obtained from extreme environments including, for example, hot sulfur pools, volcanic vents, and frozen tundra. The sample can come from a variety of sources. For example, in horticulture and agricultural testing the sample can be a plant, fertilizer, soil, liquid or other horticultural or agricultural product; in food testing the sample can be fresh food or processed food (for example infant formula, seafood, fresh produce and packaged food); and in environmental testing the sample can be liquid, soil, sewage treatment, sludge and any other sample in the environment which is considered or suspected of containing an organism or polynucleotides.

When the sample is a mixture of material containing a mixed population of organisms, for example, blood, soil or sludge, it can be treated with an appropriate ruagent which is effective to open the cells and expose or scparate the strands of nuclic acids. Although not necessary, this lysing and nucleic acid denaturing step will allow cloning, amplification or sequencing to occur more readily. Further, if desired, the mixed population can be cultured prior to analysis in order to purify or enrich a particular population or a desired isolate (e.g., an isolate of a particular species, genus, or family of organisms) and thus obtaining a purer sample. This is not necessary, however. For example, culturing of organisms in the sample can include culturing the organisms, in microdroplets and separating the cultured microdroplets with a cell sorter into individual wells of a multi-well tissue culture plate. Alternatively, the sample can be cultured on any number of selective media compositions designed to inhibit or promote growth of a particular subpopulation of organisms.

Where isolates are derived from the sample containing mixed population of organisms, nucleic acids can be obtained from the isolates as described below. The nucleic acids obtained from the isolates can be used to generate a gene library or, alternatively, be pooled with other isolate fractions of the sample wherein the pooled nucleic acids are used to generate a gene library. The isolates can be cultured prior to extraction of nucleic acids or can be uncultured. Methods of isolating specific populations of organisms present in a mixed population Accordingly, the sample comprises nucleic acids from, for example, a diverse and mixed population of organisms (e.g., microorganisms present in the gut of an insect). Nucleic acids are isolated from the sample using any number of methods for DNA and RNA isolation. Such nucleic acid isolation methods are commonly performed in the art. Where the nucleic acid is RNA, the RNA can be reversed transcribed to DNA using primers known in the art. Where the DNA is genomic DNA, the DNA can be sheared using, for example, a 25-gauge needle.

The nucleic acids can be cloned into an appropriate vector. The vector used will depend upon whether the DNA is to be expressed, amplified, sequenced or manipulated in any number of ways known in the art (see, for example, U.S. Pat. No. 6,022,716 which discloses high throughput sequencing vectors). Cloning techniques are known in the art or can be developed by one skilled in the art, without undue experimentation. The choice of a vector will also depend on the size of the polynucleotide sequence and the host cell to be employed in the methods of the invention. Thus, the vector used in the invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are typically used where the specific nucleic acid sequence to be analyzed or modified is large because these vectors are able to stably propagate large polynucleotides.

The vector containing the cloned nucleic acid sequence can then be amplified by plating (i.e., clonal amplification) or transfecting a suitable host cell with the vector (e.g., a phage on an *E. coli* host). The cloned nucleic acid sequence is used to prepare a library for screening (e.g., expression screening, PCR screening, hybridization screening or the like) by transforming a suitable organism. Hosts, known in the art are transformed by artificial introduction of the vectors containing the nucleic acid sequence by inoculation under conditions conducive for such transformation. One could transform with double stranded circular or linear nucleic acid or there may also be instances where one would transform with single stranded circular or linear nucleic acid sequences. By transform or transformation is meant a permanent or transient genetic change induced in a cell following incorporation of new DNA (e.g., DNA exogenous to the cell). Where the cell is a mammalian cell, a permanent genetic change is generally achieved by introduction of the DNA into the genome of the cell. A transformed cell or host cell generally refers to a cell (e.g., prokaryotic or eukaryotic) into which (or into an ancestor of which) has been introduced, by means of recombinant DNA techniques, a DNA molecule not normally present in the host organism.

A particular type of vector for use in the invention contains an f-factor origin replication. The f-factor (or fertility factor) in *E. coli* is a plasmid which effects high-frequency transfer of itself during conjugation and less frequent transfer of the bacterial chromosome itself. In a particular embodiment cloning vectors referred to as "fosmids" or bacterial artificial chromosome (BAC) vectors are used. These are derived from *E. coli* f-factor which is able to stably integrate large segments of DNA. When integrated with DNA from a mixed uncultured environmental sample, this makes it possible to achieve large genomic fragments in the form of a stable environmental gene library.

The nucleic acids derived from a mixed population or sample may be inserted into the vector by a variety of procedures. In general, the nucleic acid sequence is inserted into an appropriate restriction endonuclease site(s) by procedures known in the art. Such procedures and others are deemed to be within the scope of those skilled in the art. A typical cloning scenario may have DNA "blunted" with an appropriate nuclease (e.g., Mung Bean Nuclease), methylated with, for example, EcoR I Methylase and ligated to EcoR I linkers GGAATTCC. The linkers are then digested with an EcoR I Restriction Endonuclease and the DNA size fractionated (e.g., using a sucrose gradient). The resulting size fractionated DNA is then ligated into a suitable vector for sequencing, screening or expression (e.g., a lambda vector and packaged using an in vitro lambda packaging extract).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl, can be used. Transformation can also be performed after forming a protoplast of the host cell or by electroporation.

When the host is a eukaryote, methods of transfection or transformation with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be cotransfected with a second foreign DNA molecule encoding a selectable marker, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). The eukaryotic cell may be a yeast cell (e.g., *Saccharomyces cerevisiae*), an insect cell (e.g., *Drosophila* sp.) or may be a mammalian cell, including a human cell.

Eukaryotic systems, and mammalian expression systems, allow for post-translational modifications of expressed mammalian proteins to occur. Eukaryotic cells, which possess the cellular machinery for processing of the primary transcript, glycosylation, phosphorylation, or secretion of the gene product should be used. Such host cell lines may include, but are not limited to, CHO, VERO, BHK, HeLa, COS, MDCK, Jurkat, HEK-293, and W138.

In one aspect, once a library of clones is created using any number of methods, including those describe above, the clones are resuspended in a liquid media, for example, a nutrient rich broth or other growth media known in the art. Typically the media is a liquid media, which can be readily pipetted. One or more media types containing at least one clone of the library are then introduced either individually or together as a mixture, into capillaries (all or a portion thereof) in a capillary array.

In another aspect, the library is first biopanned prior to introduction or delivery into a capillary device or other screening technique. Such biopanning methods enrich the library for sequences or activities of interest. Examples of methods for biopanning or enrichment are described below.

In one aspect, the library can be screened or sorted to enrich for clones containing a sequence or activity of interested based on polynucleotide sequences present in the library or clone. Thus, the invention provides methods and compositions useful in screening organisms for a desired biological activity or biological sequence and to assist in obtaining sequences of interest that can further be used in directed evolution, molecular biology, biotechnological and industrial applications.

Accordingly, the invention provides methods to rapidly screen, enrich and/or identify sequences in a sample by screening and identifying the nucleic acid sequences present in the sample. Thus, the invention increases the repertoire of available sequences that can be used for the development of diagnostics, therapeutics or molecules for industrial applications. Accordingly, the methods of the invention can identify novel nucleic acid sequences encoding proteins or polypeptides having a desired biological activity.

After the gene libraries (e.g., an expression library) have been generated one can include the additional step of "biopanning" such libraries prior to expression screening. The "biopanning" procedure refers to a process for identifying clones having a specified biological activity by screening for sequence homology in a library of clones.

The probe sequence used for selectively interacting with the target sequence of interest in the library can be a full-length coding region sequence or a partial coding region sequence for a known bioactivity. The library can be probed using mixtures of probes comprising at least a portion of the sequence encoding a known bioactivity or having a desired bioactivity. These probes or probe libraries are preferably single-stranded. In one aspect, the library is preferably been converted into single-stranded form. The probes that are particularly suitable are those derived from DNA encoding bioactivities having an activity similar or identical to the specified bioactivity, which is to be screened. The probes can be used to PCR amplify and thus select target sequences. Alternatively, the probe sequences can be used as hybridization probes which can be used to identify sequences with substantial or a desired homology.

In another aspect, in vivo biopanning may be performed utilizing a FACS-based machine. Gene libraries or expression libraries are constructed with vectors, which contain elements, which stabilize transcribed RNA. For example, the inclusion of sequences which result in secondary structures such as hairpins, which are designed to flank the transcribed regions of the RNA would serve to enhance their stability, thus increasing their half life within the cell. The probe molecules used in the biopanning process consist of oligonucleotides labeled with detectable molecules that provide a detectable signal upon interaction with a target sequence (e.g., only fluoresce upon binding of the probe to a target molecule). Various dyes or stains well known in the art, for example those described in "Practical Flow Cytometry", 1995 Wiley-Liss, Inc., Howard M. Shapiro, M.D., can be used to intercalate or associate with nucleic acid in order to "label" the oligonucleotides. These probes are introduced into the recombinant cells of the library using one of several transformation methods. The probe molecules interact or hybridize to the transcribed target mRNA or DNA resulting in DNA/RNA heteroduplex molecules or DNA/DNA duplex molecules. Binding of the probe to a target will yield a detectable signal (e.g., a fluorescent signal), which is detected and sorted by a FACS machine, or the like, during the screening process.

The probe DNA should be at least about 10 bases and preferably at least 15 bases. In one aspect, an entire coding region of one part of a pathway may be employed as a probe. Where the probe is hybridized to the target DNA in an in vitro system, conditions for the hybridization in which target DNA is selectively isolated by the use of at least one DNA probe will be designed to provide a hybridization stringency of at least about 50% sequence identity, more particularly a stringency providing for a sequence identity of at least about 70%.

Hybridization techniques for probing a microbial DNA library to isolate target DNA of potential interest are well known in the art and any of those which are described in the literature are suitable for use herein including, for example, chip-based assays, membrane-based assays, and the like.

The resultant libraries of transformed clones can then be further screened for clones, which display an activity of interest. Clones can be shuttled in alternative hosts for expression of active compounds, or screened using methods described herein.

An alternative to the in vivo biopanning described above is an encapsulation technique such as, for example, gel microdroplets, which may be employed to localize multiple clones in one location to be screened on a FACS machine. Clones can then be broken out into individual clones to be screened again on a FACS machine to identify positive individual clones. Screening in this manner using a FACS machine is fully described in patent application Ser. No. 08/876,276 filed Jun. 16, 1997. Thus, for example, if a clone mixture has a desirable activity, then the individual clones may be recovered and rescreened utilizing a FACS machine to determine which of such clones has the specified desirable activity.

Different types of encapsulation strategies and compounds or polymers can be used with the present invention. For instance, high temperature agarose can be employed for making microdroplets stable at high temperatures, allowing stable encapsulation of cells subsequent to heat-kill steps utilized to remove all background activities when screening for thermostable bioactivities. Encapsulation can be in beads, high temperature agaroses, gel microdroplets, cells, such as ghost red blood cells or macrophages, liposomes, or any other means of encapsulating and localizing molecules.

For example, methods of preparing liposomes have been described (e.g., U.S. Pat. Nos. 5,653,996, 5393530 and 5,651,981), as well as the use of liposomes to encapsulate a variety of molecules (e.g., U.S. Pat. Nos. 5,595,756, 5,605, 703, 5,627,159, 5,652,225, 5,567,433, 4,235,871, 5,227, 170). Entrapment of proteins, viruses, bacteria and DNA in erythrocytes during endocytosis has been described, as well (see, for example, Journal of Applied Biochemistry 4, 418–435 (1982)). Erythrocytes employed as carriers in vitro or in vivo for substances entrapped during hypo-osmotic lysis or dielectric breakdown of the membrane have also been described (reviewed in Ihler, G. M. (1983) J. Pharm. Ther). These techniques are useful in the present invention to encapsulate samples in a microenvironment for screening.

"Microenvironment," as used herein, is any molecular structure, which provides an appropriate environment for facilitating the interactions necessary for the method of the invention. An environment suitable for facilitating molecular interactions includes, for example, liposomes. Liposomes can be prepared from a variety of lipids including phospholipids, glycolipids, steroids, long-chain alkyl esters; e.g., alkyl phosphates, fatty acid esters; e.g., lecithin, fatty amines and the like. A mixture of fatty material may be employed such a combination of neutral steroid, a charge amphiphile and a phospholipid. Illustrative examples of phospholipids include lecithin, sphingomyelin and dipalmitoylphos-phati-dylcholine. Representative steroids include cholesterol, cholestanol and lanosterol. Representative charged amphiphilic compounds generally contain from 12–30 carbon atoms. Exemplary compounds include mono- or dialkyl phosphate esters, or alkyl amines; e.g., diacetyl phosphate, stearyl amine, hexadecyl amine, dilauryl phosphate, and the like.

Further, it is possible to combine some or all of the above aspects such that a normalization step is performed prior to generation of the expression library, the expression library is then generated, the expression library so generated is then biopanned, and the biopanned expression library is then screened using a high throughput cell sorting and screening instrument. Thus there are a variety of options, including: (i) generating the library and then screen it; (ii) normalize the target DNA, generate the library and screen it; (iii) normalize, generate the library, biopan and screen; or (iv) generate, biopan and screen the library. The nucleic acids used to generate a library can be obtained, for example, from environmental samples, mixed populations of organisms (e.g., cultured or uncultured), enriched populations thereof, and isolates thereof. In addition, the screening techniques include, for example, hybridization screening, PCR screening, expression screening, and the like.

The gel microdroplet technology has had significance in amplifying the signals available in flow cytometric analysis, and in permitting the screening of microbial strains in strain improvement programs for biotechnology. Wittrup et al., (Biotechnolo. Bioeng. (1993) 42:351–356) developed a microencapsulation selection method which allows the rapid and quantitative screening of $>10^6$ yeast cells for enhanced secretion of *Aspergillus awamori* glucoamylase. The method provides a 400-fold single-pass enrichment for high-secretion mutants.

Gel microdroplet or other related technologies can be used in the present invention to localize, sort as well as amplify signals in the high throughput screening of recombinant libraries. Cell viability during the screening is not an issue or concern since nucleic acid can be recovered from the microdroplet.

Following any number of biopanning techniques capable of enriching the library population for clones containing sequences of interest, the enriched clones are suspended in a liquid media such as a nutrient broth or other growth media. Accordingly, the enriched clones comprise a plurality of host cells transformed with constructs comprising vectors into which have been incorporated nucleic acid sequences derived from a sample (e.g., mixed populations of organisms, isolates thereof, and the like). Liquid media containing a subset of clones and one or more substrates having a detectable molecule (e.g., an enzyme substrate) is then introduced or contacted, either individually or together as a mixture, with the enriched clones (e.g., into capillaries in a capillary array). Interaction (including reaction) of the substrate and a clone expressing an enzyme having the desire enzyme activity produces a product or a detectable signal, which can be spatially detected to identify one or more clones or capillaries containing at least one signal-producing clone. The signal-producing clones or nucleic acids contained in the signal-producing clone can then be recovered using any number of techniques.

A "substrate" as used herein includes, for example, substrates for the detection of a bioactivity or biomolecule (e.g., an enzymes and their specific enzyme activities). Such substrates are well known in the art. For example, various enzymes and suitable substrates specific for such enzymes are provided in Molecular Probes, Handbook Of Fluorescent Probes and Research Chemical (Molecular Probes, Inc.; Eugene, Oreg.), the disclosure of which is incorporated herein by reference. The substrate can have a detectable molecule associated with it including, for example, chromogenic or fluorogenic molecules. A suitable substrate for use in the present invention is any substrate that produces an optically detectable signal upon interaction (e.g., reaction) with a given enzyme having a desired activity, or a given clone encoding such enzyme.

One skilled in the art can choose a suitable substrate based on a desired enzyme activity, for example. Examples of desired enzymes/enzymatic activities include those listed herein. A desired enzyme activity may also comprise a group of enzymes in an enzymatic pathway for which there exists an optical signal substrate. One example of this is the set of carotenoid synthesis enzymes.

Substrates are known and/or are commercially available for glycosidases, proteases, phosphatases, and monoxygenases, among others. Where the desired activity is in the same class as that of other biomolecules or enzymes having a number of known substrates, the activity can be examined using a cocktail of the known substrates. For example, substrates are known for approximately 20 commercially available esterases and the combination of these known substrates can provide detectable, if not optimal, signal production.

The optical signal substrate can be a chromogenic substrate, a fluorogenic substrate, a bio-or chemi-luminescent substrate, or a fluorescence resonance energy transfer (FRET) substrate. The detectable species can be one, which results from cleavage of the substrate or a secondary molecule which is so affected by the cleavage or other substrate/biomolecule interaction as to undergo a detectable change. Innumerable examples of detectable assay formats are known from the diagnostic arts which use immunoassay, chromogenic assay, and labeled probe methodologies.

In one aspect, the optical signal substrate can be a bio- or chemi-luminescent substrate. Chemiluminescent substrates for several enzymes are available from Tropix (Bedford, Mass.). Among the enzymes having known chemiluminescent substrates are alkaline phosphatase, beta-galactosidase, beta-glucuronidase, and beta-glucosidase.

In another aspect, chromogenic substrates may be used, particularly for certain enzymes such as hydrolytic enzymes. For example, the optical signal substrate can be an indolyl derivative, which is enzymatically cleaved to yield a chromogenic product. Where chromogenic substrates are used, the optically detectable signal is optical absorbance (including changes in absorbance). In this embodiment, signal detection can be provided by an absorbance measurement using a spectrophotometer or the like.

In another aspect, a fluorogenic substrate is used, such that the optically detectable signal is fluorescence. Fluorogenic substrates provide high sensitivity for improved detection, as well as alternate detection modes. Hydroxy- and amino-substituted coumarins are the most widely used fluorophores used for preparing fluorogenic substrates. A typical coumarin-based fluorogenic substrate is 7-hydroxycoumarin, commonly known as umbelliferone (Umb). Derivatives and analogs of umbelliferone are also used. Substrate based on derivative and analogs of fluorescein (such as FDG or C12-FDG) and rhodamine are also used. Substrates derived from resorufin (e.g, resorufin beta-D -galactopyranoside or resorufin beta-D-glucouronide) are particularly useful in the present invention. Resorufin-based substrates are useful, for example, in screening for glycosidases, hydrolases and dealkylases. Lipophilic derivatives of the foregoing substrates (e.g., alkylated derivatives) may be useful in certain embodiments, since they generally load more readily into cells and may tend to associate with lipid regions of the cell. Fluorescein and resorufin are available commercially as alkylated derivatives that form products that are relatively insoluble in water (i.e., lipophilic). For example, fluorescence imaging can be performed using C12-resorufin galactoside, produced by Molecular Probes (Eugene, Oreg.) as a substrate.

The particular fluorogenic substrate used may be chosen based on the enzymatic activity being screened.

Monooxygenases (dealkylases). Several coumarin derivatives suitable as monooxygenase substrates are commercially available. Typically, in these substrates, the hydroxylation of the ethyl group in the compound results in the release of the resorufin fluorophore.

Typically, the substrates are able to enter the cell and maintain its presence within the cell for a period sufficient for analysis to occur (e.g., once the substrate is in the cell it does not "leak" back out before reacting with the enzyme being screened to an extend sufficient to produce a detectable response). Retention of the substrate in the cell can be enhanced by a variety of techniques. In one method, the substrate compound is structurally modified by addition of a hydrophobic (e.g., alkyl) tail. In another embodiment, a solvent, such as DMSO or glycerol, can be used to coat the exterior of the cell. Also the substrate can be administered to the cells at reduced temperature, which has been observed to retard leakage of substrates from cells. However, entry of the substrate into the cell is not necessary where, for example, the enzyme or polypeptide is secreted, present in a lysed cellular sample or the like, or where the substrate can act externally to the cell (e.g., an extracellular receptor-ligand complex).

The optical signal substrate can, in some embodiments, be a FRET substrate. FRET is a spectroscopic method that can monitor proximity and relative angular orientation of fluorophores. A fluorescent indicator system that uses FRET to measure the concentration of a substrate or products includes two fluorescent moieties having emission and excitation spectra that render one a "donor" fluorescent moiety and the other an "acceptor" fluorescent moiety. The two fluorescent moieties are chosen such that the excitation spectrum of the acceptor fluorescent moiety overlaps with the emission spectrum of the excited moiety (the donor fluorescence moiety). The donor moiety is excited by light of appropriate intensity within the excitation spectrum of the donor moiety and emits the absorbed energy as fluorescent light. When the acceptor fluorescent protein moiety is positioned to quench the donor moiety in the excited state, the fluorescence energy is transferred to the acceptor moiety, which can emit a second photon. The emission spectra of the donor and acceptor moieties have minimal overlap so that the two emissions can be distinguished. Thus, when acceptor emits fluorescence at longer wavelength that the donor, then the net steady state effect is that the donor's emission is quenched, and the acceptor now emits when excited at the donor's absorption maximum.

The detectable or optical signal can be measured using, for example, a fluorometer (or the like) to detect fluorescence, including fluorescence polarization, time-resolved fluorescence or FRET. In general, excitation radiation, from an excitation source having a first wavelength, causes the excitation radiation to excite the sample. In response, fluorescence compounds in the sample emit radiation having a wavelength that is different from the excitation wavelength. Methods of performing assays on fluorescent materials are well known in the art and are described, e.g, by Lakowicz (Principles of Fluorescence Spectroscopy, New York, Plenum Press, 1983) and Herman ("Resonance energy transfer microscopy," in: Fluorescence Microscopy of Living Cells in Culture, Part B, Methods in Cell Biology, vol.30, ed. Taylor & Wang, San Diego, Academic Press, 1989, pp. 219–243). Examples of fluorescence detection techniques are described in further detail below.

In addition, several methods have been described in the literature for using reporter genes to measure gene expression. Nolan et al. describes a technique to analyze beta-galactosidase expression in mammalian cells. This technique employs fluorescein-di-beta-D-glactopyranoside (FDG) as a substrate for beta-galactosidase, which releases fluorescein, a product that can be detected by its fluorescence emission upon hydrolysis (Nolan et al., 1991). Other fluorogenic substrates have been developed, such as 5-dodecanoylamino fluorescein di-beta-D-galactopyranside (C12-FDG) (Molecular Probes), which differ from FDG in that they are lipophilic fluorescein derivatives that can easily cross most cell membranes under physiological culture conditions.

The above-mentioned beta-galactosidase assays may be employed to screen single *E. coli* cells, expressing recombinant beta-D-galactosidase isolated, for example, from a hyperthermophilic archaeon such as *Sulfolobus solfataricus*. Other reporter genes may be useful as substrates and are known for beta-glucouronidase, alkaline phosphatase, chloramphenical acetyltransferase (CAT) and luciferase.

The library may, for example, be screened for a specified enzyme activity. For example, the enzyme activity screened for may be as an epoxidase or oxygenase. The recombinant enzymes may then be rescreened for a more specific enzyme activity.

Alternatively, the library may be screened for a more specialized enzyme activity. For example, instead of generically screening for epoxidase activity, the library may be screened for a more specialized activity, i.e. the type of bond on which the epoxidase acts.

As described with respect to one of the above aspects, the invention provides a process for activity screening of clones containing selected DNA derived from a microorganism which method includes: screening a library for a biomolecule of interest or bioactivity of interest, wherein the library includes a plurality of clones, the clones having been prepared by recovering nucleic acids (e.g., genomic DNA) from a mixed population of organisms, enriched populations thereof, or isolates thereof, and transforming a host with the nucleic acids to produce clones which are screened for the biomolecule or bioactivity of interest.

In another aspect, an enrichment step may be used before activity based screening. The enrichment step can be, for example, a biopanning method. This procedure of "biopanning" is described and exemplified in U.S. Pat. No. 6,054,002, issued Apr. 25, 2000, which is incorporated herein by reference.

In another aspect, polynucleotides are contained in clones, the clones having been prepared from nucleic acid sequences of a mixed population of organisms, wherein the nucleic acid sequences are used to prepare a gene library of the mixed population of organisms. The gene library is screened for a sequence of interest by transfecting a host cell containing the library with at least one nucleic acid sequence having a detectable molecule which is all or a portion of a DNA sequence encoding a bioactivity having a desirable activity and separating the library clones containing the desirable sequence by, for example, a fluorescent based analysis.

The biopanning approach described above can be used to create libraries enriched with clones carrying sequences homologous to a given probe sequence. Using this approach libraries containing clones with inserts of up to 40 kbp can be enriched approximately 1,000 fold after each round of panning. This enables one to reduce the number of clones to be screened after 1 round of biopanning enrichment. This approach can be applied to create libraries enriched for clones carrying sequence of interest related to a bioactivity of interest for example polyketide sequences.

Hybridization screening using high-density filters or biopanning has proven an efficient approach to detect homologues of pathways containing conserved genes. To discover novel bioactive molecules that may have no known counterparts, however, other approaches are necessary. Another approach of the present invention is to screen in *E. coli* for the expression of small molecule ring structures or "backbones". Because the genes encoding these polycyclic structures can often be expressed in *E. coli* the small molecule backbone can be manufactured albeit in an inactive form. Bioactivity is conferred upon transferring the molecule or pathway to an appropriate host that expresses the requisite glycosylation and methylation genes that can modify or "decorate" the structure to its active form. Thus, inactive ring compounds, recombinantly expressed in *E. coli* are detected to identify clones, which are then shuttled to a metabolically rich host, such as Streptomyces, for subsequent production of the bioactive molecule. The use of high throughput robotic systems allows the screening of hundreds of thousands of clones in multiplexed arrays in microtiter dishes.

One approach to detect and enrich for clones carrying these structures is to use the capillary screening methods or FACS screening, a procedure described and exemplified in U.S. Ser. No. 08/876,276, filed Jun. 16, 1997. Polycyclic ring compounds typically have characteristic fluorescent spectra when excited by ultraviolet light. Thus, clones expressing these structures can be distinguished from background using a sufficiently sensitive detection method. For example, high throughput FACS screening can be utilized to screen for small molecule backbones in *E. coli* libraries. Commercially available FACS machines are capable of screening up to 100,000 clones per second for UV active molecules. These clones can be sorted for further FACS screening or the resident plasmids can be extracted and shuttled to Streptomyces for activity screening.

In an alternate screening approach, after shuttling to Streptomyces hosts, organic extracts from candidate clones can be tested for bioactivity by susceptibility screening against test organisms such as *Staphylococcus aureus*, *E coli*, or *Saccharomyces cerevisiae*. FACS screening can be used in this approach by co-encapsulating clones with the test organism.

An alternative to the above-mentioned screening methods provided by the present invention is an approach termed "mixed extract" screening. The "mixed extract" screening approach takes advantage of the fact that the accessory genes needed to confer activity upon the polycyclic backbones are expressed in metabolically rich hosts, such as Streptomyces, and that the enzymes can be extracted and combined with the backbones extracted from *E. coli* clones to produce the bioactive compound in vitro. Enzyme extract preparations from metabolically rich hosts, such as Streptomyces strains, at various growth stages are combined with pools of organic extracts from *E. coli* libraries and then evaluated for bioactivity.

Another approach to detect activity in the *E. coli* clones is to screen for genes that can convert bioactive compounds to different forms.

Capillary screening, for example, can also be used to detect expression of UV fluorescent molecules in metabolically rich hosts, such as Streptomyces. Recombinant oxytetracylin retains its diagnostic red fluorescence when produced heterologously in *S. lividans* TK24. Pathway clones, which can be identified by the methods and systems of the invention, can thus be screened for polycyclic molecules in a high throughput fashion.

Recombinant bioactive compounds can also be screened in vivo using "two-hybrid" systems, which can detect enhancers and inhibitors of protein-protein or other interactions such as those between transcription factors and their activators, or receptors and their cognate targets. In this embodiment, both a small molecule pathway and a GFP reporter construct are co-expressed. Clones altered in GFP expression can then be identified and the clone isolated for characterization.

The present invention also allows for the transfer of cloned pathways derived from uncultivated samples into metabolically rich hosts for heterologous expression and downstream screening for bioactive compounds of interest using a variety of screening approaches briefly described above.

After viable or non-viable cells, each containing a different expression clone from the gene library, are screened, and positive clones are recovered, DNA can be isolated from positive clones utilizing techniques well known in the art. The DNA can then be amplified either in vivo or in vitro by utilizing any of the various amplification techniques known in the art. In vivo amplification would include transformation of the clone(s) or subclone(s) into a viable host, followed by growth of the host. In vitro amplification can be performed using techniques such as the polymerase chain reaction. Once amplified the identified sequences can be "evolved" or sequenced.

One advantage afforded by present invention is the ability to manipulate the identified biomolecules or bioactivities to generate and select for encoded variants with altered sequence, activity or specificity.

Clones found to have biomolecules or bioactivities for which the screen was performed can be subjected to directed mutagenesis to develop new biomolecules or bioactivities with desired properties or to develop modified biomolecules or bioactivities with particularly desired properties that are absent or less pronounced in nature (e.g., wild-type activity), such as stability to heat or organic solvents. Any of the known techniques for directed mutagenesis are applicable to the invention. For example, particularly preferred mutagenesis techniques for use in accordance with the invention include those described below.

Alternatively, it may be desirable to variegate a biomolecule (e.g., a peptide, protein, or polynucleotide sequence) or a bioactivity (e.g., an enzymatic activity) obtained, identified or cloned as described herein. Such variegation can modify the biomolecule or bioactivity in order to increase or decrease, for example, a polypeptide's activity, specificity, affinity, function, and the like. DNA shuffling can be used to increase variegation in a particular sample. DNA shuffling is meant to indicate recombination between substantially homologous but non-identical sequences, in some embodiments DNA shuffling may involve crossover via non-homologous recombination, such as via cer/lox and/or flp/frt systems and the like (see, for example, U.S. Pat. No. 5,939,250, issued to Dr. Jay Short on Aug. 17, 1999, and assigned to Diversa Corporation, the disclosure of which is incorporated herein by reference). Various methods for shuffling, mutating or variegating polynucleotide or polypeptide sequences are discussed below.

Nucleic acid shuffling is a method for in vitro or in vivo homologous recombination of pools of shorter or smaller polynucleotides to produce a polynucleotide or polynucleotides. Mixtures of related nucleic acid sequences or polynucleotides are subjected to sexual PCR to provide random polynucleotides, and reassembled to yield a library or mixed population of recombinant hybrid nucleic acid molecules or polynucleotides. In contrast to cassette mutagenesis, only shuffling and error-prone PCR allow one to mutate a pool of sequences blindly (without sequence information other than primers).

The advantage of the mutagenic shuffling of the invention over error-prone PCR alone for repeated selection can best be explained as follows. Consider DNA shuffling as compared with error-prone PCR (not sexual PCR). The initial library of selected or pooled sequences can consist of related sequences of diverse origin or can be derived by any type of mutagenesis (including shuffling) of a single gene. A collection of selected sequences is obtained after the first round of activity selection. Shuffling allows the free combinatorial association of all of the related sequences, for example.

This method differs from error-prone PCR, in that it is an inverse chain reaction. In error-prone PCR, the number of polymerase start sites and the number of molecules grows exponentially. However, the sequence of the polymerase start sites and the sequence of the molecules remains essentially the same. In contrast, in nucleic acid reassembly or shuffling of random polynucleotides the number of start sites and the number (but not size) of the random polynucleotides decreases over time. For polynucleotides derived from whole plasmids the theoretical endpoint is a single, large concatemeric molecule.

Since crossovers occur at regions of homology, recombination will primarily occur between members of the same sequence family. This discourages combinations of sequences that are grossly incompatible (e.g., having different activities or specificities). It is contemplated that multiple families of sequences can be shuffled in the same reaction. Further, shuffling generally conserves the relative order.

Rare shufflants will contain a large number of the best molecules (e.g., highest activity or specificity) and these rare shufflants may be selected based on their superior activity or specificity.

A pool of 100 different polypeptide sequences can be permutated in up to $10^3$ different ways. This large number of permutations cannot be represented in a single library of DNA sequences. Accordingly, it is contemplated that multiple cycles of DNA shuffling and selection may be required depending on the length of the sequence and the sequence diversity desired. Error-prone PCR, in contrast, keeps all the selected sequences in the same relative orientation, generating a much smaller mutant cloud.

The template polynucleotide, which may be used in the methods of the invention may be DNA or RNA. It may be of various lengths depending on the size of the gene or shorter or smaller polynucleotide to be recombined or reassembled. Preferably, the template polynucleotide is from 50 bp to 50 kb. It is contemplated that entire vectors containing the nucleic acid encoding the protein of interest can be used in the methods of the invention, and in fact have been successfully used.

The template polynucleotide may be obtained by amplification using the PCR reaction (U.S. Pat. Nos. 4,683,202 and 4,683,195) or other amplification or cloning methods. However, the removal of free primers from the PCR products before subjecting them to pooling of the PCR products and sexual PCR may provide more efficient results. Failure to adequately remove the primers from the original pool before sexual PCR can lead to a low frequency of crossover clones.

The template polynucleotide often is double-stranded. A double-stranded nucleic acid molecule is recommended to ensure that regions of the resulting single-stranded polynucleotides are complementary to each other and thus can hybridize to form a double-stranded molecule.

It is contemplated that single-stranded or double-stranded nucleic acid polynucleotides having regions of identity to the template polynucleotide and regions of heterology to the template polynucleotide may be added to the template polynucleotide, at this step. It is also contemplated that two different but related polynucleotide templates can be mixed at this step.

The double-stranded polynucleotide template and any added double-or single-stranded polynucleotides are subjected to sexual PCR which includes slowing or halting to provide a mixture of from about 5 bp to 5 kb or more. Preferably the size of the random polynucleotides is from about 10 bp to 1000 bp, more preferably the size of the polynucleotides is from about 20 bp to 500 bp.

Alternatively, it is also contemplated that double-stranded nucleic acid having multiple nicks may be used in the methods of the invention. A nick is a break in one strand of the double-stranded nucleic acid. The distance between such nicks is preferably 5 bp to 5 kb, more preferably between 10 bp to 1000 bp. This can provide areas of self-priming to produce shorter or smaller polynucleotides to be included with the polynucleotides resulting from random primers, for example.

The concentration of any one specific polynucleotide will not be greater than 1% by weight of the total polynucleotides, more preferably the concentration of any one specific nucleic acid sequence will not be greater than 0.1% by weight of the total nucleic acid.

The number of different specific polynucleotides in the mixture will be at least about 100, preferably at least about 500, and more preferably at least about 1000.

At this step single-stranded or double-stranded polynucleotides, either synthetic or natural, may be added to the random double-stranded shorter or smaller polynucieotides in order to increase the heterogeneity of the mixture of polynucleotides.

It is also contemplated that populations of double-stranded randomly broken polynucleotides may be mixed or combined at this step with the polynucleotides from the sexual PCR process and optionally subjected to one or more additional sexual PCR cycles.

Where insertion of mutations into the template polynucleotide is desired, single-stranded or double-stranded polynucleotides having a region of identity to the template polynucleotide and a region of heterology to the template polynucleotide may be added in a 20 fold excess by weight as compared to the total nucleic acid, more preferably the single-stranded polynucleotides may be added in a 10 fold excess by weight as compared to the total nucleic acid.

Where a mixture of different but related template polynucleotides is desired, populations of polynucleotides from each of the templates may be combined at a ratio of less than about 1:100, more preferably the ratio is less than about 1:40. For example, a backcross of the wild-type polynucleotide with a population of mutated polynucleotide may be desired to eliminate neutral mutations (e.g., mutations yielding an insubstantial alteration in the phenotypic property being selected for). In such an example, the ratio of randomly provided wild-type polynucleotides which may be added to the randomly provided sexual PCR cycle hybrid polynucleotides is approximately 1:1 to about 100:1, and more preferably from 1:1 to 40:1.

The mixed population of random polynucleotides are denatured to form single-stranded polynucleotides and then re-annealed. Only those single-stranded polynucleotides having regions of homology with other single-stranded polynucleotides will re-anneal.

The random polynucleotides may be denatured by heating. One skilled in the art could determine the conditions necessary to completely denature the double-stranded nucleic acid. Preferably the temperature is from 80 degrees Centigrade (C) to 100 degrees C., more preferably the temperature is from 90 degrees C to 96 degrees C. Other methods, which may be used to denature the polynucleotides include pressure and pH.

The polynucleotides may be re-annealed by cooling. In one aspect, the temperature is from 20° C. to 75° C., more preferably the temperature is from 40° C. to 65° C. If a high frequency of crossovers is needed based on an average of only 4 consecutive bases of homology, recombination can be forced by using a low annealing temperature, although the process becomes more difficult. The degree of renaturation, which occurs will depend on the degree of homology between the population of single-stranded polynucleotides.

Renaturation can be accelerated by the addition of polyethylene glycol ("PEG") or salt. The salt concentration is preferably from 0 mM to 200 mM, more preferably the salt concentration is from 10 mM to 100 mm. The salt may be KCl or NaCl. The concentration of PEG is preferably from 0% to 20%, more preferably from 5% to 10%.

The annealed polynucleotides are next incubated in the presence of a nucleic acid polymerase and dNTP's (i.e. dATP, dCTP, DGTP and dTTP). The nucleic acid polymerase may be the Klenow fragment, the Taq polymerase or any other DNA polymerase known in the art.

The approach to be used for the assembly depends on the minimum degree of homology that should still yield crossovers. If the areas of identity are large, Taq polymerase can be used with an annealing temperature of between 45–65° C. If the areas of identity are small, Klenow polymerase can be used with an annealing temperature of between 20–30° C. One skilled in the art could vary the temperature of annealing to increase the number of crossovers achieved.

The polymerase may be added to the random polynucleotides prior to annealing, simultaneously with annealing or after annealing. The cycle of denaturation, renaturation and incubation in the presence of polymerase is referred to herein as shuffling or reassembly of the nucleic acid. This cycle is repeated for a desired number of times. Preferably the cycle is repeated from 2 to 50 times, more preferably the sequence is repeated from 10 to 40 times. The resulting nucleic acid is a larger double-stranded polynucleotide of from about 50 bp to about 100 kb, preferably the larger polynucleotide is from 500 bp to 50 kb.

These larger polynucleotides may contain a number of copies of a polynucleotide having the same size as the template polynucleotide in tandem. This concatemeric polynucleotide is then denatured into single copies of the template polynucleotide. The result will be a population of polynucleotides of approximately the same size as the template polynucleotide. The population will be a mixed population where single or double-stranded polynucleotides having an area of identity and an area of heterology have been added to the template polynucleotide prior to shuffling. These polynucleotides are then cloned into the appropriate vector and the ligation mixture used to transform bacteria.

It is contemplated that the single polynucleotides may be obtained from the larger concatemeric polynucleotide by amplification of the single polynucleotide prior to cloning by a variety of methods including PCR (U.S. Pat. Nos. 4,683,195 and 4,683,202), rather than by digestion of the concatemer.

The vector used for cloning is not critical provided that it will accept a polynucleotide of the desired size. If expression of the particular polynucleotide is desired, the cloning vehicle should further comprise transcription and translation signals next to the site of insertion of the polynucleotide to allow expression of the polynucleotide in the host cell.

The resulting bacterial population will include a number of recombinant polynucleotides having random mutations. This mixed population may be tested to identify the desired recombinant polynucleotides. The method of selection will depend on the polynucleotide desired.

For example, if a polynucleotide, identified by the methods of described herein, encodes a protein with a first binding affinity, subsequent mutated (e.g., shuffled) sequences having an increased binding efficiency to a ligand may be desired. In such a case the proteins expressed by each of the portions of the polynucleotides in the population or library may be tested for their ability to bind to the ligand by methods known in the art (i.e. panning, affinity chromatography). If a polynucleotide, which encodes for a protein with increased drug resistance is desired, the proteins expressed by each of the polynucleotides in the population or library may be tested for their ability to confer drug resistance to the host organism. One skilled in the art, given knowledge of the desired protein, could readily test the population to identify polynucleotides, which confer the desired properties onto the protein.

It is contemplated that one skilled in the art could use a phage display system in which fragments of the protein are expressed as fusion proteins on the phage surface (Pharmacia, Milwaukee Wis.). The recombinant DNA molecules are cloned into the phage DNA at a site, which results in the transcription of a fusion protein a portion of which is encoded by the recombinant DNA molecule. The phage containing the recombinant nucleic acid molecule undergoes replication and transcription in the cell. The leader sequence of the fusion protein directs the transport of the fusion protein to the tip of the phage particle. Thus, the fusion protein, which is partially encoded by the recombinant DNA molecule is displayed on the phage particle for detection and selection by the methods described above.

It is further contemplated that a number of cycles of nucleic acid shuffling may be conducted with polynucleotides from a sub-population of the first population, which sub-population contains DNA encoding the desired recombinant protein. In this manner, proteins with even higher binding affinities or enzymatic activity could be achieved.

It is also contemplated that a number of cycles of nucleic acid shuffling may be conducted with a mixture of wild-type polynucleotides and a sub-population of nucleic acid from the first or subsequent rounds of nucleic acid shuffling in order to remove any silent mutations from the sub-population.

Any source of nucleic acid, in a purified form can be utilized as the starting nucleic acid. Thus the process may employ DNA or RNA including messenger RNA, which DNA or RNA may be single or double stranded. In addition, a DNA-RNA hybrid, which contains one strand of each may be utilized. The nucleic acid sequence may be of various lengths depending on the size of the nucleic acid sequence to be mutated. Preferably the specific nucleic acid sequence is from 50 to 50,000 base pairs. It is contemplated that entire vectors containing the nucleic acid encoding the protein of interest may be used in the methods of the invention.

Any specific nucleic acid sequence can be used to produce the population of hybrids by the present process. It is only necessary that a small population of hybrid sequences of the specific nucleic acid sequence exist or be available for the present process.

A population of specific nucleic acid sequences having mutations may be created by a number of different methods. Mutations may be created by error-prone PCR. Error-prone PCR uses low-fidelity polymerization conditions to introduce a low level of point mutations randomly over a long sequence. Alternatively, mutations can be introduced into the template polynucleotide by oligonucleotide-directed mutagenesis. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. Other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid polynucleotides so mutagenized are introduced into E. coli and propagated as a pool or library of hybrid plasmids.

Alternatively, a small mixed population of specific nucleic acids may be found in nature in that they may consist of different alleles of the same gene or the same gene from different related species (i.e., cognate genes). Alternatively, they may be related DNA sequences found within one species, for example, the immunoglobulin genes.

Once a mixed population of specific nucleic acid sequences is generated, the polynucleotides can be used directly or inserted into an appropriate cloning vector, using techniques well-known in the art.

The choice of vector depends on the size of the polynucleotide sequence and the host cell to be employed in the methods of the invention. The templates of the invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are preferred where the specific nucleic acid sequence to be mutated is larger because these vectors are able to stably propagate large polynucleotides.

If a mixed population of the specific nucleic acid sequence is cloned into a vector it can be clonally amplified. Utility can be readily determined by screening expressed polypeptides.

The DNA shuffling method of the invention can be performed blindly on a pool of unknown sequences. By adding to the reassembly mixture oligonucleotides (with ends that are homologous to the sequences being reassembled) any sequence mixture can be incorporated at any specific position into another sequence mixture. Thus, it is contemplated that mixtures of synthetic oligonucleotides, PCR polynucleotides or even whole genes can be mixed into another sequence library at defined positions. The insertion of one sequence (mixture) is independent from the insertion of a sequence in another part of the template. Thus, the degree of recombination, the homology required, and the diversity of the library can be independently and simultaneously varied along the length of the reassembled DNA.

Shuffling requires the presence of homologous regions separating regions of diversity. Scaffold-like protein structures may be particularly suitable for shuffling. The conserved scaffold determines the overall folding by self-association, while displaying relatively unrestricted loops that mediate the specific binding. Examples of such scaffolds are the immunoglobulin beta-barrel, and the four-helix bundle which are well-known in the art. This shuffling can be used to create scaffold-like proteins with various combinations of mutated sequences for binding.

The equivalents of some standard genetic matings may also be performed by shuffling in vitro. For example, a "molecular backcross" can be performed by repeatedly mixing the hybrid's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (e.g., immunogenicity). Thus it can be useful to determine which mutations in a protein are involved in the enhanced biological activity and which are not, an advantage which cannot be achieved by error-prone mutagenesis or cassette mutagenesis methods.

Large, functional genes can be assembled correctly from a mixture of small random polynucleotides. This reaction may be of use for the reassembly of genes from the highly fragmented DNA of fossils. In addition random nucleic acid fragments from fossils may be combined with polynucleotides from similar genes from related species.

It is also contemplated that the method of the invention can be used for the in vitro amplification of a whole genome from a single cell as is needed for a variety of research and diagnostic applications. DNA amplification by PCR typically includes sequences of about 40 kb. Amplification of a whole genome such as that of E. coli (5, 000 kb) by PCR would require about 250 primers yielding 125 forty kb polynucleotides. On the other hand, random production of polynucleotides of the genome with sexual PCR cycles, followed by gel purification of small polynucleotides will provide a multitude of possible primers. Use of this mix of random small polynucleotides as primers in a PCR reaction alone or with the whole genome as the template should result in an inverse chain reaction with the theoretical endpoint of a single concatamer containing many copies of the genome.

A 100 fold amplification in the copy number and an average polynucleotide size of greater than 50 kb may be obtained when only random polynucleotides are used. It is thought that the larger concatamer is generated by overlap of many smaller polynucleotides. The quality of specific PCR products obtained using synthetic primers will be indistinguishable from the product obtained from unamplified DNA. It is expected that this approach will be useful for the mapping of genomes.

The polynucleotide to be shuffled can be produced as random or non-random polynucleotides, at the discretion of the practitioner. Moreover, the invention provides a method of shuffling that is applicable to a wide range of polynucleotide sizes and types, including the step of generating polynucleotide monomers to be used as building blocks in the reassembly of a larger polynucleotide. For example, the building blocks can be fragments of genes or they can be comprised of entire genes or gene pathways, or any combination thereof.

In an aspect of in vivo shuffling, a mixed population of a specific nucleic acid sequence is introduced into bacterial or eukaryotic cells under conditions such that at least two different nucleic acid sequences are present in each host cell. The polynucleotides can be introduced into the host cells by a variety of different methods. The host cells can be transformed with the smaller polynucleotides using methods known in the art, for example treatment with calcium chloride. If the polynucleotides are inserted into a phage genome, the host cell can be transfected with the recombinant phage genome having the specific nucleic acid sequences. Alternatively, the nucleic acid sequences can be introduced into the host cell using electroporation, transfection, lipofection, biolistics, conjugation, and the like.

In general, in this aspect, specific nucleic acid sequences will be present in vectors, which are capable of stably replicating the sequence in the host cell. In addition, it is contemplated that the vectors will encode a marker gene such that host cells having the vector can be selected. This ensures that the mutated specific nucleic acid sequence can be recovered after introduction into the host cell. However, it is contemplated that the entire mixed population of the specific nucleic acid sequences need not be present on a vector sequence. Rather only a sufficient number of sequences need be cloned into vectors to ensure that after introduction of the polynucleotides into the host cells each host cell contains one vector having at least one specific nucleic acid sequence present therein. It is also contemplated that rather than having a subset of the population of the specific nucleic acids sequences cloned into vectors, this subset may be already stably integrated into the host cell.

It has been found that when two polynucleotides, which have regions of identity are inserted into the host cells homologous recombination occurs between the two polynucleotides. Such recombination between the two mutated specific nucleic acid sequences will result in the production of double or triple hybrids in some situations.

It has also been found that the frequency of recombination is increased if some of the mutated specific nucleic acid sequences are present on linear nucleic acid molecules. Therefore, in a one embodiment, some of the specific nucleic acid sequences are present on linear polynucleotides.

After transformation, the host cell transformants are placed under selection to identify those host cell transformants, which contain mutated specific nucleic acid sequences having the qualities desired. For example, if increased resistance to a particular drug is desired then the transformed host cells may be subjected to increased concentrations of the particular drug and those transformants producing mutated proteins able to confer increased drug resistance will be selected. If the enhanced ability of a particular protein to bind to a receptor is desired, then expression of the protein can be induced from the transformants and the resulting protein assayed in a ligand binding assay by methods known in the art to identify that subset of the mutated population which shows enhanced binding to the ligand. Alternatively, the protein can be expressed in another system to ensure proper processing.

Once a subset of the first recombined specific nucleic acid sequences (daughter sequences) having the desired characteristics are identified, they are then subject to a second round of recombination. In the second cycle of recombination, the recombined specific nucleic acid sequences may be mixed with the original mutated specific nucleic acid sequences (parent sequences) and the cycle repeated as described above. In this way a set of second recombined specific nucleic acids sequences can be identified which have enhanced characteristics or encode for proteins having enhanced properties. This cycle can be repeated a number of times as desired.

It is also contemplated that in the second or subsequent recombination cycle, a backcross can be performed. A molecular backcross can be performed by mixing the desired specific nucleic acid sequences with a large number of the wild-type sequences, such that at least one wild-type nucleic acid sequence and a mutated nucleic acid sequence are present in the same host cell after transformation. Recombination with the wild-type specific nucleic acid sequence will eliminate those neutral mutations that may affect unselected characteristics such as immunogenicity but not the selected characteristics.

In another aspect of the invention, it is contemplated that during the first round a subset of specific nucleic acid sequences can be generated as smaller polynucleotides by slowing or halting their PCR amplification prior to introduction into the host cell. The size of the polynucleotides must be large enough to contain some regions of identity with the other sequences so as to homoiogousiy recombine with the other sequences. The size of the polynucleotides will range from 0.03 kb to 100 kb more preferably from 0.2 kb to 10 kb. It is also contemplated that in subsequent rounds, all of the specific nucleic acid sequences other than the sequences selected from the previous round may be utilized to generate PCR polynucleotides prior to introduction into the host cells.

The shorter polynucleotide sequences can be single-stranded or double-stranded. The reaction conditions suitable for separating the strands of nucleic acid are well known in the art. The steps of this process can be repeated indefinitely, being limited only by the number of possible hybrids, which can be achieved. Therefore, the initial pool or population of mutated template nucleic acid is cloned into a vector capable of replicating in a bacteria such as *E. coli*. The particular vector is not essential, so long as it is capable of autonomous replication in *E. coli*. In a one embodiment, the vector is designed to allow the expression and production of any protein encoded by the mutated specific nucleic acid linked to the vector. It is also preferred that the vector contain a gene encoding for a selectable marker.

The population of vectors containing the pool of mutated nucleic acid sequences is introduced into the *E. coli* host cells. The vector nucleic acid sequences may be introduced by transformation, transfection or infection in the case of phage. The concentration of vectors used to transform the bacteria is such that a number of vectors is introduced into each cell. Once present in the cell, the efficiency of homologous recombination is such that homologous recombination occurs between the various vectors. This results in the generation of hybrids (daughters) having a combination of mutations, which differ from the original parent mutated sequences. The host cells are then clonally replicated and selected for the marker gene present on the vector. Only those cells having a plasmid will grow under the selection. The host cells, which contain a vector are then tested for the presence of favorable mutations.

Once a particular daughter mutated nucleic acid sequence has been identified which confers the desired characteristics, the nucleic acid is isolated either already linked to the vector or separated from the vector. This nucleic acid is then mixed with the first or parent population of nucleic acids and the cycle is repeated.

The parent mutated specific nucleic acid population, either as polynucleotides or cloned into the same vector is introduced into the host cells already containing the daughter nucleic acids. Recombination is allowed to occur in the cells and the next generation of recombinants, or granddaughters are selected by the methods described above. This cycle can be repeated a number of times until the nucleic acid or peptide having the desired characteristics is obtained. It is contemplated that in subsequent cycles, the population of mutated sequences, which are added to the hybrids may come from the parental hybrids or any subsequent generation.

In an alternative aspect, the invention provides a method of conducting a "molecular" backcross of the obtained recombinant specific nucleic acid in order to eliminate any neutral mutations. Neutral mutations are those mutations, which do not confer onto the nucleic acid or peptide the desired properties. Such mutations may however confer on the nucleic acid or peptide undesirable characteristics. Accordingly, it is desirable to eliminate such neutral mutations. The method of the invention provides a means of doing so.

In this aspect, after the hybrid nucleic acid, having the desired characteristics, is obtained by the methods of the embodiments, the nucleic acid, the vector having the nucleic acid or the host cell containing the vector and nucleic acid is isolated.

The nucleic acid or vector is then introduced into the host cell with a large excess of the wild-type nucleic acid. The nucleic acid of the hybrid and the nucleic acid of the wild-type sequence are allowed to recombine. The resulting recombinants are placed under the same selection as the hybrid nucleic acid. Only those recombinants, which retained the desired characteristics will be selected. Any silent mutations which do not provide the desired characteristics will be lost through recombination with the wild-type DNA. This cycle can be repeated a number of times until all of the silent mutations are eliminated.

In another aspect, the invention provides for a method for shuffling, assembling, reassembling, recombining, and/or concatenating at least two polynucleotides to form a progeny polynucleotide (e.g., a chimeric progeny polynucleotide that can be expressed to produce a polypeptide or a gene pathway). In a particular embodiment, a double stranded polynucleotide (e.g., two single stranded sequences hybridized to each other as hybridization partners) is treated with an exonuclease to liberate nucleotides from one of the two strands, leaving the remaining strand free of its original partner so that, if desired, the remaining strand may be used to achieve hybridization to another partner.

In a particular aspect, a double stranded polynucleotide end (that may be part of—or connected to—a polynucleotide or a non-polynucleotide sequence) is subjected to a source of exonuclease activity. Enzyme with 3' exonuclease activity, an enzyme with 5' exonuclease activity, an enzyme with both 3' exonuclease activity and 5' exonuclease activity, and any combination thereof can be used in the invention. An exonuclease can be used to liberate nucleotides from one or both ends of a linear double stranded polynucleotide, and from one to all ends of a branched polynucleotide having more than two ends.

By contrast, a non-enzymatic step may be used to shuffle, assemble, reassemble, recombine, and/or concatenate polynucleotide building blocks that is comprised of subjecting a working sample to denaturing (or "melting") conditions (for example, by changing temperature, pH, and /or salinity conditions) so as to melt a working set of double stranded polynucleotides into single polynucleotide strands. For shuffling, it is desirable that the single polynucleotide strands participate to some extent in annealment with different hybridization partners (i.e. and not merely revert to exclusive re-annealment between what were former partners before the denaturation step). The presence of the former hybridization partners in the reaction vessel, however, does not preclude, and may sometimes even favor, re-annealment of a single stranded polynucleotide with its former partner, to recreate an original double stranded polynucleotide.

In contrast to this non-enzymatic shuffling step comprised of subjecting double stranded polynucleotide building blocks to denaturation, followed by annealment, the invention further provides an exonuclease-based approach requiring no denaturation—rather, the avoidance of denaturing conditions and the maintenance of double stranded polynucleotide substrates in annealed (i.e. non-denatured) state are necessary conditions for the action of exonucleases (e.g., exonuclease III and red alpha gene product). In further contrast, the generation of single stranded polynucleotide sequences capable of hybridizing to other single stranded polynucleotide sequences is the result of covalent cleavage—and hence sequence destruction—in one of the hybridization partners. For example, an exonuclease III enzyme may be used to enzymatically liberate 3' terminal nucleotides in one hybridization strand (to achieve covalent hydrolysis in that polynucleotide strand); and this favors hybridization of the remaining single strand to a new partner (since its former partner was subjected to covalent cleavage).

It is particularly appreciated that enzymes can be discovered, optimized (e.g., engineered by directed evolution), or both discovered and optimized specifically for the instantly disclosed approach that have more optimal rates and/or more highly specific activities &/or greater lack of unwanted activities. In fact it is expected that the invention may encourage the discovery and/or development of such designer enzymes.

Furthermore, it is appreciated that one can protect the end of a double stranded polynucleotide or render it susceptible to a desired enzymatic action of an exonuclease as necessary. For example, a double stranded polynucleotide end having a 3' overhang is not susceptible to the exonuclease action of exonuclease III. However, it may be rendered susceptible to the exonuclease action of exonuclease III by a variety of means; for example, it may be blunted by treatment with a polymerase, cleaved to provide a blunt end or a 5' overhang, joined (ligated or hybridized) to another double stranded polynucleotide to provide a blunt end or a 5' overhang, hybridized to a single stranded polynucleotide to provide a blunt end or a 5' overhang, or modified by any of a variety of means).

According to one aspect, an exonuclease may be allowed to act on one or on both ends of a linear double stranded polynucleotide and proceed to completion, to near completion, or to partial completion. When the exonuclease action is allowed to go to completion, the result will be that the length of each 5' overhang will be extend far towards the middle region of the polynucleotide in the direction of what might be considered a "rendezvous point" (which may be somewhere near the polynucleotide midpoint). Ultimately, this results in the production of single stranded polynucleotides (that can become dissociated) that are each about half the length of the original double stranded polynucleotide.

Thus, the exonuclease-mediated approach is useful for shuffling, assembling and/or reassembling, recombining, and concatenating polynucleotide building blocks. The polynucleotide building blocks can be up to ten bases long or tens of bases long or hundreds of bases long or thousands of bases long or tens of thousands of bases long or hundreds of thousands of bases long or millions of bases long or even longer.

Substrates for an exonuclease may be generated by subjecting a double stranded polynucleotide to fragmentation. Fragmentation may be achieved by mechanical means (e.g., shearing, sonication, and the like), by enzymatic means (e.g., using restriction enzymes), and by any combination thereof. Fragments of a larger polynucleotide may also be generated by polymerase-mediated synthesis.

Additional examples of enzymes with exonuclease activity include red-alpha and venom phosphodiesterases. Red alpha (red alpha gene product (also referred to as lambda exonuclease) is of bacteriophage alpha origin. Red alpha gene product acts processively from 5'-phosphorylated termini to liberate mononucleotides from duplex DNA (Takahashi & Kobayashi, 1990). Venom phosphodiesterases (Laskowski, 1980) is capable of rapidly opening supercoiled DNA.

Thus, in one aspect, the invention provides a non-stochastic method of producing a set of finalized chimeric nucleic acid molecules having an overall assembly order that is chosen by design, which method is comprised of the steps of generating, by design, a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one embodiment of the invention, the annealed building pieces are treated with an enzyme, such as a ligase (e.g., T4 DNA ligase) to achieve covalent bonding of the building pieces.

In a another aspect, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related products. In a particular exemplification, the encoded products are enzymes. These exemplifications, while illustrating certain specific aspects of the invention, do not portray the limitations or circumscribe the scope of the disclosed invention.

Thus according to one aspect of the invention, the sequences of a plurality of progenitor nucleic acid templates identified using the methods of the invention are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates, and preferably at almost all of the progenitor templates. Even more preferably still a demarcation point is an area of homology that is shared by all of the progenitor templates.

In another aspect, the ligation reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the invention, the possibility of unwanted side products is greatly reduced.

In yet another aspect, the invention provides that, the ligation reassembly process is performed systematically, for example in order to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. In a particularly embodiment, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one embodiment, this polynucleotide is a gene, which may be a man-made gene. According to another embodiment, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a demarcation point.

Thus, according to another embodiment, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). Preferably, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In a preferred instance, the recombination is facilitated by, or occurs at, areas of homology between the man-made intron-containing gene and a nucleic acid with serves as a recombination partner. In a particularly preferred instance, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic ligation reassembly method of the invention utilizes a plurality of nucleic acid building blocks, each of which preferably has two ligatable ends. The two ligatable ends on each nucleic acid building block may be two blunt ends (i.e. each having an overhang of zero nucleotides), or preferably one blunt end and one overhang, or more preferably still two overhangs.

An overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

According to one aspect, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Preferred sizes for building block range from 1 base pair (not including any overhangs) to 100,000 base pairs (not including any overhangs). Other preferred size ranges are also provided, which have, lower limits of from 1 bp to 10,000 bp (including every integer value in between), and upper limits of from 2 bp to 100, 000 bp (including every integer value in between).

Many methods exist by which a double-stranded nucleic acid building block can be generated that is serviceable for the invention; and these are known in the art and can be readily performed by the skilled artisan.

According to one aspect, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another embodiment, the two strands of a double-stranded nucleic acid building block are complementary at fewer than every nucleotide apart from any that form an overhang. Thus, according to this embodiment, a double-stranded nucleic acid building block can be used to introduce codon degeneracy. Preferably the codon degeneracy is introduced using the site-saturation mutagenesis described herein, using one or more N,N, G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

The invention provides a method for selecting a subset of polynucleotides from a starting set of polynucleotides, which method is based on the ability to discriminate one or more selectable features (or selection markers) present anywhere in a working polynucleotide, so as to allow one to perform selection for (positive selection) and/or against (negative selection) each selectable polynucleotide. In a one aspect, a method is provided termed end-selection, which method is based on the use of a selection marker located in part or entirely in a terminal region of a selectable polynucleotide, and such a selection marker may be termed an "end-selection marker".

End-selection may be based on detection of naturally occurring sequences or on detection of sequences introduced experimentally (including by any mutagenesis procedure mentioned herein and not mentioned herein) or on both, even within the same polynucleotide. An end-selection marker can be a structural selection marker or a functional selection marker or both a structural and a functional selection marker. An end-selection marker may be comprised of a polynucleotide sequence or of a polypeptide sequence or of any chemical structure or of any biological or biochemical tag, including markers that can be selected using methods based on the detection of radioactivity, of enzymatic activity, of fluorescence, of any optical feature, of a magnetic property (e.g., using magnetic beads), of immunoreactivity, and of hybridization.

End-selection may be applied in combination with any method for performing mutagenesis. Such mutagenesis methods include, but are not limited to, methods described herein (supra and infra). Such methods include, by way of non-limiting exemplification, any method that may be referred herein or by others in the art by any of the following terms: "saturation mutagenesis", "shuffling", "recombination", "re-assembly", "error-prone PCR", "assembly PCR", "sexual PCR", "crossover PCR", "oligonucleotide primer-directed mutagenesis", "recursive (and/or exponential) ensemble mutagenesis (see Arkin and Youvan, 1992)", "cassette mutagenesis", "in vivo mutagenesis", and "in vitro mutagenesis". Moreover, end-selection may be performed on molecules produced by any mutagenesis and/or amplification method (see, e.g., Arnold, 1993; Caldwell and Joyce, 1992; Stemmer, 1994) following which method it is desirable to select for (including to screen for the presence of) desirable progeny molecules.

In addition, end-selection may be applied to a polynucleotide apart from any mutagenesis method. In one aspect, end-selection, as provided herein, can be used in order to facilitate a cloning step, such as a step of ligation to another polynucleotide (including ligation to a vector). The invention thus provides for end-selection as a means to facilitate library construction, selection and/or enrichment for desirable polynucleotides, and cloning in general.

In another aspect, end-selection can be based on (positive) selection for a polynucleotide; alternatively end-selection can be based on (negative) selection against a polynucleotide; and alternatively still, end-selection can be based on both (positive) selection for, and on (negative) selection against, a polynucleotide. End-selection, along with other methods of selection and/or screening, can be performed in an iterative fashion, with any combination of like or unlike selection and/or screening methods and mutagenesis or directed evolution methods, all of which can be performed in an iterative fashion and in any order, combination, and permutation. It is also appreciated that end-selection may also be used to select a polynucleotide in a: circular (e.g., a plasmid or any other circular vector or any other polynucleotide that is partly circular), and/or branched, and/or modified or substituted with any chemical group or moiety.

In one non-limiting aspect, end-selection of a linear polynucleotide is performed using a general approach based on the presence of at least one end-selection marker located at or near a polynucleotide end or terminus (that can be either a 5' end or a 3' end). In one particular non-limiting exemplification, end-selection is based on selection for a specific sequence at or near a terminus such as, but not limited to, a sequence recognized by an enzyme that recognizes a polynucleotide sequence. An enzyme that recognizes and catalyzes a chemical modification of a polynucleotide is referred to herein as a polynucleotide-acting enzyme. In a preferred embodiment, polynucleotide-acting enzymes are exemplified non-exclusively by enzymes with polynucleotide-cleaving activity, enzymes with polynucleotide-methylating activity, enzymes with polynucleotide-ligating activity, and enzymes with a plurality of distinguishable enzymatic activities (including non-exclusively, e.g., both polynucleotide-cleaving activity and polynucleotide-ligating activity).

It is appreciated that relevant polynucleotide-acting enzymes include any enzymes identifiable by one skilled in the art (e.g., commercially available) or that may be developed in the future, though currently unavailable, that are useful for generating a ligation compatible end, preferably a sticky end, in a polynucleotide. It may be preferable to use restriction sites that are not contained, or alternatively that are not expected to be contained, or alternatively that are unlikely to be contained (e.g., when sequence information regarding a working polynucleotide is incomplete) internally in a polynucleotide to be subjected to end-selection. It is recognized that methods (e.g., mutagenesis methods) can be used to remove unwanted internal restriction sites. It is also appreciated that a partial digestion reaction (i.e. a digestion reaction that proceeds to partial completion) can be used to achieve digestion at a recognition site in a terminal region while sparing a susceptible restriction site that occurs internally in a polynucleotide and that is recognized by the same enzyme. In one aspect, partial digest are useful because it is appreciated that certain enzymes show preferential cleavage of the same recognition sequence depending on the location and environment in which the recognition sequence occurs.

It is also appreciated that protection methods can be used to selectively protect specified restriction sites (e.g., internal sites) against unwanted digestion by enzymes that would otherwise cut a working polypeptide in response to the presence of those sites; and that such protection methods include modifications such as methylations and base substitutions (e.g., U instead of T) that inhibit an unwanted enzyme activity.

In another aspect of the invention, a useful end-selection marker is a terminal sequence that is recognized by a polynucleotide-acting enzyme that recognizes a specific polynucleotide sequence. In one aspect of the invention, useful polynucleotide-acting enzymes also include other enzymes in addition to classic type II restriction enzymes. According to this preferred aspect of the invention, useful polynucleotide-acting enzymes also include gyrases (e.g., topoisomerases), helicases, recombinases, relaxases, and any enzymes related thereto.

It is appreciated that, end-selection can be used to distinguish and separate parental template molecules (e.g., to be subjected to mutagenesis) from progeny molecules (e.g., generated by mutagenesis). For example, a first set of primers, lacking in a topoisomerase I recognition site, can be used to modify the terminal regions of the parental molecules (e.g., in polymerase-based amplification). A different second set of primers (e.g., having a topoisomerase I recognition site) can then be used to generate mutated progeny molecules (e.g., using any polynucleotide chimerization method, such as interrupted synthesis, template-switching polymerase-based amplification, or interrupted synthesis; or using saturation mutagenesis; or using any other method for introducing a topoisomerase I recognition site into a mutagenized progeny molecule) from the amplified template molecules. The use of topoisomerase I-based end-selection can then facilitate, not only discernment, but selective topoisomerase I-based ligation of the desired progeny molecules.

It is appreciated that an end-selection approach using topoisomerase-based nicking and ligation has several advantages over previously available selection methods. In sum, this approach allows one to achieve direction cloning (including expression cloning).

The present method can be used to shuffle, by in vitro and/or in vivo recombination by any of the disclosed methods, and in any combination, polynucleotide sequences selected by peptide display methods, wherein an associated polynucleotide encodes a displayed peptide which is screened for a phenotype (e.g., for affinity for a predetermined receptor (ligand).

An increasingly important aspect of bio-pharmaceutical drug development and molecular biology is the identification of peptide structures, including the primary amino acid sequences, of peptides or peptidomimetics that interact with biological macromolecules. One method of identifying peptides that possess a desired structure or functional property, such as binding to a predetermined biological macromolecule (e.g., a receptor), involves the screening of a large library or peptides for individual library members which possess the desired structure or functional property conferred by the amino acid sequence of the peptide.

In addition to direct chemical synthesis methods for generating peptide libraries, several recombinant DNA methods also have been reported. One type involves the display of a peptide sequence, antibody, or other protein on the surface of a bacteriophage particle or cell. Generally, in these methods each bacteriophage particle or cell serves as an individual library member displaying a single species of displayed peptide in addition to the natural bacteriophage or cell protein sequences. Each bacteriophage or cell contains the nucleotide sequence information encoding the particular displayed peptide sequence; thus, the displayed peptide sequence can be ascertained by nucleotide sequence determination of an isolated library member.

A well-known peptide display method involves the presentation of a peptide sequence on the surface of a filamentous bacteriophage, typically as a fusion with a bacteriophage coat protein. The bacteriophage library can be incubated with an immobilized, predetermined macromolecule or small molecule (e.g., a receptor) so that bacteriophage particles which present a peptide sequence that binds to the immobilized macromolecule can be differentially partitioned from those that do not present peptide sequences that bind to the predetermined macromolecule. The bacteriophage particles (i.e., library members), which are bound to the immobilized macromolecule are then recovered and replicated to amplify the selected bacteriophage sub-population for a subsequent round of affinity enrichment and phage replication. After several rounds of affinity enrichment and phage replication, the bacteriophage library members that are thus selected are isolated and the nucleotide sequence encoding the displayed peptide sequence is determined, thereby identifying the sequence(s) of peptides that bind to the predetermined macromolecule (e.g., receptor). Such methods are further described in PCT patent publications WO 91/17271, WO 91/18980, WO 91/19818 and WO 93/08278.

The present invention also provides random, pseudorandom, and defined sequence framework peptide libraries and methods for generating and screening those libraries to identify useful compounds (e.g., peptides, including single-chain antibodies) that bind to receptor molecules or epitopes of interest or gene products that modify peptides or RNA in a desired fashion. The random, pseudorandom, and defined sequence framework peptides are produced from libraries of peptide library members that comprise displayed peptides or displayed single-chain antibodies attached to a polynucleotide template from which the displayed peptide was synthesized. The mode of attachment may vary according to the specific embodiment of the invention selected, and can include encapsulation in a phage particle or incorporation in a cell.

A significant advantage of the present invention is that no prior information regarding an expected ligand structure is required to isolate peptide ligands or antibodies of interest. The peptide identified can have biological activity, which is meant to include at least specific binding affinity for a selected receptor molecule and, in some instances, will further include the ability to block the binding of other compounds, to stimulate or inhibit metabolic pathways, to act as a signal or messenger, to stimulate or inhibit cellular activity, and the like.

The invention also provides a method for shuffling a pool of polynucleotide sequences identified by the methods of the invention and selected by affinity screening a library of polysomes displaying nascent peptides (including single-chain antibodies) for library members which bind to a predetermined receptor (e.g., a mammalian proteinaceous receptor such as, for example, a peptidergic hormone receptor, a cell surface receptor, an intracellular protein which binds to other protein(s) to form intracellular protein complexes such as hetero-dimers and the like) or epitope (e.g., an immobilized protein, glycoprotein, oligosaccharide, and the like).

Polynucleotide sequences selected in a first selection round (typically by affinity selection for binding to a receptor (e.g., a ligand)) by any of these methods are pooled and the pool(s) is/are shuffled by in vitro and/or in vivo recombination to produce a shuffled pool comprising a population of recombined selected polynucleotide sequences. The recombined selected polynucleotide sequences are subjected to at least one subsequent selection round. The polynucleotide sequences selected in the subsequent selection round(s) can be used directly, sequenced, and/or subjected to one or more additional rounds of shuffling and subsequent selection. Selected sequences can also be back-crossed with polynucleotide sequences encoding neutral sequences (i.e., having insubstantial functional effect on binding), such as for example by back-crossing with a wild-type or naturally-occurring sequence substantially identical to a selected sequence to produce native-like functional peptides, which may be less immunogenic. Generally, during back-crossing subsequent selection is applied to retain the property of binding to the predetermined receptor (ligand).

Prior to or concomitant with the shuffling of selected sequences, the sequences can be mutagenized. In one embodiment, selected library members are cloned in a prokaryotic vector (e.g., plasmid, phagemid, or bacteriophage) wherein a collection of individual colonies (or plaques) representing discrete library members is produced. Individual selected library members can then be manipulated (e.g., by site-directed mutagenesis, cassette mutagenesis, chemical mutagenesis, PCR mutagenesis, and the like) to generate a collection of library members representing a kemal of sequence diversity based on the sequence of the selected library member. The sequence of an individual selected library member or pool can be manipulated to incorporate random mutation, pseudorandom mutation, defined kemal mutation (i.e., comprising variant and invariant residue positions and/or comprising variant residue positions which can comprise a residue selected from a defined subset of amino acid residues), codon-based mutation, and the like, either segmentally or over the entire length of the individual selected library member sequence. The mutagenized selected library members are then shuffled by in vitro and/or in vivo recombinatorial shuffling as disclosed herein.

The invention also provides peptide libraries comprising a plurality of individual library members of the invention, wherein (1) each individual library member of said plurality comprises a sequence produced by shuffling of a pool of selected sequences, and (2) each individual library member comprises a variable peptide segment sequence or single-chain antibody segment sequence which is distinct from the variable peptide segment sequences or single-chain antibody sequences of other individual library members in said plurality (although some library members may be present in more than one copy per library due to uneven amplification, stochastic probability, or the like).

The invention also provides a product-by-process, wherein selected polynucleotide sequences having (or encoding a peptide having) a predetermined binding specificity are formed by the process of: (1) screening a displayed peptide or displayed single-chain antibody library against a predetermined receptor (e.g., ligand) or epitope (e.g., antigen macromolecule) and identifying and/or enriching library members which bind to the predetermined receptor or epitope to produce a pool of selected library members, (2) shuffling by recombination the selected library members (or amplified or cloned copies thereof) which binds the predetermined epitope and has been thereby isolated and/or enriched from the library to generate a shuffled library, and (3) screening the shuffled library against the predetermined receptor (e.g., ligand) or epitope (e.g., antigen macromolecule) and identifying and/or enriching shuffled library members which bind to the predetermined receptor or epitope to produce a pool of selected shuffled library members.

The present method can be used to shuffle, by in vitro and/or in vivo recombination by any of the disclosed methods, and in any combination, polynucleotide sequences selected by antibody display methods, wherein an associated polynucleotide encodes a displayed antibody which is screened for a phenotype (e.g., for affinity for binding a predetermined antigen (ligand)).

Various molecular genetic approaches have been devised to capture the vast immunological repertoire represented by the extremely large number of distinct variable regions, which can be present in immunoglobulin chains. The naturally-occurring germ line immunoglobulin heavy chain locus is composed of separate tandem arrays of variable segment genes located upstream of a tandem array of diversity segment genes, which are themselves located upstream of a tandem array of joining (i) region genes, which are located upstream of the constant region genes. During B lymphocyte development, V-D-J rearrangement occurs wherein a heavy chain variable region gene (VH) is formed by rearrangement to form a fused D segment followed by rearrangement with a V segment to form a V-D-J joined product gene which, if productively rearranged, encodes a functional variable region (VH) of a heavy chain. Similarly, light chain loci rearrange one of several V segments with one of several J segments to form a gene encoding the variable region (VL) of a light chain.

The vast repertoire of variable regions possible in immunoglobulins derives in part from the numerous combinatorial possibilities of joining V and i segments (and, in the case of heavy chain loci, D segments) during rearrangement in B cell development. Additional sequence diversity in the heavy chain variable regions arises from non-uniform rearrangements of the D segments during V-D-J joining and from N region addition. Further, antigen-selection of specific B cell clones selects for higher affinity variants having non-germline mutations in one or both of the heavy and light chain variable regions; a phenomenon referred to as "affinity maturation" or "affinity sharpening". Typically, these "affinity sharpening" mutations cluster in specific areas of the variable region, most commonly in the complementarity-determining regions (CDRs).

In order to overcome many of the limitations in producing and identifying high-affinity immunoglobulins through antigen-stimulated β cell development (i.e., immunization), various prokaryotic expression systems have been developed that can be manipulated to produce combinatorial antibody libraries which may be screened for high-affinity antibodies to specific antigens. Recent advances in the expression of antibodies in *Escherichia coli* and bacteriophage systems (see "alternative peptide display methods", infra) have raised the possibility that virtually any specificity can be obtained by either cloning antibody genes from characterized hybridomas or by de novo selection using antibody gene libraries (e.g., from Ig cDNA).

Combinatorial libraries of antibodies have been generated in bacteriophage lambda expression systems which may be screened as bacteriophage plaques or as colonies of lysogens (Huse et al., 1989); Caton and Koprowski, 1990; Mullinax et al., 1990; Persson et al., 1991). Various embodiments of bacteriophage antibody display libraries and lambda phage expression libraries have been described (Kang et al., 1991; Clackson et al., 1991; McCafferty et al., 1990; Burton et al., 1991; Hoogenboom et al., 1991; Chang et al., 1991; Breitling et al., 1991; Marks et al., 1991, p. 581; Barbas et al., 1992; Hawkins and Winter, 1992; Marks et al., 1992, p. 779; Marks et al., 1992, p. 16007; and Lowman et al., 1991; Lerner et al., 1992; all incorporated herein by reference). Typically, a bacteriophage antibody display library is screened with a receptor (e.g., polypeptide, carbohydrate, glycoprotein, nucleic acid) that is immobilized (e.g., by covalent linkage to a chromatography resin to enrich for reactive phage by affinity chromatography) and/or labeled (e.g., to screen plaque or colony lifts).

One particularly advantageous approach has been the use of so-called single-chain fragment variable (scfv) libraries (Marks et al., 1992, p. 779; Winter and Milstein, 1991; Clackson et al., 1991; Marks et al., 1991, p. 581; Chaudhary et al., 1990; Chiswell et al., 1992; McCafferty et al., 1990; and Huston et al., 1988). Various embodiments of scfv libraries displayed on bacteriophage coat proteins have been described.

Beginning in 1988, single-chain analogues of Fv fragments and their fusion proteins have been reliably generated by antibody engineering methods. The first step generally involves obtaining the genes encoding VH and VL domains with desired binding properties; these V genes may be isolated from a specific hybridoma cell line, selected from a combinatorial V-gene library, or made by V gene synthesis. The single-chain Fv is formed by connecting the component V genes with an oligonucleotide that encodes an appropriately designed linker peptide, such as (Gly-Gly-Gly-Gly-Ser (SEQ ID NO:57)) or equivalent linker peptide(s). The linker bridges the C-terminus of the first V region and N-terminus of the second, ordered as either VH-linker-VL or VL-linker-VH' In principle, the scfv binding site can faithfully replicate both the affinity and specificity of its parent antibody combining site.

Thus, scfv fragments are comprised of VH and VL domains linked into a single polypeptide chain by a flexible linker peptide. After the scfv genes are assembled, they are cloned into a phagemid and expressed at the tip of the M13 phage (or similar filamentous bacteriophage) as fusion proteins with the bacteriophage PIII (gene 3) coat protein. Enriching for phage expressing an antibody of interest is accomplished by panning the recombinant phage displaying a population scfv for binding to a predetermined epitope (e.g., target antigen, receptor).

The linked polynucleotide of a library member provides the basis for replication of the library member after a screening or selection procedure, and also provides the basis for the determination, by nucleotide sequencing, of the identity of the displayed peptide sequence or VH and VL amino acid sequence. The displayed peptide (s) or single-chain antibody (e.g., scfv) and/or its VH and VL domains or their CDRs can be cloned and expressed in a suitable expression system. Often polynucleotides encoding the isolated VH and VL domains will be ligated to polynucleotides encoding constant regions (CH and CL) to form polynucleotides encoding complete antibodies (e.g., chimeric or fully-human), antibody fragments, and the like. Often polynucleotides encoding the isolated CDRs will be grafted into polynucleotides encoding a suitable variable region framework (and optionally constant regions) to form polynucleotides encoding complete antibodies (e.g., humanized or fully-human), antibody fragments, and the like. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like.

Various methods have been reported for increasing the combinatorial diversity of a scfv library to broaden the repertoire of binding species (idiotype spectrum) The use of PCR has permitted the variable regions to be rapidly cloned either from a specific hybridoma source or as a gene library from non-immunized cells, affording combinatorial diversity in the assortment of VH and VL cassettes which can be combined. Furthermore, the VH and VL cassettes can themselves be diversified, such as by random, pseudorandom, or directed mutagenesis. Typically, VH and VL cassettes are diversified in or near the complementarity-determining regions (CDRS), often the third CDR, CDR3. Enzymatic inverse PCR mutagenesis has been shown to be a simple and reliable method for constructing relatively large libraries of scfv site-directed hybrids (Stemmer et al., 1993), as has error-prone PCR and chemical mutagenesis (Deng et al., 1994). Riechmann (Riechmann et al., 1993) showed semi-rational design of an antibody scfv fragment using site-directed randomization by degenerate oligonucleotide PCR and subsequent phage display of the resultant scfv hybrids. Barbas (Barbas et al., 1992) attempted to circumvent the problem of limited repertoire sizes resulting from using biased variable region sequences by randomizing the sequence in a synthetic CDR region of a human tetanus toxoid-binding Fab.

CDR randomization has the potential to create approximately $1 \times 10^{20}$ CDRs for the heavy chain CDR3 alone, and a roughly similar number of variants of the heavy chain CDR1 and CDR2, and light chain CDR1–3 variants. Taken individually or together, the combination possibilities of CDR randomization of heavy and/or light chains requires generating a prohibitive number of bacteriophage clones to produce a clone library representing all possible combinations, the vast majority of which will be non-binding. Generation of such large numbers of primary transformants is not feasible with current transformation technology and bacteriophage display systems. For example, Barbas (Barbas et al., 1992) only generated $5 \times 10^7$ transformants, which represents only a tiny fraction of the potential diversity of a library of thoroughly randomized CDRs.

Despite these substantial limitations, bacteriophage display of scfv have already yielded a variety of useful antibodies and antibody fusion proteins. A bispecific single chain antibody has been shown to mediate efficient tumor cell lysis (Gruber et al., 1994). Intracellular expression of an anti-Rev scfv has been shown to inhibit HIV-1 virus replication in vitro (Duan et al., 1994), and intracellular expression of an anti-p21rar, scfv has been shown to inhibit meiotic maturation of *Xenopus oocytes* (Biocca et al., 1993). Recombinant scfv, which can be used to diagnose HIV infection have also been reported, demonstrating the diagnostic utility of scfv (Lilley et al., 1994). Fusion proteins wherein an scFv is linked to a second polypeptide, such as a toxin or fibrinolytic activator protein, have also been reported (Holvost et al., 1992; Nicholls et al., 1993).

If it were possible to generate scfv libraries having broader antibody diversity and overcoming many of the limitations of conventional CDR mutagenesis and randomization methods, which can cover only a very tiny fraction of the potential sequence combinations, the number and quality of scfv antibodies suitable for therapeutic and diagnostic use could be vastly improved. To address this, the in vitro and in vivo shuffling methods of the invention are used to recombine CDRs, which have been obtained (typically via PCR amplification or cloning) from nucleic acids obtained from selected displayed antibodies. Such displayed antibodies can be displayed on cells, on bacteriophage particles, on polysomes, or any suitable antibody display system wherein the antibody is associated with its encoding nucleic acid(s). In a variation, the CDRs are initially obtained from mRNA (or cDNA) from antibody-producing cells (e.g., plasma cells/splenocytes from an immunized wild-type mouse, a human, or a transgenic mouse capable of making a human antibody as in WO 92/03918, WO 93/12227, and WO 94/25585), including hybridomas derived therefrom.

Polynucleotide sequences selected in a first selection round (typically by affinity selection for displayed antibody binding to an antigen (e.g., a ligand) by any of these methods are pooled and the pool(s) is/are shuffled by in vitro and/or in vivo recombination, especially shuffling of CDRs (typically shuffling heavy chain CDRs with other heavy chain CDRs and light chain CDRs with other light chain CDRs) to produce a shuffled pool comprising a population of recombined selected polynucleotide sequences. The recombined selected polynucleotide sequences are expressed in a selection format as a displayed antibody and subjected to at least one subsequent selection round. The polynucleotide sequences selected in the subsequent selection round(s) can be used directly, sequenced, and/or subjected to one or more additional rounds of shuffling and subsequent selection until an antibody of the desired binding affinity is obtained. Selected sequences can also be back-crossed with polynucleotide sequences encoding neutral antibody framework sequences (i.e., having insubstantial functional effect on antigen binding), such as for example by back-crossing with a human variable region framework to produce human-like sequence antibodies. Generally, during back-crossing subsequent selection is applied to retain the property of binding to the predetermined antigen.

Alternatively, or in combination with the noted variations, the valency of the target epitope may be varied to control the average binding affinity of selected scfv library members. The target epitope can be bound to a surface or substrate at varying densities, such as by including a competitor epitope, by dilution, or by other method known to those in the art. A high density (valency) of predetermined epitope can be used to enrich for scfv library members, which have relatively low affinity, whereas a low density (valency) can preferentially enrich for higher affinity scfv library members.

For generating diverse variable segments, a collection of synthetic oligonucleotides encoding random, pseudorandom, or a defined sequence kernal set of peptide sequences can be inserted by ligation into a predetermined site (e.g., a CDR). Similarly, the sequence diversity of one or more CDRs of the single-chain antibody cassette(s) can be expanded by mutating the CDR(s) with site-directed mutagenesis, CDR-replacement, and the like. The resultant DNA molecules can be propagated in a host for cloning and amplification prior to shuffling, or can be used directly (i.e., may avoid loss of diversity which may occur upon propagation in a host cell) and the selected library members subsequently shuffled.

Displayed peptide/polynucleotide complexes (library members) which encode a variable segment peptide sequence of interest or a single-chain antibody of interest are selected from the library by an affinity enrichment technique. This is accomplished by means of a immobilized macromolecule or epitope specific for the peptide sequence of interest, such as a receptor, other macromolecule, or other epitope species. Repeating the affinity selection procedure provides an enrichment of library members encoding the desired sequences, which may then be isolated for pooling and shuffling, for sequencing, and/or for further propagation and affinity enrichment.

The library members without the desired specificity are removed by washing. The degree and stringency of washing required will be determined for each peptide sequence or single-chain antibody of interest and the immobilized predetermined macromolecule or epitope. A certain degree of control can be exerted over the binding characteristics of the nascent peptide/DNA complexes recovered by adjusting the conditions of the binding incubation and the subsequent washing. The temperature, pH, ionic strength, divalent cations concentration, and the volume and duration of the washing will select for nascent peptide/DNA complexes within particular ranges of affinity for the immobilized macromolecule. Selection based on slow dissociation rate, which is usually predictive of high affinity, is often the most practical route. This may be done either by continued incubation in the presence of a saturating amount of free predetermined macromolecule, or by increasing the volume, number, and length of the washes. In each case, the rebinding of dissociated nascent peptide/DNA or peptide/RNA complex is prevented, and with increasing time, nascent peptide/DNA or peptide/RNA complexes of higher and higher affinity are recovered.

Additional modifications of the binding and washing procedures may be applied to find peptides with special characteristics. The affinities of some peptides are dependent on ionic strength or cation concentration. This is a useful characteristic for peptides that will be used in affinity purification of various proteins when gentle conditions for removing the protein from the peptides are required.

One variation involves the use of multiple binding targets (multiple epitope species, multiple receptor species), such that a scfv library can be simultaneously screened for a multiplicity of scfv which have different binding specificities. Given that the size of a scfv library often limits the diversity of potential scfv sequences, it is typically desirable to us scfv libraries of as large a size as possible. The time and economic considerations of generating a number of very large polysome scFv-display libraries can become prohibitive. To avoid this substantial problem, multiple predetermined epitope species (receptor species) can be concomitantly screened in a single library, or sequential screening against a number of epitope species can be used. In one variation, multiple target epitope species, each encoded on a separate bead (or subset of beads), can be mixed and incubated with a polysome-display scfv library under suitable binding conditions. The collection of beads, comprising multiple epitope species, can then be used to isolate, by affinity selection, scfv library members. Generally, subsequent affinity screening rounds can include the same mixture of beads, subsets thereof, or beads containing only one or two individual epitope species. This approach affords efficient screening, and is compatible with laboratory automation, batch processing, and high throughput screening methods.

A variety of techniques can be used in the present invention to diversify a peptide library or single-chain antibody library, or to diversify, prior to or concomitant with shuffling, around variable segment peptides found in early rounds of panning to have sufficient binding activity to the predetermined macromolecule or epitope. In one approach, the positive selected peptide/polynucleotide complexes (those identified in an early round of affinity enrichment) are sequenced to determine the identity of the active peptides. Oligonucleotides are then synthesized based on these active peptide sequences, employing a low level of all bases incorporated at each step to produce slight variations of the primary oligonucleotide sequences. This mixture of (slightly) degenerate oligonucleotides is then cloned into the variable segment sequences at the appropriate locations. This method produces systematic, controlled variations of the starting peptide sequences, which can then be shuffled. It requires, however, that individual positive nascent peptide/polynucleotide complexes be sequenced before mutagenesis, and thus is useful for expanding the diversity of small numbers of recovered complexes and selecting variants having higher binding affinity and/or higher binding specificity. In a variation, mutagenic PCR amplification of positive selected peptide/polynucleotide complexes (especially of the variable region sequences, the amplification products of which are shuffled in vitro and/or in vivo and one or more additional rounds of screening is done prior to sequencing. The same general approach can be employed with single-chain antibodies in order to expand the diversity and enhance the binding affinity/specificity, typically by diversifying CDRs or adjacent framework regions prior to or concomitant with shuffling. If desired, shuffling reactions can be spiked with mutagenic oligonucleotides capable of in vitro recombination with the selected library members can be included. Thus, mixtures of synthetic oligonucleotides and PCR produced polynucleotides (synthesized by error-prone or high-fidelity methods) can be added to the in vitro shuffling mix and be incorporated into resulting shuffled library members (shufflants).

The invention of shuffling enables the generation of a vast library of CDR-variant single-chain antibodies. One way to generate such antibodies is to insert synthetic CDRs into the single-chain antibody and/or CDR randomization prior to or concomitant with shuffling. The sequences of the synthetic CDR cassettes are selected by referring to known sequence data of human CDR and are selected in the discretion of the practitioner according to the following guidelines: synthetic CDRs will have at least 40 percent positional sequence identity to known CDR sequences, and preferably will have at least 50 to 70 percent positional sequence identity to known CDR sequences. For example, a collection of synthetic CDR sequences can be generated by synthesizing a collection of oligonucleotide sequences on the basis of naturally-occurring human CDR sequences listed in Kabat (Kabat et al., 1991); the pool (s) of synthetic CDR sequences are calculated to encode CDR peptide sequences having at least 40 percent sequence identity to at least one known naturally-occurring human CDR sequence. Alternatively, a collection of naturally-occurring CDR sequences may be compared to generate consensus sequences so that amino acids used at a residue position frequently (i.e., in at least 5 percent of known CDR sequences) are incorporated into the synthetic CDRs at the corresponding position(s). Typically, several (e.g., 3 to about 50) known CDR sequences are compared and observed natural sequence variations between the known CDRs are tabulated, and a collection of oligonucleotides encoding CDR peptide sequences encompassing all or most permutations of the observed natural sequence variations is synthesized. For example but not for limitation, if a collection of human VH CDR sequences have carboxy-terminal amino acids which are either Tyr, Val, Phe, or Asp, then the pool(s) of synthetic CDR oligonucleotide sequences are designed to allow the carboxy-terminal CDR residue to be any of these amino acids. In some embodiments, residues other than those which naturally-occur at a residue position in the collection of CDR sequences are incorporated: conservative amino acid substitutions are frequently incorporated and up to 5 residue positions may be varied to incorporate non-conservative amino acid substitutions as compared to known naturally-occurring CDR sequences. Such CDR sequences can be used in primary library members (prior to first round screening) and/or can be used to spike in vitro shuffling reactions of selected library member sequences. Construction of such pools of defined and/or degenerate sequences will be readily accomplished by those of ordinary skill in the art.

The collection of synthetic CDR sequences comprises at least one member that is not known to be a naturally-occurring CDR sequence. It is within the discretion of the practitioner to include or not include a portion of random or pseudorandom sequence corresponding to N region addition in the heavy chain CDR; the N region sequence ranges from 1 nucleotide to about 4 nucleotides occurring at V-D and D-J junctions. A collection of synthetic heavy chain CDR sequences comprises at least about 100 unique CDR sequences, typically at least about 1,000 unique CDR sequences, preferably at least about 10,000 unique CDR sequences, frequently more than 50,000 unique CDR sequences; however, usually not more than about $1\times10^6$ unique CDR sequences are included in the collection, although occasionally $1\times10^7$ to $1\times10^8$ unique CDR sequences are present, especially if conservative amino acid substitutions are permitted at positions where the conservative amino acid substituent is not present or is rare (i.e., less than 0.1 percent) in that position in naturally-occurring human CDRS. In general, the number of unique CDR sequences included in a library should not exceed the expected number of primary transformants in the library by more than a factor of 10. Such single-chain antibodies generally bind of about at least $1\times10$ m-, preferably with an affinity of about at least $5\times10^7$ M-1, more preferably with an affinity of at least $1\times10^8$ M-1 to $1\times10^9$ M-1 or more, sometimes up to $1\times10^{10}$ M-1 or more. Frequently, the predetermined antigen is a human protein, such as for example a human cell surface antigen (e.g., CD4, CD8, IL-2 receptor, EGF receptor, PDGF receptor), other human biological macromolecule (e.g., thrombomodulin, protein C, carbohydrate antigen, sialyl Lewis antigen, L-selectin), or nonhuman disease associated macromolecule (e.g., bacterial LPS, virion capsid protein or envelope glycoprotein) and the like.

High affinity single-chain antibodies of the desired specificity can be engineered and expressed in a variety of systems. For example, scfv have been produced in plants (Firek et al., 1993) and can be readily made in prokaryotic systems (Owens and Young, 1994; Johnson and Bird, 1991). Furthermore, the single-chain antibodies can be used as a basis for constructing whole antibodies or various fragments thereof (Kettleborough et al., 1994). The variable region encoding sequence may be isolated (e.g., by PCR amplification or subcloning) and spliced to a sequence encoding a desired human constant region to encode a human sequence antibody more suitable for human therapeutic uses where immunogenicity is preferably minimized. The polynucleotide(s) having the resultant fully human encoding sequence(s) can be expressed in a host cell (e.g., from an expression vector in a mammalian cell) and purified for pharmaceutical formulation.

Once expressed, the antibodies, individual mutated immunoglobulin chains, mutated antibody fragments, and other immunoglobulin polypeptides of the invention can be purified according to standard procedures of the art, including ammonium sulfate precipitation, fraction column chromatography, gel electrophoresis and the like (see, generally, Scopes, 1982). Once purified, partially or to homogeneity as desired, the polypeptides may then be used therapeutically or in developing and performing assay procedures, immunofluorescent stainings, and the like (see, generally, Lefkovits and Pernis, 1979 and 1981; Lefkovits, 1997).

The antibodies generated by the method of the present invention can be used for diagnosis and therapy. By way of illustration and not limitation, they can be used to treat cancer, autoimmune diseases, or viral infections. For treatment of cancer, the antibodies will typically bind to an antigen expressed preferentially on cancer cells, such as erbB-2, CEA, CD33, and many other antigens and binding members well known to those skilled in the art.

Shuffling can also be used to recombinatorially diversify a pool of selected library members obtained by screening a two-hybrid screening system to identify library members which bind a predetermined polypeptide sequence. The selected library members are pooled and shuffled by in vitro and/or in vivo recombination. The shuffled pool can then be screened in a yeast two hybrid system to select library members which bind said predetermined polypeptide sequence (e.g., and SH2 domain) or which bind an alternate predetermined polypeptide sequence (e.g., an SH2 domain from another protein species).

An approach to identifying polypeptide sequences which bind to a predetermined polypeptide sequence has been to use a so-called "two-hybrid" system wherein the predetermined polypeptide sequence is present in a fusion protein (Chien et al., 1991). This approach identifies protein-protein interactions in vivo through reconstitution of a transcriptional activator (Fields and Song, 1989), the yeast Gal4 transcription protein. Typically, the method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacz, HIS3) which is operably linked to a Gal4 binding site. Typically, the two-hybrid method is used to identify novel polypeptide sequences which interact with a known protein (Silver and Hunt, 1993; Durfee et al., 1993; Yang et al., 1992; Luban et al., 1993; Hardy et al., 1992; Bartel et al., 1993; and Vojtek et al., 1993). However, variations of the two-hybrid method have been used to identify mutations of a known protein that affect its binding to a second known protein (Li and Fields, 1993; Lalo et al., 1993; Jackson et al., 1993; and Madura et al., 1993). Two-hybrid systems have also been used to identify interacting structural domains of two known proteins (Bardwell et al., 1993; Chakrabarty et al., 1992; Staudinger et al., 1993; and Milne and Weaver 1993) or domains responsible for oligomerization of a single protein (Iwabuchi et al., 1993; Bogerd et al., 1993). Variations of two-hybrid systems have been used to study the in vivo activity of a proteolytic enzyme (Dasmahapatra et al., 1992). Alternatively, an E. coli/BCCP interactive screening system (Germino et al., 1993; Guarente, 1993) can be used to identify interacting protein sequences (i.e., protein sequences which heterodimerize or form higher order heteromultimers). Sequences selected by a two-hybrid system can be pooled and shuffled and introduced into a two-hybrid system for one or more subsequent rounds of screening to identify polypeptide sequences which bind to the hybrid containing the predetermined binding sequence. The sequences thus identified can be compared to identify consensus sequence(s) and consensus sequence kernals.

One microgram samples of template DNA are obtained and treated with U.V. light to cause the formation of dimers, including TT dimers, particularly purine dimers. U.V. exposure is limited so that only a few photoproducts are generated per gene on the template DNA sample. Multiple samples are treated with U.V. light for varying periods of time to obtain template DNA samples with varying numbers of dimers from U.V. exposure.

A random priming kit which utilizes a non-proofreading polymerase (for example, Prime-It II Random Primer Labeling kit by Stratagene Cloning Systems) is utilized to generate different size polynucleotides by priming at random sites on templates which are prepared by U.V. light (as described above) and extending along the templates. The priming protocols such as described in the Prime-It II Random Primer Labeling kit may be utilized to extend the primers. The dimers formed by U.V. exposure serve as a roadblock for the extension by the non-proofreading polymerase. Thus, a pool of random size polynucleotides is present after extension with the random primers is finished.

The invention is further directed to a method for generating a selected mutant polynucleotide sequence (or a population of selected polynucleotide sequences) typically in the form of amplified and/or cloned polynucleotides, whereby the selected polynucleotide sequences(s) possess at least one desired phenotypic characteristic (e.g., encodes a polypeptide, promotes transcription of linked polynucleotides, binds a protein, and the like) which can be selected for. One method for identifying hybrid polypeptides that possess a desired structure or functional property, such as binding to a predetermined biological macromolecule (e.g., a receptor), involves the screening of a large library of polypeptides for individual library members which possess the desired structure or functional property conferred by the amino acid sequence of the polypeptide.

In one aspect, the present invention provides a method for generating libraries of displayed polypeptides or displayed antibodies suitable for affinity interaction screening or phenotypic screening. The method comprises (1) obtaining a first plurality of selected library members comprising a displayed polypeptide or displayed antibody and an associated polynucleotide encoding said displayed polypeptide or displayed antibody, and obtaining said associated polynucleotides or copies thereof wherein said associated polynucleotides comprise a region of substantially identical sequences, optimally introducing mutations into said polynucleotides or copies, (2) pooling the polynucleotides or copies, (3) producing smaller or shorter polynucleotides by interrupting a random or particularized priming and synthesis process or an amplification process, and (4) performing amplification, preferably PCR amplification, and optionally mutagenesis to homologously recombine the newly synthesized polynucleotides.

It is an object of the invention to provide a process for producing hybrid polynucleotides which express a useful hybrid polypeptide by a series of steps comprising:

(a) producing polynucleotides by interrupting a polynucleotide amplification or synthesis process with a means for blocking or interrupting the amplification or synthesis process and thus providing a plurality of smaller or shorter polynucleotides due to the replication of the polynucleotide being in various stages of completion;

(b) adding to the resultant population of single- or double-stranded polynucleotides one or more single- or double-stranded oligonucleotides, wherein said added oligonucleotides comprise an area of identity in an area of heterology to one or more of the single- or double-stranded polynucleotides of the population;

(c) denaturing the resulting single- or double-stranded oligonucleotides to produce a mixture of single-stranded polynucleotides, optionally separating the shorter or smaller polynucleotides into pools of polynucleotides having various lengths and further optionally subjecting said polynucleotides to a PCR procedure to amplify one or more oligonucleotides comprised by at least one of said polynucleotide pools;

(d) incubating a plurality of said polynucleotides or at least one pool of said polynucleotides with a polymerase under conditions which result in annealing of said single-stranded polynucleotides at regions of identity between the single-stranded polynucleotides and thus forming of a mutagenized double-stranded polynucleotide chain;

(e) optionally repeating steps (c) and (d);

(f) expressing at least one hybrid polypeptide from said polynucleotide chain, or chains; and (g) screening said at least one hybrid polypeptide for a useful activity.

In one aspect of the invention, the means for blocking or interrupting the amplification or synthesis process is by utilization of UV light, DNA adducts, DNA binding proteins.

In one aspect of the invention, the DNA adducts, or polynucleotides comprising the DNA adducts, are removed from the polynucleotides or polynucleotide pool, such as by a process including heating the solution comprising the DNA fragments prior to further processing.

In another aspect, clones which are identified as having a biomolecule or bioactivity of interest may also be sequenced to identify the DNA sequence encoding a polypeptide (e.g., an enzyme) or the polypeptide sequence itself having the specified activity, for example. Thus, in accordance with the present invention it is possible to isolate and identify: (i) DNA encoding a bioactivity of interest (e.g., an enzyme having a specified enzyme activity), (ii) biomolecules (e.g., polynucleotides or enzymes having such activity (including the amino acid sequence thereof)) and (iii) produce recombinant biomolecules or bioactivities.

Suitable clones (e.g., 1–1000 or more clones) from the library are identified by the methods of the invention and sequenced using, for example, high through-put sequencing techniques. The exact method of sequencing is not a limiting factor of the invention. Any method useful in identifying the sequence of a particular cloned DNA sequence can be used. In general, sequencing is an adaptation of the natural process of DNA replication. Therefore, a template (e.g., the vector) and primer sequences are used. One general template preparation and sequencing protocol begins with automated picking of bacterial colonies, each of which contains a separate DNA clone which will function as a template for the sequencing reaction. The selected clones are placed into media, and grown overnight. The DNA templates are then purified from the cells and suspended in water. After DNA quantification, high-throughput sequencing is performed using a sequencers, such as Applied Biosystems, Inc., Prism 377 DNA Sequencers. The resulting sequence data can then be used in additional methods, including searching a database or databases.

A number of source databases are available that contain either a nucleic acid sequence and/or a deduced amino acid sequence for use with the invention in identifying or determining the activity encoded by a particular polynucleotide sequence. All or a representative portion of the sequences (e.g., about 100 individual clones) to be tested are used to search a sequence database (e.g., GenBank, PFAM or ProDom), either simultaneously or individually. A number of different methods of performing such sequence searches are known in the art. The databases can be specific for a particular organism or a collection of organisms. For example, there are databases for the C. elegans, Arabadopsis. sp., M. genitalium, M.jannaschii, E. coli, H. influenzae, S. cerevisiae and others. The sequence data of the clone is then aligned to the sequences in the database or databases using algorithms designed to measure homology between two or more sequences.

Sequence homology means that two polynucleotide sequences are homologous (i.e., on a nucleotide-by-nucleotide basis) over the window of comparison. A percentage of sequence identity or homology is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence homology. This substantial homology denotes a characteristic of a polynucleotide sequence, wherein the polynucleotide comprises a sequence having at least 60 percent sequence homology, typically at least 70 percent homology, often 80 to 90 percent sequence homology, and most commonly at least 99 percent sequence homology as compared to a reference sequence of a comparison window of at least 25–50 nucleotides, wherein the percentage of sequence homology is calculated by comparing the reference sequence to the polynucleotide sequence which may include deletions or additions which total 20 percent or less of the reference sequence over the window of comparison.

Sequences having sufficient homology can the be further identified by any annotations contained in the database, including, for example, species and activity information. Accordingly, in a typical environmental sample, a plurality of nucleic acid sequences will be obtained, cloned, sequenced and corresponding homologous sequences from a database identified. This information provides a profile of the polynucleotides present in the sample, including one or more features associated with the polynucleotide including the organism and activity associated with that sequence or any polypeptide encoded by that sequence based on the database information. As used herein "fingerprint" or "profile" refers to the fact that each sample will have associated with it a set of polynucleotides characteristic of the sample and the environment from which it was derived. Such a profile can include the amount and type of sequences present in the sample, as well as information regarding the potential activities encoded by the polynucleotides and the organisms from which polynucleotides were derived. This unique pattern is each sample's profile or fingerprint.

In some instances it may be desirable to express a particular cloned polynucleotide sequence once its identity or activity is determined or a suggested identity or activity is associated with the polynucleotide. In such instances the desired clone, if not already cloned into an expression vector, is ligated downstream of a regulatory control element (e.g., a promoter or enhancer) and cloned into a suitable host cell. Expression vectors are commercially available along with corresponding host cells for use in the invention.

As representative examples of expression vectors which may be used there may be mentioned viral particles, baculovirus, phage, plasmids, phagemids, cosmids, phosmids, bacterial artificial chromosomes, viral nucleic acid (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, Aspergillus, yeast, and the like) Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE70, pQE60, pQE-9 (Qiagen), psiX174, pBluescript SK, pBluescript KS, pNH8A, pNH16a, pNH18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene), pSVK3, pBPV, pMSG, pSVL (Pharmacia). However, any other plasmid or vector may be used as long as they are replicable and viable in the host.

The nucleic acid sequence in the expression vector is operatively linked to an appropriate expression control sequence(s) (promoter) to direct mRNA synthesis. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors typically contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The nucleic acid sequence(s) selected, cloned and sequenced as hereinabove described can additionally be introduced into a suitable host to prepare a library, which is screened for the desired biomolecule or bioactivity. The selected nucleic acid is preferably already in a vector which includes appropriate control sequences whereby a selected nucleic acid encoding a biomolecule or bioactivity may be expressed, for detection of the desired activity. The host cell can be a higher eukaryotic cell, such as a mammalian cell, or a lower eukaryotic cell, such as a yeast cell, or the host cell can be a prokaryotic cell, such as a bacterial cell. The selection of an appropriate host is deemed to be within the scope of those skilled in the art from the teachings herein.

In some instances it may be desirable to perform an amplification of the nucleic acid sequence present in a sample or a particular clone that has been isolated. In this embodiment, the nucleic acid sequence is amplified by PCR reaction or similar reaction known to those of skill in the art. Commercially available amplification kits are available to carry out such amplification reactions.

In addition, it is important to recognize that the alignment algorithms and searchable database can be implemented in computer hardware, software or a combination thereof. Accordingly, the isolation, processing and identification of nucleic acid or polypeptide sequences can be implemented in an automated system.

In addition to the sequence-based techniques described above, a number of traditional assay system exist for measuring an enzymatic activity using multi-well plates. For example, existing screening technology usually relies on two-dimensional well (e.g., 96-, 384- and 1536-well) plates. The present invention also provides a capillary array-based approach of that has numerous advantages over well-based screening techniques, including the elimination of the need for fluid dispensers for dispensing fluids (e.g., reactants) into individual well reservoirs, and the reduced cost per array (e.g., glass capillaries are reusable) (see, for example, U.S. patent application Ser. No. 09/444,112, filed Nov. 22, 1999, which is incorporated herein by reference in its entirety).

Accordingly, the capillaries, capillary array and systems of the invention are particularly well suited for screening libraries for activity or biomolecules of interest including polynucleotides. The screening for activity may be effected on individual expression clones or may be initially effected on a mixture of expression clones to ascertain whether or not the mixture has one or more specified activities. If the mixture has a specified activity, then the individual clones may be rescreened for such activity or for a more specific activity after collection from the capillary array.

All headings and subheading used herein are provided for the convenience of the reader and should not be construed to limit the invention.

As used herein and in the appended claims, the singular forms "a," "and," and "the" include plural referents unless the context clearly dictates otherwise. Thus, for example, reference to "a clone" includes a plurality of clones and reference to "the nucleic acid sequence" generally includes reference to one or more nucleic acid sequences and equivalents thereof known to those skilled in the art, and so forth.

Unless defined otherwise, all technical and scientific terms used herein have the same meaning as commonly understood to one of ordinary skill in the art to which the invention belongs. Although any methods, devices and materials similar or equivalent to those described herein can be used in the practice or testing of the invention, the preferred methods, devices and materials described.

All publications mentioned herein are incorporated herein by reference in full for the purpose of describing and disclosing the databases, proteins, and methodologies, which are described in the publications, which might be used in connection with the described invention. The publications discussed above and throughout the text are provided solely for their disclosure prior to the filing date of the present application. Nothing herein is to be construed as an admission that the inventors are not entitled to antedate such disclosure by virtue of prior invention.

The invention will now be described in greater detail by reference to the following non-limiting examples.

EXAMPLES

Example 1

DNA Isolation

DNA is isolated using the IsoQuick Procedure as per manufacture's instructions (Orca Research Inc., Bothell, Wash.). The isolated DNA can optionally be normalized according to Example 2 (below). Upon isolation, the DNA is sheared by pushing and pulling the DNA through a 25-gauge double-hub needle and a 1-cc syringe about 500 times. A small amount is run on a 0.8% agarose gel to make sure the majority of the DNA is in the desired size range (about 3–6 kb).

Blunt-ending DNA. The DNA is blunt-ended by mixing 45 µl of 10× Mung Bean Buffer, 2.0 µl Mung Bean Nuclease (1050 u/µl) and water to a final volume of 405 µl. The mixture is incubated at 37° C. for 15 minutes. The mixture is phenol;chloroform extracted, followed by an additional chloroform extraction. One ml of ice cold ethanol is added to the final extract to precipitate the DNA. The DNA is precipitated for 10 minutes on ice. The DNA is removed by centrifugation in a microcentrifuge for 30 minutes. The pellet is washed with 1 ml of 70% ethanol and repelleted in the microcentrifuge. Following centrifugation, the DNA is dried and gently resuspended in 26 µl of TE buffer.

Methylation of DNA. The DNA is methylated by mixing 4 µl of 10×EcoRI Methylase Buffer, 0.5 µl SAM (32 mM), 5.0 µl EcoRI Methylase (40 u/µl) and incubating at 37° C. for 1 hour. In order to insure blunt ends, the following can be added to the methylation reaction: 5.0 µl of 100 mM $MgCl_2$, 8.0 µl of dNTP mix (2.5 mM of each dGTP, dATP, dTTP, dCTP), 4.0 µl of Klenow (5 u/µl). The mixture is then incubated at 12° C. for 30 minutes.

After incubating for 30 minutes 450 µl 1×STE is added. The mixture is phenol/chloroform extracted once followed by an additional chloroform extraction. One ml of ice cold ethanol is added to the final extract to precipitate the DNA. The DNA is precipitated for 10 minutes on ice. The DNA is removed by centrifugation in a microcentrifuge for 30 minutes. The pellet is washed with 1 ml of 70% ethanol, repelleted in the microcentrifuge and allowed to dry for 10 minutes.

Ligation. The DNA is ligated by gently resuspending the DNA in 8 µl EcoRI adapters (from Stratagene's cDNA Synthesis Kit), 1.0 µl of 10× ligation buffer, 1.0 µl of 10 mM rATP, 1.0 µl of T4 DNA Ligase (4 Wu/µl) and incubating at 4° C. for 2 days. The ligation reaction is terminated by heating for 30 minutes at 70° C.

Phosphorylation of adapters. The adapter ends are phosphorylated by mixing the ligation reaction with 1.0 µl of 10× Ligation Buffer, 2.0 µl of 10 mM rATP, 6.0 µl of $H_2O$, 1.0 µl of polynucleotide kinase (PNK), and incubating at 37° C. for 30 minutes. After incubating for 30 minutes, 31 µl of $H_2O$ and 5 ml of 10×STE are added to the reaction and the sample is size fractionated on a Sephacryl S-500 spin column. The pooled fractions (1–3) are phenol/chloroform extracted once, followed by an additional chloroform extraction. The DNA is precipitated by the addition of ice cold ethanol on ice for 10 minutes. The precipitate is pelleted by centrifugation in a microcentrifuge at high speed for 30 minutes. The resulting pellet is washed with 1 ml 70% ethanol, repelleted by centrifugation and allowed to dry for 10 minutes. The sample is resuspended in 10.5 µl TE buffer. The sample is not plated, but is ligated directly to lambda arms as described above, except 2.5 µl of DNA and no water is used.

Sucrose Gradient (2.2 ml) Size Fractionation. Ligation is stopped by heating the sample to 65° C. for 10 minutes. The sample is gently loaded on a 2.2 ml sucrose gradient and centrifuged in a mini-ultracentrifuged 45 k rpm at 20° C. for 4 hours (no brake). Fractions are collected by puncturing the bottom of the gradient tube with a 20—gauge needle and allowing the sucrose to flow through the needle. The first 20 drops are collected in a Falcon 2059 tube, and then ten 1-drop fractions (labeled 1–10) are collected. Each drop is about 60 µl in volume. Five µl of each fraction are run on a 0.8% agarose gel to check the size. Fractions 1–4 (about 10–1.5 kb) are pooled and, in a separate tube, fractions 5–7 (about 5–0.5 kb) are pooled. One ml of ice cold ethanol is added to precipitate the DNA and then placed on ice for 10 minutes. The precipitate is pelleted by centrifugation in a microcentrifuge at high speed for 30 minutes. The pellets are washed by resuspending them in 1 ml of 70% ethanol and repelleting them by centrifugation in a microcentrifuge at high speed for 10 minutes, and then dried. Each pellet is then resuspended in 10 µl of TE buffer.

Test Ligation to Lambda Arms. The assay is plated by spotting 0.5 µl of the sample on agarose containing ethidium bromide along with standards (DNA sample of known concentration) to get an approximate concentration. The samples are then viewed using UV light and the estimated concentration is compared to the standards. The following ligation reaction (5 µl reactions) are prepared and incubated at 4° C. overnight, as shown in Table 1 below:

are about pin-head in size. The plates are overlaid with 8–10 ml SM Buffer and placed at 4° C. overnight (with gentle rocking if possible).

Harvest Phage. The phage suspension is recovered by pouring the SM buffer off each plate into a 50 ml conical tube. About 3 ml of chloroform are added, shaken vigorously and incubated at room temperature for 15 minutes. The tubes are centrifuged at 2K rpm for 10 minutes to remove cell debris. The supernatant is poured into a sterile flask, 500 µl chloroform are added and stored at 4° C.

Titer Amplified Library. Serial dilutions of the harvested phage are made (for example, $10^{-5}$=1 µl amplified phage in 1 ml SM Buffer; $10^{-6}$=1 µl of the $10^{-3}$ dilution in 1 ml SM Buffer and the like), and 200 µl host (in 10 mM $MgSO_4$) are added to two tubes. One tube is inoculated with 10 µl of $10^{-6}$ dilution ($10^{-5}$). The other tube is inoculated with 1 µl of $10^{-6}$ dilution ($10^{-6}$), and incubated at 37° C. for 15 minutes.

About 3 ml of 48° C. top agar (50 ml stock containing 150 µl IPTG (0.5 M) and 37 µl X-GAL (350 mg/ml)) are added to each tube and plated on 100 mm plates. The plates are incubated overnight at 37° C.

The ZAP II library is excised to create the pBLUE-SCRIPT library according to manufacturer's protocols (Stratagene).

The DNA library can be transformed into host cells (e.g., E. coli) to generate an expression library of clones.

Example 2

Normalization

Prior to library generation, purified DNA can be normalized. DNA is first fractionated according to the following protocol A sample composed of genomic DNA is purified on a cesium-chloride gradient. The cesium chloride (Rf=1.3980) solution is filtered through a 0.2 µm filter and

TABLE 1

| Sample | $H_2O$ | 10× Ligase | 10 mM rATP | Lambda arms (ZAP) | Insert DNA | T4 DNA Ligase |
|---|---|---|---|---|---|---|
| Fraction 1–4 | 0.5 µl | 0.5 µl | 0.5 µl | 1.0 µl | 2.0 µl | 0.5 µl |
| Fraction 5–7 | 0.5 µl | 0.5 µl | 0.5 µl | 1.0 µl | 2.0 µl | 0.5 µl |

Test Package and Plate. The ligation reactions are packaged following manufacturer's protocol. Packaging reactions are stopped with 500 µl SM buffer and pooled with packaging that came from the same ligation. One µl of each pooled reaction is titered on an appropriate host ($OD_{600}$=1.0) (XL1-Blue MRF). 200 µl host (in $MgSO_4$) are added to Falcon 2059 tubes, inoculated with 1 µl packaged phage and incubated at 37° C. for 15 minutes. About 3 ml of 48° C. top agar (50 ml stock containing 150 µl IPTG (0.5 M) and 300 µl X-GAL (350 mg/ml)) are added and plated on 100 mm plates. The plates are incubated overnight at 37° C.

Amplification of Libraries ($5.0 \times 10^5$ recombinants from each library). About 3.0 ml host cells ($OD_{600}$=1.0) are added to two 50 ml conical tubes, inoculated with $2.5 \times 10^5$ pfu of phage per conical tube, and then incubated at 37° C. for 20 minutes. Top agar is added to each tube to a final volume of 45 ml. Each tube is plated across five 150 mm plates. The plates are incubated at 37° C. for 6–8 hours or until plaques 15 ml is loaded into a 35 ml OptiSeal tube (Beckman) The DNA is added and thoroughly mixed. Ten micrograms of bis-benzimide (Sigma; Hoechst 33258) is added and mixed thoroughly. The tube is then filled with the filtered cesium chloride solution and spun in a Bti50 rotor in a Beckman L8-70 Ultracentrifuge at 33 k rpm for 72 hours. Following centrifugation, a syringe pump and fractionator (Brandel Model 186) are used to drive the gradient through an ISCO UA-5UV absorbance detector set to 280 nm. Peaks representing the DNA from the organisms present in an environmental sample are obtained. Eubacterial sequences can be detected by PCR amplification of DNA encoding rRNA from a 10 fold dilution of the E. coli peak using the following primers to amplify:

Forward primer: 5'-AGAGTTTGATCCTGGCTCAG-3' (SEQ ID NO:58)

Reverse primer: 5'-GGTTACCTTGTTACGACTT-3' (SEQ ID NO:59)

Recovered DNA is sheared or enzymatically digested to 3–6 kb fragments. Lone-linker primers are ligated and the DNA is size-selected. Size-selected DNA is amplified by PCR, if necessary.

Normalization is then accomplished by resuspending the double-stranded DNA sample in hybridization buffer (0.12 M NaH$_2$PO$_4$, pH 6.8/0.82 M NaCl/1 mM EDTA/0.1% SDS). The sample is overlaid with mineral oil and denatured by boiling for 10 minutes. The sample is incubated at 68° C. for 12–36 hours. Double-stranded DNA is separated from single-stranded DNA according to standard protocols (Sambrook, 1989) on hydroxyapatite at 60° C. The single-stranded DNA fraction is desalted and amplified by PCR. The process is repeated for several more rounds (up to 5 or more).

Example 3

Enzymatic Activity Assay

The following is a representative example of a procedure for screening an expression library, prepared in accordance with Example 1, for epoxidase activity.

Plates of the library prepared as described in Example 1 are used to multiply inoculate a single plate containing 200 μl of LB Amp/Meth, glycerol in each well. This step is performed using the High Density Replicating Tool (HDRT) of the Beckman BIOMEK.RTM. with a 1% bleach, water, isopropanol, air-dry sterilization cycle between each inoculation. The single plate is grown for 2 h at 37° C. and is then used to inoculate two white 96-well Dynatech microtiter daughter plates containing 250 μl of LB Amp/Meth, glycerol in each well. The original single plate is incubated at 37° C. for 18 h, then stored at –80° C. The two condensed daughter plates are incubated at 37° C. also for 18 h. The condensed daughter plates are then heated at 70° C. for 45 min. to kill the cells and inactivate the host E. coli enzymes. A stock solution of 5 mg/mL morphourea phenylalanyl-7-amino-4-trifluoromethyl coumarin (MuPheAFC, the "substrate") in DMSO is diluted to 600 μM with 50 mM pH 7.5 Hepes buffer containing 0.6 mg/mL of the detergent dodecyl maltoside. Fifty μl of the 600 μM MuPheAFC solution is added to each of the wells of the white condensed plates with one 100 μl mix cycle using the BIOMEK to yield a final concentration of substrate of about 100 μM. The fluorescence values are recorded (excitation=400 nm, emission=505 nm) on a plate reading fluorometer immediately after addition of the substrate (t=0). The plate is incubated at 70° C. for 100 min, then allowed to cool to ambient temperature for 15 additional minutes. The fluorescence values are recorded again (t–100). The values at t–0 are subtracted from the values at t–100 to determine if an active clone is present.

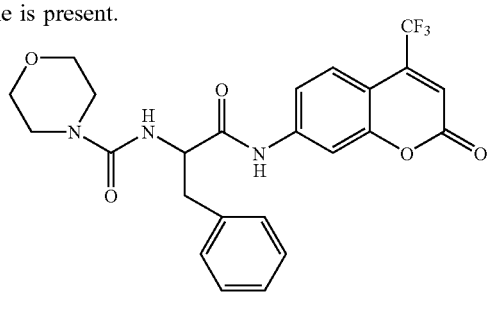

MuPheAFC

The data will indicate whether one of the clones in a particular well is hydrolyzing the substrate. In order to determine the individual clone which carries the activity, the source library plates are thawed and the individual clones are used to singly inoculate a new plate containing LB Amp/Meth, glycerol. As above, the plate is incubated at 37° C. to grow the cells, heated at 70° C. to inactivate the host enzymes, and 50 μl of 600 μM MuPheAFC is added using the Biomek.

After addition of the substrate the t=0 fluorescence values are recorded, the plate is incubated at 70° C., and the t=100 min. values are recorded as above. These data indicate which plate the active clone is in.

The enantioselectivity value, E, for the substrate is determined according to the equation below:

$$E = \frac{\ln[(1 - c(1 + ee_p)]}{\ln[(1 - c(1 + ee_p)]}$$

where ee$_p$=the enantiomeric excess (ee) of the hydrolyzed product and c=the percent conversion of the reaction. See Wong and Whitesides, Enzymes in Synthetic Organic Chemistry, 1994, Elsevier, Tarrytown, N.Y., pp. 9–12.

The enantiomeric excess is determined by either chiral high performance liquid chromatography (HPLC) or chiral capillary electrophoresis (CE). Assays are performed as follows: two hundred μl of the appropriate buffer is added to each well of a 96-well white microtiter plate, followed by 50 μl of partially or completely purified enzyme solution; 50 μl of substrate is added and the increase in fluorescence monitored versus time until 50% of the substrate is consumed or the reaction stops, whichever comes first.

Example 4

Directed Mutagenesis of Positive Enzyme Activity Clones

Directed mutagenesis was performed on two different enzymes (alkaline phosphatase and β-glycosidase) to generate new enzymes which exhibit a higher degree of activity than the wild-type enzymes.

Alkaline Phosphatase

The XL1-Red strain (Stratagene) was transformed with genomic clone 27a3a (in plasmid pBluescript) encoding the alkaline phosphatase gene from the organism OC9a, an organism isolated from the surface of a whale bone, according to the manufacturer's protocol. A 5 ml culture of LB+0.1 mg/ml ampicillin was inoculated with 200 μl of the transformation and the culture was allowed to grow at 37° C. for 30 hours. A miniprep was then performed on the culture, and the isolated DNA screened by transforming 2 μl of the resulting DNA into XL-1 Blue cells (Stratagene) according to the manufacturer's protocol and following the assay procedure outlined below. The mutated OC9a phosphatase took 10 minutes to develop color and the wild type enzyme took 30 minutes to develop color in the screening assay.

Standard Alkaline Phosphatase Screening Assay

Transformed XL1 Blue cells were plated on LB/amp plates. The resulting colonies were lifted with Duralon UV (Stratagene) or HATF (Millipore) membranes and lysed in chloroform vapors for 30 seconds. Cells were heat killed by incubating for 30 minutes at 85° C. The filters were developed at room temperature in BCIP buffer and the fastest developing colonies ("positives") were selected for restreaking the "positives" onto a BCIP plate (BCIP Buffer: 20 mm CAPS pH 9.0, 1 mm MgCl$_2$, 0.01 mm ZnCl$_2$, 0.1 mg/ml BCIP).

Beta-Glycosidase

This protocol was used to mutagenize Thermococcus 9N2 Beta-Glycosidase.

PCR was carried out by incubating 2 microliters dNTP's (10 mM Stocks); 10 microliters 10×PCR Buffer; 0.5 microliters Vector DNA-31G1A-100 nanograms; 20 microliters 3' Primer (100 pmol); 20 microliters 5' Primer (100 pmol); 16 microliters MnCl 4H$_2$O (1.25 mM Stock); 24.5 microliters H$_2$O; and 1 microliter Taq Polymerase (5.0 Units) in a total volume of 100 microliters. The PCR cycle was: 95° C. 15 seconds; 58° C. 30 seconds; 72° C. 90 seconds; 25 cycles (10 minute extension at 72° C.–4° C. incubation).

Five microliters of the PCR product was run on a 1% agarose gel to check the reaction. Purify on a QIAQUICK column (Qiagen). Resuspend in 50 microliters H$_2$O.

Twenty-five microliters of purified PCR product; 10 microliters NEB Buffer #2; 3 microliters Kpn I (1 OU/microliter); 3 microliters EcoRl (20 U/microliter); and 59 microliters H$_2$O. were incubated for 2 hours at 37° C. to digest the PCR products and purified on a QIAQUICK column (Qiagen). Elute with 35 microliters H$_2$O.

Ten microliters of digested PCR product, 5 microliters Vector (cut with EcoRI/KpnI and phosphatased with shrimp alkaline phosphatase, 4 microliters 5× Ligation Buffer, and 1 microliter T4 DNA Ligase (BRL) were incubated overnight to ligate the PCR products into the vector.

The resulting vector was transformed into M15pREP4 cells using electroporation. 100 or 200 microliters of the cells were plated onto LB amp meth kan plates, and grown overnight at 37° C.

Beta-galactosidase was assayed by (1) Perform colony lifts using Millipore HATF membrane filters; (2) lyse colonies with chloroform vapor in 150 mm glass petri dishes; (3) transfer filters to 100 mm glass petri dishes containing a piece of Whatman 3 MM filter paper saturated with Z buffer containing 1 mg/ml XGLU (After transferring filter bearing lysed colonies to the glass petri dish, maintain dish at room temperature); and (4) "Positives" were observed as blue spots on the filter membranes ("positives" are spots which appear early). A Pasteur pipette (or glass capillary tube) was used to core blue spots on the filter membrane. Place the small filter disk in an Eppendorf tube containing 20 µl water. Incubate the Eppendorf tube at 75° C. for 5 minutes followed by vortexing to elute plasmid DNA off filter. Transform this DNA into electrocompetent E. coli cells and repeat filter-lift assay on transformation plates to identify "positives." Return transformation plates to 37° C. incubator after filter lift to regenerate colonies. Inoculate 3 ml LBamp liquid with repurified positives and incubate at 37° C. overnight. Isolate plasmid DNA from these cultures and sequence plasmid insert. The filter assay uses buffer Z (see recipe below) containing 1 mg/ml of the substrate 5-bromo-4-chloro-3-indolyl-.beta.-o-glucopyranoside (XGLU) (Diagnostic Chemicals Limited or Sigma). Z-Buffer: (referenced in Miller, J. H. (1992) A Short Course in Bacterial Genetics, p. 445.) per liter:

Na$_2$HPO$_4$–7H$_2$O 16.1 g
Na$_2$HPO$_4$–4H$_2$O 5.5 g
KCl 0.75 g
Na$_2$HPO$_4$–7H$_2$O 0.246 g
6-mercaptoethanol 2.7 ml
Adjust pH to 7.0

Example 5

Construction of a Stable, Large Insert DNA Library of Picoplankton Genomic DNA

Cell collection and preparation of DNA. Agarose plugs containing concentrated picoplankton cells were prepared from samples collected on an oceanographic cruise from Newport, Oregon to Honolulu, Hawaii. Seawater (30 liters) was collected in Niskin bottles, screened through 10 µm Nitex, and concentrated by hollow fiber filtration (Amicon DC10) through 30,000 MW cutoff polyfulfone filters. The concentrated bacterioplankton cells were collected on a 0.22 µm, 47 mm Durapore filter, and resuspended in 1 ml of 2×STE buffer (1 M NaCl, 0.1 M EDTA, 10 mM Tris, pH 8.0) to a final density of approximately 1×10$^{10}$ cells per ml. The cell suspension was mixed with one volume of 1% molten Seaplaque LMP agarose (FMC) cooled to 40° C., and then immediately drawn into a 1 ml syringe. The syringe was sealed with parafilm and placed on ice for 10 min. The cell-containing agarose plug was extruded into 10 ml of Lysis Buffer (10 mM Tris pH 8.0, 50 mM NaCl, 0.1 M EDTA, 1% Sarkosyl, 0.2% sodium deoxycholate, 1 mg/ml lysozyme) and incubated at 37° C. for one hour. The agarose plug was then transferred to 40 mls of ESP Buffer (1% Sarkosyl, 1 mg/ml proteinase K, in 0.5 M EDTA), and incubated at 55° C. for 16 hours. The solution was decanted and replaced with fresh ESP Buffer, and incubated at 55° C. for an additional hour. The agarose plugs were then placed in 50 mM EDTA and stored at 4° C. shipboard for the duration of the oceanographic cruise.

One slice of an agarose plug (72 µl) prepared from a sample collected off the Oregon coast was dialyzed overnight at 4° C. against 1 mL of buffer A (100 mM NaCl, 10 mM Bis Tris Propane-HCl, 100 µg/ml acetylated BSA: pH 7.0 at 25° C.) in a 2 mL microcentrifuge tube. The solution was replaced with 250 µl of fresh buffer A containing 10 mM MgCl$_2$ and 1 mM DTT and incubated on a rocking platform for 1 hr at room temperature. The solution was then changed to 250 µl of the same buffer containing 4U of Sau3A1 (NEB), equilibrated to 37° C. in a water bath, and then incubated on a rocking platform in a 37° C. incubator for 45 min. The plug was transferred to a 1.5 ml microcentrifuge tube and incubated at 68° C. for 30 min to inactivate the enzyme and to melt the agarose. The agarose was digested and the DNA dephosphorylated using Gelase and HK-phosphatase (Epicentre), respectively, according to the manufacturer's recommendations. Protein was removed by gentle phenol/chloroform extraction and the DNA was ethanol precipitated, pelleted, and then washed with 70% ethanol. This partially digested DNA was resuspended in sterile H$_2$O to a concentration of 2.5 ng/µl for ligation to the pFOS1 vector.

PCR amplification results from several of the agarose plugs indicated the presence of significant amounts of archaeal DNA. Quantitative hybridization experiments using rRNA extracted from one sample, collected at 200 m of depth off the Oregon Coast, indicated that planktonic archaea in (this assemblage comprised approximately 4.7% of the total picoplankton biomass (this sample corresponds to "PACI"-200 m in Table 1 of DeLong et al., Nature, 371:695–698, 1994). Results from archaeal-biased rDNA PCR amplification performed on agarose plug lysates confirmed the presence of relatively large amounts of archaeal DNA in this sample. Agarose plugs prepared from this picoplankton sample were chosen for subsequent fosmid library preparation. Each 1 ml agarose plug from this site contained approximately 7.5×10⁵ cells, therefore approximately 5.4×10⁵ cells were present in the 72 µl slice used in the preparation of the partially digested DNA.

Vector arms were prepared from pFOS1 as described (Kim et al., Stable propagation of cosmid sized human DNA inserts in an F factor based vector, Nucl. Acids Res., 20:10832–10835, 1992). Briefly, the plasmid was completely digested with AstII, dephosphorylated with HK phosphatase, and then digested with BamHI to generate two arms, each of which contained a cos site in the proper orientation for cloning and packaging ligated DNA between 35–45 kbp. The partially digested picoplankton DNA was ligated overnight to the PFOS1 arms in a 15 µl ligation reaction containing 25 ng each of vector and insert and 1U of T4 DNA ligase (Boehringer-Mannheim). The ligated DNA in four microliters of this reaction was in vitro packaged using the Gigapack XL packaging system (Stratagene), the fosmid particles transfected to *E. coli* strain DH10B (BRL), and the cells spread onto $LB_{cm15}$ plates. The resultant fosmid clones were picked into 96-well microliter dishes containing $LB_{cm15}$ supplemented with 7% glycerol. Recombinant fosmids, each containing ca. 40 kb of picoplankton DNA insert, yielded a library of 3.552 fosmid clones, containing approximately 1.4×10⁸ base pairs of cloned DNA. All of the clones examined contained inserts ranging from 38 to 42 kbp. This library was stored frozen at −80° C. for later analysis.

Numerous modifications and variations of the present invention are possible in light of the above teachings; therefore, within the scope of the claims, the invention may be practiced other than as particularly described. While the invention has been described in detail with reference to certain aspects thereof, it will be understood that modifications and variations are within the spirit and scope of that which is described and claimed.

All publications, patents, patent applications, GenBank sequences and ATCC deposits, cited herein are hereby expressly incorporated by reference for all purposes.

A number of aspects of the invention have been described. Nevertheless, it will be understood that various modifications may be made without departing from the spirit and scope of the invention. Accordingly, other aspects are within the scope of the following claims.

What is claimed is:

1. An isolated, synthetic or recombinant nucleic acid, wherein the nucleic acid comprises
   (a) a sequence that hybridizes under stringent conditions to the complement of the polynucleotide comprising the nucleic acid sequence of SEQ ID NO:23, wherein the nucleic acid encodes a polypeptide having cytochrome P450 activity, and the stringent conditions comprise a wash step comprising a wash in 0.2×SSC at a temperature of about 65° C. for about 15 minutes, or
   (b) a sequence which is the complete complement of the polynucleotide of (a).

2. The isolated, synthetic or recombinant nucleic acid of claim 1, wherein the nucleic acid comprises the nucleic acid sequence of SEQ ID NO:23.

3. The isolated, synthetic or recombinant nucleic acid of claim 1, wherein the nucleic acid encodes the polypeptide having the amino acid sequence of SEQ ID NO:24.

4. The isolated, synthetic or recombinant nucleic acid of claim 1, wherein P450 activity comprises catalysis of incorporation of oxygen into a substrate.

5. The isolated, synthetic or recombinant nucleic acid of claim 4, wherein the P450 activity comprises epoxidation.

6. The isolated, synthetic or recombinant nucleic acid of claim 5, wherein the epoxidase activity further comprises epoxidation of an alkene substrate.

7. The isolated, synthetic or recombinant nucleic acid of claim 5, wherein the epoxidase activity further comprises production of a chiral product.

8. The isolated, synthetic or recombinant nucleic acid of claim 5, wherein the epoxidase activity is enantioselective.

9. The isolated, synthetic or recombinant nucleic acid of claim 1, wherein the P450 activity is thermostable at a temperature in the range from greater than about 37° C. to about 90° C.

10. The isolated, synthetic or recombinant nucleic acid of claim 1, wherein the polypeptide retains a P450 activity under conditions comprising a temperature range of between about 37° C. to about 70° C.

11. The isolated, synthetic or recombinant nucleic acid of claim 1, wherein the P450 activity is thermotolerant, retaining a P450 activity after exposure to a temperature in the range from greater than 37° C. to about 50° C.

12. The isolated, synthetic or recombinant nucleic acid of claim 11, wherein the polypeptide retains a P450 activity after exposure to a temperature in the range from greater than 37° C. to about 90° C.

13. The isolated, synthetic or recombinant nucleic acid of claim 1, wherein the stringent conditions comprise hybridization in a buffer comprising 6×SSC, 25% formamide at a temperature of 42° C.

14. An expression cassette comprising the nucleic acid of claim 1.

15. A vector comprising a nucleic acid comprising the nucleic acid of claim 1.

16. A cloning vehicle comprising the vector as set forth in claim 15, wherein the cloning vehicle comprises a viral vector, a plasmid, a phage, a phagemid, a cosmid, a fosmid, a bacteriophage or an artificial chromosome.

17. The cloning vehicle of claim 16, wherein the viral vector comprises an adenovirus vector, a retroviral vector or an adeno-associated viral vector.

18. The cloning vehicle of claim 17, comprising a bacterial artificial chromosome (BAC), a plasmid, a bacteriophage P1-derived vector (PAC), a yeast artificial chromosome (YAC), or a mammalian artificial chromosome (MAC).

19. An isolated cell transformed with a vector, wherein the vector comprises the nucleic acid of claim 1.

20. The isolated, synthetic or recombinant nucleic acid of claim 1, wherein the nucleic acid comprises a nucleic acid sequence having at least 95% sequence identity to SEQ ID NO:23.

21. An isolated, synthetic or recombinant nucleic acid encoding a fusion protein comprising: (a) an epoxidase and an N-terminal or a carboxy-terminal heterologous peptide,
   wherein the epoxidase comprises a sequence having at least 95% sequence identity to SEQ ID NO:24, and wherein the fusion protein continues to have epoxidase activity.

22. An isolated, synthetic or recombinant nucleic acid comprising a nucleic acid sequence having at least 95% sequence identity to SEQ ID NO:23, wherein the nucleic acid encodes a polypeptide having a P450 activity.

23. An isolated, synthetic or recombinant nucleic acid comprising a nucleic acid sequence having at least 95% sequence identity to SEQ ID NO:23, wherein the nucleic acid encodes a polypeptide having epoxidation activity and has a sequence comprising a variation of SEQ ID NO:24, wherein one or more amino acid residues of SEQ ID NO:24 are replaced with a conservative substitution.

24. An isolated, synthetic or recombinant nucleic acid comprising a polypeptide coding sequence having at least 95% sequence identity to SEQ ID NO:23, wherein the nucleic acid encodes a polypeptide having epoxidation activity, and a bacterial, a viral or a eukaryotic promoter, wherein the coding sequence is operably linked to the promoter.

25. An isolated, synthetic or recombinant nucleic acid comprising a nucleic acid sequence having at least 95% sequence identity to SEQ ID NO:23, wherein the nucleic acid encodes a polypeptide having epoxidation activity, and a nucleic acid sequence encoding a detection or a purification domain.

26. An isolated, synthetic or recombinant nucleic acid comprising a nucleic acid sequence having at least 95% sequence identity to SEQ ID NO:23, wherein the nucleic acid encodes a polypeptide having epoxidation activity.

27. An isolated, synthetic or recombinant nucleic acid comprising a nucleic acid sequence having at least 98% sequence identity to SEQ ID NO:23, wherein the nucleic acid encodes a polypeptide having epoxidation activity.

28. An isolated, synthetic or recombinant nucleic acid comprising a nucleic acid sequence having at least 99% sequence identity to SEQ ID NO:23, wherein the nucleic acid encodes a polypeptide having epoxidation activity.

29. An isolated, synthetic or recombinant nucleic acid, wherein the nucleic acid comprises the a nucleic acid sequence of SEQ ID NO:23, wherein the nucleic acid encodes a polypeptide having a P450 activity and the P450 activity comprises an epoxidation activity.

30. The isolated, synthetic or recombinant nucleic acid of claim 26, wherein the sequence identities are determined by analysis with a sequence comparison algorithm.

31. The isolated, synthetic or recombinant nucleic acid of claim 26, wherein the sequence comparison algorithm is a BLAST version 2.2.2 algorithm where a filtering setting is set to blastall -p blastp -d "nr pataa" -F F, and all other options are set to default.

32. An isolated cell transformed with the nucleic acid of claim 26.

33. The transformed cell of claim 19 or claim 32, wherein the cell is a bacterial cell, a mammalian cell, a fungal cell, a yeast cell, an insect cell or a plant cell.

34. An array comprising an immobilized nucleic acid as set forth in claim 26 or claim 1.

35. A method of producing a recombinant cytochrome P450 polypeptide comprising the steps of:
  (a) providing a nucleic acid operably linked to a promoter; wherein the nucleic acid comprises the sequence of claim 26 or claim 1; and
  (b) expressing the nucleic acid of step (a) under conditions that allow expression of the polypeptide, thereby producing arecombinant polypeptide encoded by the nucleic acid.

36. The method of claim 35, further comprising transforming a host cell with the nucleic acid of step (a) followed by expressing the nucleic acid of step (a), thereby producing a recombinant polypeptide in a transformed cell.

37. A method for overexpressing a recombinant cytochrome P450 polypeptide in a cell comprising expressing a vector comprising the nucleic acid of claim 26 or claim 1, wherein overexpression is effected by use of a high activity promoter, a dicistronic vector or by gene amplification of the vector.

38. The isolated, synthetic or recombinant nucleic acid of claim 1, wherein the cytochrome P450 activity comprises a monooxygenation reaction.

39. The isolated, synthetic or recombinant nucleic acid of claim 1, wherein the cytochrome P450 activity comprises catalysis of incorporation of oxygen into a substrate.

40. The isolated, synthetic or recombinant nucleic acid of claim 1, wherein the cytochrome P450 activity comprises hydroxylation of aliphatic or aromatic carbons.

41. The isolated, synthetic or recombinant nucleic acid of claim 1, wherein the cytochrome P450 activity comprises epoxidation.

42. The isolated, synthetic or recombinant nucleic acid of claim 1, wherein the cytochrome P450 activity comprises N—, O—, or S-dealkylation.

43. The isolated, synthetic or recombinant nucleic acid of claim 1, wherein the cytochrome P450 activity comprises dehalogenation.

44. The isolated, synthetic or recombinant nucleic acid of claim 1, wherein the cytochrome P450 activity comprises oxidative deamination.

45. The isolated, synthetic or recombinant nucleic acid of claim 1, wherein the cytochrome P450 activity comprises N-oxidation or N-hydroxylation.

46. The isolated, synthetic or recombinant nucleic acid of claim 1, wherein the cytochrome P450 activity comprises sulphoxide formation.

47. The isolated, synthetic or recombinant nucleic acid of claim 1, wherein the cytochrome P450 activity comprises a monooxygenation reaction.

48. The isolated, synthetic or recombinant nucleic acid of claim 22, wherein the cytochrome P450 activity comprises catalysis of incorporation of oxygen into a substrate.

49. The isolated, synthetic or recombinant nucleic acid of claim 22, wherein the cytochrome P450 activity comprises hydroxylation of aliphatic or aromatic carbons.

50. The isolated, synthetic or recombinant nucleic acid of claim 22, wherein the cytochrome P450 activity comprises epoxidation.

51. The isolated, synthetic or recombinant nucleic acid of claim 22, wherein the cytochrome P450 activity comprises N—, O—, or S-dealkylation.

52. The isolated, synthetic or recombinant nucleic acid of claim 22, wherein the cytochrome P450 activity comprises dehalogenation.

53. The isolated, synthetic or recombinant nucleic acid of claim 22, wherein the cytochrome P450 activity comprises oxidative deamination.

54. The isolated, synthetic or recombinant nucleic acid of claim 22, wherein the cytochrome P450 activity comprises N-oxidation or N-hydroxylation.

55. The isolated, synthetic or recombinant nucleic acid of claim 22, wherein the cytochrome P450 activity comprises sulphoxide formation.

\* \* \* \* \*

SEQUENCE LISTING

<160> NUMBER OF SEQ ID NOS: 59

<210> SEQ ID NO 1
<211> LENGTH: 1221
<212> TYPE: DNA
<213> ORGANISM: Bacterial

<400> SEQUENCE: 1

```
gtgaccacca ccacgaccaa cgaccccgac acccccagg tccacttctg ggccgtcccc    60
gacctcaccg gcctcgactt cgacccgctg ctcgccaaac tgctgcacga ggaccccgtc   120
acccgcgtcc ggctgccgca cggcgaaggc cacgcctggc tcgtcacccg ctacgaggac   180
gtcaagttcg tctccgtcga cccgcgcttc agccgccagg ccgtctgggg ccgttccatc   240
acccgcgtag ccccccactt catcccgatg gagggcgccg tcggcttcgc cgacccgccg   300
gaccacaccc ggatgcgccg cgtcgtcgcc cgcgccttca gcgcccgcgc cctgcgctcc   360
ctgcgcgacc acgcccagga cgtcatggac cggctcctcg accgggtcga ggagcacggc   420
gcgcccgccg acctcatgga gctcgtcaac cgccccttcc ccctcgccat ggtcagcgaa   480
ctcatgggcg tccccgaggg cgaccagccg ctgatgcgcc actggtccga caccatcatc   540
tcggccggcg ccggccggga ggccagcgag acggccaagg ccgagatggg ccggtacttc   600
accgaactca tcggccgcaa ccacggcacc ggcaaggaga ccctcgccgc cgtcctcgcc   660
gacgccgtcg acgacgacac cctcaccgag cacgaggccg tcggcctcgc cgtcctcatc   720
cagatcggcg gcgcccacgc cgtccggaac aacagccgcca acatggtgta cgcgctgctc   780
acccaccccg agcacctcgc ccggctgcgc gcggagccgg agctcgtccc ccaggccgtc   840
gacgagctcc tccgctacat cccgcaccgc aacgccgtcg gcctctcccg gatcgccctg   900
gaggacgtcg aggtcggcgg ggtcaccatc ccctccggcg accccgtcta cgtctcctac   960
ctgacggcca accgcgaccc cgccgtcttc cccgacccct agcggctcga cttcgaccgc  1020
gcgtacaacc cccacgtcgc cttcggccac ggccccact actgccccgg ctccgccctc  1080
gcccgcatcg agtcggagat cctcgtcgac acgctgtgga cccgcttccc gaacctgcgg  1140
```

```
ctcgccgtcc ccgaggacca gctgcgctgg cagcgcggcg ccctcatccg cggccccgag    1200
acccttccgg tcacctggtg a                                              1221
```

<210> SEQ ID NO 2
<211> LENGTH: 406
<212> TYPE: PRT
<213> ORGANISM: Bacterial

<400> SEQUENCE: 2

```
Met Thr Thr Thr Thr Thr Asn Asp Pro Asp Thr Pro Gln Val His Phe
 1               5                  10                  15

Trp Ala Val Pro Asp Leu Thr Gly Leu Asp Phe Asp Pro Leu Leu Ala
                20                  25                  30

Lys Leu Leu His Glu Asp Pro Val Thr Arg Val Arg Leu Pro His Gly
            35                  40                  45

Glu Gly His Ala Trp Leu Val Thr Arg Tyr Glu Asp Val Lys Phe Val
        50                  55                  60

Ser Val Asp Pro Arg Phe Ser Arg Gln Ala Val Trp Gly Arg Ser Ile
65                  70                  75                  80

Thr Arg Val Ala Pro His Phe Ile Pro Met Glu Gly Ala Val Gly Phe
                85                  90                  95

Ala Asp Pro Pro Asp His Thr Arg Met Arg Arg Val Val Ala Arg Ala
            100                 105                 110

Phe Ser Ala Arg Ala Leu Arg Ser Leu Arg Asp His Ala Gln Asp Val
        115                 120                 125

Met Asp Arg Leu Leu Asp Arg Val Glu Glu His Gly Ala Pro Ala Asp
    130                 135                 140

Leu Met Glu Leu Val Asn Arg Pro Phe Pro Leu Ala Met Val Ser Glu
145                 150                 155                 160

Leu Met Gly Val Pro Glu Gly Asp Gln Pro Leu Met Ala His Trp Ser
                165                 170                 175

Asp Thr Ile Ile Ser Ala Gly Ala Gly Arg Glu Ala Ser Glu Thr Ala
            180                 185                 190

Lys Ala Glu Met Gly Arg Tyr Phe Thr Glu Leu Ile Gly Arg Asn His
        195                 200                 205

Gly Thr Gly Lys Glu Thr Leu Ala Ala Val Leu Ala Asp Ala Val Asp
    210                 215                 220

Asp Asp Thr Leu Thr Glu His Glu Ala Val Gly Leu Ala Val Leu Ile
225                 230                 235                 240

Gln Ile Gly Gly Ala His Ala Val Arg Asn Asn Ser Ala Asn Met Val
                245                 250                 255

Tyr Ala Leu Leu Thr His Pro Glu His Leu Ala Arg Leu Arg Ala Glu
            260                 265                 270

Pro Glu Leu Val Pro Gln Ala Val Asp Glu Leu Leu Arg Tyr Ile Pro
        275                 280                 285

His Arg Asn Ala Val Gly Leu Ser Arg Ile Ala Leu Glu Asp Val Glu
    290                 295                 300

Val Gly Gly Val Thr Ile Pro Ser Gly Asp Pro Val Tyr Val Ser Tyr
305                 310                 315                 320

Leu Thr Ala Asn Arg Asp Pro Ala Val Phe Pro Asp Pro Glu Arg Leu
                325                 330                 335

Asp Phe Asp Arg Ala Tyr Asn Pro His Val Ala Phe Gly His Gly Pro
            340                 345                 350

His Tyr Cys Pro Gly Ser Ala Leu Ala Arg Ile Glu Ser Glu Ile Leu
```

|   |   | 355 |   |   | 360 |   |   |   | 365 |   |   |
|---|---|---|---|---|---|---|---|---|---|---|---|

Val Asp Thr Leu Trp Thr Arg Phe Pro Asn Leu Arg Leu Ala Val Pro
    370                 375                 380

Glu Asp Gln Leu Arg Trp Gln Arg Gly Ala Leu Ile Arg Gly Pro Glu
385                 390                 395                 400

Thr Leu Pro Val Thr Trp
            405

<210> SEQ ID NO 3
<211> LENGTH: 1227
<212> TYPE: DNA
<213> ORGANISM: Bacterial
<400> SEQUENCE: 3

```
atgaccggtc aagaccagac aatcgttcac gatgtcccgg taaacgtcgc tcaacagccc      60
aacccctacc cgctcttcga acgcatccgc gagcacggcg tcgtccagcg ggtacggctg     120
aatcccactc ttgaagtctg gatggtcacc ggatacgacg aggcggtggc ggcgctcacc     180
gaccccggc tcagcagcag ccccgtcggc gtcaacggac tcgaggagga gatggcccac     240
caggagcgca ccaacgtcct gatggccagc atgctcgtcg ccaacggcga ggaccacacc     300
cggctgcgca acctcgtctc gaaggccttc accgcccgcc gggtggagca gctcgcgccg     360
cgcgtccagg cgcacaccga cgccttcctc gacgcggtcg cggcgcgcgg atccgccgac     420
ctggtctcgg agttcgccct gccgctcccc atggccgtac tcagcgacct catcggcatc     480
ccggccgagg ggcagcccga cttcgcccgc ctcgcggtcg gcctcatcat gccgccgaac     540
accccgagc ggctcgccaa gggagcccgc gcccgcgccg aactcaccga gttcttcgag     600
ccgttgatcg cccagcgcaa gaaggagccg aaggacgacc tgctgagcgc gctctgcgcg     660
gcgcaggccg aggagcggat cagcgaccgc gagctgacgg cgatgacgat cctgctcacg     720
ctcgccgggc acgagacgac ggccagcctg atcgccaacg cgtgcacgc cctgctgcgg     780
caccccgagc agttcgccac cctgcgcgac gaccccctcgc tgctgccggg cgcgatcgag     840
gaactcctgc gctacgaggg cccggtgagc cggggcgtcg cccgcttcac cacccgaccccg     900
tacgagatcg gcggggtcac cgtaccggcc ggcgagatga tcatcatcgg gctcgccgcg     960
gccaatcgcg acccggcccg ctacgaccgt cccgacatcc tcgacgttgc acgccgtgag    1020
gtgccgcaac agctcgcttt cggccatggc gtgcacttct gcctgggtgc gccgctggcc    1080
cgcgcggagg cccggatcgc catcggcacc ctgctgcgcc gcttccccga tctgcggctc    1140
gccgacccgg acgcggacct cagccggcgc gagggcatcc tgcgcggcat ggcgaccctg    1200
cccgtgacct tcacgcccga ggcctga                                       1227
```

<210> SEQ ID NO 4
<211> LENGTH: 408
<212> TYPE: PRT
<213> ORGANISM: Bacterial
<400> SEQUENCE: 4

Met Thr Gly Gln Asp Gln Thr Ile Val His Asp Val Pro Val Asn Val
1               5                   10                  15

Ala Gln Gln Pro Asn Pro Tyr Pro Leu Phe Glu Arg Ile Arg Glu His
                20                  25                  30

Gly Val Val Gln Arg Val Arg Leu Asn Pro Thr Leu Glu Val Trp Met
            35                  40                  45

Val Thr Gly Tyr Asp Glu Ala Val Ala Ala Leu Thr Asp Pro Arg Leu

|    |    |    |    |    | 50  |    |    |    | 55  |    |    |    | 60  |    |    |
|----|----|----|----|----|-----|----|----|----|-----|----|----|----|-----|----|----|

Ser Ser Ser Pro Val Gly Val Asn Gly Leu Glu Glu Met Ala His
65                  70                  75                  80

Gln Glu Arg Thr Asn Val Leu Met Ala Ser Met Leu Val Ala Asn Gly
                85                  90                  95

Glu Asp His Thr Arg Leu Arg Asn Leu Val Ser Lys Ala Phe Thr Ala
                100                 105                 110

Arg Arg Val Glu Gln Leu Ala Pro Arg Val Gln Ala His Thr Asp Ala
                115                 120                 125

Phe Leu Asp Ala Val Ala Arg Gly Ser Ala Asp Leu Val Ser Glu
130                 135                 140

Phe Ala Leu Pro Leu Pro Met Ala Val Leu Ser Asp Leu Ile Gly Ile
145                 150                 155                 160

Pro Ala Glu Gly Gln Pro Asp Phe Ala Arg Leu Ala Val Gly Leu Ile
                165                 170                 175

Met Pro Pro Asn Thr Pro Glu Arg Leu Ala Lys Gly Ala Arg Ala Arg
                180                 185                 190

Ala Glu Leu Thr Glu Phe Phe Glu Pro Leu Ile Ala Gln Arg Lys Lys
                195                 200                 205

Glu Pro Lys Asp Asp Leu Leu Ser Ala Leu Cys Ala Ala Gln Ala Glu
210                 215                 220

Glu Arg Ile Ser Asp Arg Glu Leu Thr Ala Met Thr Ile Leu Leu Thr
225                 230                 235                 240

Leu Ala Gly His Glu Thr Thr Ala Ser Leu Ile Ala Asn Gly Val His
                245                 250                 255

Ala Leu Leu Arg His Pro Glu Gln Phe Ala Thr Leu Arg Asp Asp Pro
                260                 265                 270

Ser Leu Leu Pro Gly Ala Ile Glu Glu Leu Leu Arg Tyr Glu Gly Pro
                275                 280                 285

Val Ser Arg Gly Val Ala Arg Phe Thr Thr Asp Pro Tyr Glu Ile Gly
                290                 295                 300

Gly Val Thr Val Pro Ala Gly Glu Met Ile Ile Ile Gly Leu Ala Ala
305                 310                 315                 320

Ala Asn Arg Asp Pro Ala Arg Tyr Asp Arg Pro Asp Ile Leu Asp Val
                325                 330                 335

Ala Arg Arg Glu Val Pro Gln Gln Leu Ala Phe Gly His Gly Val His
                340                 345                 350

Phe Cys Leu Gly Ala Pro Leu Ala Arg Ala Glu Ala Arg Ile Ala Ile
                355                 360                 365

Gly Thr Leu Leu Arg Arg Phe Pro Asp Leu Arg Leu Ala Asp Pro Asp
370                 375                 380

Ala Asp Leu Ser Arg Arg Glu Gly Ile Leu Arg Gly Met Ala Thr Leu
385                 390                 395                 400

Pro Val Thr Phe Thr Pro Glu Ala
                405

<210> SEQ ID NO 5
<211> LENGTH: 1116
<212> TYPE: DNA
<213> ORGANISM: Bacterial

<400> SEQUENCE: 5
atgagcgacg agccgaaccg cgagccgggc cggggcatag cgggcgaccg ggcggcggcg        60
ccgcccgggg acccctggac gcggctgccg tccatggcgc cggcggagcc ggtggccgac       120

-continued

```
ggtaagggcg gccccggtc cgccgccgcg ccgggacggg tgcggaccgt gcccgatccg        180
gccgtcctcg gtggctcccg ggccaggacc gtcgcgccca gtccctcga ccccggcgcc        240 tcgcgcgacc cgcaccgcat ccaccggacg ctgcggagg acttcccgct cacgtacgac        300
ccgctgctgc gggcctgggt gctcagccgg tacgccgacg tggccaccgc cctcaccgac        360
agccgcttca cccacgggca ccggcccggc gaccgccgt gcgcgcgggc ccatgtcgac         420
gtcgacgtgg cggccctgcg gtcggtcacg gagcgcaccg cgtacgtgct ggcccgccgg        480
atcgccgagc ggccccaggc cgatctggtg gccgacttct gccactggct gcccgccggg        540
accgtggccg ccgccgtcgg cgtcccctac cgcgacatga tgcggctcgt ccgcggccgg        600
gcggccggcg ctctcgcggg ggagtgcggc gggcagatcg ccgtacggga gaaggcgctt        660
gcgtccttcc tcggcaacgt cctcgccgat cccgatcagg tcgccgccct gcgggacgcg        720
ccggccgggc tggtggcccg cgcctggacg gagtcgctgc gccgcgaccc gcccgtgcag        780
atcgccgtgc gcaggacgag cgccgaggtg ccggtgagcg gcggtgtcgt cccggcgggc        840
gtgcccgtgg cgctgctcgt gggctcggcg ggccgggacc cggagcggtt ccgcgagccg        900
gaccgtttcg atcccttccg tgccgacccg ggccagttga cgtacggctc cggcttctgc        960
ccggcggtgc tcctggccgg tcttgaggcg gagtacgcgc tgcgggccct gttcacggcg       1020
atgccccggc tccgcctcgc cgagggcttc cgcccggtgt gggcgggtct catcacgcgg       1080
gcgccgcgga gcctgatcgt ccggccggga ggctga                                1116
```

<210> SEQ ID NO 6
<211> LENGTH: 371
<212> TYPE: PRT
<213> ORGANISM: Bacterial

<400> SEQUENCE: 6

```
Met Ser Asp Glu Pro Asn Arg Glu Pro Gly Arg Gly Ile Ala Gly Asp
 1               5                  10                  15

Arg Ala Ala Pro Pro Gly Asp Pro Trp Thr Arg Leu Pro Ser Met
             20                  25                  30

Ala Pro Ala Glu Pro Val Ala Asp Gly Lys Gly Pro Arg Ser Ala
         35                  40                  45

Ala Ala Pro Gly Arg Val Arg Thr Val Pro Asp Pro Ala Val Leu Gly
     50                  55                  60

Gly Ser Arg Ala Arg Thr Val Ala Pro Ser Pro Leu Asp Pro Gly Ala
 65                  70                  75                  80

Ser Arg Asp Pro His Arg Ile His Arg Thr Leu Arg Glu Asp Phe Pro
                 85                  90                  95

Leu Thr Tyr Asp Pro Leu Leu Arg Ala Trp Val Leu Ser Arg Tyr Ala
            100                 105                 110

Asp Val Ala Thr Ala Leu Thr Asp Ser Arg Phe Thr His Gly His Arg
        115                 120                 125

Pro Gly Asp Pro Pro Cys Ala Arg Ala His Val Asp Val Asp Val Ala
    130                 135                 140

Ala Leu Arg Ser Val Thr Glu Arg Thr Ala Tyr Val Leu Ala Arg Arg
145                 150                 155                 160

Ile Ala Glu Arg Pro Gln Ala Asp Leu Val Ala Asp Phe Cys His Trp
                165                 170                 175

Leu Pro Ala Gly Thr Val Ala Ala Val Gly Val Pro Tyr Arg Asp
            180                 185                 190
```

```
Met Met Arg Leu Val Arg Gly Arg Ala Ala Gly Ala Leu Ala Gly Glu
        195                 200                 205

Cys Gly Gly Gln Ile Ala Val Arg Glu Lys Ala Leu Ala Ser Phe Leu
        210                 215                 220

Gly Asn Val Leu Ala Asp Pro Asp Gln Val Ala Leu Arg Asp Ala
225                 230                 235                 240

Pro Ala Gly Leu Val Ala Arg Ala Trp Thr Glu Ser Leu Arg Arg Asp
                245                 250                 255

Pro Pro Val Gln Ile Ala Val Arg Arg Thr Ser Ala Glu Val Pro Val
                260                 265                 270

Ser Gly Gly Val Val Pro Ala Gly Val Pro Val Ala Leu Leu Val Gly
                275                 280                 285

Ser Ala Gly Arg Asp Pro Glu Arg Phe Arg Glu Pro Asp Arg Phe Asp
        290                 295                 300

Pro Phe Arg Ala Asp Pro Gly Gln Leu Thr Tyr Gly Ser Gly Phe Cys
305                 310                 315                 320

Pro Ala Val Leu Leu Ala Gly Leu Glu Ala Glu Tyr Ala Leu Arg Ala
                325                 330                 335

Leu Phe Thr Ala Met Pro Arg Leu Arg Leu Ala Glu Gly Phe Arg Pro
                340                 345                 350

Val Trp Ala Gly Leu Ile Thr Arg Ala Pro Arg Ser Leu Ile Val Arg
        355                 360                 365

Pro Gly Gly
        370

<210> SEQ ID NO 7
<211> LENGTH: 1392
<212> TYPE: DNA
<213> ORGANISM: Bacterial

<400> SEQUENCE: 7
atgcccccca acaccgtccc gaccccggtg ccaggaggcc gaccgctgat cgggcacgcc      60
cgccaactgc tgtggcgcag gctgccgttc ctggagtcgc tgcgggacca cggcgacatc     120
gtggtgatcc gcctcggccc gtggcggatc catgtgctca acgacccggc gctcgtccgc     180
gacgtcctca ccaaacgctc cccggacttc gggctgagcc cccagttcca ggtgatgaaa     240
cgcgtcatcg gcaacgggct cctcgccacc gacggcccct ccaccgccg gcagcgcaaa      300 ctgatcctcc ccgccctgca ccacaccagg atccgcgcct acgcccgcac catgacccgc     360
ctcgccgacg cccgtaccgc ccgctggcag gacgggcaga ccctgcgcgt cgacgcggag     420
ttcaccgaac tggccaccga gatcgtgctg cgctgcctgt ctccaccga gatcggcggc     480 gccgacgtgg ccgccgtggt ggccgccctg cccgacctga tgagctgggc cggcagccgc     540
ggcctcgacc cgaccgggct gctcggcgcc gtccccaccc cgctgggccg ccgcttccgg     600
cgctccatgg cggtgctgga cgcgctgctc gcccgggtca tcggggcccg ccgggcggac     660
ggcccggcca ccgaccaccc cgacctgctc gccgcgctgc tcgccgcccg gacgcggag      720 accggggagc ccatgtccga ccggcagatc gcgacgagg ccatgtcgtt cctggtggcc     780
ggggccgaat cggtctcccg caccctgacc tggagcgccc tgctgctggc cggcgacccc     840
gaggcggccc ccggctccca ccaggaggcc gatcgcgaac tgtccggccg cccggcccac     900
ttcgaggacc tgccgaggct gcgccacacc cgcatggtgc tccaggaggc gctgcgcctg     960
tacccgcccg gctacctgat ctcccgggcg gcgctgcgcg acaccacgct cggcccctac    1020
cgcatcccgg ccggcgccac cgtgatgttc tcctactacg ccctccagcg ggaccccgc    1080
```

-continued

```
cgcttcccgg acccggcccg gttcgacccg ttgcgctggt cgcccaagcg cggcggcgcc    1140
gaccgggagg cgttcacgcc gttcggcctc ggcccgcacg gctgcctcgg cgagagcttc    1200
gcgtggaccg agatgtccat cgtgctcgcc accctcgccg cccgctggga gctgcgctcc    1260
gcctcgccgc gcccggtgcg gccggtgccc accttctccc tgaccatggc cggcgccccg    1320
atgaccgtca ccgcgcggcc ggtgcgcacc ggccccgtcc acaccctgct ggccagccgt    1380
aacggaggat ga                                                        1392
```

<210> SEQ ID NO 8
<211> LENGTH: 463
<212> TYPE: PRT
<213> ORGANISM: Bacterial

<400> SEQUENCE: 8

```
Met Pro Pro Asn Thr Val Pro Thr Pro Val Pro Gly Gly Arg Pro Leu
  1               5                  10                  15

Ile Gly His Ala Arg Gln Leu Leu Trp Arg Arg Leu Pro Phe Leu Glu
                 20                  25                  30

Ser Leu Arg Asp His Gly Asp Ile Val Ile Arg Leu Gly Pro Trp
             35                  40                  45

Arg Ile His Val Leu Asn Asp Pro Ala Leu Val Arg Asp Val Leu Thr
 50                  55                  60

Lys Arg Ser Pro Asp Phe Gly Leu Ser Pro Gln Phe Gln Val Met Lys
 65                  70                  75                  80

Arg Val Ile Gly Asn Gly Leu Leu Ala Thr Asp Gly Pro Phe His Arg
                 85                  90                  95

Arg Gln Arg Lys Leu Ile Leu Pro Ala Leu His His Thr Arg Ile Arg
                100                 105                 110

Ala Tyr Ala Arg Thr Met Thr Arg Leu Ala Asp Ala Arg Thr Ala Arg
            115                 120                 125

Trp Gln Asp Gly Gln Thr Leu Arg Val Asp Ala Glu Phe Thr Glu Leu
130                 135                 140

Ala Thr Glu Ile Val Leu Arg Cys Leu Phe Ser Thr Glu Ile Gly Gly
145                 150                 155                 160

Ala Asp Val Ala Ala Val Val Ala Ala Leu Pro Asp Leu Met Ser Trp
                165                 170                 175

Ala Gly Ser Arg Gly Leu Asp Pro Thr Gly Leu Leu Gly Ala Val Pro
            180                 185                 190

Thr Pro Leu Gly Arg Arg Phe Arg Arg Ser Met Ala Val Leu Asp Ala
        195                 200                 205

Leu Leu Ala Arg Val Ile Gly Ala Arg Arg Ala Asp Gly Pro Ala Thr
    210                 215                 220

Asp His Pro Asp Leu Leu Ala Leu Leu Ala Ala Arg Asp Ala Glu
225                 230                 235                 240

Thr Gly Glu Pro Met Ser Asp Arg Gln Ile Arg Asp Glu Ala Met Ser
                245                 250                 255

Phe Leu Val Ala Gly Ala Glu Ser Ser Arg Thr Leu Thr Trp Ser
            260                 265                 270

Ala Leu Leu Leu Ala Gly Asp Pro Glu Ala Ala Arg Leu His Gln
        275                 280                 285

Glu Ala Asp Arg Glu Leu Ser Gly Arg Pro Ala His Phe Glu Asp Leu
    290                 295                 300

Pro Arg Leu Arg His Thr Arg Met Val Leu Gln Glu Ala Leu Arg Leu
```

-continued

```
                305                 310                 315                 320
            Tyr Pro Pro Gly Tyr Leu Ile Ser Arg Ala Ala Leu Arg Asp Thr Thr
                            325                 330                 335
            Leu Gly Pro Tyr Arg Ile Pro Ala Gly Ala Thr Val Met Phe Ser Tyr
                        340                 345                 350
            Tyr Ala Leu Gln Arg Asp Pro Arg Phe Pro Asp Pro Ala Arg Phe
                        355                 360                 365
            Asp Pro Leu Arg Trp Ser Pro Lys Arg Gly Gly Ala Asp Arg Glu Ala
                    370                 375                 380
            Phe Thr Pro Phe Gly Leu Gly Pro His Gly Cys Leu Gly Glu Ser Phe
            385                 390                 395                 400
            Ala Trp Thr Glu Met Ser Ile Val Leu Ala Thr Leu Ala Ala Arg Trp
                            405                 410                 415
            Glu Leu Arg Ser Ala Ser Pro Arg Pro Val Arg Pro Val Pro Thr Phe
                        420                 425                 430
            Ser Leu Thr Met Ala Gly Ala Pro Met Thr Val Thr Ala Arg Pro Val
                        435                 440                 445
            Arg Thr Gly Pro Val His Thr Leu Leu Ala Ser Arg Asn Gly Gly
                    450                 455                 460

<210> SEQ ID NO 9
<211> LENGTH: 1173
<212> TYPE: DNA
<213> ORGANISM: Bacterial

<400> SEQUENCE: 9
gtggacccga ttctggatct ggcccgaccg tcgatcctgc ggaaccccta cccctcgtac      60
gaccggatgc gcgagaccgg cccggtcttc tggcacgaac tgctcggttc gtgggtcctg     120
acccggcacg ccgactgcct cgcggtgctc accgacagca accgtttcgc ctccgactgg     180
cgccgggccg gggaggacat ccccgccccg ctgctcagcg tgcagaccct cgacccgccg     240
gagcacaccg ccatccggca cctcctcctc gacggtttcc gggcccagga ccggcgggcg     300
ctccatgacg acctggaggg gcagatcgcc gatctgctcg cggagttggc cggccggccg     360
tccttcgacc tggtcgggga gctcgccgaa ccgatcgccc tccgcttcgt gaccgccttc     420
ctcggcgtcc cggcccccgc gctcgactgg ttcgtgccca tgtcccgtac cgtcgtcgac     480
ggcatggacg ccgggctgtg cccgagaag cacgagccgg ccgtcgccgc ccgcgcccag     540
ctcgcggagt acgcgggcgg ctggctcgcc gaccgcgcga aggacggcct catcgcctac     600
gtggccgagc acgcggcgga cagcggcgtg gcagaaacgg ttctgcggaa cagtctgcgc     660
gccgttctcc acgcgggcta cgaatccgcc tcccggctgc tcggcaacgc cgcggccgcc     720
ctcctcacca ccccggcgc gctcgccgcg ttccgggcga ccccggccac ggccgtggac     780
gaactcatcc ggtacgacgc acccgtccag gcggacgccc gggtctgcgt caccgacacc     840
gaactgggtg gcgtcacgat gaaggcgggt gatccggtca cgctcttcct gggcgcggcc     900
aaccacgacc gctccgcttc gaccaccccc acagagctgc gactcgaccg cgccccgaac     960
ccgcacctcg ggttcggccg cggggcccat gcctgtctgg gcgcgtccat ggcgatccgg    1020
ctcaccggat cggtcctcgg gaccctggcc acggaccacc ccggcgcacg ggcggtcgcg    1080
gaaccggaac accggcgcaa cctgaccctt cgcggtctcg accgcttcga ggtctgcctg    1140
cgtccagaca cgggggagga ggtacgacca tga                                 1173

<210> SEQ ID NO 10
```

```
<211> LENGTH: 390
<212> TYPE: PRT
<213> ORGANISM: Bacterial

<400> SEQUENCE: 10

Met Asp Pro Ile Leu Asp Leu Ala Arg Pro Ser Ile Leu Arg Asn Pro
1               5                   10                  15

Tyr Pro Ser Tyr Asp Arg Met Arg Glu Thr Gly Pro Val Phe Trp His
            20                  25                  30

Glu Leu Leu Gly Ser Trp Val Leu Thr Arg His Ala Asp Cys Leu Ala
        35                  40                  45

Val Leu Thr Asp Ser Asn Arg Phe Ala Ser Asp Trp Arg Arg Ala Gly
    50                  55                  60

Glu Asp Ile Pro Ala Pro Leu Leu Ser Val Gln Thr Leu Asp Pro Pro
65                  70                  75                  80

Glu His Thr Ala Ile Arg His Leu Leu Leu Asp Gly Phe Arg Ala Gln
                85                  90                  95

Asp Arg Arg Ala Leu His Asp Asp Leu Glu Gly Gln Ile Ala Asp Leu
            100                 105                 110

Leu Ala Glu Leu Ala Gly Arg Pro Ser Phe Asp Leu Val Gly Glu Leu
        115                 120                 125

Ala Glu Pro Ile Ala Leu Arg Phe Val Thr Ala Phe Leu Gly Val Pro
    130                 135                 140

Ala Pro Ala Leu Asp Trp Phe Val Pro Met Ser Arg Thr Val Val Asp
145                 150                 155                 160

Gly Met Asp Ala Gly Leu Trp Pro Glu Lys His Glu Pro Ala Val Ala
                165                 170                 175

Ala Arg Ala Gln Leu Ala Glu Tyr Ala Gly Gly Trp Leu Ala Asp Pro
            180                 185                 190

Pro Lys Asp Gly Leu Ile Ala Tyr Val Ala Glu His Ala Ala Asp Ser
        195                 200                 205

Gly Val Ala Glu Thr Val Leu Arg Asn Ser Leu Arg Ala Val Leu His
    210                 215                 220

Ala Gly Tyr Glu Ser Ala Ser Arg Leu Leu Gly Asn Ala Ala Ala Ala
225                 230                 235                 240

Leu Leu Thr Thr Pro Gly Ala Leu Ala Ala Phe Arg Ala Thr Pro Ala
                245                 250                 255

Thr Ala Val Asp Glu Leu Ile Arg Tyr Asp Ala Pro Val Gln Ala Asp
            260                 265                 270

Ala Arg Val Cys Val Thr Asp Thr Glu Leu Gly Gly Val Thr Met Lys
        275                 280                 285

Ala Gly Asp Pro Val Thr Leu Phe Leu Gly Ala Ala Asn His Asp Pro
    290                 295                 300

Leu Arg Phe Asp His Pro Thr Glu Leu Arg Leu Asp Arg Ala Pro Asn
305                 310                 315                 320

Pro His Leu Gly Phe Gly Arg Gly Ala His Ala Cys Leu Gly Ala Ser
                325                 330                 335

Met Ala Ile Arg Leu Thr Gly Ser Val Leu Gly Thr Leu Ala Thr Asp
            340                 345                 350

His Pro Gly Ala Arg Ala Val Ala Glu Pro Glu His Arg Arg Asn Leu
        355                 360                 365

Thr Leu Arg Gly Leu Asp Arg Phe Glu Val Cys Leu Arg Pro Asp Thr
    370                 375                 380

Gly Glu Glu Val Arg Pro
```

-continued

```
<210> SEQ ID NO 11
<211> LENGTH: 1188
<212> TYPE: DNA
<213> ORGANISM: Unknown
<220> FEATURE:
<223> OTHER INFORMATION: Obtained from an environmental sample

<400> SEQUENCE: 11
atgactttga agttcaaccc ctactgcgaa gagttttacc agaacccgtg gcagaacttc      60
cgggcgcttc gaacgcagga cccggtccac tatatcgagg aattcgatgc ctgggctctg     120
ttcggtttcg aggatgtgtg gcgcgcgggc atggaccggg aaagcttcac cgctacctac     180
ggcagctctc cacaggcgct gctgatcgac cgggtaaagc agccggagat cttcctgttc     240
atggacatac cgaaccacat gatccaccgc ggcattattg cgaaggatta cggccgcaac     300
gccatgccgc ttctcgaggg gaagatccgc gccacggcaa agaggcgat tacgccctac      360
ctgaagtccg gtgagatgga cgtttacgcc ttcgcccgta cagtggcgct tttcaccatc     420
gctgacatga tcggtctgcg gccggaagag gtcgtccgta ccggtccct tatcgatatt      480
ttcttcgggc gcacaccagg ccatcgaggc acaaccccgg acggcgtggc ggcctttcac     540
gaagtaaccg cctacgtcct tgatctgatc ggccactacc gggcgaaggg cgcaccggag     600
ggcagccaca tcgacaactg gctcaaggca gagccggatg gccggcccct cgacgatcag     660
gcgctgtgcg ccaatatctt ttcgctgtcg attacgggct cggacaccgt gcccctgtca     720
tcggcggcgg caatctatta tctgtcggag catccggcgc agctggaggc ggtgcgctcc     780
gaccgcgcgc tgattcccgc cgccttcgct gagaccgtgc gctacgatca gccgaccaat     840
gtactgggcc gactgcttgc cattgacacc gacaaatacg gcaagccgat gaaaaaaggt     900
caagcggtcc tgttcatgta tgcgtcggca accgtgacc cgctggaatt cgaacacccc      960
gacacgttca atatataccg cgatccccgg cgcaccctgt ccttcggctc cggcatccat    1020
atctgtctgg gccagcttct ggccaaactg gaaggtcaga tcattctgga acgctgtttt    1080
gagcatatcc cggactttac ggtccagtat aaggaggtgc ggcgcattcc cggcgaattt    1140
ctccagggt tcgggtcat gccgatccgc ttcccgctgc gaacctga              1188

<210> SEQ ID NO 12
<211> LENGTH: 395
<212> TYPE: PRT
<213> ORGANISM: Unknown
<220> FEATURE:
<223> OTHER INFORMATION: Obtained from an environmental sample

<400> SEQUENCE: 12

Met Thr Leu Lys Phe Asn Pro Tyr Cys Glu Glu Phe Tyr Gln Asn Pro
 1               5                  10                  15

Trp Gln Asn Phe Arg Ala Leu Arg Thr Gln Asp Pro Val His Tyr Ile
            20                  25                  30

Glu Glu Phe Asp Ala Trp Ala Leu Phe Gly Phe Glu Asp Val Trp Arg
        35                  40                  45

Ala Gly Met Asp Arg Glu Ser Phe Thr Ala Thr Tyr Gly Ser Ser Pro
    50                  55                  60

Gln Ala Leu Leu Ile Asp Arg Val Lys Gln Pro Glu Ile Phe Leu Phe
65                  70                  75                  80

Met Asp Ile Pro Asn His Met Ile His Arg Gly Ile Ile Ala Lys Asp
                85                  90                  95
```

```
Tyr Gly Arg Asn Ala Met Pro Leu Leu Glu Gly Lys Ile Arg Ala Thr
            100                 105                 110

Ala Lys Glu Ala Ile Thr Pro Tyr Leu Lys Ser Gly Glu Met Asp Val
        115                 120                 125

Tyr Ala Phe Ala Arg Thr Val Ala Leu Phe Thr Ile Ala Asp Met Ile
    130                 135                 140

Gly Leu Arg Pro Glu Glu Val Val Arg Ile Arg Ser Leu Ile Asp Ile
145                 150                 155                 160

Phe Phe Gly Arg Thr Pro Gly His Arg Gly Thr Thr Pro Asp Gly Val
                165                 170                 175

Ala Ala Phe His Glu Val Thr Ala Tyr Val Leu Asp Leu Ile Gly His
            180                 185                 190

Tyr Arg Ala Lys Gly Ala Pro Glu Gly Ser His Ile Asp Asn Trp Leu
        195                 200                 205

Lys Ala Glu Pro Asp Gly Arg Pro Leu Asp Asp Gln Ala Leu Cys Ala
    210                 215                 220

Asn Ile Phe Ser Leu Ser Ile Thr Gly Ser Asp Thr Val Pro Leu Ser
225                 230                 235                 240

Ser Ala Ala Ile Tyr Tyr Leu Ser Glu His Pro Ala Gln Leu Glu
                245                 250                 255

Ala Val Arg Ser Asp Arg Ala Leu Ile Pro Ala Ala Phe Ala Glu Thr
            260                 265                 270

Val Arg Tyr Asp Gln Pro Thr Asn Val Leu Gly Arg Leu Leu Ala Ile
        275                 280                 285

Asp Thr Asp Lys Tyr Gly Lys Pro Met Lys Lys Gly Gln Ala Val Leu
290                 295                 300

Phe Met Tyr Ala Ser Ala Asn Arg Asp Pro Leu Glu Phe Glu His Pro
305                 310                 315                 320

Asp Thr Phe Asn Ile Tyr Arg Asp Pro Arg Arg Thr Leu Ser Phe Gly
                325                 330                 335

Ser Gly Ile His Ile Cys Leu Gly Gln Leu Leu Ala Lys Leu Glu Gly
            340                 345                 350

Gln Ile Ile Leu Glu Thr Leu Phe Glu His Ile Pro Asp Phe Thr Val
        355                 360                 365

Gln Tyr Lys Glu Val Arg Arg Ile Pro Gly Glu Phe Leu Gln Gly Phe
    370                 375                 380

Gly Val Met Pro Ile Arg Phe Pro Leu Arg Thr
385                 390                 395

<210> SEQ ID NO 13
<211> LENGTH: 1191
<212> TYPE: DNA
<213> ORGANISM: Bacterial

<400> SEQUENCE: 13
atgagcgagt ccctccacac cgtcaccacg ctgccgaccg agcgtcagac cgggtgcccc     60
ttcgacccgc cggcggaact gatcgacgca cgccaacacg gtggcatcag ccggtgcacc    120
catcccggcg gcaagcccgg ctatctgatc accggttacg acctcgtccg atccgtactg    180
gccgatcccc ggttcagctc gcgcaaggac ctcctgaacg tcgtcgactt cgagctcccg    240
cccgcccctc cgggcgagtt cctcctcatg gacgagcccc agcattcgcg ctaccggaag    300
ccgctcgtcg gcaagttcac cgtgcggcgc atgcgactgc tcaccgaacg catcgagcag    360
atcaccacgg aatgcctgga cgccatggag gaggccgggc cgtcggcgga cctcgtggcc    420
```

```
gcgttcgcca agccgatccc caccatcgtc atctgcgagc tgctgggcgt tccgtacgag      480
gaccgtgcct cgttccagga gcagatcgac acgttcatga gcggcgagac gagcgacgag      540
gacctcatcg cggcgtacac cgccacccag acctacctcg ccgagctggt ggccgccaag      600
cgcgcgaaac ccaccgacga cgtgctgagc gaactgaccg acagcgacct caccgacgag      660
gaactgcagg gcatcagcct gatcctgctc gcggccggct cgacacgac cgcgaacatg       720 ctctccctcg gtaccttcgc ccttctgcag cacccggccc aactggccgc gctgcaggcc      780
gaccccggcc tcatcgacca ggccgtcgaa gagctgctgc ggtacctcag cgtcgcgaag      840
acgttcatgc ggaccgcgct cgtcgacgtc gaggtcggcg ccacaccgt cgaggcgggc       900 acgaccgtcg tcctgtcgta cagcacggcc aaccgcgacc ccgagcgctt cgacgacccc      960
cacgtgctcg acgtgcaccg gaagcagggc gggcacctgg ccttcggcca cggcatccac     1020
ctgtgcctgg tcagcaact cgcccgcgtc gagatgcgga tcgcgatcgc cgcgctgctc       1080
gaccgcttcc ccacgctgcg cctcgccgtc ccgccgagg aggtcgccct gcggcccgag       1140
accgcggaca tctacggggt gaagagcctt cccgtcacct gggacgtatg a               1191
```

<210> SEQ ID NO 14
<211> LENGTH: 396
<212> TYPE: PRT
<213> ORGANISM: Bacterial

<400> SEQUENCE: 14

```
Met Ser Glu Ser Leu His Thr Val Thr Thr Leu Pro Thr Glu Arg Gln
1               5                   10                  15

Thr Gly Cys Pro Phe Asp Pro Pro Ala Glu Leu Ile Asp Ala Arg Gln
                20                  25                  30

His Gly Gly Ile Ser Arg Cys Thr His Pro Gly Gly Lys Pro Gly Tyr
            35                  40                  45

Leu Ile Thr Gly Tyr Asp Leu Val Arg Ser Val Leu Ala Asp Pro Arg
        50                  55                  60

Phe Ser Ser Arg Lys Asp Leu Leu Asn Val Val Asp Phe Glu Leu Pro
65                  70                  75                  80

Pro Ala Pro Pro Gly Glu Phe Leu Leu Met Asp Glu Pro Gln His Ser
                85                  90                  95

Arg Tyr Arg Lys Pro Leu Val Gly Lys Phe Thr Val Arg Arg Met Arg
            100                 105                 110

Leu Leu Thr Glu Arg Ile Glu Gln Ile Thr Thr Glu Cys Leu Asp Ala
        115                 120                 125

Met Glu Glu Ala Gly Pro Ser Ala Asp Leu Val Ala Ala Phe Ala Lys
    130                 135                 140

Pro Ile Pro Thr Ile Val Ile Cys Glu Leu Leu Gly Val Pro Tyr Glu
145                 150                 155                 160

Asp Arg Ala Ser Phe Gln Glu Gln Ile Asp Thr Phe Met Ser Gly Glu
                165                 170                 175

Thr Ser Asp Glu Asp Leu Ile Ala Ala Tyr Thr Ala Thr Gln Thr Tyr
            180                 185                 190

Leu Ala Glu Leu Val Ala Ala Lys Arg Ala Lys Pro Thr Asp Asp Val
        195                 200                 205

Leu Ser Glu Leu Thr Asp Ser Asp Leu Thr Asp Glu Leu Gln Gly
        210                 215                 220

Ile Ser Leu Ile Leu Leu Ala Ala Gly Phe Asp Thr Thr Ala Asn Met
225                 230                 235                 240
```

```
Leu Ser Leu Gly Thr Phe Ala Leu Leu Gln His Pro Ala Gln Leu Ala
                245                 250                 255
Ala Leu Gln Ala Asp Pro Gly Leu Ile Asp Gln Ala Val Glu Glu Leu
            260                 265                 270
Leu Arg Tyr Leu Ser Val Ala Lys Thr Phe Met Arg Thr Ala Leu Val
        275                 280                 285
Asp Val Glu Val Gly Gly His Thr Val Glu Ala Gly Thr Thr Val Val
    290                 295                 300
Leu Ser Tyr Ser Thr Ala Asn Arg Asp Pro Glu Arg Phe Asp Asp Pro
305                 310                 315                 320
His Val Leu Asp Val His Arg Lys Gln Gly Gly His Leu Ala Phe Gly
                325                 330                 335
His Gly Ile His Leu Cys Leu Gly Gln Gln Leu Ala Arg Val Glu Met
                340                 345                 350
Arg Ile Ala Ile Ala Ala Leu Leu Asp Arg Phe Pro Thr Leu Arg Leu
            355                 360                 365
Ala Val Pro Ala Glu Glu Val Ala Leu Arg Pro Glu Thr Ala Asp Ile
        370                 375                 380
Tyr Gly Val Lys Ser Leu Pro Val Thr Trp Asp Val
385                 390                 395
```

<210> SEQ ID NO 15
<211> LENGTH: 1215
<212> TYPE: DNA
<213> ORGANISM: Bacterial

<400> SEQUENCE: 15

```
gtggccgctt ccgccgccgc cccgccggcg gcccgcacct gggcggtgga cgacctgccc      60
gccctcgcct tcgacccgct gctcaccgaa ctcctggaga aggagcccgt cgcccgcatc     120
aggctgccgt tcgccgcgcg gaacgaggcc tggctggtga cgcggtacga ggacgtgcgc     180
gcggtgacct ccgaccccg gttcagccgg acggcgctgc tcgaccagca ggtcaccaag     240
atgaccggcc acatggtggc ctcgaaggcg cccctcaact acgccgatcc gccgtaccac     300
acccagctgc gcaaggcggt gaccaaggcg ttcaccgggc agagcaccag gcggctgcgt     360
ccgcttgccc aggcgggcac cgaccggctc ctggacgcga tggaggcggc gggccgcccc     420
gccgacctga tgaagcatct gcacggcccg ctgccgatgg cggtggtgtg cgatctgctc     480
ggcatcccgg aggaggaccg ggcggagctg gcctcctggc cggacctgat cctgtcctcg     540
ggccccggcc cggagagcag caaggcggcc aaggcccaga tccacggcta cgtcatccgg     600
ctgctcgacc ggcggcgcgc ggagcccag gacgatctgg cgggcgtgct cgcggagtcc     660
ctcgccgagg ggcggatcac cgccgaggag gccgtctccc tggcgatggc gatcctgatc     720
agcggcgcgc acgcggtacg gaacaacagc gccaacatgg tgtacgtgct gctcacccgg     780
ccggagctcg cggaccggct gcgcgccgag cccggactgc tcccgcaggc cgtggacgag     840
ctgctgcgct ggatcccgca ccgcaacggc gtcgggctgc ccggatcgc acgaggac      900
gtcgaggtcg gcggggtgct gatccgggcg ggtgaggcgg tctacgcctc ctacctcgcg     960
gccaaccggg acccgcggc cttcgaggac cggaccgcc tcgacttcga ccggagggc     1020
atcgggcacg tgtcgttcgg tcacggcccg caccactgca tgggcgcgat gctcacccgc     1080
atggagtccg aggtgatgct gtcgacgctg ctcgaccgct atccgcggct gcggctcgcg     1140
gggagcgccg aggacgtggt gtggcagtcg aaggggctca tccgcggccc gaaggaactc     1200
```

```
ctcgtgacct ggtga                                              1215
```

<210> SEQ ID NO 16
<211> LENGTH: 404
<212> TYPE: PRT
<213> ORGANISM: Bacterial

<400> SEQUENCE: 16

```
Met Ala Ser Ala Ala Pro Pro Ala Ala Arg Thr Trp Ala Val
 1               5                  10                  15

Asp Asp Leu Pro Ala Leu Ala Phe Asp Pro Leu Leu Thr Glu Leu Leu
                20                  25                  30

Glu Lys Glu Pro Val Ala Arg Ile Arg Leu Pro Phe Ala Ala Arg Asn
            35                  40                  45

Glu Ala Trp Leu Val Thr Arg Tyr Glu Asp Val Arg Ala Val Thr Ser
    50                  55                  60

Asp Pro Arg Phe Ser Arg Thr Ala Leu Leu Asp Gln Gln Val Thr Lys
65                  70                  75                  80

Met Thr Gly His Met Val Ala Ser Lys Ala Ala Leu Asn Tyr Ala Asp
                85                  90                  95

Pro Pro Tyr His Thr Gln Leu Arg Lys Ala Val Thr Lys Ala Phe Thr
            100                 105                 110

Gly Gln Ser Thr Arg Arg Leu Arg Pro Leu Ala Gln Ala Gly Thr Asp
        115                 120                 125

Arg Leu Leu Asp Ala Met Glu Ala Ala Gly Arg Pro Ala Asp Leu Met
130                 135                 140

Lys His Leu His Gly Pro Leu Pro Met Ala Val Val Cys Asp Leu Leu
145                 150                 155                 160

Gly Ile Pro Glu Glu Asp Arg Ala Glu Leu Ala Ser Trp Pro Asp Leu
                165                 170                 175

Ile Leu Ser Ser Gly Pro Gly Pro Glu Ser Ser Lys Ala Ala Lys Ala
            180                 185                 190

Gln Ile His Gly Tyr Val Ile Arg Leu Leu Asp Arg Arg Ala Glu
        195                 200                 205

Pro Gln Asp Asp Leu Ala Gly Val Leu Ala Glu Ser Leu Ala Glu Gly
210                 215                 220

Arg Ile Thr Ala Glu Glu Ala Val Ser Leu Ala Met Ala Ile Leu Ile
225                 230                 235                 240

Ser Gly Ala His Ala Val Arg Asn Asn Ser Ala Asn Met Val Tyr Val
                245                 250                 255

Leu Leu Thr Arg Pro Glu Leu Ala Asp Arg Leu Arg Ala Glu Pro Gly
            260                 265                 270

Leu Leu Pro Gln Ala Val Asp Glu Leu Leu Arg Trp Ile Pro His Arg
        275                 280                 285

Asn Gly Val Gly Leu Pro Arg Ile Ala Thr Glu Asp Val Glu Val Gly
    290                 295                 300

Gly Val Leu Ile Arg Ala Gly Glu Ala Val Tyr Ala Ser Tyr Leu Ala
305                 310                 315                 320

Ala Asn Arg Asp Pro Ala Ala Phe Glu Asp Pro Asp Arg Leu Asp Phe
                325                 330                 335

Asp Arg Glu Gly Ile Gly His Val Ser Phe Gly His Gly Pro His His
            340                 345                 350

Cys Met Gly Ala Met Leu Thr Arg Met Glu Ser Glu Val Met Leu Ser
        355                 360                 365
```

| Thr | Leu | Leu | Asp | Arg | Tyr | Pro | Arg | Leu | Arg | Leu | Ala | Gly | Ser | Ala | Glu |
| --- | --- | --- | --- | --- | --- | --- | --- | --- | --- | --- | --- | --- | --- | --- | --- |
| | 370 | | | | 375 | | | | 380 | | | | | | |

| Asp | Val | Val | Trp | Gln | Ser | Lys | Gly | Leu | Ile | Arg | Gly | Pro | Lys | Glu | Leu |
| --- | --- | --- | --- | --- | --- | --- | --- | --- | --- | --- | --- | --- | --- | --- | --- |
| 385 | | | | | 390 | | | | | 395 | | | | | 400 |

| Leu | Val | Thr | Trp |
| --- | --- | --- | --- |

<210> SEQ ID NO 17
<211> LENGTH: 1266
<212> TYPE: DNA
<213> ORGANISM: Bacterial

<400> SEQUENCE: 17

```
atggccgcct gccccatct ccccgaaggg caccttcccg aggggttcga cgccaccgac      60
cccgacctgc tgcgcgaacg cgtccccttc ccggagttca cccggctgcg cagaccgca    120
ccggtgtggt ggtgcccgca gccgcccggc gtcaccggct cgcggacgg cgggtactgg    180
gccgtcacgc gccacgccga cgtcaagtac gtctccaccc accccgagct gttctcctcg    240
aacgagaaca ccgccgtcat ccgcttcaac gagcacatca cccgggacca gatcgaggtc    300
cagaagctga tcatgctcaa catggacccg cccgagcaca cccgggtccg ccagatcgtc    360
cagcgcggct tcaccccccg cgcgatccgc agcctggaaa ccgccctgcg cgaccgggcc    420
cacgccatcg tcgacgaggc ccggcgcggc gggacgccg acggcacctt cgacttcgtc    480
acccgggtcg ccgtcgaact gccccctccag gccatcgccg aactcatcgg cgtccccag    540
gaggaccgct cccggatctt cgactggtcg aacaagatgg tcgcgtacga cgaccccgaa    600
tacgccatca ccgaggagat cggcgccgag ccgccatgg aactcatcgg ctactcgatg    660
aacatggccg ccgcccgcaa ggagtgcccc gccgccgaca tcgtcagcca gctcgtcgcc    720
gccgagggcc agggcaacct ctcctccgac gagttcggct tcttcgtgct gctgctcgcc    780
gtcgccggga acgagaccac ccgcaacgcc atcagccacg gcatgcacgc cttcctcacc    840
caccccgacg agtgggagct cttcaagcgc gagcggcccg cgaccgccgc cgaggagatc    900
gtccgctggg ccacccccgt cgtctccttc agcggaccg cgacccagga caccgaactc    960
ggcggacaga agatcaccaa gggcgaccgc gtcggcctct ctactcctc cgccaacaac   1020
gaccccgagg tcttcaccga ccccgaacgc ttcgacatca cccgcgaccc caaccccac   1080
ctcggcttcg gcggcggcgg cccccacttc tgcctcggca gtccctcgc catcaaggag   1140
atcgagctga tcttcaacgc gatcgcggac gccctgcccg acctcaccct cgcgggcgaa   1200
ccgcgccgac tgcgggccgc ctggctgaac ggcgtcaagg aactccgggt ccgcgcctcc   1260
gcgtga                                                              1266
```

<210> SEQ ID NO 18
<211> LENGTH: 421
<212> TYPE: PRT
<213> ORGANISM: Bacterial

<400> SEQUENCE: 18

| Met | Ala | Ala | Cys | Pro | His | Leu | Pro | Glu | Gly | His | Leu | Pro | Glu | Gly | Phe |
| --- | --- | --- | --- | --- | --- | --- | --- | --- | --- | --- | --- | --- | --- | --- | --- |
| 1 | | | | 5 | | | | | 10 | | | | | 15 | |

| Asp | Ala | Thr | Asp | Pro | Asp | Leu | Leu | Arg | Glu | Arg | Val | Pro | Phe | Pro | Glu |
| --- | --- | --- | --- | --- | --- | --- | --- | --- | --- | --- | --- | --- | --- | --- | --- |
| | | | 20 | | | | | 25 | | | | | 30 | | |

| Phe | Thr | Arg | Leu | Arg | Gln | Thr | Ala | Pro | Val | Trp | Trp | Cys | Pro | Gln | Pro |
| --- | --- | --- | --- | --- | --- | --- | --- | --- | --- | --- | --- | --- | --- | --- | --- |
| | | | | 35 | | | | | 40 | | | | 45 | | |

| Pro | Gly | Val | Thr | Gly | Phe | Ala | Asp | Gly | Gly | Tyr | Trp | Ala | Val | Thr | Arg |
| --- | --- | --- | --- | --- | --- | --- | --- | --- | --- | --- | --- | --- | --- | --- | --- |
| | 50 | | | | | 55 | | | | | 60 | | | | |

```
His Ala Asp Val Lys Tyr Val Ser Thr His Pro Glu Leu Phe Ser Ser
 65                  70                  75                  80

Asn Glu Asn Thr Ala Val Ile Arg Phe Asn Glu His Ile Thr Arg Asp
                 85                  90                  95

Gln Ile Glu Val Gln Lys Leu Ile Met Leu Asn Met Asp Pro Pro Glu
            100                 105                 110

His Thr Arg Val Arg Gln Ile Val Gln Arg Gly Phe Thr Pro Arg Ala
        115                 120                 125

Ile Arg Ser Leu Glu Thr Ala Leu Arg Asp Arg Ala His Ala Ile Val
    130                 135                 140

Asp Glu Ala Arg Arg Gly Ala Asp Ala Asp Gly Thr Phe Asp Phe Val
145                 150                 155                 160

Thr Arg Val Ala Val Glu Leu Pro Leu Gln Ala Ile Ala Glu Leu Ile
                165                 170                 175

Gly Val Pro Gln Glu Asp Arg Ser Arg Ile Phe Asp Trp Ser Asn Lys
            180                 185                 190

Met Val Ala Tyr Asp Asp Pro Glu Tyr Ala Ile Thr Glu Glu Ile Gly
        195                 200                 205

Ala Glu Ala Ala Met Glu Leu Ile Gly Tyr Ser Met Asn Met Ala Ala
    210                 215                 220

Ala Arg Lys Glu Cys Pro Ala Ala Asp Ile Val Ser Gln Leu Val Ala
225                 230                 235                 240

Ala Glu Gly Gln Gly Asn Leu Ser Ser Asp Glu Phe Gly Phe Phe Val
                245                 250                 255

Leu Leu Leu Ala Val Ala Gly Asn Glu Thr Thr Arg Asn Ala Ile Ser
            260                 265                 270

His Gly Met His Ala Phe Leu Thr His Pro Asp Glu Trp Glu Leu Phe
        275                 280                 285

Lys Arg Glu Arg Pro Ala Thr Ala Ala Glu Ile Val Arg Trp Ala
    290                 295                 300

Thr Pro Val Val Ser Phe Gln Arg Thr Ala Thr Gln Asp Thr Glu Leu
305                 310                 315                 320

Gly Gly Gln Lys Ile Thr Lys Gly Asp Arg Val Gly Leu Phe Tyr Ser
                325                 330                 335

Ser Ala Asn Asn Asp Pro Glu Val Phe Thr Asp Pro Glu Arg Phe Asp
            340                 345                 350

Ile Thr Arg Asp Pro Asn Pro His Leu Gly Phe Gly Gly Gly Pro
        355                 360                 365

His Phe Cys Leu Gly Lys Ser Leu Ala Ile Lys Glu Ile Glu Leu Ile
    370                 375                 380

Phe Asn Ala Ile Ala Asp Ala Leu Pro Asp Leu Thr Leu Ala Gly Glu
385                 390                 395                 400

Pro Arg Arg Leu Arg Ala Ala Trp Leu Asn Gly Val Lys Glu Leu Arg
                405                 410                 415

Val Arg Ala Ser Ala
            420

<210> SEQ ID NO 19
<211> LENGTH: 1278
<212> TYPE: DNA
<213> ORGANISM: Bacterial

<400> SEQUENCE: 19
gtgagcacca cccccgaacc cgcctcctgc cccgtgtcgt ccccgctcc cgagctcttc      60
```

-continued

```
acctgggagt tcgcgagcga tccgtatccc gcgtacgcct ggctgcggga gcacgcgccc    120
gtgcaccgga cgacgctgcc cagcggggtc gaggcgtggc tggtgacgcg gtacggggac    180
gcccggcagg cgctggccga ccagcggctc tccaagaacc cggcgcacca cgacgagtcc    240
ccgcacgcca agggcaagac gggcattccg ggcgagcgca aggccgagct gatgacgcat    300
ctgctcaaca tcgacccgcc ggaccacacc cggctgcggc ggctcgtctc gaaggccttc    360
accccgcgcc gggtcgccga gttcacgccg cgggtgcagg agctgaccga ccggctgatc    420
gacgccttcg tgacgaaggg gagcgcggac ctcatccacg acttcgcctt cccgctgccc    480
atctacgcga tctgcgacct gctcggcgtg cccgaggagg accaggacga cttccgggac    540
tgggccggga tgatgatccg gcacggcggc gggccgcgcg gcggggtcgc gcggtcggtg    600
aagaagatgc gcggctatct cgccgagctg atccaccgca agcgcgaagc gcccggggac    660
gacctcatct cggggctcat caaggcctcc gaccacgggg agcacctcac cgagaacgag    720
gcggccgcca tggccttcat cctgctcttc gccggcttcg agaccaccgt caacctcatc    780
ggcaacggcg tgtaccagct gctgcgccac cccgggcagc gcgagcggct gcagacctcg    840
ctcgcggccg gcgagaccgg gctcctggag accgggatcg aggagctgct gcggtacgac    900
gggccggtgg agatggccac ctggcggtac gcgaccgagc cgctgaccct cggcgggcag    960
gacatcccgg cgggcgaccc ggtgctcgtg gtcctcgcgg ccgccgaccg ggaccccggag   1020
cggttcgacc ggccggacgt gctcgacctc gcccggcgcg acaaccagca cctggggtac   1080
gggcacggca tccactactg cctgggcgcg ccgctcgcgc ggctcgaagg gcagaccgcg   1140
ctcgcgaccc tgctgactcg gcttccggac ctgcgacttg ccgccgatcc ggccgaactg   1200
cggtggcgcg gcgggctcat catgcggggt ttgcgcacgc ttccggtgga gttctcccct   1260
tccgtacggg tccactga                                                 1278
```

<210> SEQ ID NO 20
<211> LENGTH: 425
<212> TYPE: PRT
<213> ORGANISM: Bacterial

<400> SEQUENCE: 20

```
Met Ser Thr Thr Pro Glu Pro Ala Ser Cys Pro Val Ser Ser Pro Ala
 1               5                  10                  15

Pro Glu Leu Phe Thr Trp Glu Phe Ala Ser Asp Pro Tyr Pro Ala Tyr
            20                  25                  30

Ala Trp Leu Arg Glu His Ala Pro Val His Arg Thr Thr Leu Pro Ser
        35                  40                  45

Gly Val Glu Ala Trp Leu Val Thr Arg Tyr Gly Asp Ala Arg Gln Ala
    50                  55                  60

Leu Ala Asp Gln Arg Leu Ser Lys Asn Pro Ala His His Asp Glu Ser
65                  70                  75                  80

Pro His Ala Lys Gly Lys Thr Gly Ile Pro Gly Glu Arg Lys Ala Glu
                85                  90                  95

Leu Met Thr His Leu Leu Asn Ile Asp Pro Pro Asp His Thr Arg Leu
            100                 105                 110

Arg Arg Leu Val Ser Lys Ala Phe Thr Pro Arg Val Ala Glu Phe
        115                 120                 125

Thr Pro Arg Val Gln Glu Leu Thr Asp Arg Leu Ile Asp Ala Phe Val
    130                 135                 140

Thr Lys Gly Ser Ala Asp Leu Ile His Asp Phe Ala Phe Pro Leu Pro
```

-continued

```
            145                 150                 155                 160
        Ile Tyr Ala Ile Cys Asp Leu Leu Gly Val Pro Glu Glu Asp Gln Asp
                        165                 170                 175
        Asp Phe Arg Asp Trp Ala Gly Met Met Ile Arg His Gly Gly Gly Pro
                    180                 185                 190
        Arg Gly Gly Val Ala Arg Ser Val Lys Lys Met Arg Gly Tyr Leu Ala
                    195                 200                 205
        Glu Leu Ile His Arg Lys Arg Glu Ala Pro Gly Asp Asp Leu Ile Ser
                210                 215                 220
        Gly Leu Ile Lys Ala Ser Asp His Gly Glu His Leu Thr Glu Asn Glu
        225                 230                 235                 240
        Ala Ala Ala Met Ala Phe Ile Leu Leu Phe Ala Gly Phe Glu Thr Thr
                        245                 250                 255
        Val Asn Leu Ile Gly Asn Gly Val Tyr Gln Leu Leu Arg His Pro Gly
                        260                 265                 270
        Gln Arg Glu Arg Leu Gln Thr Ser Leu Ala Ala Gly Thr Gly Leu
                    275                 280                 285
        Leu Glu Thr Gly Ile Glu Glu Leu Leu Arg Tyr Asp Gly Pro Val Glu
                    290                 295                 300
        Met Ala Thr Trp Arg Tyr Ala Thr Glu Pro Leu Thr Leu Gly Gly Gln
        305                 310                 315                 320
        Asp Ile Pro Ala Gly Asp Pro Val Leu Val Val Leu Ala Ala Ala Asp
                        325                 330                 335
        Arg Asp Pro Glu Arg Phe Asp Arg Pro Asp Val Leu Asp Leu Ala Arg
                    340                 345                 350
        Arg Asp Asn Gln His Leu Gly Tyr Gly His Gly Ile His Tyr Cys Leu
                    355                 360                 365
        Gly Ala Pro Leu Ala Arg Leu Glu Gly Gln Thr Ala Leu Ala Thr Leu
                370                 375                 380
        Leu Thr Arg Leu Pro Asp Leu Arg Leu Ala Ala Asp Pro Ala Glu Leu
        385                 390                 395                 400
        Arg Trp Arg Gly Gly Leu Ile Met Arg Gly Leu Arg Thr Leu Pro Val
                        405                 410                 415
        Glu Phe Ser Pro Ser Val Arg Val His
                    420                 425

<210> SEQ ID NO 21
<211> LENGTH: 1257
<212> TYPE: DNA
<213> ORGANISM: Unknown
<220> FEATURE:
<223> OTHER INFORMATION: Obtained from an environmental sample

<400> SEQUENCE: 21
atgtacacca ttcccccctac gccacagttc gacaacgaac ttgtcgatcc ggcgacctgg      60
gccgacgagg ccagaatcca tgcctacctg gcctggctgc gggagcacga cccggtgcgc     120
cggctcgagc ctgagggcta cgagcccttc tacgccatca cgaagcatgc cgacctgatg     180
gccatcgaac gcgacaagca ggtgttcatc aacgacccgc gcctacccct ggcgccggaa     240
gcggtcaccg cggcgatcga gcaactcacc gggcgccggc acctggtccg gtcgctggtg     300
cagatggacg agccggacca catgaagtac cggatgctcc ccgcgtcctt cttcacccgt     360
cagaagctcg cggcgatgaa gccggaggtg gagcgtctcg cggcgcacta tgtggatcgg     420
atggcggagt tcggcggcga atgcgacttc gttcgggacg tggcggtctg gtacccgctg     480
```

-continued

| | |
|---|---|
| cgggtggtga tgagtgcgct cggcgttccg ccggaggacg agccgctgat gatgaagctg | 540 |
| acccaggagt tgttcggatc cagcgacccc gaggtccagc ggtccttcga catcatggcg | 600 |
| atcggcgacg tggtacggga cttcgaggcg tacttcaccg gcatctcgga agatcgccgg | 660 |
| cgcaatcccc gtgacgacat cgccacgctc attgcccacg ccaaaatcga cggggaaccc | 720 |
| attggtgacc tggaggcggc aggctattac atcatcatcg ccaccgccgg ccacgacacc | 780 |
| acctcctcga gtacggccgg cgggctgctc gcgctgatgg agaaccccga ggagttccag | 840 |
| aaactgcgcg cgacacgga tcggcatgtg gccggcgcgg tcgacgaaat gattcgctgg | 900 |
| gtatccccag tgcgtcactt catgcgcacc gccaccgagg actacgcaat ccgcggcaag | 960 |
| accatcgcca gggcgaatc ggtgatcctg tggtatccgt cggcgaaccg cgatgccgag | 1020 |
| gtgttcaacg acccgttcgc gttccgcgtc gagcggccgg cggcgcgcaa tttgccttc | 1080 |
| ggctacggcg ctcacgtctg tctcggtcaa catctggcgc ggatggaaat gcagacgttc | 1140 |
| taccgcgaac tgctgtcgcg ggtggggcac gtagagctgg cggcgagcc ccgctacgcc | 1200 |
| caggctgcct tcgtcggcgg actcaagagc ctgccgattc gctaccgcat gaagtga | 1257 |

<210> SEQ ID NO 22
<211> LENGTH: 418
<212> TYPE: PRT
<213> ORGANISM: Unknown
<220> FEATURE:
<223> OTHER INFORMATION: Obtained from an environmental sample

<400> SEQUENCE: 22

Met Tyr Thr Ile Pro Pro Thr Pro Gln Phe Asp Asn Glu Leu Val Asp
1               5                   10                  15

Pro Ala Thr Trp Ala Asp Glu Ala Arg Ile His Ala Tyr Leu Ala Trp
            20                  25                  30

Leu Arg Glu His Asp Pro Val Arg Arg Leu Glu Pro Glu Gly Tyr Glu
        35                  40                  45

Pro Phe Tyr Ala Ile Thr Lys His Ala Asp Leu Met Ala Ile Glu Arg
    50                  55                  60

Asp Lys Gln Val Phe Ile Asn Asp Pro Arg Thr Leu Ala Pro Glu
65                  70                  75                  80

Ala Val Thr Ala Ala Ile Glu Gln Leu Thr Gly Arg Arg His Leu Val
                85                  90                  95

Arg Ser Leu Val Gln Met Asp Glu Pro Asp His Met Lys Tyr Arg Met
            100                 105                 110

Leu Thr Ala Ser Phe Phe Thr Arg Gln Lys Leu Ala Ala Met Lys Pro
        115                 120                 125

Glu Val Glu Arg Leu Ala Ala His Tyr Val Asp Arg Met Ala Glu Phe
    130                 135                 140

Gly Gly Glu Cys Asp Phe Val Arg Asp Val Ala Val Trp Tyr Pro Leu
145                 150                 155                 160

Arg Val Val Met Ser Ala Leu Gly Val Pro Pro Glu Asp Glu Pro Leu
                165                 170                 175

Met Met Lys Leu Thr Gln Glu Leu Phe Gly Ser Ser Asp Pro Glu Val
            180                 185                 190

Gln Arg Ser Phe Asp Ile Met Ala Ile Gly Asp Val Val Arg Asp Phe
        195                 200                 205

Glu Ala Tyr Phe Thr Gly Ile Ser Glu Asp Arg Arg Arg Asn Pro Arg
    210                 215                 220

Asp Asp Ile Ala Thr Leu Ile Ala His Ala Lys Ile Asp Gly Glu Pro

-continued

```
                225                 230                 235                 240
Ile Gly Asp Leu Glu Ala Ala Gly Tyr Tyr Ile Ile Ala Thr Ala
                    245                 250                 255
Gly His Asp Thr Thr Ser Ser Thr Ala Gly Gly Leu Leu Ala Leu
                260                 265                 270
Met Glu Asn Pro Glu Glu Phe Gln Lys Leu Arg Gly Asp Thr Asp Arg
                275                 280                 285
His Val Ala Gly Ala Val Asp Glu Met Ile Arg Trp Val Ser Pro Val
            290                 295                 300
Arg His Phe Met Arg Thr Ala Thr Glu Asp Tyr Ala Ile Arg Gly Lys
305                 310                 315                 320
Thr Ile Ala Lys Gly Glu Ser Val Ile Leu Trp Tyr Pro Ser Ala Asn
                    325                 330                 335
Arg Asp Ala Glu Val Phe Asn Asp Pro Phe Ala Phe Arg Val Glu Arg
                340                 345                 350
Pro Ala Ala Arg Asn Leu Ala Phe Gly Tyr Gly Ala His Val Cys Leu
                355                 360                 365
Gly Gln His Leu Ala Arg Met Glu Met Gln Thr Phe Tyr Arg Glu Leu
            370                 375                 380
Leu Ser Arg Val Gly His Val Glu Leu Ala Gly Glu Pro Arg Tyr Ala
385                 390                 395                 400
Gln Ala Ala Phe Val Gly Gly Leu Lys Ser Leu Pro Ile Arg Tyr Arg
                    405                 410                 415
Met Lys
```

<210> SEQ ID NO 23
<211> LENGTH: 3234
<212> TYPE: DNA
<213> ORGANISM: Unknown
<220> FEATURE:
<223> OTHER INFORMATION: Obtained from an environmental sample

<400> SEQUENCE: 23

```
atggcgtcca ccaacagatt gagcccgatc ccgcatccgc cgactaaacc ggtggtcggc    60
aacatgctgt cgctggactc gacggcgccg gtgcagaacc tggcacggct ggcgaaggaa   120
ctggggccga tcttctggtt ggacatgatg ggggcgccga tcgtcatcgt ctccggccac   180
gatctcgtgg aagagctcag cgacgagaaa cgtttcgaca aggcggtacg cggggcgctg   240
cgccgcgtac gtgcggtcgg cggcgacggg ctgttcaccg ccgatacgtc ggagccgaac   300
tggagcaagg cgcataacat cctgctgcag ccgttcggca accgcgccat gcagtcctac   360
cacccgagca tggtcgatat cgccgaacag ctcgtgaaga atgggagcg gctgaacgtc   420
gacgacgaga tcgacgtcgt tcatgatatg accgcattga cgctcgacac catcggactg   480
tgcgggttcg attaccgctt caattcattt taccggcgtg attaccatcc gttcgtcgcg   540
tcgttggtcc gttcgctcga aaccatcatg atgatccgcg gcctgccgtt ggaaaatctg   600
tggatgcaga agcgtcggcg cgacctcgcc gccgacgttg gcttcatgaa caaaatggtc   660
gacgagatca ttgccgagcg gcgcaggagc gctgaagccg agggcaagaa agacatgctc   720
ggcgcaatga tgaccggcgt cgaccgcacc accggtgaac agcttgatga cgtcaacatc   780
cgctatcaga tcaacacgtt tctgatcgcg gggcatgaaa ccaccagcgg cctgttgtcg   840
tgcacgctgt atgcgttgtt gaagcatcct gaaattctca ggaaggccta cgaggaagtc   900
gaccgggtgc tcgggcccga tatcaacgcc aggccgacct atcagcaggt gacacagctc   960
```

-continued

```
acgtacatca cgcagattct gaaggaggcg ctgcggttgt ggccgccggc gccggcctat    1020
ggcatctcgc cgctcaagga cgagaccatc ggcggcaagt acaaattaaa gaagaacacg    1080
ttcatcaccg tattggtgct ggcactgcac cgcgatcgca cgtgtgggg atccaatccc     1140 gatgcgttcg atccggaaaa tttcagccgc gaggccgagg cggcgcggcc catcaacgcc    1200
tggaagccgt tcggcaacgg tcagcgcgcc tgcatcggcc gtggctttgc gatgcatgaa    1260
gcggcgcttg cgatcggtat gatcctgcaa cgcttcaagc tggtcgacgt caaccgttac    1320
cagatggtgt tgaaggagac gctgacgatc aagcctgacg gcttcaagat caaggtgcgg    1380
ccgcgggccg aacgggatcg cggcgcttac ggcggcgcgg catctgtagc gatggccccg    1440
aacacgccga cggcgcccca cgagcgaacg cgtctggggc acaacacgcc gctgttggtg    1500
ctttatggat cgaacctcgg caccgcggaa gaactcgcga cccgcgttgc cgatctcgcc    1560
gaagtcaacg gctttgccac caaactggcg ccgctcgatg atttcgtcgg caagctgccg    1620
gagcaaggcg gcgttctgat tttctgtgcg tcctacaatg gtgtaccgcc cgacaacgcc    1680
acgcagttcg tcaaatggct tggcggcgat atcccaaagg atagttttgc caaggtgcgt    1740
tacgcggtgt tcggctgcgg caacagcgac tgggccgcga cctatcagtc agtgccgcgc    1800
ctgatcgacg agcaattggc ggcgcacggc gcgcgcagcg tttatacgcg aggcgagggc    1860
gacgcccgca gcgatcttga cgggcaattc gagagctggt ttgcagccgc agctccggcg    1920
gcaaccaggg agtttggtct cgagtcgaat tcagccgca gcgctgatga tgcgccgctc     1980
tacacgatcg aaccggtggc accatcagtg gtcaatacga tcgtcaccca gggcggcgtc    2040
ttgccgatga aggtagtggc caactccgaa ctgcaaaaca agctgggcac caatccctct    2100
gatcgttcga cccggcatgt cgaggtgcag ctacctccag gcatcagcta tcgtgtcggc    2160
gatcatctca gcgtcgtgcc gcgcaatgat ccggcgctgg tcgatgccgt cgcgcgccgc    2220
ttcggctttc tgccggccga ccagatccgg ttgcaggtcg ccgaaggccg ccgtgcgcaa    2280
ctgccggtcg gcgacgccgt tcggtcgggg cggctgttga ccgagttcgt cgagttgcag    2340
caggtcgcga cccgcaagca aatccagatc ttgtcggaac acacgcgttg tccgatgacc    2400
aagcccaaac tggtgggcct ggccggagac gacgcagctt ccgcggaacg ctaccgcgcc    2460
gaggtgctcg gcaagcgcaa atcggtgttc gacctgctgg aggaacatcc ggcctgcgaa    2520
ttgccgttcc acgcgtttct ggaaatgctg tcgctgctgg cgccgcgcta ttattcgatc    2580
tcgtcgtcgc cggcgggcga gcccgcgcgt tgcagcgtta ccgcggccgt ggtcgcatcg    2640
cctgcgagtt cgggacgcgg tatctaccgg ggcgtctgtt cgaactatct tgccgggcgc    2700
cgcgcaggtg acaccatcca cgccaccgtg cgcgaaacca aggccggctt ccggctgccg    2760
aatgatccgt ccgtgccgat catcatgatc ggccccggca cgggtctggc gccgtttcgt    2820
ggtttcctgc aggagcgtgc cgcgttgcag gcaaagggcg ctacgcttgg tccggcgatg    2880 ctgttttttcg gctgccgtca ccccgaacag gattatctct atgccgatga actaaaggcg    2940
ttcgccgccg acgggattac cgagttgcac accgcgttct cgcgcggcga cggaccgaag    3000
acgtatgtgc agcatctgat cgtggccgag aaggatcggg tctgcagcct gatcgagcaa    3060
ggcgcgatca tctacgtttg tggcgacggc ggacggatgg aaccggacgt gaaagccacg    3120
cttgtcggga tctatcgcga acgctccggc gccgatgccg gcactgcgca cgctggatc     3180 gaagacctcg cgccaaaaaa ccgctacgtc ctcgacgtct gggcaggtgg ataa          3234
```

<210> SEQ ID NO 24
<211> LENGTH: 1077

```
<212> TYPE: PRT
<213> ORGANISM: Unknown
<220> FEATURE:
<223> OTHER INFORMATION: Obtained from an environmental sample

<400> SEQUENCE: 24
```

| | | | | | | | | | | | | | | |
|---|---|---|---|---|---|---|---|---|---|---|---|---|---|---|
| Met | Ala | Ser | Thr | Asn | Arg | Leu | Ser | Pro | Ile | Pro | His | Pro | Pro | Thr | Lys |
| 1 | | | | 5 | | | | | 10 | | | | | 15 | |
| Pro | Val | Val | Gly | Asn | Met | Leu | Ser | Leu | Asp | Ser | Thr | Ala | Pro | Val | Gln |
| | | | 20 | | | | | 25 | | | | | 30 | | |
| Asn | Leu | Ala | Arg | Leu | Ala | Lys | Glu | Leu | Gly | Pro | Ile | Phe | Trp | Leu | Asp |
| | | 35 | | | | | 40 | | | | | 45 | | | |
| Met | Met | Gly | Ala | Pro | Ile | Val | Ile | Val | Ser | Gly | His | Asp | Leu | Val | Glu |
| 50 | | | | | 55 | | | | | 60 | | | | | |
| Glu | Leu | Ser | Asp | Glu | Lys | Arg | Phe | Asp | Lys | Ala | Val | Arg | Gly | Ala | Leu |
| 65 | | | | | 70 | | | | | 75 | | | | | 80 |
| Arg | Arg | Val | Arg | Ala | Val | Gly | Gly | Asp | Gly | Leu | Phe | Thr | Ala | Asp | Thr |
| | | | | 85 | | | | | 90 | | | | | 95 | |
| Ser | Glu | Pro | Asn | Trp | Ser | Lys | Ala | His | Asn | Ile | Leu | Leu | Gln | Pro | Phe |
| | | | 100 | | | | | 105 | | | | | 110 | | |
| Gly | Asn | Arg | Ala | Met | Gln | Ser | Tyr | His | Pro | Ser | Met | Val | Asp | Ile | Ala |
| | | 115 | | | | | 120 | | | | | 125 | | | |
| Glu | Gln | Leu | Val | Lys | Lys | Trp | Glu | Arg | Leu | Asn | Val | Asp | Asp | Glu | Ile |
| | 130 | | | | | 135 | | | | | 140 | | | | |
| Asp | Val | Val | His | Asp | Met | Thr | Ala | Leu | Thr | Leu | Asp | Thr | Ile | Gly | Leu |
| 145 | | | | | 150 | | | | | 155 | | | | | 160 |
| Cys | Gly | Phe | Asp | Tyr | Arg | Phe | Asn | Ser | Phe | Tyr | Arg | Arg | Asp | Tyr | His |
| | | | | 165 | | | | | 170 | | | | | 175 | |
| Pro | Phe | Val | Ala | Ser | Leu | Val | Arg | Ser | Leu | Glu | Thr | Ile | Met | Met | Ile |
| | | | 180 | | | | | 185 | | | | | 190 | | |
| Arg | Gly | Leu | Pro | Leu | Glu | Asn | Leu | Trp | Met | Gln | Lys | Arg | Arg | Arg | Asp |
| | | 195 | | | | | 200 | | | | | 205 | | | |
| Leu | Ala | Ala | Asp | Val | Gly | Phe | Met | Asn | Lys | Met | Val | Asp | Glu | Ile | Ile |
| 210 | | | | | 215 | | | | | 220 | | | | | |
| Ala | Glu | Arg | Arg | Arg | Ser | Ala | Glu | Ala | Glu | Gly | Lys | Lys | Asp | Met | Leu |
| 225 | | | | | 230 | | | | | 235 | | | | | 240 |
| Gly | Ala | Met | Met | Thr | Gly | Val | Asp | Arg | Thr | Thr | Gly | Glu | Gln | Leu | Asp |
| | | | | 245 | | | | | 250 | | | | | 255 | |
| Asp | Val | Asn | Ile | Arg | Tyr | Gln | Ile | Asn | Thr | Phe | Leu | Ile | Ala | Gly | His |
| | | | 260 | | | | | 265 | | | | | 270 | | |
| Glu | Thr | Thr | Ser | Gly | Leu | Leu | Ser | Cys | Thr | Leu | Tyr | Ala | Leu | Leu | Lys |
| | | 275 | | | | | 280 | | | | | 285 | | | |
| His | Pro | Glu | Ile | Leu | Arg | Lys | Ala | Tyr | Glu | Glu | Val | Asp | Arg | Val | Leu |
| | 290 | | | | | 295 | | | | | 300 | | | | |
| Gly | Pro | Asp | Ile | Asn | Ala | Arg | Pro | Thr | Tyr | Gln | Gln | Val | Thr | Gln | Leu |
| 305 | | | | | 310 | | | | | 315 | | | | | 320 |
| Thr | Tyr | Ile | Thr | Gln | Ile | Leu | Lys | Glu | Ala | Leu | Arg | Leu | Trp | Pro | Pro |
| | | | | 325 | | | | | 330 | | | | | 335 | |
| Ala | Pro | Ala | Tyr | Gly | Ile | Ser | Pro | Leu | Lys | Asp | Glu | Thr | Ile | Gly | Gly |
| | | | 340 | | | | | 345 | | | | | 350 | | |
| Lys | Tyr | Lys | Leu | Lys | Lys | Asn | Thr | Phe | Ile | Thr | Val | Leu | Val | Leu | Ala |
| | | 355 | | | | | 360 | | | | | 365 | | | |
| Leu | His | Arg | Asp | Arg | Ser | Val | Trp | Gly | Ser | Asn | Pro | Asp | Ala | Phe | Asp |
| | 370 | | | | | 375 | | | | | 380 | | | | |

-continued

Pro Glu Asn Phe Ser Arg Glu Ala Glu Ala Arg Pro Ile Asn Ala
385                 390                 395                 400

Trp Lys Pro Phe Gly Asn Gly Gln Arg Ala Cys Ile Gly Arg Gly Phe
            405                 410                 415

Ala Met His Glu Ala Ala Leu Ala Ile Gly Met Ile Leu Gln Arg Phe
            420                 425                 430

Lys Leu Val Asp Val Asn Arg Tyr Gln Met Val Leu Lys Glu Thr Leu
            435                 440                 445

Thr Ile Lys Pro Asp Gly Phe Lys Ile Lys Val Arg Pro Arg Ala Glu
        450                 455                 460

Arg Asp Arg Gly Ala Tyr Gly Gly Ala Ala Ser Val Ala Met Ala Pro
465                 470                 475                 480

Asn Thr Pro Thr Ala Pro His Glu Arg Thr Arg Leu Gly His Asn Thr
                485                 490                 495

Pro Leu Leu Val Leu Tyr Gly Ser Asn Leu Gly Thr Ala Glu Glu Leu
            500                 505                 510

Ala Thr Arg Val Ala Asp Leu Ala Glu Val Asn Gly Phe Ala Thr Lys
            515                 520                 525

Leu Ala Pro Leu Asp Asp Phe Val Gly Lys Leu Pro Glu Gln Gly Gly
530                 535                 540

Val Leu Ile Phe Cys Ala Ser Tyr Asn Gly Val Pro Pro Asp Asn Ala
545                 550                 555                 560

Thr Gln Phe Val Lys Trp Leu Gly Gly Asp Ile Pro Lys Asp Ser Phe
                565                 570                 575

Ala Lys Val Arg Tyr Ala Val Phe Gly Cys Gly Asn Ser Asp Trp Ala
            580                 585                 590

Ala Thr Tyr Gln Ser Val Pro Arg Leu Ile Asp Glu Gln Leu Ala Ala
        595                 600                 605

His Gly Ala Arg Ser Val Tyr Thr Arg Gly Glu Gly Asp Ala Arg Ser
    610                 615                 620

Asp Leu Asp Gly Gln Phe Glu Ser Trp Phe Ala Ala Ala Pro Ala
625                 630                 635                 640

Ala Thr Arg Glu Phe Gly Leu Glu Ser Asn Phe Ser Arg Ser Ala Asp
                645                 650                 655

Asp Ala Pro Leu Tyr Thr Ile Glu Pro Val Ala Pro Ser Val Val Asn
            660                 665                 670

Thr Ile Val Thr Gln Gly Gly Val Leu Pro Met Lys Val Val Ala Asn
        675                 680                 685

Ser Glu Leu Gln Asn Lys Leu Gly Thr Asn Pro Ser Asp Arg Ser Thr
690                 695                 700

Arg His Val Glu Val Gln Leu Pro Pro Gly Ile Ser Tyr Arg Val Gly
705                 710                 715                 720

Asp His Leu Ser Val Val Pro Arg Asn Asp Pro Ala Leu Val Asp Ala
            725                 730                 735

Val Ala Arg Arg Phe Gly Phe Leu Pro Ala Asp Gln Ile Arg Leu Gln
            740                 745                 750

Val Ala Glu Gly Arg Arg Ala Gln Leu Pro Val Gly Asp Ala Val Ser
            755                 760                 765

Val Gly Arg Leu Leu Thr Glu Phe Val Glu Leu Gln Gln Val Ala Thr
        770                 775                 780

Arg Lys Gln Ile Gln Ile Leu Ser Glu His Thr Arg Cys Pro Met Thr
785                 790                 795                 800

Lys Pro Lys Leu Val Gly Leu Ala Gly Asp Asp Ala Ala Ser Ala Glu

-continued

```
                     805                 810                 815
Arg Tyr Arg Ala Glu Val Leu Gly Lys Arg Lys Ser Val Phe Asp Leu
                 820                 825                 830
Leu Glu Glu His Pro Ala Cys Glu Leu Pro Phe His Ala Phe Leu Glu
             835                 840                 845
Met Leu Ser Leu Leu Ala Pro Arg Tyr Tyr Ser Ile Ser Ser Ser Pro
         850                 855                 860
Ala Gly Glu Pro Ala Arg Cys Ser Val Thr Ala Val Val Ala Ser
865                 870                 875                 880
Pro Ala Ser Ser Gly Arg Gly Ile Tyr Arg Gly Val Cys Ser Asn Tyr
                 885                 890                 895
Leu Ala Gly Arg Arg Ala Gly Asp Thr Ile His Ala Thr Val Arg Glu
             900                 905                 910
Thr Lys Ala Gly Phe Arg Leu Pro Asn Asp Pro Ser Val Pro Ile Ile
         915                 920                 925
Met Ile Gly Pro Gly Thr Gly Leu Ala Pro Phe Arg Gly Phe Leu Gln
     930                 935                 940
Glu Arg Ala Ala Leu Gln Ala Lys Gly Ala Thr Leu Gly Pro Ala Met
945                 950                 955                 960
Leu Phe Phe Gly Cys Arg His Pro Glu Gln Asp Tyr Leu Tyr Ala Asp
                 965                 970                 975
Glu Leu Lys Ala Phe Ala Ala Asp Gly Ile Thr Glu Leu His Thr Ala
             980                 985                 990
Phe Ser Arg Gly Asp Gly Pro Lys Thr Tyr Val Gln His Leu Ile Val
         995                 1000                1005
Ala Glu Lys Asp Arg Val Cys Ser Leu Ile Glu Gln Gly Ala Ile Ile
     1010                1015                1020
Tyr Val Cys Gly Asp Gly Gly Arg Met Glu Pro Asp Val Lys Ala Thr
1025                1030                1035                1040
Leu Val Gly Ile Tyr Arg Glu Arg Ser Gly Ala Asp Ala Gly Thr Ala
                 1045                1050                1055
Gln Arg Trp Ile Glu Asp Leu Gly Ala Lys Asn Arg Tyr Val Leu Asp
             1060                1065                1070
Val Trp Ala Gly Gly
     1075
```

<210> SEQ ID NO 25
<211> LENGTH: 1254
<212> TYPE: DNA
<213> ORGANISM: Bacterial

<400> SEQUENCE: 25

| | | | | | |
|---|---|---|---|---|---|
| gtgaacgcac | cgaagagcac | cgcccccggc | cgccgcgcgc | ccaccgcct | cgaccccacc | 60 |
| ggccctgcc | cgcacgccgt | caacgcccgc | ctcctcgcgg | agggcgccgt | cacccccgta | 120 |
| ctcctccccg | gcgacatcga | cggcatggcc | gtcctcggcc | acgacgccct | ccgtgacttc | 180 |
| ctctcccacc | ccgacgtcgc | caagggcccc | cagcacttca | ccgccctctc | cgagggccga | 240 |
| ataccgacg | gctggcccct | gcgcaccttc | gccaccctcc | cgggcatgat | gaccgccgac | 300 |
| ggcgccgacc | accgccgtct | cgcgcccctg | gtgagcagcg | ccttcaccgc | cgccgggtg | 360 |
| gaggaactgc | gccccgcgt | cgcgacggtc | gccgccggac | tcctcgacgg | actcgccgag | 420 |
| gccgccgaac | ggggcgacgg | cgtcgcggac | ctcgccgcc | actacgccct | ccgctgccg | 480 |
| ctcggcgtca | tctgcgaact | cctcggcgtc | gaccgggccc | accaggaccg | gctgcacgag | 540 |

```
ctctccgcgc tggtcgtcgc gaccgacatc gggcccgacc gcgccgtcgc cgtcaaccgc    600
gagctcctcg aactcctcac cgccatcgcc gccgccaagg ccgccgatcc gcgcgacgac    660
ctcaccagcg cgctcatcgc ggcccgcgac gaggacggcg accggctcgg cccgcacgag    720
ctgatcggca ccctgctcct gctgatcgtc gccggccacg agaccaccct gaacctggtg    780
accaacgccg tgcgggcgct ctgctcccac cgcgaccaac tcgccctggt cctcgacggc    840
cgggcgagct ggtcggacgt ggtggaggag acgctccgct gggacagccc ggtcagctac    900
ttcccgttcc gctatcccac ccgggacctc accgtcgacg caccctcat ccccggggc    960 accccgtcc tcgccggcta tgcggcggcg ggccgggaca ccaaggccca cggcccggac   1020
gccgaccgct cgacctcac gcgtacggcg acggtgaagc acctgtcact cggccacggc   1080
ccgcactact gcctgggcgc cccgctcgcc cggatggagg cggccgtcgc cctggagacg   1140
ctgttcaccc gcttccccgg cctggacctg gccgtcccgg agtccgagtt gccccggcac   1200
tccgggttcg tcggcaacag cgtccggacg ctcccggtcc ggcccggcgg ctga         1254
```

<210> SEQ ID NO 26
<211> LENGTH: 417
<212> TYPE: PRT
<213> ORGANISM: Bacterial

<400> SEQUENCE: 26

```
Met Asn Ala Pro Lys Ser Thr Ala Pro Gly Arg Arg Ala Pro His Arg
 1               5                  10                  15

Leu Asp Pro Thr Gly Pro Cys Pro His Ala Val Asn Ala Arg Leu Leu
            20                  25                  30

Ala Glu Gly Ala Val Thr Pro Val Leu Leu Pro Gly Asp Ile Asp Gly
        35                  40                  45

Met Ala Val Leu Gly His Asp Ala Leu Arg Asp Phe Leu Ser His Pro
    50                  55                  60

Asp Val Ala Lys Gly Pro Gln His Phe Thr Ala Leu Ser Glu Gly Arg
65                  70                  75                  80

Ile Pro Asp Gly Trp Pro Leu Arg Thr Phe Ala Thr Leu Pro Gly Met
                85                  90                  95

Met Thr Ala Asp Gly Ala Asp His Arg Arg Leu Arg Ala Leu Val Ser
            100                 105                 110

Ser Ala Phe Thr Ala Arg Arg Val Glu Glu Leu Arg Pro Arg Val Ala
        115                 120                 125

Thr Val Ala Ala Gly Leu Leu Asp Gly Leu Ala Glu Ala Ala Glu Arg
    130                 135                 140

Gly Asp Gly Val Ala Asp Leu Arg Arg His Tyr Ala Leu Pro Leu Pro
145                 150                 155                 160

Leu Gly Val Ile Cys Glu Leu Leu Gly Val Asp Arg Ala His Gln Asp
                165                 170                 175

Arg Leu His Glu Leu Ser Ala Leu Val Val Ala Thr Asp Ile Gly Pro
            180                 185                 190

Asp Arg Ala Val Ala Val Asn Arg Glu Leu Leu Glu Leu Leu Thr Ala
        195                 200                 205

Ile Ala Ala Ala Lys Ala Ala Asp Pro Arg Asp Asp Leu Thr Ser Ala
    210                 215                 220

Leu Ile Ala Ala Arg Asp Glu Asp Gly Asp Arg Leu Gly Pro His Glu
225                 230                 235                 240

Leu Ile Gly Thr Leu Leu Leu Leu Ile Val Ala Gly His Glu Thr Thr
                245                 250                 255
```

```
Leu Asn Leu Val Thr Asn Ala Val Arg Ala Leu Cys Ser His Arg Asp
            260                 265                 270

Gln Leu Ala Leu Val Leu Asp Gly Arg Ala Ser Trp Ser Asp Val Val
        275                 280                 285

Glu Glu Thr Leu Arg Trp Asp Ser Pro Val Ser Tyr Phe Pro Phe Arg
    290                 295                 300

Tyr Pro Thr Arg Asp Leu Thr Val Asp Gly Thr Leu Ile Pro Arg Gly
305                 310                 315                 320

Thr Pro Val Leu Ala Gly Tyr Ala Ala Gly Arg Asp Thr Lys Ala
                325                 330                 335

His Gly Pro Asp Ala Asp Arg Phe Asp Leu Thr Arg Thr Ala Thr Val
            340                 345                 350

Lys His Leu Ser Leu Gly His Gly Pro His Tyr Cys Leu Gly Ala Pro
        355                 360                 365

Leu Ala Arg Met Glu Ala Val Ala Leu Glu Thr Leu Phe Thr Arg
    370                 375                 380

Phe Pro Gly Leu Asp Leu Ala Val Pro Glu Ser Glu Leu Pro Arg His
385                 390                 395                 400

Ser Gly Phe Val Gly Asn Ser Val Arg Thr Leu Pro Val Arg Pro Gly
                405                 410                 415

Gly

<210> SEQ ID NO 27
<211> LENGTH: 1200
<212> TYPE: DNA
<213> ORGANISM: Bacterial

<400> SEQUENCE: 27
atggacgccg ctgctgaccc cgtgtacgac ccctggtccc ccgagttcgt cgccgatccc      60
taccccgcct acgccgggct gcgcgcggcc ggccgcgcgc actggcacgg ccgacgcgg     120
cagtggctga tcccgcacca cgaggacgtg tcggcactgc tcagggaccg gcggctcggc     180
cgtacgtaca cccatcgctt cacgcacgag gagttcgggc aggaggcccc ggacgccgcg     240
tacgagccgt ccacacgct caacgaccac gggctgctcg acctggaggg cgccgaccac     300
agccgcatcc ggcggctggt gtcgaaggcg ttcaccccga ggaccgtgga ggacctggcg     360
ccgaccgtac ggcggctggc cgccgacctg gtcggcggtc tggtcgcggc cggcggcggc     420
gacctccagg cggcggtggc ggaaccctg ccggtcgcgg tgatcgccga gatgctgggc     480
gtccccgagg gcgacgagga gcgggcgcgg ctgcgcccct ggtcggcggc gatctgcggg     540
atgttcgagc tgaatccctc ggaggagacg gcgcggcggg cggtggcggc ctctgtggag     600
ttctccggct atctgcggga gctgatcgcc cggcggcgca aggagccggg ggacgatctg     660
atctcgtcgc tgatcgcggt ggaggagctg accgagcagg agatgatctc cacctgtgtg     720
ctcctcctga acgcgggtca cgaggcgacc gtgaacacca cggtcaacgg ctggtggacg     780
ctgctcagag agggcgtccg gcccgatccc gaaaagttgt ccacagctgt ggaagaactt     840
ctgcgctacg acacccgct ccagatgttc gagcggtggg tcctcgacga catcgagatc     900
ggcggccaca cccttccgcg cggctccgag gtggccctgc tcctcggctc cgccaaccgc     960
gacccgccc gcttcggccc gacgccgac acctcgacc tcaccgcgc cgacaacccc    1020
cacatcacct tcggcgccgg catccactac tgcctcggcg cccgctcgc cgtctcgaa     1080
ctgacggcgg tcttcggcga gttgctccgc caggcgccgg gcctccggct cgcggcggag    1140
```

-continued cccgtacgca agccgggata cgtgatccgc ggcttcgagg agctgctcgt cgagctgtga    1200

<210> SEQ ID NO 28
<211> LENGTH: 399
<212> TYPE: PRT
<213> ORGANISM: Bacterial

<400> SEQUENCE: 28

Met Asp Ala Ala Ala Asp Pro Val Tyr Asp Pro Trp Ser Pro Glu Phe
1               5                   10                  15

Val Ala Asp Pro Tyr Pro Ala Tyr Ala Gly Leu Arg Ala Ala Gly Arg
            20                  25                  30

Ala His Trp His Gly Pro Thr Arg Gln Trp Leu Ile Pro His His Glu
        35                  40                  45

Asp Val Ser Ala Leu Leu Arg Asp Arg Leu Gly Arg Thr Tyr Thr
    50                  55                  60

His Arg Phe Thr His Glu Glu Phe Gly Gln Glu Ala Pro Asp Ala Ala
65                  70                  75                  80

Tyr Glu Pro Phe His Thr Leu Asn Asp His Gly Leu Leu Asp Leu Glu
                85                  90                  95

Gly Ala Asp His Ser Arg Ile Arg Arg Leu Val Ser Lys Ala Phe Thr
            100                 105                 110

Pro Arg Thr Val Glu Asp Leu Ala Pro Thr Val Arg Arg Leu Ala Ala
        115                 120                 125

Asp Leu Val Gly Gly Leu Val Ala Ala Gly Gly Asp Leu Gln Ala
    130                 135                 140

Ala Val Ala Glu Pro Leu Pro Val Ala Val Ile Ala Glu Met Leu Gly
145                 150                 155                 160

Val Pro Glu Gly Asp Glu Arg Ala Arg Leu Arg Pro Trp Ser Ala
                165                 170                 175

Ala Ile Cys Gly Met Phe Glu Leu Asn Pro Ser Glu Glu Thr Ala Arg
            180                 185                 190

Arg Ala Val Ala Ala Ser Val Glu Phe Ser Gly Tyr Leu Arg Glu Leu
        195                 200                 205

Ile Ala Arg Arg Lys Glu Pro Gly Asp Asp Leu Ile Ser Ser Leu
    210                 215                 220

Ile Ala Val Glu Glu Leu Thr Glu Gln Glu Met Ile Ser Thr Cys Val
225                 230                 235                 240

Leu Leu Leu Asn Ala Gly His Glu Ala Thr Val Asn Thr Thr Val Asn
                245                 250                 255

Gly Trp Trp Thr Leu Leu Arg Glu Gly Val Arg Pro Asp Pro Glu Lys
            260                 265                 270

Leu Ser Thr Ala Val Glu Glu Leu Leu Arg Tyr Asp Thr Pro Leu Gln
        275                 280                 285

Met Phe Glu Arg Trp Val Leu Asp Asp Ile Glu Ile Gly Gly His Thr
    290                 295                 300

Leu Pro Arg Gly Ser Glu Val Ala Leu Leu Gly Ser Ala Asn Arg
305                 310                 315                 320

Asp Pro Ala Arg Phe Gly Pro Thr Ala Asp Thr Leu Asp Leu Thr Arg
                325                 330                 335

Ala Asp Asn Pro His Ile Thr Phe Gly Ala Gly Ile His Tyr Cys Leu
            340                 345                 350

Gly Ala Pro Leu Ala Arg Leu Glu Leu Thr Ala Val Phe Gly Glu Leu
        355                 360                 365

Leu Arg Gln Ala Pro Gly Leu Arg Leu Ala Ala Glu Pro Val Arg Lys
    370                 375                 380

Pro Gly Tyr Val Ile Arg Gly Phe Glu Glu Leu Leu Val Glu Leu
385                 390                 395

<210> SEQ ID NO 29
<211> LENGTH: 1527
<212> TYPE: DNA
<213> ORGANISM: Bacterial

<400> SEQUENCE: 29

| | | | | | |
|---|---|---|---|---|---|
| atgaccctcc | cacccgccga | acacaccgcc | gagaaggcag | gggcggtccc | gccccgggc | 60 |
| tgcccggccc | acgcctccaa | gggacccggc | ggagcgaccc | ggctctacgg | ccccgccgcc | 120 |
| gagacggacc | ccatgggcct | gtacgaggca | ctgcgcgccg | aacacggccc | ggtcgccccc | 180 |
| gtgctgctcg | acggagacgt | ccgcgcctgg | ctcgtgctcg | gctacctgga | gaaccgcgac | 240 |
| gtggccagcc | gccgacgca | gtactcccgc | gacccgcgcg | tctggcacgg | ctggcggagc | 300 |
| ggcgagatcg | accccgccac | ctcgccctc | gtcccgatga | tcggctggcg | tcccgactgc | 360 |
| gtgtgcgccg | acggcgagga | gcaccagcgg | ctgcgcgggg | cggtcacggc | cgggctcagc | 420 |
| cagttcgacc | accgggggt | ccgccgccac | atcacccgct | tcgcgcacca | gctgatcgac | 480 |
| acgttctgcg | aggacggcga | ggtggagctg | gtcgggcagt | tcaccgagca | cctgccgatg | 540 |
| ctcacgctga | cccatctgct | cggcatgtcg | gacgagtccg | gccccggct | cgtgcacgcc | 600 |
| gcccgtgacc | tcttcaaggc | caccgagacc | tcgctcgcca | gcaacgccta | cgtgatcgag | 660 |
| tgcctcgaac | agctcgtcgt | cgccaagcgg | tcccggccgg | ggcaggacat | cgcctccgcg | 720 |
| ctgatggcac | ccccgccgg | gctcaccgac | gaggaggtgc | tgcaccacct | gcgcctcatc | 780 |
| ctcctcgcgg | ggtacgagac | gaccgccaac | ctcatgtcca | acgtcctgcg | catggtggtc | 840 |
| accgaccccc | ggttccgagg | atcgctggcc | ggcggccaga | tgaccctgcc | cgaggccgtc | 900 |
| gagcaggtcc | tctgggacga | gccgccgctg | atggtgtgcc | ccggccggtg | ggccaacggc | 960 |
| gacaccaccc | tcggcggccg | gcagatcaag | gcgggcgaca | tgctgctgct | cggcctggcc | 1020 |
| gccgggaacg | tcgacaaggc | gatccgcccg | gacgcctcga | ccccgtcca | ccacaaccgc | 1080 |
| gcccacctgt | cgttcagcgc | cggcacccac | gagtgccccg | gccaggacat | cggccgcatc | 1140 |
| atcgccgacg | ccggcatcga | catcctgctc | accggctgc | cgacatcgc | cctggccgtc | 1200 |
| cccgaggaga | gcctgtcctg | gcgctcctcc | acctgggccc | ggcacctgac | ggcgctgccc | 1260 |
| gtgcacttcg | cccccgcgt | ccccgagggg | cacgacgtcc | cgaacccgct | gcccgccccg | 1320 |
| ccggccccga | gcttcgggcc | ccgtcggcg | ccgctgtggc | cgtcgcccgg | ccccggaccc | 1380 |
| gcccgcccgt | cggatcaggc | gccgccgccc | ggcccggtcc | ccggcggcgg | ggccacggga | 1440 |
| ggggcgtccg | gccccgcgtc | ggaacacggc | cccggacccc | gcgccacctg | cgtacgagg | 1500 |
| gtcatgcgct | tcctgcggag | gcggtag | | | | 1527 |

<210> SEQ ID NO 30
<211> LENGTH: 508
<212> TYPE: PRT
<213> ORGANISM: Bacterial

<400> SEQUENCE: 30

Met Thr Leu Pro Pro Ala Glu His Thr Ala Glu Lys Ala Gly Ala Val
1               5                   10                  15

Pro Pro Pro Gly Cys Pro Ala His Ala Ser Lys Gly Pro Gly Gly Ala
                20                  25                  30

-continued

```
Thr Arg Leu Tyr Gly Pro Ala Ala Glu Thr Asp Pro Met Gly Leu Tyr
         35                  40                  45

Glu Ala Leu Arg Ala Glu His Gly Pro Val Ala Pro Val Leu Leu Asp
     50                  55                  60

Gly Asp Val Arg Ala Trp Leu Val Leu Gly Tyr Leu Glu Asn Arg Asp
 65                  70                  75                  80

Val Ala Ser Arg Pro Thr Gln Tyr Ser Arg Asp Pro Arg Val Trp His
                 85                  90                  95

Gly Trp Arg Ser Gly Glu Ile Asp Pro Ala Thr Ser Pro Leu Val Pro
                100                 105                 110

Met Ile Gly Trp Arg Pro Asp Cys Val Cys Ala Asp Gly Glu Glu His
             115                 120                 125

Gln Arg Leu Arg Gly Ala Val Thr Ala Gly Leu Ser Gln Phe Asp His
         130                 135                 140

Arg Gly Val Arg Arg His Ile Thr Arg Phe Ala His Gln Leu Ile Asp
145                 150                 155                 160

Thr Phe Cys Glu Asp Gly Glu Val Glu Leu Val Gly Gln Phe Thr Glu
                165                 170                 175

His Leu Pro Met Leu Thr Leu Thr His Leu Leu Gly Met Ser Asp Glu
                180                 185                 190

Ser Gly Pro Arg Leu Val His Ala Ala Arg Asp Leu Phe Lys Ala Thr
            195                 200                 205

Glu Thr Ser Leu Ala Ser Asn Ala Tyr Val Ile Glu Cys Leu Glu Gln
    210                 215                 220

Leu Val Val Ala Lys Arg Ser Arg Pro Gly Gln Asp Ile Ala Ser Ala
225                 230                 235                 240

Leu Met Ala His Pro Ala Gly Leu Thr Asp Glu Val Leu His His
                245                 250                 255

Leu Arg Leu Ile Leu Leu Ala Gly Tyr Glu Thr Thr Ala Asn Leu Met
            260                 265                 270

Ser Asn Val Leu Arg Met Val Val Thr Asp Pro Arg Phe Arg Gly Ser
                275                 280                 285

Leu Ala Gly Gly Gln Met Thr Leu Pro Glu Ala Val Glu Gln Val Leu
    290                 295                 300

Trp Asp Glu Pro Pro Leu Met Val Cys Pro Gly Arg Trp Ala Asn Gly
305                 310                 315                 320

Asp Thr Thr Leu Gly Gly Arg Gln Ile Lys Ala Gly Asp Met Leu Leu
                325                 330                 335

Leu Gly Leu Ala Ala Gly Asn Val Asp Lys Ala Ile Arg Pro Asp Ala
            340                 345                 350

Ser Thr Pro Val His His Asn Arg Ala His Leu Ser Phe Ser Ala Gly
    355                 360                 365

Thr His Glu Cys Pro Gly Gln Asp Ile Gly Arg Ile Ala Asp Ala
    370                 375                 380

Gly Ile Asp Ile Leu Leu Thr Arg Leu Pro Asp Ile Ala Leu Ala Val
385                 390                 395                 400

Pro Glu Glu Ser Leu Ser Trp Arg Ser Ser Thr Trp Ala Arg His Leu
                405                 410                 415

Thr Ala Leu Pro Val His Phe Ala Pro Arg Val Pro Glu Gly His Asp
            420                 425                 430

Val Pro Asn Pro Leu Pro Ala Pro Ala Pro Ser Phe Gly Pro Pro
                435                 440                 445
```

```
Ser Ala Pro Leu Trp Pro Ser Pro Gly Pro Gly Pro Ala Arg Pro Ser
    450                 455                 460

Asp Gln Ala Pro Pro Gly Pro Val Pro Gly Gly Ala Thr Gly
465                 470                 475                 480

Gly Ala Ser Gly Pro Ala Ser Glu His Gly Pro Gly Pro Arg Ala Thr
                485                 490                 495

Trp Arg Thr Arg Val Met Arg Phe Leu Arg Arg Arg
                500                 505
```

<210> SEQ ID NO 31
<211> LENGTH: 1179
<212> TYPE: DNA
<213> ORGANISM: Bacterial

<400> SEQUENCE: 31

```
atgtccgtca tcgaactggg ggagtacggc gcggacttca ccgcgaatcc gtaccnctac      60
tacgcgaaac tccgcgaagc gggacccgtc cacgaggtcc ggatgcccga cggcttccag     120
ttctggctgg tcgtcggcca cgaggagggg cgcgccgcac tcgccgaccc ccggctcgcc     180
aagtcccccct ccgtgatcgg cgtacggccc cggaggaggg acatcatcgg cgtccacctc    240
ctcgccgcgg acgcgcccga ccacacccgg ctgcgccgcc tggtcaccgg tgagttcacc     300
ggccgtcggg tggagggcct cgcccccgc atccagcagc tgaccacgga gctcgccgac      360
gccatggaac cggcaggccg tgccgacctc gtcgacgcct cgcctaccc gctgccgatc      420
atcgtcatct gcgagctcct cggcgtcccc gccgaggacc gcgacacctt ccgccgctgg     480
tcgaaccagc tggtcacgcc caccggcgac caggagttcg ccaggcgat ggtggacttc      540
gcggcctatc tcgacgcgct catcgaggac aagcggccg ccggaccac cgacgacctg       600
ctctccgccc tgatcaccgc ccgcgccgag gacggcgacc ggctctccgg ccccgaactc     660
cgcgccatgg cctatctgct gctcatcgcg ggccacgaga ccaccgtcaa cctgatcgcc     720
aacaccgtcc gcaacctgct cacccacccc gagcagctcg cggccctccg cgccgacccg     780
gacctcctgg acgggacgat cgaggagtcc ctgcggtacg acggaccggt ggagaccggc     840
acgttccgct tcacccggga ggccgtcacc atcggcgggc gggagatcgc ggcgggccag     900
tacgtgctcg tcggcatcgg ggcgctcgac cgcgaccccg cccgcttccc cgaccccgac     960
cgcttcgaca tccgccggga cacccgcggc cacctcgcct tcggccacgg catccactac    1020
tgcctgggcg ccccgctggc ccgcctggag ggccggatcg ccctccgtac cctcctcgac    1080
cgcttcccgg acctggaact cgaccccgag gcgagccct gggaatggct ccccggcctc    1140
ctgatgcgcg gcgtccgaca cctcccggtc aggtggtga                          1179
```

<210> SEQ ID NO 32
<211> LENGTH: 392
<212> TYPE: PRT
<213> ORGANISM: Bacterial

<400> SEQUENCE: 32

```
Met Ser Val Ile Glu Leu Gly Glu Tyr Gly Ala Asp Phe Thr Ala Asn
  1               5                  10                  15

Pro Tyr Pro Tyr Tyr Ala Lys Leu Arg Glu Ala Gly Pro Val His Glu
                20                  25                  30

Val Arg Met Pro Asp Gly Phe Gln Phe Trp Leu Val Val Gly His Glu
                35                  40                  45

Glu Gly Arg Ala Ala Leu Ala Asp Pro Arg Leu Ala Lys Ser Pro Ser
     50                  55                  60
```

-continued

Val Ile Gly Val Arg Pro Pro Glu Glu Asp Ile Ile Gly Val His Leu
65                  70                  75                  80

Leu Ala Ala Asp Ala Pro Asp His Thr Arg Leu Arg Arg Leu Val Thr
            85                  90                  95

Gly Glu Phe Thr Gly Arg Arg Val Glu Gly Leu Arg Pro Arg Ile Gln
            100                 105                 110

Gln Leu Thr Thr Glu Leu Ala Asp Ala Met Glu Pro Ala Gly Arg Ala
            115                 120                 125

Asp Leu Val Asp Ala Phe Ala Tyr Pro Leu Pro Ile Ile Val Ile Cys
            130                 135                 140

Glu Leu Leu Gly Val Pro Ala Glu Asp Arg Asp Thr Phe Arg Arg Trp
145                 150                 155                 160

Ser Asn Gln Leu Val Thr Pro Thr Gly Asp Gln Glu Phe Gly Gln Ala
            165                 170                 175

Met Val Asp Phe Ala Ala Tyr Leu Asp Ala Leu Ile Glu Asp Lys Arg
            180                 185                 190

Ala Ala Gly Pro Thr Asp Asp Leu Leu Ser Ala Leu Ile Thr Ala Arg
            195                 200                 205

Ala Glu Asp Gly Asp Arg Leu Ser Gly Pro Glu Leu Arg Ala Met Ala
210                 215                 220

Tyr Leu Leu Leu Ile Ala Gly His Glu Thr Thr Val Asn Leu Ile Ala
225                 230                 235                 240

Asn Thr Val Arg Asn Leu Leu Thr His Pro Glu Gln Leu Ala Ala Leu
            245                 250                 255

Arg Ala Asp Pro Asp Leu Leu Asp Gly Thr Ile Glu Glu Ser Leu Arg
            260                 265                 270

Tyr Asp Gly Pro Val Glu Thr Gly Thr Phe Arg Phe Thr Arg Glu Ala
            275                 280                 285

Val Thr Ile Gly Gly Arg Glu Ile Ala Ala Gly Gln Tyr Val Leu Val
            290                 295                 300

Gly Ile Gly Ala Leu Asp Arg Asp Pro Ala Arg Phe Pro Asp Pro Asp
305                 310                 315                 320

Arg Phe Asp Ile Arg Arg Asp Thr Arg Gly His Leu Ala Phe Gly His
            325                 330                 335

Gly Ile His Tyr Cys Leu Gly Ala Pro Leu Ala Arg Leu Glu Gly Arg
            340                 345                 350

Ile Ala Leu Arg Thr Leu Leu Asp Arg Phe Pro Asp Leu Glu Leu Asp
            355                 360                 365

Pro Glu Gly Glu Pro Trp Glu Trp Leu Pro Gly Leu Leu Met Arg Gly
370                 375                 380

Val Arg His Leu Pro Val Arg Trp
385                 390

<210> SEQ ID NO 33
<211> LENGTH: 1194
<212> TYPE: DNA
<213> ORGANISM: Bacterial

<400> SEQUENCE: 33
atgagcgtcg ccgtcgagac cctgccggcc ttccccttcg actgggacgg gacccggctg     60
cccgccgagg tcgaggcgct ccgcgccgaa cccgtacgcc gggtgcggac gatcgccggg    120
gccgaggcct ggctggtctc ctcgtacgag ctgtgcaggc aggtcctgga ggacccgcgg    180
ttcagcctga aggacacctc ggcgccgggc gcgccgcggc agtacgcgct gacgatcccg    240

```
ccgcacgtgg tgaacaacat gggcaacatc accggggccg ggctgcgcaa ggccgtgatg      300
aaggcgatca acccgaaggc gcccggcctg gaggagtggc tgcgggcgcg ggccggggcc      360
ctggtggacg cgctggtcgc cgagggcgcg cccggggagc tgcggggcgc ctacgccgac      420
ccgtactcgt cggggctgca ctgccggatg ctgggcatcc cggaggagga cgggccgcgg      480
ctgctgcgca gcctggacgt ggccttcatg aacgccccgt ccgagatcga ggcggcccgg      540
ctccactggg accgggacat cgcgtacatg accgagcgtc tcgacgatcc ggcgacgggc      600
gggctgatgg cggagctcgc ggcgctgcgc gaggatcccg agtacgcgca tctgacggac      660
gagatgctgg cgacggtggg cgtgacgctg ttcggggccg gggtgatctc caccgccggg      720
ttcctgacga tggcgctcgt gtcggtgctg accggccgg acgtgcgggc ggcgctgacc       780
gccggcggcg ggcacggggt cgccggggcg atggacgaac tgctgcgggt gaacctgtcc      840
atcggcgacg gctgccccg gctcgcccctg gaggacgtgc ggctcggcga cgtcgaggtg      900
cgggccggtg aactggtcct ggtgctggtg gaggccgcga accacgatcc gctgcacttc      960
ccggacccgc tggccttccg gccggaccgg gagaacgccg ccgaccacct ctccttcggc     1020
ggcggtcggc actactgccc ggcgacgccg ctgggcaagc ggcacgccga gatcgccctg     1080
gagacgctcc tcgaccggct gccggagctg cggctcgcgg tgccggtcga gcagctggtg     1140
tggcgcacca acttcatgaa gcggctcccg gagcggctgc cggtggcctg gtag           1194
```

<210> SEQ ID NO 34
<211> LENGTH: 397
<212> TYPE: PRT
<213> ORGANISM: Bacterial

<400> SEQUENCE: 34

```
Met Ser Val Ala Val Glu Thr Leu Pro Ala Phe Pro Phe Asp Trp Asp
  1               5                  10                  15

Gly Thr Arg Leu Pro Ala Glu Val Glu Ala Leu Arg Ala Glu Pro Val
                 20                  25                  30

Arg Arg Val Arg Thr Ile Ala Gly Ala Glu Ala Trp Leu Val Ser Ser
             35                  40                  45

Tyr Glu Leu Cys Arg Gln Val Leu Glu Asp Pro Arg Phe Ser Leu Lys
         50                  55                  60

Asp Thr Ser Ala Pro Gly Ala Pro Arg Gln Tyr Ala Leu Thr Ile Pro
 65                  70                  75                  80

Pro His Val Val Asn Asn Met Gly Asn Ile Thr Gly Ala Gly Leu Arg
                 85                  90                  95

Lys Ala Val Met Lys Ala Ile Asn Pro Lys Ala Pro Gly Leu Glu Glu
                100                 105                 110

Trp Leu Arg Ala Arg Ala Gly Ala Leu Val Asp Ala Leu Val Ala Glu
            115                 120                 125

Gly Ala Pro Gly Glu Leu Arg Gly Ala Tyr Ala Asp Pro Tyr Ser Ser
        130                 135                 140

Gly Leu His Cys Arg Met Leu Gly Ile Pro Glu Glu Asp Gly Pro Arg
145                 150                 155                 160

Leu Leu Arg Ser Leu Asp Val Ala Phe Met Asn Ala Pro Ser Glu Ile
                165                 170                 175

Glu Ala Ala Arg Leu His Trp Asp Arg Asp Ile Ala Tyr Met Thr Glu
            180                 185                 190

Arg Leu Asp Asp Pro Ala Thr Gly Gly Leu Met Ala Glu Leu Ala Ala
        195                 200                 205
```

-continued

```
Leu Arg Glu Asp Pro Glu Tyr Ala His Leu Thr Asp Glu Met Leu Ala
            210                 215                 220
Thr Val Gly Val Thr Leu Phe Gly Ala Gly Val Ile Ser Thr Ala Gly
225                 230                 235                 240
Phe Leu Thr Met Ala Leu Val Ser Val Leu Thr Arg Pro Asp Val Arg
                245                 250                 255
Ala Ala Leu Thr Ala Gly Gly Gly His Gly Val Ala Gly Ala Met Asp
                260                 265                 270
Glu Leu Leu Arg Val Asn Leu Ser Ile Gly Asp Gly Leu Pro Arg Leu
            275                 280                 285
Ala Leu Glu Asp Val Arg Leu Gly Asp Val Glu Val Arg Ala Gly Glu
        290                 295                 300
Leu Val Leu Val Leu Val Glu Ala Ala Asn His Asp Pro Leu His Phe
305                 310                 315                 320
Pro Asp Pro Leu Ala Phe Arg Pro Asp Arg Glu Asn Ala Ala Asp His
                325                 330                 335
Leu Ser Phe Gly Gly Gly Arg His Tyr Cys Pro Ala Thr Ala Leu Gly
                340                 345                 350
Lys Arg His Ala Glu Ile Ala Leu Glu Thr Leu Leu Asp Arg Leu Pro
            355                 360                 365
Glu Leu Arg Leu Ala Val Pro Val Glu Gln Leu Val Trp Arg Thr Asn
        370                 375                 380
Phe Met Lys Arg Leu Pro Glu Arg Leu Pro Val Ala Trp
385                 390                 395

<210> SEQ ID NO 35
<211> LENGTH: 1239
<212> TYPE: DNA
<213> ORGANISM: Bacterial

<400> SEQUENCE: 35
gtgatcccgg ccacggagga gaacccggcc gcggcgccgc gggtgccgga cctgtccgac     60
ccgctgctcc accagcgcgg cgaggccgga ccggtcctgg cgcgactgcg gcgcgaggaa    120
ccggtctgcc aggtcacccg ggcggacggc tcgacgttct gggccgtcct gtcgtacgag    180
ctgatcaccc aggtcctcgc cgacgccgcc accttcagct ccaccggcgg gatgcggctc    240
gacgccgatc cggtggcgac cgccgccgcg accggcaaga tgatggtcat caccgacccg    300
ccgctgcacg gcatgatccg ccgggtcgtc agctcggcgt tcaccccccg catggtgctc    360
cgcctcgagg agaccatgcg gaccatctcg gtcgaggtca tcgaggccgc cctcgggcag    420
gactcgatcg acttcaccga ggtggcggcc cggctgccgc tgtcggtcat ctgcgacatg    480
ctcggcgtgc gcgcgccga ctgggacttc atgctgtccc gcacgatgac ggccttcggg    540
gtgaacggcg acgacgggcc cgagcagcag cagcgggtgg cgacgcccca caccgacatc    600
ttcctgtact acgacgagct gatgcggctg cgcaggaagg agccgcagga ggacatcatc    660
agcgccctcg tgcacggccg gatcgacggc aggccgctga ccgaggagga gatcatcctc    720
aactgcaacg ggctgatctc cggcggcaac gagaccaccc ggcacgccac catcggcgga    780
ctgctcgcgc tcatcgagca ccccgagcag tggcgccggc tccaggagga gccggaggtg    840
ctgccgaccg cggtgcagga gatcctgcgg ttcacgacgc cgccatgca cgtgctgcgc    900
accgccaccc gggaaacgga actggcgggg cgccggatca aggcgggcga catggtcgcg    960
ctctggctgg cctcgggcaa ccgggacgag accgtcttcg cggaccccgga ccgctttgac   1020
```

```
atcgggcggc gcgaggtgaa ccgcaaccct ccttcgcgt acggcagtca cttctgcatc    1080
ggttcggcgc tcgccaccac ggagctgaac accttcttcg acgtcctcag acagcgggtc    1140
gcacggcccg aactgaccgg agaggtacgg cgcatgcgct ccaacctcat cggcggcatc    1200
gagcacctgc cggtccgcct ggtccccgg accgctga                             1239
```

<210> SEQ ID NO 36
<211> LENGTH: 412
<212> TYPE: PRT
<213> ORGANISM: Bacterial

<400> SEQUENCE: 36

```
Met Ile Pro Ala Thr Glu Glu Asn Pro Ala Ala Pro Arg Val Pro
 1               5                  10                  15

Asp Leu Ser Asp Pro Leu Leu His Gln Arg Gly Glu Ala Gly Pro Val
            20                  25                  30

Leu Ala Arg Leu Arg Arg Glu Glu Pro Val Cys Gln Val Thr Arg Ala
        35                  40                  45

Asp Gly Ser Thr Phe Trp Ala Val Leu Ser Tyr Glu Leu Ile Thr Gln
    50                  55                  60

Val Leu Ala Asp Ala Ala Thr Phe Ser Ser Thr Gly Gly Met Arg Leu
65                  70                  75                  80

Asp Ala Asp Pro Val Ala Thr Ala Ala Thr Gly Lys Met Met Val
                85                  90                  95

Ile Thr Asp Pro Pro Leu His Gly Met Ile Arg Arg Val Val Ser Ser
            100                 105                 110

Ala Phe Thr Pro Arg Met Val Leu Arg Leu Glu Glu Thr Met Arg Thr
        115                 120                 125

Ile Ser Val Glu Val Ile Glu Ala Ala Leu Gly Gln Asp Ser Ile Asp
    130                 135                 140

Phe Thr Glu Val Ala Ala Arg Leu Pro Leu Ser Val Ile Cys Asp Met
145                 150                 155                 160

Leu Gly Val Pro Arg Ala Asp Trp Asp Phe Met Leu Ser Arg Thr Met
                165                 170                 175

Thr Ala Phe Gly Val Asn Gly Asp Asp Gly Pro Glu Gln Gln Gln Arg
            180                 185                 190

Val Ala Thr Ala His Thr Asp Ile Phe Leu Tyr Tyr Asp Glu Leu Met
        195                 200                 205

Arg Leu Arg Arg Lys Glu Pro Gln Glu Asp Ile Ile Ser Ala Leu Val
    210                 215                 220

His Gly Arg Ile Asp Gly Arg Pro Leu Thr Glu Glu Ile Ile Leu
225                 230                 235                 240

Asn Cys Asn Gly Leu Ile Ser Gly Gly Asn Glu Thr Thr Arg His Ala
                245                 250                 255

Thr Ile Gly Gly Leu Leu Ala Leu Ile Glu His Pro Glu Gln Trp Arg
            260                 265                 270

Arg Leu Gln Glu Glu Pro Glu Val Leu Pro Thr Ala Val Gln Glu Ile
        275                 280                 285

Leu Arg Phe Thr Thr Pro Ala Met His Val Leu Arg Thr Ala Thr Arg
    290                 295                 300

Glu Thr Glu Leu Ala Gly Arg Arg Ile Lys Ala Gly Asp Met Val Ala
305                 310                 315                 320

Leu Trp Leu Ala Ser Gly Asn Arg Asp Glu Thr Val Phe Ala Asp Pro
                325                 330                 335
```

-continued

```
Asp Arg Phe Asp Ile Gly Arg Arg Glu Val Asn Arg Asn Leu Thr Phe
            340                 345                 350

Ala Tyr Gly Ser His Phe Cys Ile Gly Ser Ala Leu Ala Thr Thr Glu
        355                 360                 365

Leu Asn Thr Phe Phe Asp Val Leu Arg Gln Arg Val Ala Arg Pro Glu
    370                 375                 380

Leu Thr Gly Glu Val Arg Arg Met Arg Ser Asn Leu Ile Gly Gly Ile
385                 390                 395                 400

Glu His Leu Pro Val Arg Leu Val Pro Arg Asp Arg
                405                 410
```

<210> SEQ ID NO 37
<211> LENGTH: 1218
<212> TYPE: DNA
<213> ORGANISM: Bacterial

<400> SEQUENCE: 37

```
gtgcagaacg aacagacccc tgccaccgca cccgtcacgc ttcccaccgg gcgagccgcc     60
ggctgcccct tcgacccgcc cgccggactc gccgaggtcc gcgccaccgg cccgctggcc    120
cggatgacgt accccgacgg acacatcggc tggctggcca ccggccacgc cgcggtgcgc    180
tccgtcctgg cgaccccg gttcagctcg cggtacgagc tgatgcacta ccccttcccc      240
ggcggccccg agggcccgcc ggcacccgcc ccgtcggcg acatgaccgg gatggacgca     300
cccgagcaca cccgcttccg gcggctgctc accggcaagt tcaccgtccg ccggatgcgg    360
cagctcaccg accgggtcgc ggagctcacc gccgggcacc tggacgcgat ggagcgcggc    420
ggcccgggcg tcgacctggt cgaggccttc gcacgaccgc tgcccgcgct gatgatctgc    480
gagctgctcg gcgtgccgta cgcggaccgc gagcgcttcc aggagcacgc tcagacgatc    540
atgtcgatgg acgtgtcgcc gaggagatg gaggccgcgt tcaccgcgtt cctcgggtac     600
atggcggagc tggtcgcggc caagcgggcc gagccctccg acgacctgct cggcgacctg    660
gcccaggact ccgacctcac cgacgaggaa ctcgtcggcg tcggaggctt cctgctcgcc    720
gccggcctcg acaccaccgc caacatgatc gcccacggaa cgttcgcgct cctcacccac    780
ccggaacagg cggacgcgct gcgcgcggac ccggcccttg ccccgggcgc cgtggaggag    840
ctgatgcgct atctgaccgt cgcccacacc ggagtgcgga ccgccctgga ggacgtcgag    900
gtggaaggcg tgctcatcag ggcgggcgag agcgtcaccc tctcccttga ggccgccaac    960
cgggacccgg agcggttccc cgaccccgac ccctcgacg tacaccgcaa ggccacgggg   1020
cacctgggct tcgggcacgg catccaccag tgcctgggcc agcaactggc ccgcgtcgag   1080
atgacggtgg ccctgcccgc gctgctgagg cggttcccca cgctgcggct cgacgtgccg   1140
gccgaggagg tgccgctgcg gaccgagatg aacgtgtacg gcgtgcaccg gctgcccgtc   1200
acctgggacg aggtctga                                                 1218
```

<210> SEQ ID NO 38
<211> LENGTH: 405
<212> TYPE: PRT
<213> ORGANISM: Bacterial

<400> SEQUENCE: 38

```
Met Gln Asn Glu Gln Thr Pro Ala Thr Ala Pro Val Thr Leu Pro Thr
  1               5                  10                  15

Gly Arg Ala Ala Gly Cys Pro Phe Asp Pro Pro Ala Gly Leu Ala Glu
             20                  25                  30
```

Val Arg Ala Thr Gly Pro Leu Ala Arg Met Thr Tyr Pro Asp Gly His
         35                  40                  45

Ile Gly Trp Leu Ala Thr Gly His Ala Val Arg Ser Val Leu Gly
 50                  55                  60

Asp Pro Arg Phe Ser Ser Arg Tyr Glu Leu Met His Tyr Pro Phe Pro
 65                  70                  75                  80

Gly Gly Pro Glu Gly Pro Ala Pro Ala Pro Val Gly Asp Met Thr
                 85                  90                  95

Gly Met Asp Ala Pro Glu His Thr Arg Phe Arg Leu Leu Thr Gly
             100                 105                 110

Lys Phe Thr Val Arg Arg Met Arg Gln Leu Thr Asp Arg Val Ala Glu
             115                 120                 125

Leu Thr Ala Gly His Leu Asp Ala Met Glu Arg Gly Pro Gly Val
         130                 135                 140

Asp Leu Val Glu Ala Phe Ala Arg Pro Leu Pro Ala Leu Met Ile Cys
145                 150                 155                 160

Glu Leu Leu Gly Val Pro Tyr Ala Asp Arg Glu Arg Phe Gln Glu His
                 165                 170                 175

Ala Gln Thr Ile Met Ser Met Asp Val Ser Pro Glu Glu Met Glu Ala
             180                 185                 190

Ala Phe Thr Ala Phe Leu Gly Tyr Met Ala Glu Leu Val Ala Ala Lys
         195                 200                 205

Arg Ala Glu Pro Ser Asp Asp Leu Leu Gly Asp Leu Ala Gln Asp Ser
    210                 215                 220

Asp Leu Thr Asp Glu Glu Leu Val Gly Val Gly Gly Phe Leu Leu Ala
225                 230                 235                 240

Ala Gly Leu Asp Thr Thr Ala Asn Met Ile Ala His Gly Thr Phe Ala
                 245                 250                 255

Leu Leu Thr His Pro Glu Gln Ala Asp Ala Leu Arg Ala Asp Pro Ala
             260                 265                 270

Leu Ala Pro Gly Ala Val Glu Glu Leu Met Arg Tyr Leu Thr Val Ala
         275                 280                 285

His Thr Gly Val Arg Thr Ala Leu Glu Asp Val Glu Val Glu Gly Val
    290                 295                 300

Leu Ile Arg Ala Gly Glu Ser Val Thr Leu Ser Leu Glu Ala Ala Asn
305                 310                 315                 320

Arg Asp Pro Glu Arg Phe Pro Asp Pro Asp Thr Leu Asp Val His Arg
                 325                 330                 335

Lys Ala Thr Gly His Leu Gly Phe Gly His Gly Ile His Gln Cys Leu
             340                 345                 350

Gly Gln Gln Leu Ala Arg Val Glu Met Thr Val Ala Leu Pro Ala Leu
         355                 360                 365

Leu Arg Arg Phe Pro Thr Leu Arg Leu Asp Val Pro Ala Glu Glu Val
    370                 375                 380

Pro Leu Arg Thr Glu Met Asn Val Tyr Gly Val His Arg Leu Pro Val
385                 390                 395                 400

Thr Trp Asp Glu Val
                405

<210> SEQ ID NO 39
<211> LENGTH: 1215
<212> TYPE: DNA
<213> ORGANISM: Bacterial

<400> SEQUENCE: 39

-continued

```
atgcgcttac acacagcaga accggccggg accgccgacg ccgaacccgt tccgtacccg      60
ttcaacgagg cggacggcat ctccctggcc gacgcctacg aggaggcccg cgagcagccc     120
gggctgctgc gggtccggat ggcctacggt gagccggcct ggctcgccac ccggtacgcc     180
gacgcccggc tggtcctggg cgaccggcgc ttcagccggg ccgagggcgc ccggcacgac     240
gagccgcgcc agtccgaggg cgccgcgac agcgggatcc tcagcatgga cccgccggac      300
cacacccggt tgcgcaccct ggtggccaag gcgttcacca tgcaccaggt ggagaagttg     360
cgccccggcg tgcgggagct ggccgacgag ctgatcgaca agatggtcgc caccggcgcc     420
ccggtcgacc tggtcgagga gttcgcgctg ccggtgccgg tcggggtgat ctgccagctg     480
ctcggcgtgc cggtcgagga ccgtccgcgc ttccgggcgt ggagcgacgc ggcgctgtcc     540
accagttccc tgacggccga ggagttcgac gccaaccagg aggaactgcg ggcctacatg     600 cggggggttga tcgaggatca ccgggcgcgt ccgcgtgagg acctgatcac cgggctgatc     660
gaggcccggg accgcgacga ccggctgacc gagcaggagt tggtggacct gtgcgtcggc     720
atcctggtgg ccggccacga gaccaccgcc acgcagatcc ccaacttcgt ggtgacgctg     780
ctggaccggc ccgagcagtg gaaccggctg cgggaggacc cggagctggt cccgaccgcg     840
gtcgaggagc tgatgcgttt cgtgccgctg ggcagcggtg cctcgttccc gcggtacgcc     900
accgaggacg tggaggtcgg cggcacgctg gtgcgcgccg gggagccggt gctggtggcg     960
gtcggggcgg ccaaccgcga cccggccagg ttcgacgcgc cgcaggagct ggacctggcc    1020
cgggagggca accagcacct cgggttcggc catggcgtcc accactgcct cggggcgccg    1080
ctggcccggc tggagttgca ggaggcgctg ggcgcgctgc tgcggcggct gccgggtctg    1140
cggatcgccg gtgacatcga gtggaagacg cagatgctgg tccgcgggcc gcgcacgctg    1200
ccggtggggt ggtga                                                    1215
```

<210> SEQ ID NO 40
<211> LENGTH: 404
<212> TYPE: PRT
<213> ORGANISM: Bacterial

<400> SEQUENCE: 40

Met Arg Leu His Thr Ala Glu Pro Ala Gly Thr Ala Asp Ala Glu Pro
1               5                   10                  15

Val Pro Tyr Pro Phe Asn Glu Ala Asp Gly Ile Ser Leu Ala Asp Ala
            20                  25                  30

Tyr Glu Glu Ala Arg Glu Gln Pro Gly Leu Leu Arg Val Arg Met Ala
        35                  40                  45

Tyr Gly Glu Pro Ala Trp Leu Ala Thr Arg Tyr Ala Asp Ala Arg Leu
    50                  55                  60

Val Leu Gly Asp Arg Arg Phe Ser Arg Ala Glu Gly Ala Arg His Asp
65                  70                  75                  80

Glu Pro Arg Gln Ser Glu Gly Arg Arg Asp Ser Gly Ile Leu Ser Met
                85                  90                  95

Asp Pro Pro Asp His Thr Arg Leu Arg Thr Leu Val Ala Lys Ala Phe
            100                 105                 110

Thr Met His Gln Val Glu Lys Leu Arg Pro Ala Val Arg Glu Leu Ala
        115                 120                 125

Asp Glu Leu Ile Asp Lys Met Val Ala Thr Gly Ala Pro Val Asp Leu
    130                 135                 140

Val Glu Glu Phe Ala Leu Pro Val Pro Val Gly Val Ile Cys Gln Leu

-continued

```
            145                 150                 155                 160
Leu Gly Val Pro Val Glu Asp Arg Pro Arg Phe Arg Ala Trp Ser Asp
                165                 170                 175
Ala Ala Leu Ser Thr Ser Ser Leu Thr Ala Glu Glu Phe Asp Ala Asn
            180                 185                 190
Gln Glu Glu Leu Arg Ala Tyr Met Arg Gly Leu Ile Glu Asp His Arg
        195                 200                 205
Ala Arg Pro Arg Glu Asp Leu Ile Thr Gly Leu Ile Glu Ala Arg Asp
    210                 215                 220
Arg Asp Asp Arg Leu Thr Glu Gln Glu Leu Val Asp Leu Cys Val Gly
225                 230                 235                 240
Ile Leu Val Ala Gly His Glu Thr Thr Ala Thr Gln Ile Pro Asn Phe
                245                 250                 255
Val Val Thr Leu Leu Asp Arg Pro Glu Gln Trp Asn Arg Leu Arg Glu
            260                 265                 270
Asp Pro Glu Leu Val Pro Thr Ala Val Glu Glu Leu Met Arg Phe Val
        275                 280                 285
Pro Leu Gly Ser Gly Ala Ser Phe Pro Arg Tyr Ala Thr Glu Asp Val
    290                 295                 300
Glu Val Gly Gly Thr Leu Val Arg Ala Gly Glu Pro Val Leu Val Ala
305                 310                 315                 320
Val Gly Ala Ala Asn Arg Asp Pro Ala Arg Phe Asp Ala Pro Gln Glu
                325                 330                 335
Leu Asp Leu Ala Arg Glu Gly Asn Gln His Leu Gly Phe Gly His Gly
            340                 345                 350
Val His His Cys Leu Gly Ala Pro Leu Ala Arg Leu Glu Leu Gln Glu
        355                 360                 365
Ala Leu Gly Ala Leu Leu Arg Arg Leu Pro Gly Leu Arg Ile Ala Gly
    370                 375                 380
Asp Ile Glu Trp Lys Thr Gln Met Leu Val Arg Gly Pro Arg Thr Leu
385                 390                 395                 400
Pro Val Gly Trp
```

<210> SEQ ID NO 41
<211> LENGTH: 1164
<212> TYPE: DNA
<213> ORGANISM: Bacterial

<400> SEQUENCE: 41

| | | | | | |
|---|---|---|---|---|---|
| atgaggagca | tcgcgtttct | cgcccccgac | ttcctcgcca | acccctggcc | ccggtacgcc | 60 |
| cgcttccgcg | ccgagcagcc | ggtctggtgg | tccgacgaga | tccggatgtt | ctgcgtcttc | 120 |
| cgccaccggg | acatccgcgc | ctgcctcacc | ggagcggact | acaccgtcga | gtacccttc | 180 |
| cgggtcagcc | gccaggtctt | cggcgagacc | ctgctcgacc | tcgacggccc | ccgccaccag | 240 |
| cggctgcgcc | gcccgctcgc | cgggctgctg | ctcggacagc | gcgacaacat | cgcgttccgc | 300 |
| gcggccgccg | agaacgggc | caggaccgcc | gtggcggcgc | tcccggcgga | caccgtgctc | 360 |
| gacatggtgg | ccggaccggc | ccgcgccgtc | ccgctcaccg | cgaccgccac | cttcctcggc | 420 |
| gtccccgccg | aacggcacga | ctggctgctg | cacaccgtgg | agtacctggt | cggccatctg | 480 |
| gacggcagca | gcggggactt | cggccgtgcc | tccgcgctcc | gggccgagct | cgaggagtac | 540 |
| ctgctcgggc | tgatcacctc | gggagcgccc | cccgctcca | tgctcggcga | ggtgcacggc | 600 |
| tgggtgcgtg | acggcgagat | caccgcccgg | gaggcggtcg | tctcgccac | cctcacctc | 660 |

-continued

```
gccgcgggct tcgagacctc gaccggcctc atctccaaca ccctgcactg cctggcccgt    720
caccccgggc acgcggccgc ggcggccgcc gaccccggcc ggctgcgggc gttcgtcaag    780
gagacgctcc gctgggagcc gccgcagcac gacaccgtgc ggttcgcccg gcgggacacc    840
acgctggccg gcgtacccgt accggcgggc agcgcgctca aactcatgct ggccagtggc    900
aaccgggacg ccgaagtctt cgagcacgcc gaggagttcc gccggagcg gtccacccac     960 ggctcgctga ccttcgggca cggcgcccat tcctgcctcg gcacccacat cgcgctcgat   1020
gtggccgagg ccttcgtcgg ggccctgctg gcccgcttcc ccgggctgcg cgcggtggac   1080
gacccgctgc cgccgatcac cggctcgacc ttccgcaggc cccaggccct gcggatgcgg   1140
ctgggaccca aggagagtc atga                                          1164
```

<210> SEQ ID NO 42
<211> LENGTH: 387
<212> TYPE: PRT
<213> ORGANISM: Bacterial

<400> SEQUENCE: 42

```
Met Arg Ser Ile Ala Phe Leu Ala Pro Asp Phe Leu Ala Asn Pro Trp
  1               5                  10                  15

Pro Arg Tyr Ala Arg Phe Arg Ala Glu Gln Pro Val Trp Trp Ser Asp
                 20                  25                  30

Glu Ile Arg Met Phe Cys Val Phe Arg His Arg Asp Ile Arg Ala Cys
             35                  40                  45

Leu Thr Gly Ala Asp Tyr Thr Val Glu Tyr Pro Phe Arg Val Ser Arg
         50                  55                  60

Gln Val Phe Gly Glu Thr Leu Leu Asp Leu Asp Gly Pro Arg His Gln
 65                  70                  75                  80

Arg Leu Arg Arg Pro Leu Ala Gly Leu Leu Leu Gly Gln Arg Asp Asn
                 85                  90                  95

Ile Ala Phe Arg Ala Ala Ala Gly Glu Arg Ala Arg Thr Ala Val Ala
            100                 105                 110

Ala Leu Pro Ala Asp Thr Val Leu Asp Met Val Ala Gly Pro Ala Arg
        115                 120                 125

Ala Val Pro Leu Thr Ala Thr Ala Thr Phe Leu Gly Val Pro Ala Glu
    130                 135                 140

Arg His Asp Trp Leu Leu His Thr Val Glu Tyr Leu Val Gly His Leu
145                 150                 155                 160

Asp Gly Ser Ser Gly Asp Phe Gly Arg Ala Ser Ala Leu Arg Ala Glu
                165                 170                 175

Leu Glu Glu Tyr Leu Leu Gly Leu Ile Thr Ser Gly Ala Pro Pro Arg
            180                 185                 190

Ser Met Leu Gly Glu Val His Gly Trp Val Arg Asp Gly Glu Ile Thr
        195                 200                 205

Ala Arg Glu Ala Val Gly Leu Ala Thr Leu Thr Leu Ala Ala Gly Phe
    210                 215                 220

Glu Thr Ser Thr Gly Leu Ile Ser Asn Thr Leu His Cys Leu Ala Arg
225                 230                 235                 240

His Pro Gly His Ala Ala Ala Ala Ala Asp Pro Gly Arg Leu Arg
                245                 250                 255

Ala Phe Val Lys Glu Thr Leu Arg Trp Glu Pro Pro Gln His Asp Thr
            260                 265                 270

Val Arg Phe Ala Arg Arg Asp Thr Thr Leu Ala Gly Val Pro Val Pro
        275                 280                 285
```

-continued

```
Ala Gly Ser Ala Leu Lys Leu Met Leu Ala Ser Gly Asn Arg Asp Ala
        290                 295                 300

Glu Val Phe Glu His Ala Glu Glu Phe Arg Pro Glu Arg Ser Thr His
305                 310                 315                 320

Gly Ser Leu Thr Phe Gly His Gly Ala His Ser Cys Leu Gly Thr His
                325                 330                 335

Ile Ala Leu Asp Val Ala Glu Ala Phe Val Gly Ala Leu Leu Ala Arg
            340                 345                 350

Phe Pro Gly Leu Arg Ala Val Asp Asp Pro Leu Pro Pro Ile Thr Gly
        355                 360                 365

Ser Thr Phe Arg Arg Pro Gln Ala Leu Arg Met Arg Leu Gly Pro Lys
    370                 375                 380

Gly Glu Ser
385

<210> SEQ ID NO 43
<211> LENGTH: 1224
<212> TYPE: DNA
<213> ORGANISM: Bacterial

<400> SEQUENCE: 43
atgtgggccc ggttccgcgc cgagagcccg gtccaccggc accgcgccac cccgggcgcg     60
cccccgttct gggtgctgtc ccggcacgcc gacgtcgtcg ccgtctaccg ggacgacaaa    120
cgcttcacct ccgaacgcgg caacgtcctc gccacccctg cccagggcga ggactcggcg    180
tccgggaaga tgctcgccgt caccgacggg ccccgccacc gcgagatccg caacctcatg    240
ctcaagtcct tctcccccg gtcctcgccc cggtcgtgg agggcgtgaa ccgccgtacc    300
gtcgcgctcc tcgacgaggc cctggagcgc ggcgcgttcg acttcgtcgt cgaccttgcg    360
gaccacatcc cgatcaacac catcggcgac ctcatgggcg tcccggtcgc ggaccgcgag    420
cagctcgtcc actggaacac catgaccctc tcccgtacga gcgcggagca cggggcggag    480
gaggagtggc tcgcgcgcaa cgagatcctc ctgtacttct ccgagctcgc cgccaagcgc    540
cgccgggacc ccggcgagga cgtcatcagc gccctggcca ccggcaccgt cgacggacgg    600
ccgctgaccg aggacgagat cgtcttcaac tgctacagcc tcatcctcgg cggcgacgag    660
tccagccgga tgtcctccgt cggcgccgtg atcgccctgg ccgaacaccc cgaccagtgg    720
aaggcgttga aggagggcct cgtcgacacc gccaccgcca cggaggaggt gctgcgctgg    780
acgaccccgg ccatgcactt cggccggcgc gcgctcaccg acgtcgagat ccgcggccgc    840
acgatcgcct cgggcgacgt ggtcacgctg tggaacagct cggccaactt cgacgaggag    900
gtcttcgccg acccggagcg cttcgacctg cccgtacgc ccaacaaaca cgtggcgttc    960
ggccacgggc cgcacttctg catcggcgcg ttcctcggcc gcacccacgt cgaggcgatg   1020
ctccgcgccc tccgggacaa ggccggacac ctcgaactcc tcggcagacc gcggctgctc   1080
cactcgaact tcgtgtacgg gtacaccagc ctcccggtcc gcatcgaccg ccccgccgcg   1140
tccggcacca gcggcatcag cccggtgtca gcgcccctg ccacagtcga ccggacccgc   1200
gagtccgcga cagatgggaa gtga                                          1224

<210> SEQ ID NO 44
<211> LENGTH: 407
<212> TYPE: PRT
<213> ORGANISM: Bacterial

<400> SEQUENCE: 44
```

-continued

```
Met Trp Ala Arg Phe Arg Ala Glu Ser Pro Val His Arg His Arg Ala
 1               5                  10                  15

Thr Pro Gly Ala Pro Pro Phe Trp Val Leu Ser Arg His Ala Asp Val
             20                  25                  30

Val Ala Val Tyr Arg Asp Asp Lys Arg Phe Thr Ser Glu Arg Gly Asn
             35                  40                  45

Val Leu Ala Thr Leu Leu Gln Gly Glu Asp Ser Ala Ser Gly Lys Met
 50                  55                  60

Leu Ala Val Thr Asp Gly Pro Arg His Arg Glu Ile Arg Asn Leu Met
65                   70                  75                  80

Leu Lys Ser Phe Ser Pro Arg Val Leu Ala Pro Val Val Glu Gly Val
                 85                  90                  95

Asn Arg Arg Thr Val Ala Leu Leu Asp Glu Ala Leu Glu Arg Gly Ala
             100                 105                 110

Phe Asp Phe Val Val Asp Leu Ala Asp His Ile Pro Ile Asn Thr Ile
             115                 120                 125

Gly Asp Leu Met Gly Val Pro Val Ala Asp Arg Glu Gln Leu Val His
130                 135                 140

Trp Asn Thr Met Thr Leu Ser Arg Thr Ser Ala Glu His Gly Ala Glu
145                 150                 155                 160

Glu Glu Trp Leu Ala Arg Asn Glu Ile Leu Leu Tyr Phe Ser Glu Leu
                 165                 170                 175

Ala Ala Lys Arg Arg Arg Asp Pro Gly Glu Asp Val Ile Ser Ala Leu
             180                 185                 190

Ala Thr Gly Thr Val Asp Gly Arg Pro Leu Thr Glu Asp Glu Ile Val
             195                 200                 205

Phe Asn Cys Tyr Ser Leu Ile Leu Gly Gly Asp Glu Ser Ser Arg Met
             210                 215                 220

Ser Ser Val Gly Ala Val Ile Ala Leu Ala Glu His Pro Asp Gln Trp
225                 230                 235                 240

Lys Ala Leu Lys Glu Gly Leu Val Asp Thr Ala Thr Ala Thr Glu Glu
                 245                 250                 255

Val Leu Arg Trp Thr Thr Pro Ala Met His Phe Gly Arg Arg Ala Leu
             260                 265                 270

Thr Asp Val Glu Ile Arg Gly Arg Thr Ile Ala Ser Gly Asp Val Val
             275                 280                 285

Thr Leu Trp Asn Ser Ser Ala Asn Phe Asp Glu Glu Val Phe Ala Asp
             290                 295                 300

Pro Glu Arg Phe Asp Leu Ala Arg Thr Pro Asn Lys His Val Ala Phe
305                 310                 315                 320

Gly His Gly Pro His Phe Cys Ile Gly Ala Phe Leu Gly Arg Thr His
                 325                 330                 335

Val Glu Ala Met Leu Arg Ala Leu Arg Asp Lys Ala Gly His Leu Glu
             340                 345                 350

Leu Leu Gly Arg Pro Arg Leu Leu His Ser Asn Phe Val Tyr Gly Tyr
             355                 360                 365

Thr Ser Leu Pro Val Arg Ile Asp Arg Pro Ala Ala Ser Gly Thr Ser
             370                 375                 380

Gly Ile Ser Pro Val Ser Ala Pro Pro Ala Thr Val Asp Arg Thr Arg
385                 390                 395                 400

Glu Ser Ala Thr Asp Gly Lys
                 405
```

<210> SEQ ID NO 45
<211> LENGTH: 1248
<212> TYPE: DNA
<213> ORGANISM: Bacterial

<400> SEQUENCE: 45

```
atgaccgacc cgacccagga gcccgactcc cgccagaatt cctccccggc ccatccgcct      60
cacccggcat acgcggccca cccggcccat ccgcctcacc cggcatacgc ggcctacgcg     120
gccctgcgct ccacctgccc cgtgcggccc gccccggca ccggggagcg ccccggtttt      180
ctggtcacgg gttacgcgga ggcccgggag cgctcggcg actcccgcct ctcgaaggac      240
acggccgcgt tcttcgcggg caaggggtcg cggcgccggc tccaccccgc ggtcgcccac     300
acgatgctgg ccagcgaccc gccccggcac accaggctcc gcaagctggt gacgagggcg     360
ttcaccaccg gggccgtcgc ggagctgcgt cccttcatcg cccgcgtcac ggacgaactg     420
ctggaccagt ggccggacgg cgagccgttc gacgtcgtgg cgggcctcgc ggtgccgctc     480
ccggtgatcg tgatctgccg gctgctcggg atccccagc acgaccggcc cgaagtacag      540
cgctggtcgg ggcagctctt cgcggccggg cggcccgacg tcgtcgacgc ggcctcgcac     600
gcgctggccg agtacatgac cggcctcatc gccaccaagc gccgggaccc cggcggttcg     660
ctgctcgacc ggctcgtcgt ggctcgcgac ggcgacgacc gtctgagcga ggaggagctg     720
gtctcgctgg ccgtgctcct gctcgtggcc ggccacgaga ccaccaccaa caccctcggc     780
aacgccctcc tggccctgct ccagcatccg gccgcgctgg cccgcctcgg cgcggacccc     840
gacggcgtcc ccgccgcgct ggacgaactg ctgcgcttcg actcggcggt gagcacggcc     900
accttccggt tcaccacgga acccgtcacg ctcggcggca ccgacatccc cgcgggcgtc     960
ccggtcctga tcgccctcgg agcggccaac cgggaccccg tacggttccc ggccccggac    1020
cgactcgacc tggaccgcga cgcgtccgcc cacctcgcgt tcggccacgg catccaccgc    1080
tgcgtcggcg cgcccctggc gagggcggag acggagatcg ccctacgagc cctgctgacc    1140
cgcttcccgg gcatccgtct cgccgtaccg ccggacgaac tgacatggcg ccccacccga    1200
ctcgtccgcg gtctggagtc cctcccggtc ctcgcgtcga cgccctag                 1248
```

<210> SEQ ID NO 46
<211> LENGTH: 415
<212> TYPE: PRT
<213> ORGANISM: Bacterial

<400> SEQUENCE: 46

Met Thr Asp Pro Thr Gln Glu Pro Asp Ser Arg Gln Asn Ser Ser Pro
1               5                   10                  15

Ala His Pro Pro His Pro Ala Tyr Ala Ala His Pro Ala His Pro Pro
            20                  25                  30

His Pro Ala Tyr Ala Ala Tyr Ala Ala Leu Arg Ser Thr Cys Pro Val
        35                  40                  45

Arg Pro Ala Pro Gly Thr Gly Glu Arg Pro Gly Phe Leu Val Thr Gly
    50                  55                  60

Tyr Ala Glu Ala Arg Glu Ala Leu Gly Asp Ser Arg Leu Ser Lys Asp
65                  70                  75                  80

Thr Ala Ala Phe Phe Ala Gly Lys Gly Ser Arg Arg Leu His Pro
                85                  90                  95

Ala Val Ala His Thr Met Leu Ala Ser Asp Pro Pro Arg His Thr Arg
            100                 105                 110

```
Leu Arg Lys Leu Val Thr Arg Ala Phe Thr Thr Gly Ala Val Ala Glu
            115                 120                 125

Leu Arg Pro Phe Ile Ala Arg Val Thr Asp Glu Leu Leu Asp Gln Trp
        130                 135                 140

Pro Asp Gly Glu Pro Phe Asp Val Val Ala Gly Leu Ala Val Pro Leu
145                 150                 155                 160

Pro Val Ile Val Ile Cys Arg Leu Leu Gly Ile Pro Gln His Asp Arg
                165                 170                 175

Pro Glu Val Gln Arg Trp Ser Gly Gln Leu Phe Ala Ala Gly Arg Pro
            180                 185                 190

Asp Val Asp Ala Ala Ser His Ala Leu Ala Glu Tyr Met Thr Gly
            195                 200                 205

Leu Ile Ala Thr Lys Arg Arg Asp Pro Gly Gly Ser Leu Leu Asp Arg
        210                 215                 220

Leu Val Val Ala Arg Asp Gly Asp Arg Leu Ser Glu Glu Leu
225                 230                 235                 240

Val Ser Leu Ala Val Leu Leu Val Ala Gly His Glu Thr Thr Thr
                245                 250                 255

Asn Thr Leu Gly Asn Ala Leu Leu Ala Leu Leu Gln His Pro Ala Ala
            260                 265                 270

Leu Ala Arg Leu Gly Ala Asp Pro Asp Gly Val Pro Ala Ala Leu Asp
        275                 280                 285

Glu Leu Leu Arg Phe Asp Ser Ala Val Ser Thr Ala Thr Phe Arg Phe
290                 295                 300

Thr Thr Glu Pro Val Thr Leu Gly Gly Thr Asp Ile Pro Ala Gly Val
305                 310                 315                 320

Pro Val Leu Ile Ala Leu Gly Ala Ala Asn Arg Asp Pro Val Arg Phe
                325                 330                 335

Pro Ala Pro Asp Arg Leu Asp Leu Asp Arg Asp Ala Ser Ala His Leu
            340                 345                 350

Ala Phe Gly His Gly Ile His Arg Cys Val Gly Ala Pro Leu Ala Arg
        355                 360                 365

Ala Glu Thr Glu Ile Ala Leu Arg Ala Leu Leu Thr Arg Phe Pro Gly
        370                 375                 380

Ile Arg Leu Ala Val Pro Pro Asp Glu Leu Thr Trp Arg Pro Thr Arg
385                 390                 395                 400

Leu Val Arg Gly Leu Glu Ser Leu Pro Val Leu Ala Ser Thr Pro
                405                 410                 415

<210> SEQ ID NO 47
<211> LENGTH: 1353
<212> TYPE: DNA
<213> ORGANISM: Bacterial

<400> SEQUENCE: 47
atgactccgg ccacggttcc ggttgtcgtc gacggcccgc gcggcatgcc actcctcggc      60
agcctccccg ccttcggcaa gaaccccctc gccttcttcg aacaactcag ggaccgcggg     120
gacatcgtcc gctggcgctt cggccgcaaa ccctccctct tcatcgccca ccccgacacc     180
gtcggcgaac tcctcaccga ggtcgagcgc agcttcgacc agcccgacct cggcatcgcc     240
ttccgcaccc tcctcgggaa cggcgtcatc gtctccaagg cgccgactg gcgccgcaag     300 cgctcccctcg tccaaccctc cgtccgcccc aaacaggtcc gctcctacgc cgcgaccatg     360
gccgactgcg ccgtcgccct cgccgaccgc tggaccgacg acagcacat cgacatcaag     420
```

-continued

```
aaggagatgg cggccctcac ccagctcatc gccgtccgca ccatcttcgg cgtcgacacc      480
gcggccgacg ccgaagccat cggcgccgcc atggacgtcg cacagaagga gatcggcgcc      540
gagttcagcg gcatcggagc cgtcctgccc gactgggtgc caccccggg acgcgcccgc       600 atcaaacgtg ccaccgccgt catcgacgcc gaggtctccc gcgtcgtctc ccgtcaccgc      660
gacggcgaga ccgaacgccc cgacctcctc agccgactgc tcgccgcccg cgacgagacc      720
ggcgcgcccc tctccgacca ggagatccgc gacgagaccc tcaccctcta catcggcggc      780
cacgagacca ccagctccac cctcgtctgg gcctggtacc tcctctcccg caaccccgg      840 gtccgcgacg ccctcaccga gaactcgac cgcgtcctcg ccgaccacga acccggctac      900
gacgactacg ccgccctcac ctacacccag gcggtcatca aggagaccct gcgcctctac      960
ccgacgatct ggctcatcac cggcctcgcc aaggaaggcg ccgtgctcgg tggcacgccc     1020
gtacccgccg gcacccgcgt ctggtccagc cagtgggcca cccagcggga ccccgctgg     1080 tacggcgacg cggaggcctt ccgccccgag cgctggatcg agcgggaggg cgaacccgcc     1140
gagcagatac ccgagtacgc ctggttcccc ttcggcggcg gccccgcgt ctgcctcggc      1200 acccgcttcg ccctcgtgga agccgtcctc gtcctgcgg tcctcgcccg ccgctaccac      1260
ctgaacctga cgaccgaaga actcctcccg gtccccagcc tcaccctcca accggaccgc     1320
gacgtcctgg ccacggtacg gacccgggac tga                                  1353
```

<210> SEQ ID NO 48
<211> LENGTH: 450
<212> TYPE: PRT
<213> ORGANISM: Bacterial

<400> SEQUENCE: 48

```
Met Thr Pro Ala Thr Val Pro Val Val Val Asp Gly Pro Arg Gly Met
  1               5                  10                  15

Pro Leu Leu Gly Ser Leu Pro Ala Phe Gly Lys Asn Pro Leu Ala Phe
                 20                  25                  30

Phe Glu Gln Leu Arg Asp Arg Gly Asp Ile Val Arg Trp Arg Phe Gly
             35                  40                  45

Arg Lys Pro Ser Leu Phe Ile Ala His Pro Asp Thr Val Gly Glu Leu
         50                  55                  60

Leu Thr Glu Val Glu Arg Ser Phe Asp Gln Pro Asp Leu Gly Ile Ala
 65                  70                  75                  80

Phe Arg Thr Leu Leu Gly Asn Gly Val Ile Val Ser Lys Gly Ala Asp
                 85                  90                  95

Trp Arg Arg Lys Arg Ser Leu Val Gln Pro Ser Val Arg Pro Lys Gln
            100                 105                 110

Val Arg Ser Tyr Ala Ala Thr Met Ala Asp Cys Ala Val Ala Leu Ala
        115                 120                 125

Asp Arg Trp Thr Asp Gly Gln His Ile Asp Ile Lys Lys Glu Met Ala
    130                 135                 140

Ala Leu Thr Gln Leu Ile Ala Val Arg Thr Ile Phe Gly Val Asp Thr
145                 150                 155                 160

Ala Ala Asp Ala Glu Ala Ile Gly Ala Ala Met Asp Val Ala Gln Lys
                165                 170                 175

Glu Ile Gly Ala Glu Phe Ser Gly Ile Gly Ala Val Leu Pro Asp Trp
            180                 185                 190

Val Pro Thr Pro Gly Arg Ala Arg Ile Lys Arg Ala Thr Ala Val Ile
        195                 200                 205
```

```
Asp Ala Glu Val Ser Arg Val Ser Arg His Arg Asp Gly Glu Thr
210                 215                 220

Glu Arg Pro Asp Leu Leu Ser Arg Leu Leu Ala Ala Arg Asp Glu Thr
225                 230                 235                 240

Gly Ala Pro Leu Ser Asp Gln Glu Ile Arg Asp Glu Thr Val Thr Leu
            245                 250                 255

Tyr Ile Gly Gly His Glu Thr Thr Ser Ser Thr Leu Val Trp Ala Trp
        260                 265                 270

Tyr Leu Leu Ser Arg Asn Pro Arg Val Arg Asp Ala Leu Thr Glu Glu
            275                 280                 285

Leu Asp Arg Val Leu Ala Asp His Glu Pro Gly Tyr Asp Asp Tyr Ala
290                 295                 300

Ala Leu Thr Tyr Thr Gln Ala Val Ile Lys Glu Thr Leu Arg Leu Tyr
305                 310                 315                 320

Pro Thr Ile Trp Leu Ile Thr Gly Leu Ala Lys Glu Gly Ala Val Leu
            325                 330                 335

Gly Gly Thr Pro Val Pro Ala Gly Thr Arg Val Trp Ser Ser Gln Trp
            340                 345                 350

Ala Thr Gln Arg Asp Pro Arg Trp Tyr Gly Asp Ala Glu Ala Phe Arg
            355                 360                 365

Pro Glu Arg Trp Ile Glu Arg Gly Glu Pro Ala Glu Gln Ile Pro
370                 375                 380

Glu Tyr Ala Trp Phe Pro Phe Gly Gly Pro Arg Val Cys Leu Gly
385                 390                 395                 400

Thr Arg Phe Ala Leu Val Glu Ala Val Leu Val Leu Ala Val Leu Ala
            405                 410                 415

Arg Arg Tyr His Leu Asn Leu Thr Thr Glu Glu Leu Leu Pro Val Pro
            420                 425                 430

Ser Leu Thr Leu Gln Pro Asp Arg Asp Val Leu Ala Thr Val Arg Thr
            435                 440                 445

Arg Asp
450

<210> SEQ ID NO 49
<211> LENGTH: 1215
<212> TYPE: DNA
<213> ORGANISM: Bacterial

<400> SEQUENCE: 49
atggagatca cgccggagtt cctccgcgac ccctacccgc gtaccagcg gatgcgggag      60 accggccgaa tgcacctgag ctcggccaac accgggcgca cctggttcct tccgcaccac    120
gccgacatcc gtaccgcgct gcgcgacgaa cggttctccg cgtcccgcaa ggccggcggg    180
ttcgtcaacc agttcccggc cgaggtgcgc cccgagttcg cccgcttcaa cgaggccatc    240
agccgctgga tcgtgctgca cgaccagccc gagcaccgcc agctgcgcca gctgatgcag    300
cagggcttca cccgccggct catcaccacc atggagccca gatccagcg gtctgcgac     360 gacctgatcg acgccttcgt caaacgcggc agcaccgagt tcatgacgga gtacgcacac    420
cccttccccg ccaaggtgat cgccgagatg ctcggcgtga accggagga ctacccggcc    480 ttcgtcgtct ggtccgagga cctgctcaac ttcgccggct cgctgcgccc caccctggag    540
atgttccggg ccgcgcagga cgggctcctc gcgatgatgg actacttcgc ccgactcctg    600
cccgagcggc gggagaaccc cggcgacgac ctggtcagcc tgctgctcag cgccgagagc    660
gagggcgagt ggatgaccgc cgagcaggtc ctggcgaact gcacccagat catcgtcgcc    720
```

-continued

```
ggacacgaga ccacccgcaa cctcgtggcc aacggcgtcg aactcctcct ccgctacccg    780
gagcagcgcg ccctcctgga atcccgcccg gagctgatgc cgagcgcggt ccgcgagatc    840
atgcgcttcg agagcccgct ccagttcatc cggcgggtgg cccgcgagga cttcgagttc    900
ggcggcgccg aggtgcgcga gggcgacggg ctcgtcctga tgctgggctc ggcgaaccgc    960
gaccccgagg ccttcgacga ccccgacacc ttcgacctca cccgcaaccc cacgggccat   1020
ctcgccttcg ggtggggccc gcacgtctgc gtcggcgccg ccctggccga gctcgagggc   1080
caggtgtcct tccggaccct gctcgaccgc ctccccggcc tggaactccg gacgcacgag   1140
cccgagcgca tccccaaccc gatgctgagg ggcttcgcct ccctcgacct gggcttccgg   1200
gaatccgccg gatga                                                    1215
```

<210> SEQ ID NO 50
<211> LENGTH: 404
<212> TYPE: PRT
<213> ORGANISM: Bacterial

<400> SEQUENCE: 50

```
Met Glu Ile Thr Pro Glu Phe Leu Arg Asp Pro Tyr Pro Val Tyr Gln
  1               5                  10                  15

Arg Met Arg Glu Thr Gly Arg Met His Leu Ser Ser Ala Asn Thr Gly
             20                  25                  30

Arg Thr Trp Phe Leu Pro His His Ala Asp Ile Arg Thr Ala Leu Arg
         35                  40                  45

Asp Glu Arg Phe Ser Ala Ser Arg Lys Ala Gly Phe Val Asn Gln
     50                  55                  60

Phe Pro Ala Glu Val Arg Pro Glu Phe Ala Arg Phe Asn Glu Ala Ile
 65                  70                  75                  80

Ser Arg Trp Ile Val Leu His Asp Gln Pro Glu His Arg Gln Leu Arg
                 85                  90                  95

Gln Leu Met Gln Gln Gly Phe Thr Arg Arg Leu Ile Thr Thr Met Glu
            100                 105                 110

Pro Lys Ile Gln Arg Val Cys Asp Asp Leu Ile Asp Ala Phe Val Lys
        115                 120                 125

Arg Gly Ser Thr Glu Phe Met Thr Glu Tyr Ala His Pro Phe Pro Ala
    130                 135                 140

Lys Val Ile Ala Glu Met Leu Gly Val Asn Pro Glu Asp Tyr Pro Ala
145                 150                 155                 160

Phe Val Val Trp Ser Glu Asp Leu Leu Asn Phe Ala Gly Ser Leu Arg
                165                 170                 175

Pro Thr Leu Glu Met Phe Arg Ala Ala Gln Asp Gly Leu Leu Ala Met
            180                 185                 190

Met Asp Tyr Phe Ala Arg Leu Leu Pro Glu Arg Arg Glu Asn Pro Gly
        195                 200                 205

Asp Asp Leu Val Ser Leu Leu Leu Ser Ala Glu Ser Glu Gly Glu Trp
    210                 215                 220

Met Thr Ala Glu Gln Val Leu Ala Asn Cys Thr Gln Ile Ile Val Ala
225                 230                 235                 240

Gly His Glu Thr Thr Arg Asn Leu Val Ala Asn Gly Val Glu Leu Leu
                245                 250                 255

Leu Arg Tyr Pro Glu Gln Arg Ala Leu Leu Glu Ser Arg Pro Glu Leu
            260                 265                 270

Met Pro Ser Ala Val Arg Glu Ile Met Arg Phe Glu Ser Pro Leu Gln
```

```
                275              280              285
     Phe Ile Arg Arg Val Ala Arg Glu Asp Phe Glu Phe Gly Gly Ala Glu
                 290              295              300
     Val Arg Glu Gly Asp Gly Leu Val Leu Met Leu Gly Ser Ala Asn Arg
     305              310              315              320
     Asp Pro Glu Ala Phe Asp Pro Asp Thr Phe Asp Leu Thr Arg Asn
                     325              330              335
     Pro Thr Gly His Leu Ala Phe Gly Trp Gly Pro His Val Cys Val Gly
                 340              345              350
     Ala Ala Leu Ala Glu Leu Glu Gly Gln Val Ser Phe Arg Thr Leu Leu
                 355              360              365
     Asp Arg Leu Pro Gly Leu Glu Leu Arg Thr His Glu Pro Glu Arg Ile
                 370              375              380
     Pro Asn Pro Met Leu Arg Gly Phe Ala Ser Leu Asp Leu Gly Phe Arg
     385              390              395              400
     Glu Ser Ala Gly

<210> SEQ ID NO 51
<211> LENGTH: 1254
<212> TYPE: DNA
<213> ORGANISM: Bacterial

<400> SEQUENCE: 51
gtggcggagc cgagcgaggt gcccgacgtc ttcgaccccc ggatctacgc gaccgggatc      60
ccgcacgacc gcttccgcct cctgcgcgat acgcccccgt cgcctggca ggaggagccc     120
gagatcctcg ggtggccgc cgggagcggg ttctggcgg tcacccggca cgccgacgtc     180
gtccgggtgc tcaaggactc cggcacgtac tcctcgtgtc tcggcgccac ccagatacgc     240
gaccccgacc ccgccgacct ccccttcatc cggcgcatga tgctcaatca ggaccctccc     300
gcccacggca ggctgcggcg cctcgtgagc cgggccttca cccgggggcg gatcgagcgc     360
ttcgaggcca ccgtgcggaa cgggcccgg cagctgctcg ccggggccgt cgacgcgggc     420
gaggtcgacc tcgtccgggc cgtcaccgac gactacgccc tgctcaacct gaccgacctg     480
ctcggggtgc ccgcgagcga ccggggcctg ctgcacgcct ggaccgagcg cgtcatcgcg     540
taccaggacc ccgacgagcc gccgccctc gacgagcggg gcggccggt caacccgcgc     600
tcgcccgcca tgctcgccga gatgttcggc tacgcccagg agctcgccgc ccacaagcgg     660
gcccgtcccg ccgacgacgt gatgagcgtg ctcgccggct ccgcactcgc cgacgcggaa     720
ctggagatgt tcttcttcct gctgaccgtc gccgggaacg acacggtccg cgccgccgcc     780
cccggcggac tcctcgccct cgccgaacac cccggcgaac agcgcaggtt gtggcgcggc     840
gaggtcgaca ccggtacggc ggtggacgaa ctcctgcggg tgcacccgcc cgtgctctcc     900
ttccggcgca ccgccgccac cgacaccgag ctcgccggcc ggcgatccg ccggggcgac     960
aaggtcgtcg tcttccacgc ctccgccaat tacgacgagc gcgtcttccc cgacccgcac    1020
cggctggacc tcagccgcgg tccgaacccg cacgtctcct cggcgacgg cccgcacgtc    1080
tgcctcggag cccacttcgc ccggcttcag ctccgggtgc tccacgagga actgcgccgc    1140
gcctgcggcg gcctggagct cgccggaccg ccccgccgcc tcgtctcgaa cttcatcaac    1200
ggcgtcaagt cgctgccggt acggcttcgg gagccgtccg cgccgccgc gtga          1254

<210> SEQ ID NO 52
<211> LENGTH: 419
<212> TYPE: PRT
```

<213> ORGANISM: Bacterial

<400> SEQUENCE: 52

```
Gly Asn Met Ala Glu Pro Ser Glu Val Pro Asp Val Phe Asp Pro Arg
  1               5                  10                  15
Ile Tyr Ala Thr Gly Ile Pro His Asp Arg Phe Arg Leu Leu Arg Asp
             20                  25                  30
His Ala Pro Val Ala Trp Gln Glu Pro Glu Ile Leu Gly Trp Pro
         35                  40                  45
Ala Gly Ser Gly Phe Trp Ala Val Thr Arg His Ala Asp Val Val Arg
     50                  55                  60
Val Leu Lys Asp Ser Gly Thr Tyr Ser Ser Cys Leu Gly Ala Thr Gln
 65                  70                  75                  80
Ile Arg Asp Pro Asp Pro Ala Asp Leu Pro Phe Ile Arg Arg Met Met
                 85                  90                  95
Leu Asn Gln Asp Pro Pro Ala His Gly Arg Leu Arg Arg Leu Val Ser
                100                 105                 110
Arg Ala Phe Thr Pro Gly Arg Ile Glu Arg Phe Glu Ala Thr Val Arg
            115                 120                 125
Lys Arg Ala Arg Gln Leu Leu Ala Gly Ala Val Asp Ala Gly Glu Val
130                 135                 140
Asp Leu Val Arg Ala Val Thr Asp Asp Tyr Ala Leu Leu Asn Leu Thr
145                 150                 155                 160
Asp Leu Leu Gly Val Pro Ala Ser Asp Arg Gly Leu Leu His Ala Trp
                165                 170                 175
Thr Glu Arg Val Ile Ala Tyr Gln Asp Pro Asp Glu Pro Pro Ala Leu
            180                 185                 190
Asp Glu Arg Gly Arg Pro Val Asn Pro Arg Ser Pro Ala Met Leu Ala
        195                 200                 205
Glu Met Phe Gly Tyr Ala Gln Glu Leu Ala Ala His Lys Arg Ala Arg
210                 215                 220
Pro Ala Asp Asp Val Met Ser Val Leu Ala Gly Ser Ala Leu Ala Asp
225                 230                 235                 240
Ala Glu Leu Glu Met Phe Phe Leu Leu Thr Val Ala Gly Asn Asp
                245                 250                 255
Thr Val Arg Ala Ala Pro Gly Gly Leu Leu Ala Leu Ala Glu His
            260                 265                 270
Pro Gly Glu Gln Arg Arg Leu Trp Arg Gly Glu Val Asp Thr Gly Thr
        275                 280                 285
Ala Val Asp Glu Leu Leu Arg Val His Pro Val Leu Ser Phe Arg
290                 295                 300
Arg Thr Ala Ala Thr Asp Thr Glu Leu Ala Gly Arg Pro Ile Arg Arg
305                 310                 315                 320
Gly Asp Lys Val Val Phe His Ala Ser Ala Asn Tyr Asp Glu Arg
                325                 330                 335
Val Phe Pro Asp Pro His Arg Leu Asp Leu Ser Arg Gly Pro Asn Pro
            340                 345                 350
His Val Ser Phe Gly Asp Gly Pro His Val Cys Leu Gly Ala His Phe
        355                 360                 365
Ala Arg Leu Gln Leu Arg Val Leu His Glu Leu Arg Arg Ala Cys
370                 375                 380
Gly Gly Leu Glu Leu Ala Gly Pro Pro Arg Arg Leu Val Ser Asn Phe
385                 390                 395                 400
```

```
Ile Asn Gly Val Lys Ser Leu Pro Val Arg Leu Arg Glu Pro Ser Ala
            405                 410                 415

Pro Pro Ala

<210> SEQ ID NO 53
<211> LENGTH: 1377
<212> TYPE: DNA
<213> ORGANISM: Bacterial

<400> SEQUENCE: 53
atggccatca ccaccggcac cgaagcaccc gaactcgccg gcatccact  gctcggctcc     60 atgtccgacc tcaagaacga ctcgctgggc accttcctgc gggcccggcg cgagcacggc    120
gacgtcgtcc gcatcgtcgc gggaccgccc ggcatccgcg ccaccgtcta cggcgtcttc    180
tccgccgagg gcgcgcagca ggtcctcgcc ggggagtccg ccaacttccg caaggacaac    240
gccttctacc aggagatccg cgagtccttc ggcaacggcc tgctcaccag ccaggacgag    300
gactacctcc gccagcgccg gctcgtccag cccctcttca cccgccgccg ggtcgacggc    360
tacgccgccg ccatcgccgc cgaggtcacc accctcaccg aggagtggcg ggacgccggc    420
gccgagcccg tcgacgtcct cgacgagatg gcccgcctcg ccctgcgcgc cgtggcccgc    480
atcctcttcg gcacggacgt cgacgcggcc gtcgagatcg tcggaagcgc cttccccgag    540
ctcggcgcgt acgtgctccg ccgcggctac agcccgctca cgtcccccg  cagctggccc    600 accccgccca accggcgcgc ggccgccgtc accgggcgc  tgtacgaggt ctgcgaccgc    660
atcatcgccg gcgtcggag  ctccgacggg gcgtcccccg cgacggcca  ggacctgctc    720 accctcctcg tcgaggccga gagcgccgag acggcagct  tcgacgcgac cgagctgcgc    780
gaacaggtcc tcgtcttcct gctcgccgga cacgagacca ccgccacctc gctcggcttc    840
gccctgcacc tcctcgccct ccaccggccg gagcagaagc gggcccacga ggaggtcgac    900
cgggtgctcg gcggccgtac ccccggcgcc ggcgacctcg acgccctgcc ctacgtcacc    960
caggtgctca aggaggccat gcggctcttc ccgccgccg  cggtcatcgg cgccgggcc    1020 gtcgtcgaga cccggatcgg cggtgtcacc gtcccggccg gtcggacgt  gatcgtcgcc    1080 ccctgggtca cccaccgcca cccggactac tgggaggacg ccgagcgctt cgaccccgac    1140
cgcttcactc ccgaggcgga ggccgcccgc cccgctacg  cctggttccc cttcggcggc    1200
ggcccgcgcg cctgcatcgg ccagcacttc tcgatgctgg agtcggtgat cgcgctggcg    1260
atgatcctcc agcggtacga gttcgaggcc gtcgacaccg aggtgccggt ggcccccgcg    1320
atcaccctcc aggcgatggg cccggcgcgc tgccgcctca gccccggca  ggcgtag      1377

<210> SEQ ID NO 54
<211> LENGTH: 458
<212> TYPE: PRT
<213> ORGANISM: Bacterial

<400> SEQUENCE: 54

Met Ala Ile Thr Thr Gly Thr Glu Ala Pro Glu Leu Ala Gly His Pro
1               5                   10                  15

Leu Leu Gly Ser Met Ser Asp Leu Lys Asn Asp Ser Leu Gly Thr Phe
            20                  25                  30

Leu Arg Ala Arg Arg Glu His Gly Asp Val Val Arg Ile Val Ala Gly
        35                  40                  45

Pro Pro Gly Ile Arg Ala Thr Val Tyr Gly Val Phe Ser Ala Glu Gly
    50                  55                  60
```

```
Ala Gln Gln Val Leu Ala Gly Glu Ser Ala Asn Phe Arg Lys Asp Asn
 65                  70                  75                  80

Ala Phe Tyr Gln Glu Ile Arg Glu Ser Phe Gly Asn Gly Leu Leu Thr
                 85                  90                  95

Ser Gln Asp Glu Asp Tyr Leu Arg Gln Arg Leu Val Gln Pro Leu
            100                 105                 110

Phe Thr Arg Arg Arg Val Asp Gly Tyr Ala Ala Ile Ala Ala Glu
        115                 120                 125

Val Thr Thr Leu Thr Glu Glu Trp Arg Asp Ala Gly Ala Glu Pro Val
    130                 135                 140

Asp Val Leu Asp Glu Met Ala Arg Leu Ala Leu Arg Ala Val Ala Arg
145                 150                 155                 160

Ile Leu Phe Gly Thr Asp Val Asp Ala Ala Val Glu Ile Val Gly Ser
                165                 170                 175

Ala Phe Pro Glu Leu Gly Ala Tyr Val Leu Arg Arg Gly Tyr Ser Pro
            180                 185                 190

Leu Asn Val Pro Arg Ser Trp Pro Thr Pro Ala Asn Arg Arg Ala Ala
        195                 200                 205

Ala Val His Arg Ala Leu Tyr Glu Val Cys Asp Arg Ile Ile Ala Gly
210                 215                 220

Arg Arg Ser Ser Asp Gly Ala Ser Pro Gly Asp Gly Gln Asp Leu Leu
225                 230                 235                 240

Thr Leu Leu Val Glu Ala Glu Ser Ala Glu Asp Gly Ser Phe Asp Ala
                245                 250                 255

Thr Glu Leu Arg Glu Gln Val Leu Val Phe Leu Leu Ala Gly His Glu
            260                 265                 270

Thr Thr Ala Thr Ser Leu Gly Phe Ala Leu His Leu Leu Ala Leu His
        275                 280                 285

Pro Ala Glu Gln Lys Arg Ala His Glu Glu Val Asp Arg Val Leu Gly
290                 295                 300

Gly Arg Thr Pro Gly Ala Gly Asp Leu Asp Ala Leu Pro Tyr Val Thr
305                 310                 315                 320

Gln Val Leu Lys Glu Ala Met Arg Leu Phe Pro Ala Ala Val Ile
                325                 330                 335

Gly Arg Arg Ala Val Glu Thr Arg Ile Gly Gly Val Thr Val Pro
            340                 345                 350

Ala Gly Ser Asp Val Ile Val Ala Pro Trp Val Thr His Arg His Pro
        355                 360                 365

Asp Tyr Trp Glu Asp Ala Glu Arg Phe Asp Pro Asp Arg Phe Thr Pro
370                 375                 380

Glu Ala Glu Ala Ala Arg Pro Arg Tyr Ala Trp Phe Pro Phe Gly Gly
385                 390                 395                 400

Gly Pro Arg Ala Cys Ile Gly Gln His Phe Ser Met Leu Glu Ser Val
                405                 410                 415

Ile Ala Leu Ala Met Ile Leu Gln Arg Tyr Glu Phe Glu Ala Val Asp
            420                 425                 430

Thr Glu Val Pro Val Ala Pro Ala Ile Thr Leu Gln Ala Met Gly Pro
        435                 440                 445

Ala Arg Cys Arg Leu Lys Pro Arg Gln Ala
450                 455

<210> SEQ ID NO 55
<211> LENGTH: 1248
<212> TYPE: DNA
```

<213> ORGANISM: Bacterial

<400> SEQUENCE: 55

```
atgaacgggg cgggcggggt gggggtgttc gatccggtgg ggctcgacct ggccgacccg    60
tacccggtct accggcggta ccgggaggcc ggttcggtgc atccggggcg ccgaccgac    120
cgggcagggc cgaccacctg gtacgtcttc gggtacgcgg aggtcgcgcg ggtcctcacg    180
gaccggggct tcggccgggc gtcgccgtcg gcggcgagcg cggcgccgat ccccgaggga    240
tacgggacgc tgcgccggat cgtcgagaac tggctcgtct tcctggaccc gccccggcac    300
acgcggctgc gcgcccaggt ggccccgccg ctgagcgctc cggccgtacg ggccttgcgt    360
ccccgcgtac gggagatcgc ggaggaactc gtacggcccc tcgcgcggcg gcccgtggtc    420
gaactggtcg agggcttcgc cgccccgttc ccgctgctgg tcgtggcggg gctgctcggg    480
gtcgaccccg gtcggtggcc gtggttccgg gaggaggcgc tcgccctcca gcggtccggc    540
gggaccaggg gcgaccggtc gccggccgcg ctcgcacggg ccgaccgcgc ggcggcgcac    600
cttgacgcgt acttccgggc ggagctggcg gcgcgccgct cggaggaccg ggggggacctg   660
ctctcggcgc tggcggcggc cggcgccgag gaccctcgc tggggacgac cgcgctgacg    720
tcgacctgcg tccacctcct gacggccggg cacgagacga cgacgggcct gctgggcaag    780
gcggtgctcg cgctgctggc gcggccgag gtggcggagg aactgcgcgc ggaccccggc    840
ctgttgccga acgccgtgga cgagttcctg cgccacgacc cacccgtgca gatggtcacg    900
cggtgggcgc ggcgggacgc ggagctcgcc ggccgagcgg tccgccgggg cgaccgggtc    960
cagctggtgc tgggttcggc ccaccgcgac ccggcccgct tcccggaccc cgaccggctg   1020
gacatccgcc gggacaccgg ccggcactgc gcgttcggtc tgggcatcca ctactgcgtg   1080
ggggcggcgc tggcacgcgc ggaggcggag atcggcctgg ggctcctgct ggaacggctg   1140
ccggcgctcc ggaccggcgc ccgtccacgg gtggaggtgg agtacgcccc ggactgggtg   1200
ttccacggcc cgtcccgcct gacgctgacc tcgcgggagc gtccctga                1248
```

<210> SEQ ID NO 56
<211> LENGTH: 415
<212> TYPE: PRT
<213> ORGANISM: Bacterial

<400> SEQUENCE: 56

```
Met Asn Gly Ala Gly Gly Val Gly Val Phe Asp Pro Val Gly Leu Asp
  1               5                  10                  15

Leu Ala Asp Pro Tyr Pro Val Tyr Arg Arg Tyr Arg Glu Ala Gly Ser
             20                  25                  30

Val His Pro Gly Arg Pro Thr Asp Arg Ala Gly Pro Thr Thr Trp Tyr
         35                  40                  45

Val Phe Gly Tyr Ala Glu Val Ala Arg Val Leu Thr Asp Arg Gly Phe
     50                  55                  60

Gly Arg Ala Ser Pro Ser Ala Ala Ser Ala Ala Pro Ile Pro Glu Gly
 65                  70                  75                  80

Tyr Gly Thr Leu Arg Arg Ile Val Glu Asn Trp Leu Val Phe Leu Asp
                 85                  90                  95

Pro Pro Arg His Thr Arg Leu Arg Ala Gln Val Ala Pro Pro Leu Ser
            100                 105                 110

Ala Pro Ala Val Arg Ala Leu Arg Pro Arg Val Arg Glu Ile Ala Glu
        115                 120                 125

Glu Leu Val Arg Pro Leu Ala Arg Arg Pro Val Val Glu Leu Val Glu
```

```
            130                 135                 140
Gly Phe Ala Ala Pro Phe Pro Leu Leu Val Val Ala Gly Leu Leu Gly
145                 150                 155                 160

Val Asp Pro Gly Arg Trp Pro Trp Phe Arg Glu Glu Ala Leu Ala Leu
                165                 170                 175

Gln Arg Ser Gly Gly Thr Arg Gly Asp Arg Ser Pro Ala Ala Leu Ala
            180                 185                 190

Arg Ala Asp Arg Ala Ala Ala His Leu Asp Ala Tyr Phe Arg Ala Glu
        195                 200                 205

Leu Ala Ala Arg Arg Ser Glu Asp Arg Gly Asp Leu Leu Ser Ala Leu
210                 215                 220

Ala Ala Ala Gly Ala Glu Asp Pro Ser Leu Gly Thr Thr Ala Leu Thr
225                 230                 235                 240

Ser Thr Cys Val His Leu Leu Thr Ala Gly His Glu Thr Thr Thr Gly
                245                 250                 255

Leu Leu Gly Lys Ala Val Leu Ala Leu Ala Arg Pro Glu Val Ala
            260                 265                 270

Glu Glu Leu Arg Ala Asp Pro Gly Leu Leu Pro Asn Ala Val Asp Glu
        275                 280                 285

Phe Leu Arg His Asp Pro Pro Val Gln Met Val Thr Arg Trp Ala Arg
290                 295                 300

Arg Asp Ala Glu Leu Ala Gly Arg Ala Val Arg Arg Gly Asp Arg Val
305                 310                 315                 320

Gln Leu Val Leu Gly Ser Ala His Arg Asp Pro Ala Arg Phe Pro Asp
                325                 330                 335

Pro Asp Arg Leu Asp Ile Arg Arg Asp Thr Gly Arg His Cys Ala Phe
            340                 345                 350

Gly Leu Gly Ile His Tyr Cys Val Gly Ala Ala Leu Ala Arg Ala Glu
        355                 360                 365

Ala Glu Ile Gly Leu Gly Leu Leu Glu Arg Leu Pro Ala Leu Arg
370                 375                 380

Thr Gly Ala Arg Pro Arg Val Glu Val Glu Tyr Ala Pro Asp Trp Val
385                 390                 395                 400

Phe His Gly Pro Ser Arg Leu Thr Leu Thr Ser Arg Glu Arg Pro
                405                 410                 415

<210> SEQ ID NO 57
<211> LENGTH: 5
<212> TYPE: PRT
<213> ORGANISM: Artificial Sequence
<220> FEATURE:
<223> OTHER INFORMATION: linker peptide

<400> SEQUENCE: 57

Gly Gly Gly Gly Ser
 1               5

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
agagtttgat cctggctcag                                            20
```

```
-continued

<210> SEQ ID NO 59
<211> LENGTH: 19
<212> TYPE: DNA
<213> ORGANISM: Artificial Sequence
<220> FEATURE:
<223> OTHER INFORMATION: primer

<400> SEQUENCE: 59
ggttaccttg ttacgactt                                                    19
```